United States Patent
Thomashow et al.

(10) Patent No.: US 6,417,428 B1
(45) Date of Patent: Jul. 9, 2002

(54) PLANT HAVING ALTERED ENVIRONMENTAL STRESS TOLERANCE

(76) Inventors: Michael F. Thomashow, 805 Southlawn; Eric J. Stockinger, 1360 Burcham Dr., both of East Lansing, MI (US) 48823; Kirsten Jaglo-Ottosen, 307 S. Clemens Ave., Lansing, MI (US) 48912; Sarah Jane Gilmour, 1830 Barnes Rd., Leslie, MI (US) 49251; Daniel Zarka, 2101 Barritt St., Lansing, MI (US) 48912; Cai-Zhong Jiang, 1301 Orchard Park Cir., Apt. C-4, Davis, CA (US) 94516

( * ) Notice: Subject to any disclaimer, the term of this patent is extended or adjusted under 35 U.S.C. 154(b) by 0 days.

(21) Appl. No.: 09/198,119

(22) Filed: Nov. 23, 1998

Related U.S. Application Data

(63) Continuation-in-part of application No. 09/018,233, filed on Feb. 3, 1998, now abandoned, and a continuation-in-part of application No. 09/017,816, filed on Feb. 3, 1998, now abandoned, and a continuation-in-part of application No. 09/018,235, filed on Feb. 3, 1998, now abandoned, and a continuation-in-part of application No. 09/017,575, filed on Feb. 3, 1998, now abandoned, and a continuation-in-part of application No. 09/018,227, filed on Feb. 3, 1998, now abandoned, and a continuation-in-part of application No. 09/018,234, filed on Feb. 3, 1998, now abandoned, and a continuation-in-part of application No. 08/706,270, filed on Sep. 4, 1996, now Pat. No. 5,892,009.

(51) Int. Cl.⁷ .............................. A01H 1/00; C12Q 1/68; C07H 19/00
(52) U.S. Cl. ...................... 800/260; 435/6; 536/22.1; 536/23.1
(58) Field of Search .............................. 435/6; 536/22.1, 536/23.1; 800/205

(56) References Cited

U.S. PATENT DOCUMENTS

| | | |
|---|---|---|
| 5,296,462 A | 3/1994 | Thomashow .................. 514/2 |
| 5,356,816 A | 10/1994 | Thomashow ............. 435/320.1 |

OTHER PUBLICATIONS

Yamaguchi–Shinozaki et al., The Plant Cell, 6:251–264 (1994).
Baker, S.S. et al., Plant Mol. Biol., 24:701–713 (1994).
Jiang, C. et al., Plant Mol. Biol., 30:679–684 (1996).
Horvath, D.P. et al., Plant Physiol., 103:1047–1053 (1993).
Wang, H. et al., Plant Mol. Biol., 28:605–617 (1995).
Okme–Takagi, M. et al., The Plant Cell, 7:173–182 (1995).
Klucher, K.M. et al., The Plant Cell, 8:137–153 (1996).
Wilson, K. et al., The Plant Cell, 8:659–671 (1996).
Li, J.J. et al., Science, 262:1870–1874 (1993).
Guy, C.L., Annu. Rev. Plant Physiol. Plant Mol. Biol. 41:187–223 (1990).
Monroy, A.F. et al., Plant Physiol., 102:1227–1235 (1993).
Monroy, A.F. et al., The Plant Cell, 7:321–331 (1995).

(List continued on next page.)

*Primary Examiner*—Jezia Riley
(74) *Attorney, Agent, or Firm*—Karen Guerrero

(57) ABSTRACT

A transformed plant is provided which comprises one or more environmental stress tolerance genes; a DNA regulatory sequence which regulates expression of the one or more environmental stress tolerance genes; a sequence encoding a binding protein capable of binding to the DNA regulatory sequence and inducing expression of the one or more environmental stress tolerance genes; and a recombinant promoter which regulates expression of the gene encoding the binding protein. A method for altering an environmental stress tolerance of a plant is also provided which comprises the steps of transforming a plant with a promoter which regulates expression of at least one copy of a gene encoding a binding protein capable of binding to a DNA regulatory sequence which regulates one or more environmental stress tolerance genes in the plant; expressing the binding protein encoded by the gene; and stimulating expression of at least one environmental stress tolerance gene through binding of the binding protein to the DNA regulatory sequence.

33 Claims, 43 Drawing Sheets

(1 of 43 Drawing Sheet(s) Filed in Color)

OTHER PUBLICATIONS

Knight et al., The Plant Cell, 8:489–503 (1996).
Knight, M.R. et al., Nature, 352:524–526 (1991).
Ding, J.P. et al., Plant J., 3:713–720 (1993).
White, T.C. et al., Plant Physiol., 106:917–928 (1994).
Hajela, R.K. et al., Plant Physiol., 93:1246–1252 (1990).
Gilmour, S.J., Plant Physiol., 87:745–750 (1988).
Schiestl, R.H. et al., Current Genetics, 16:339–346 (1989). (Abstract).
Berger, S.L. et al., Cell, 70:251–265 (1992).
Stockinger, E.J., et al., J. Heredity, 87:214–218 (1996). (Abstract).
Walling, L. et al., Nucleic Acids Res., 16:10477–10492 (1988). (Abstract).
Raikhel, N., Plant Physiol., 100:1627–1632 (1992).
Hahn, S., Cell 72:481–483 (1993).
Foster et al., FASEBJ, 8:192–200 (1994).
Ma, J. et al., Cell, 51:113–199 (1987).
Ma, J. et al., Nature, 334:631–633 (1988).
McCarty, D.R., et al., Cell, 66:895–905 (1991).
Guarente, L., Trends Biochem. Sci., 20:517–521 (1995).
Horiuchi, J. et al., Mol. Cell Biol., 15:1203–1209 (1995).
Wolffe, A.P., Trends Biochem. Sci., 19:240–244 (1994). (Abstract).
Brownell, J.E. et al., Cell, 84:843–851 (1996).
Jofuku, K.D. et al., The Plant Cell, 6:1211–1225 (1994).
Elliot, R.C. et al., The Plant Cell, 8;155–168 (1996).
Weigel, D., The Plant Cell, 7:388–389 (1995).
Choi, S.Y. et al., Plant Physiol., 108:849 (1995).

Activity of "positive" plasmids in reporter strains

| UAS Replacement Sequence | | | Yeast colony color on X-gal filters |
|---|---|---|---|
| Oligo | C-repeat/DRE | Inserts | |
| MT50 | COR15a | →→→→→← | Blue |
| MT50 | COR15a | →←←←←← | Blue |
| MT66 | COR78 | ←→→ | Blue |
| MT52 | M1 COR15a | →←← | White |

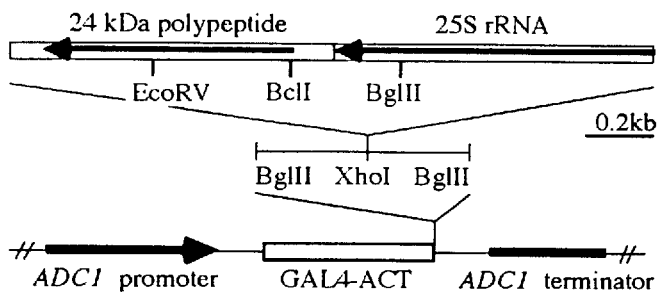

FIGURE 2A

```
AAAAAGAATCTACCTGAAAAGAAAAAAAAGAGAGAGAGATATAAATAGCTTACCAAGACAGATATACTATC    71
TTTTATTAATCCAAAAAGACTGAGAACTCTAGTAACTACGTACTACTTAAACCTTATCCAGTTTCTTGAAA   142
CAGAGTACTCTGATCAATG AAC TCA TTT TCA GCT TTT TCT GAA ATG TTT GGC TCC GAT   200
                     M   N   S   F   S   A   F   S   E   M   F   G   S   D    14

TAC GAG CCT CAA GGC GGA GAT TAT TGT CCG ACG TTG GCC ACG AGT TGT CCG AAG   254
 Y   E   P   Q   G   G   D   Y   C   P   T   L   A   T   S   C   P   K    32
                                                                   *
AAA CCG GCG GGC CGT AAG AAG TTT CGT GAG ACT CGT CAC CCA ATT TAC AGA GGA   308
 K   P   A   G   R   K   K   F   R   E   T   R   H   P   I   Y   R   G    50
 *           *   *   *                                   =   =   =   =
GTT CGT CAA AGA AAC TCC GGT AAG TGG GTT TCT GAA GTG AGA GAG CCA AAC AAG   362
 V   R   Q   R   N   S   G   K   W   V   S   E   V   R   E   P   N   K    68
 =   =   =   =   =   =   =   =   =   =   =   =   =   =   =   =   =   =
AAA ACC AGG ATT TGG CTC GGG ACT TTC CAA ACC GCT GAG ATG GCA GCT CGT GCT   416
 K   T   R   I   W   L   G   T   F   Q   T   A   E   M   A   A   R   A    86
 =   =   =   =   =   =   =   =   =   =   =   =   =   =   =   =   =   =
CAC GAC GTC GCT GCA TTA GCC CTC CGT GCC CGA TCA GCA TGT CTC AAC TTC GCT   470
 H   D   V   A   A   L   A   L   R   G   R   S   A   C   L   N   F   A   104
 =   =   =   =   =   =   =   =   =   =   =   =   =   =   =   =   =   =
GAC TCG GCT TGG CGG CTA CGA ATC CCG GAG TCA ACA TGC GCC AAG GAT ATC CAA   524
 D   S   A   W   R   L   R   I   P   E   S   T   C   A   K   D   I   Q   122
 =   =
AAA GCG GCT GCT GAA GCG GCG TTG GCT TTT CAA GAT GAG ACG TGT GAT ACG ACG   578
 K   A   A   A   E   A   A   L   A   F   Q   D   E   T   C   D   T   T   140

ACC ACG GAT CAT GGC CTG GAC ATG GAG GAG ACG ATG GTG GAA GCT ATT TAT ACA   632
 T   T   D   H   G   L   D   M   E   E   T   M   V   E   A   I   Y   T   158

CCG GAA CAG AGC GAA GGT GCG TTT TAT ATG GAT GAG GAG ACA ATG TTT GGG ATG   686
 P   E   Q   S   E   G   A   F   Y   M   D   E   E   T   M   F   G   M   176

CCG ACT TTG TTG GAT AAT ATG GCT GAA GGC ATG CTT TTA CCG CCG CCG TCT GTT   740
 P   T   L   L   D   N   M   A   E   G   M   L   L   P   P   P   S   V   194

CAA TGG AAT CAT AAT TAT GAC GGC GAA GGA GAT GGT GAC GTG TCG CTT TGG AGT   794
 Q   W   N   H   N   Y   D   G   E   G   D   G   D   V   S   L   W   S   212

TAC TAA TATTCGATAGTCGTTTCCATTTTTTGTACTATAGTTTGAAAAATATTCTAGTTCCTTTTTTAGAA 863
 Y                                                                        213

TGGTTCCTTCATTTTTATTTTATTTTTATTGTTGTAGAAACGAG                               905
```

FIGURE 2B

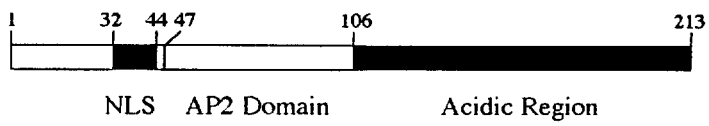

NLS   AP2 Domain        Acidic Region

FIGURE 2C

```
                                              
CBF1    IYRGVRQRNSGKWVSEVREPNKKT.RIWLGT    76
        ||||||| ||:  :|:|:|  |  : |:||||
EREBP2  HYRGVRQRPWGKFAAEIRDPAKNGARVWLGT    98

**    ^    .  *      **
CBF1    FQTAEMAARAHDVAALALRGRSACLNFADS   106
        ::||| ||  |:  ||   :|| | |||:
EREBP2  YETAEEAALAYDKAAYRMRGSKALLNFPHR   158
```

FIGURE 2D

```
ATGAACTCATTTTCTGCCTTTTCTGAAATGTTTGGCTCCGATTACGAGTCTCCGGTTCC  60
Met Asn Ser Phe Ser Ala Phe Ser Glu Met Phe Gly Ser Asp Tyr Glu Ser Pro Val Ser
TCAGGCGGTGATTACAGTCCGAAGCTTGCCACGAGCTGCCCCAAGAAACCAGCGGGAAGG  120
Ser Gly Gly Asp Tyr Ser Pro Lys Leu Ala Thr Ser Cys Pro Lys Lys Pro Ala Gly Arg
AAGAAGTTTCGTGAGACTCGTCACCCAATTTACAGAGGAGTTCGTCAAAGAAACTCCGGT  180
Lys Lys Phe Arg Glu Thr Arg His Pro Ile Tyr Arg Gly Val Arg Gln Arg Asn Ser Gly
AAGTGGGTGTGTGAGTTGAGAGAGCCAAAACAAGAAACGAGGATTTGGCTCGGGACTTTC  240
Lys Trp Val Cys Glu Leu Arg Glu Pro Asn Lys Lys Thr Arg Ile Trp Leu Gly Thr Phe
CAAACCGCTGAGATGGCAGCTCGTGCTGCTCACGACGTCGCCGCCATAGCTCTCCGTGGCAGA  300
Gln Thr Ala Glu Met Ala Ala Arg Ala His Asp Val Ala Ala Ile Ala Leu Arg Gly Arg
TCTGCCTGTCTCAATTTCGCTGACTCGGCTTGGCGGCTACGAATCCCGGAATCAACCTGT  360
Ser Ala Cys Leu Asn Phe Ala Asp Ser Ala Trp Arg Leu Arg Ile Pro Glu Ser Thr Cys
GCCAAGGAAATCCAAAAGGGCGGCTGAAGCCGCGTTGAATTTTCAAGATGAGATGTGT  420
Ala Lys Glu Ile Gln Lys Gly Ala Ala Ala Glu Ala Ala Leu Asn Phe Gln Asp Met Cys
CATATGACGACGGATGCTCATGGTCTTGACATGGAGGAGACCTTGGTGGAGGCTATTTAT  480
His Met Thr Thr Asp Ala His Gly Leu Asp Met Glu Glu Thr Leu Val Glu Ala Ile Tyr
ACGCCGGAACAGAGCCAAGATGCGTTTATGGATGAAGAGGCGATGTTGGGGATGCT  540
Thr Pro Glu Gln Ser Gln Asp Ala Phe Tyr Met Asp Glu Glu Ala Met Leu Gly Met Ser
AGTTTGTTGGATAACATGGCCGAAGGGATGCTTTTACCGTCGCCGTCGGTTCAATGGAAC  600
Ser Leu Leu Asp Asn Met Ala Glu Gly Met Leu Leu Pro Ser Pro Ser Val Gln Trp Asn
TATAATTTTGATGTCGGAGGAGATGATGACGTGTCCTTATGGAGCTATTAA  651
Tyr Asn Phe Asp Val Gly Glu Gly Asp Asp Asp Val Ser Leu Trp Ser Tyr •
```

FIGURE 12

```
ATGAACTCATTTTCTGCTTTTTCTGAAATGTTTGGCTCCGATTACGAGTCTTCGGTTCC  60
Met Asn Ser Phe Ser Ala Phe Leu Lys Met Phe Gly Ser Asp Tyr Glu Ser Ser Val Ser

TCAGGCGGTGATTATATTCCGACGCTTGCGAGCAGCTGCCCAAGAAACCGGGGTCGT   120
Ser Gly Gly Asp Tyr Ile Pro Thr Leu Ala Ser Ser Cys Pro Lys Pro Ala Gly Arg

AAGAAGTTTCGTGAGACTCGTCACCAATATACAGAGGAGTTCGTGGAGAAACTCCGGT   180
Lys Lys Phe Arg Glu Thr Arg His Pro Ile Tyr Arg Gly Val Arg Arg Asn Ser Gly

AAGTGGGTTTGTGAGGTTAGAGAACCAAAGAAAACAAGGATTTGGCTCGGAACATTT   240
Lys Trp Val Cys Glu Val Arg Glu Pro Asn Lys Lys Thr Arg Ile Trp Leu Gly Thr Phe

CAAACCGCTGAGATGGCAGCTCGAGTCACGACGTTGCCGCTTAGCCCTTCGTGGCCGA   300
Gln Thr Ala Glu Met Ala Ala Arg Ala His Asp Val Ala Ala Leu Ala Leu Arg Gly Arg

TCAGCCTGTCTCAATTTCGCTGACTCGGCTTGGAGACTCCGAATCCCGGAATCAACTTGC   360
Ser Ala Cys Leu Asn Phe Ala Asp Ser Ala Trp Arg Leu Arg Ile Pro Glu Ser Thr Cys

GCTAAGGACATCCAAAAGGCGGCTTGCCGTTGGCGTTCAGGATGAGATGTGT   420
Ala Lys Asp Ile Gln Lys Ala Ala Ala Glu Ala Ala Leu Ala Phe Gln Asp Glu Met Cys

GATGCGACGACGATCATGGCTTCGACATGGAGGAGACGTTGGTGGAGGCTATTTACACG   480
Asp Ala Thr Thr Asp His Gly Phe Asp Met Glu Glu Thr Leu Val Glu Ala Ile Tyr Thr

GCGGAACAGAGCGAAAATGCGTTTATATGCACGACTTTTCGCTTCCGTCCGTACAGTGCCGAGT   540
Ala Glu Gln Ser Glu Asn Ala Phe Tyr Met His Asp Glu Ala Met Phe Glu Met Pro Ser

TTGTTGGCTAATATGGCAGAAGGATGCTTTTGCGCTTCCGTCCTCCGTACAGTGGAATCAT   600
Leu Leu Ala Asn Met Ala Glu Gly Met Leu Leu Pro Leu Pro Ser Val Gln Trp Asn His

AATCATGAAGTCGACGGCGATGATGACGACGTATCGTTATGGAGTTATTAA  651
Asn His Glu Val Asp Gly Asp Asp Asp Val Ser Leu Trp Ser Tyr •
```

FIGURE 13

```
             MNSFSAFSEMFGSDYESKVSSGGDYXPTLATSCPKKPAGRKKFRETRHPI
                      10        20        30        40        50
cbf1.pro     MNSFSAFSEMFGSDYEPQ---GGDYCPTLATSCPKKPAGRKKFRETRHPI    47
cbf2.PRO     MNSFSAFSEMFGSDYESPVSSGGDYSPKLATSCPKKPAGRKKFRETRHPI    50
cbf3.PRO     MNSFSAFSEMFGSDYESSVSSGGDYIPTLASSCPKKPAGRKKFRETRHPI    50

YRGVRQRNSGKWVCEVREPNKKTRIWLGTFQTAEMAARAHDVAALALRGR
                      60        70        80        90       100
cbf1.pro     YRGVRQRNSGKWVSEVREPNKKTRIWLGTFQTAEMAARAHDVAAIALRGR    97
cbf2.PRO     YRGVRQRNSGKWVCELREPNKKTRIWLGTFQTAEMAARAHDVAAIALRGR   100
cbf3.PRO     YRGVRRRNSGKWVCEVREPNKKTRIWLGTFQTAEMAARAHDVAALALRGR   100

SACLNFADSAWRLRIPESTCAKDIQKAAAEAALAFQDEMCDXTTDXHGLD
                     110       120       130       140       150
cbf1.pro     SACLNFADSAWRLRIPESTCAKDIQKAAAEAALAFQDETCDTTTDHGLD    147
cbf2.PRO     SACLNFADSAWRLRIPESTCAKEIQKAAAEAALNFQDEMCHMTYDAHGLD   150
cbf3.PRO     SACLNFADSAWRLRIPESTCAKDIQKAAAEAALAFQDEMCDATTD-NGFD   149

MEETLVEAIYTPEQSEXAFYMDEEAMFGMPSLLDNMAEGMLLPXPSVQWN
                     160       170       180       190       200
cbf1.pro     MEETMVEAIYTPEQSEGAFYMDEETMFGMPTLLDNMAEGMLLPPSVQWN    197
cbf2.PRO     MEETLVEAIYTPEQSQDAFYMDKEAMLGMSSLLDNMAEGMLLPSPSVQWN   200
cbf3.PRO     MEETLVEAIYTAEQSENAFYMHDEAMFEMPSLLANMAEGMLLPLPSVQWN   199

HNXDVEGDDD-VSLWSY
                     210
cbf1.pro     HNYDGEGDGD-VSLWSY                                     213
cbf2.PRO     YNFDVEGDDD-VSLWSY                                     216
cbf3.PRO     HNHEVDGDDDDVSLWSY                                     216
```

FIGURE 14

```
Plurality:  2.00   Threshold:  4   AveWeight  1.00   AveMatch  2.91   AvMisMatch  -2.00
PRETTY of: at-nap{*}    January 29, 1998 23:04

1                                                            50
       at-nap{cbf1}    mnsfsafsem  fgsdyepqgg  dycptlatsc  pkkpagrkkf  retrHPIYRG
at-nap{napus-homolog}  ----------  ----------  ----------  ----------  ----HPIYRG
          Consensus    ----------  ----------  ----------  ----------  ----HPIYRG 51                                                          100
       at-nap{cbf1}    VRqRnSGKWV  sEVREPNKKt  RIWLGTFqTA  EMAARAHDVA  ALALRGRsAC
at-nap{napus-homolog}  VRlRkSGKWV  cEVREPNKKs  RIWLGTFkTA  EMAARAHDVA  ALALRGRgAC
          Consensus    VR-R-SGKWV  -EVREPNKK-  RIWLGTF-TA  EMAARAHDVA  ALALRGR-AC 101                                                         150
       at-nap{cbf1}    .LNfADSAWRL RIPEsTCaKD  IQKAAAEAAL  AFq.......  .......dET
at-nap{napus-homolog}  LNyADSAWRL  RIPEtTChKD  IQKAAAEAAL  AFeaeksdvt  mqngqnmeET
          Consensus    LN-ADSAWRL  RIPE-TC-KD  IQKAAAEAAL  AF--------  -------ET 151                                                         200
       at-nap{cbf1}    c.........  DT........  ..........  ....TTTDHG  lDMEETMVEA
at-nap{napus-homolog}  tavasqaevn  DTttehgmnm  eeatavasqa  evndTTTDHG  vDMEETMVEA
          Consensus    ----------  DT--------  ----------  ----TTTDHG  -DMEETMVEA 201                                                         250
       at-nap{cbf1}    iyTpEQSEG.  ..........  .........a  fYMDEEtMfg  MPTLLdnMAE
at-nap{napus-homolog}  vfTgEQSEGf  nmakestvea  avvteepskg  sYMDEEwMle  MPTLLadMAE
          Consensus    --T-EQSEG-  ----------  ----------  -YMDEE-M--  MPTLL--MAE 251                   278
       at-nap{cbf1}    GMLLpppsvq  wnhnydgegd  gdvslwsy
at-nap{napus-homolog}  GMLL......  ..........  ........
          Consensus    GMLL------  ----------  --------
```

FIGURE 16

FIGURE 18A bjCBF1 Species=Brassica juncea Length=577 [SEQ ID No. 38]
TTTCACCCTATCTACCGGGGAGTTCGCCTGAGAAAGTCAGGTAAGTGGGTGTGTGAAGTG
AGGGAGCCAAACAAGAAATCTAGGATTTGGCTTGGAACTTTCAAAACCGCAGAGATCGCT
GCTCGTGCTCACGACGTTGCCGCCTTAGCCCTCCGTGGAAGAGCGGCCTGTCTCAACTTC
GCCGACTCGGCTTGGCGGCTCCGTATCCCGGAGACAACTTGCGCCAAGGATATCCAGAAG
GCTGCTGCTGAAGCTGCGTTGGCTTTTGGGGCCGAAAAGAGTGATACCACGACGAATGAT
CAAGGCATGAACATGGAGGAGATGACGGTGGTGGCTTCTCAGGCTGAGGTGAGCGACACG
ACGACATATCATGGCCTGGACATGGAGGAGACTATGGTGGAGGCTGTTTTTGCTGAGGAA
CAGAGAGAAGGGTTTTACTTGGCGGAGGAGACGACGGTGGAGGGTGTTGTTACGGAGGAA
CAGAGCAAAGGGTTTTATATGTACGAGGAGTGGACGTTCGGGATGCAGTCCTTTTTGGCC
GATATGGCTGAAGGCATGCTCTTTTCAAAGGGCGAAT bjCBF2 Species=Brassica juncea Length=431 [SEQ ID No. 40]
CATCCGATCTACAGGGGAGTTCGTCTGAGAAAATCAGGTAAGTGGGTGTGTGAAGTGAGG
GAACCAAACAAGAGATCTAGGATCTGGCTCGGTACTTTCCTAACCGCCGAGATCGCAGCT
CGCGCTCACGACGTCGCCGCCATAGCCCTCCGTGGCAAATCCGCATGTCTCAATTTCGCT
GACTCGGCTTGGCGGCTCCGTATCTCGGAGACAACATGCCCTAAGGAGATTCAGAAGGCT
GCTGCTGAAGCCGCGGTGGCTTTTCAGGCTGAGCTAAATGATACGACGGCCGATCATGGC
CTTGACGTGGAGGAGACGATCGTGGAGGCTATTTTCACGGAGGAAAGCAGCGAAGGGTTT
TATATGGACGAGGAGTTCATGTTCGGGATGCCGACCTTGTGGGCTAGTATGGCAGAAGGG
ATGCTTCTTCC bjCBF3 Species=Brassica juncea Length=431 [SEQ ID No. 42]
CATCCAATTTACCGTGGAGTTCGTCTGAGAAAATCAGGTAAGTGGGTGTGTGAAGTGAGG
GAGCCAAACAAGAAATCTAGGATCTGGCCCGGTACTTTCCTAACCGCCGAGATCGCAGCT
CGCGCTCACGACGTCGCCGCCATAGCCCTCCGTGGCAAATCCGCATGTCTCAATTTCGCT
GACTCGGCTTGGCGGCTCCGTATCCCGGAGACAACATGCCCTAAGGAGATTCAGAAGGCT
GCTGCTGAAGCCGCGGTGGCTTTTCAGGCTGAGCTAAATGATACGACGGCCGATCATGGC
CTTGACGTGGAGGAGACGATCGTGGAGGCTATTTTCACGGAGGAAAGCAGCGAAGGGTTT
TATATGGACGAGGAGTTCATGTTCGGGATGCCGACCTTGTGGGCTAGTATGGCGGAGGGC
ATGCTCCTTCC bjCBF4 Species=Brassica juncea Length=425 [SEQ ID No. 44]
CATCCAATCTACCGGGGTGTTCGACAGAGAAACTCAGGGAAATGGGTTTGTGAAGTTAGG
GAGCCTAATAAGAAATCTAGGATCTGGTTAGGGACTTTTCCGACCGTCGAAATGGCCGCT
CGTGCTCACGACGTCGCCGCTTTAGCCCTTCGTGGCCGCTCCGCTTGTCTTAATTTCGCC
GACTCGGCGTGGTGTCTACGGATTCCCGAGTCTACTTGTCCTAAAGAGATTCAGAAAGCT
GCGGCCGAAGCTGCAATGGCGTTTCAGAACGAGACGGCTACGACTGAGACGACTATGGTT
GAGGGAGTCATACCGGCGGAGGAGACGGTGGGGCAGACGCGTGTGGAGACAGCAGAGGAG
AACGGTGTGTTTTATATGGACGATCCAAGGTTTCTTGAGAATATGGCAGAGGGCATGTTC
CTACC bnCBF1 Species=Brassica napus Length=632 [SEQ ID No. 46]
CACCCGATATACCGGGGAGTTCGTCTGAGAAAGTCAGGTAAGTGGGTGTGTGAAGTGAGG
GAACCAAACAAGAAATCTAGAATTTGGCTTGGAACTTTCAAAACAGCTGAGATGGCAGCT
CGTGCTCACGACGTCGCTGCCCTAGCCCTCCGTGGAAGAGGCGCCTGCCTCAATTATGCG
GACTCGGCTTGGCGGCTCCGCATCCCGGAGACAACCTGCCACAAGGATATCCAGAAGGCT
GCTGCTGAAGCCGCATTGGCTTTTGAGGCTGAGAAAAGTGATGTGACGATGCAAAATGGC
CAGAACATGGAGGAGACGACGGCGGTGGCTTCTCAGGCTGAAGTGAATGACACGACGACA
GAACATGGCATGAACATGGAGGAGGCAACGGCAGTGGCTTCTCAGGCTGAGGTGAATGAC
ACGACGACGGATCATGGCGTAGACATGGAGGAGACAATGGTGGAGGCTGTTTTTACTGGG
GAACAAAGTGAAGGGTTTAACATGGCGAAGGAGTCGACGGTGGAGGCTGCTGTTGTTACG
GAGGAACCGAGCAAAGGATCTTACATGGACGAGGAGTGGATGCTCGAGATGCCGACCTTG
TTGGCTGATATGGCAGAAGGGATGCTCCTGCC bnCBF2 Species=Brassica napus Length=876 [SEQ ID No. 48]
ACCGCTCGAGCAACAATGAACACATTCCCTGCTTCCACTGAAATGGTTGGCTCCGAGAAC
GAGTCTCCGGTTACTACGGTAGTAGGAGGTGATTATTATCCCATGTTGGCGGCAAGCTGT
CCGAAGAAGCCAGCGGGTAGGAAGAAGTTTCAGGAGACACGTCACCCCATTTACCGAGGA
GTTCGTCTGAGAAAGTCAGGTAAGTGGGTGTGTGAAGTGAGGGAACCAAACAAGAAATC

FIGURE 18A-continued

AGAATTTGGCCCGGAACTTTCAAAACAGCTGAGATGGCAGCTCGTGCTCACGACGTCGCT
GCCCTAGCCCTCCGTGGAAGAGGCGCCTGCCTCAATTATGCGGACTCGGCTTGGCGGCTC
CGCATCCCGGAAACAACCTGCCACAAGGATATCCAGAAGGCTGCTGCTGAAGCCGCATTG
GCTTTTGAGGCTGAGAAAAGTGATGTGACGATGCAAAATGGCCTGAACATGGAGGAGACG
ACGGCGGTGGCTTCTCAGGCTGAAGTGAATGACACGACGACAGAACATGGCATGAACATG
GAGGAGGCAACAGCGGTGGCTTCTCAGGCTGAGGTGAATGACACGACGACAGATCATGGC
GTAGACATGGAGGAGACGATGGTGGAGGCTGTTTTTACGGAGGAACAAAGTGAAGGGTTC
AACATGGCGGAGGAGTCGACGGTGGAGGCTGCTGTTGTTACGGATGAACTGAGCAAAGGA
TTTTACATGGACGAGGAGTGGACGTACGAGATGCCGACCTTGTTGGCTGATATGGCGGCA
GGGATGCTTTTGCCGCCACCATCTGTACAATGGGGACATAATGATGACTTGGAAGGAGAT
GCGGACATGAACCTCTGGAGTTATTAAGGATCCGCG bnCBF3 Species=Brassica napus Length=884 [SEQ ID No. 50]
ACTACACTCAGCCTTATCCAGTTTTTTTCAAAAGATTTTTCAACAATGAACACATTCCCT
GCGTCCACTGAAATGGTTGGCTCCGAGAACGAGTCTCCGGTTACTACGGTAGCAGGAGGT
GATTATTATCCCATGTTGGCGGCAAGCTGTCCGAAGAAGCCAGCAGGTAGGAAGAAGTTT
CAGGAGACACGTCACCCCATTTACCGAGGAGTTCGTCTGAGAAAGTCAGGTAAGTGGGTG
TGTGAAGTGAGGGAACCAAACAAGAAATCTAGAATTTGGCCCGGAACTTTCAAAACAGCT
GAGATGGCAGCTCGTGCTCACGACGTCGCTGCCCTAGCCCTCCGTGGAAGAGGCGCCTGC
CTCAATTATGCGGACTCGGCTTGGCGGCTCCGCATCCCGGAGACAACCTGCCACAAGGAT
ATCCAGAAGGCTGCTGCTGAAGCCGCATTGGCTTTTGAGGCTGAGAAAAGTGATGTGACG
ATGCAAAATGGCCTGAACATGGAGGAGACGACGGCGGTGGCTTCTCAGGCTGAAGTGAAT
GACACGACGACAGAACATGGCATGAACATGGAGGAGGCAACGGCAGTGGCTTCTCAGGCT
GAGGTGAATGACACGACGACGGATCATGGCGTAGACATGGAGGAGACAATGGTGGAGCT
GTTTTTACTGGGGAACAAAGTGAAGGGTTTAACATGGCGAAGGAGTCGACGGTGGAGGCT
GCTGTTGTTACGGAGGAACCGAGCAAAGGATCTTACATGGACGAGGAGTGGATGCTCGAG
ATGCCGACCTTGTTGGCTGATATGGCGGAAGGGATGCTTTTGCCGCCGCCGTCCGTACAA
TGGGGACAGAATGATGACTTCGAAGGAGATGCTGACATGAACCT bnCBF4 Species=Brassica napus Length=874 [SEQ ID No. 52]
GTAATTCGATTACCGCTCGAGTACTTACTATACTACACTCAGCCTTATCCAGTTTTTCAA
AAGAAGTTTTCAACTATGAACTCAGTCTCTACTTTTTCTGAACTTCTTGGCTCTGAGAAC
GAGTCTCCGGTAGGTGGTGATTACTGTCCCATGTTGGCGGCGAGCTGTCCGAAGAAGCCG
GCGGGTAGGAAGAAGTTTCGGGAGACACGTCACCCCATTTACCGAGGAGTTCGCCTTAGA
AAATCAGGTAAGTGGGTGTGTGAAGTGAGGGAACCAAACAAAAAATCTAGGATTTGGCTC
GGAACTTTCAAAACAGCTGAGATCGCAGCTCGTGCTCACGACGTCGCCGCCTTAGCTCTC
CGTGGAAGAGGCGCCTGCCTCAACTTCGCCGACTCGGCTTGGCGGCTCCGTATCCCGGAG
ACAACCTGCGCCAAGGATATCCAGAAGGCTGCTGCTGAAGCCGCATTGGCTTTTGAGGCC
GAGAAGAGTGATACCACGACGAATGATCATGGCATGAACATGGCTTCTCAGGCCGAGGTT
AATGACACAACGGATCATGGCCTGGACATGGAGGAGACGATGGTGGAGGCTGTTTTTACT
GAGGAGCAGAGAGACGGGTTTTACATGGCGGAGGAGACGACGGTGGAGGGTGTTGTTCCG
GAGGAACAGATGAGCAAAGGGTTTTACATGGACGAGGAGTGGATGTTCGGGATGCCGACC
TTGTTGGCTGATATGGCGGCAGGGATGCTCTTACCGCCGCCGTCCGTACAATGGGGACAT
AATGATGACTTCGAAGGAGATGTTGACATGAACCTCTGGAATTATTAGTACTCATATTTT
TTTAAATTATTTTTTGAACGAATAATATTTTATT bnCBF1 Species=Brassica napus Length=898 [SEQ ID No. 54]
AATAAATATCTTATCAAACCAGTCAGAACAGAGATCTTGTTACTTACTATACTACACTCA
GCCTTATCCAGTTTTCAAAAAAGTATTCAACGATGAACTCAGTCTCTACTTTTTCTGAA
CTGCTCCGCTCCGAGAACGAGTCTCCGGTTAATACGGAAGGTGGTGATTACATTTTGGCG
GCGAGCTGTCCCAAGAAACCTGCTGGTAGGAAGAAGTTTCAGGAGACACGCCACCCCATT
TACAGAGGAGTTCGTCTGAGGAAGTCAGGTAAGTGGGTGTGTGAAGTGAGGGAACCAAAC
AAGAAATCTAGAATTTGGCTCGGAACTTTCAAAACAGCTGAGATCGCAGCTCGTGCTCAC
GACGTTGCCGCCTTAGCTCTCCGTGGAAGAGGCGCCTGCCTCAACTTCGCCGACTCGGCT
TGGCGGCTCCGTATCCCGGAGACGACCTGCGCCAAGGATATCCAGAAGGCTGCTGCTGAA
GCCGCATTGGCTTTTGAGGCCGAGAAGAGTGATACCACGACGAATGATCATGGCATGAAC
ATGGCTTCTCAGGTTGAGGTTAATGACACGACGGATCATGACCTGGACATGGAGGAGACG
ATAGTGGAGGCTGTTTTTAGGGAGGAACAGAGAGAAGGGTTTTACATGGCGGAGGAGACG
ACGGTTGTGGGTGTTGTTCCGGAGGAACAGATGAGCAAAGGGTTTTACATGGACGAGGAG
TGGATGTTCGGGATGCCGACCTTGTTGGCTGATATGGCGGCAGGGATGCTCTTACCGCTG
CCGTCCGTACAATGGGACATAATGATGACTTCGAAGGAGATGCTGACATGAACCTCTGG
AATTATTAGTACTCATATTTTTTAAATTATTTTTGAACGAATAATATTTTATTGAA bnCBF6 Species=Brassica napus Length=1132 [SEQ ID No. 56]
GATTACCGCTCGAGTACTTACTATACTACACTCAGCCTTATCCAGTTTTTCTCAAAAGAT
TTTTCAACAATGAACACATTCCCTGCTTCCACTGAAATGGTTGGCTCCGAGAACGAGTCT FIGURE 18A-continued

```
CCGGTTACTACGGTAGTAGGAGGTGATTATTATCCCATGTTGGCGGCAAGCTGTCCGAAG
AAGCCAGCGGGTAGGAAGAAGTTTCAGGAGACACGTCACCCCATTTACCGAGGAGTTCGT
CTGAGAAAGTCAGGTAAGTGGGTGTGTGAAGTGAGGGAACCAAACAAGAAATCTAGAATT
TGGCTTGGAACTTTCAAAACAGCTGAGATGGCAGCTCGTGCTCACGACGTGGCTGCCCTA
GCCCTCCGTGGAAGAGGCGCCTGCCTCAATTATGCGGACTCGGCTTCGCGGCTCCGCATC
CCGGAGACAACCTGCCACAAGGATATCCAGAAGGCTGCTGCTGAAGCCGCATTGGCTTTT
GAGGCTGAGAAAAGTGATGTGACGATGGAGGAGACGATGGCGGTGGCTTCTCAGGCTGAA
GTGAATGACACGACGACAGATCATGGCATGAACATGGAGGAGGCAACAGCGGTGGCTTCT
CAGGCTGAGGTGAATGACACGACGACAGATCATGGCGTAGACATGGAGGAGACGATGGTG
GAGGCTGTTTTTACGGAGGAACAAAGTGAAGGGTTCAACATGGCGGAGGAGTCGACGGTG
GAGGCTGCTGTTGTTACGGATGAACTGAGCAAAGGATTTTACATGGACGAGGAGTGGACG
TACGAGATGCCGACCTTGTTGGCTGATATGGCGGCAGGGATGCTTTTGCCGCCACCATCT
GTACAATGGGACATAATGATGACTTGGAAGGAGATGCTGACATGAACCTCTGGAATTAT
TAATACTCGTGTTTTAAAAATTATACATTGTGCAATAATATTTTATCGAATTTCTAATTC
TGCCTTTAACTTTTAATGGGATCTTTATTAGTGTAGGAAACGAGTGTAAATGTTCCGCC
GTGGTGTTGTCAAAATGCTGATTATTTTTGTGTGCAGCATAATCACGTTTGGTTTCCTT
TACACTCCAAATTTAGTTGAAATACAAATAGAATAGAAAAGTGAAAAAATGT
``` bnCBF7 Species=Brassica napus Length=768 [SEQ ID No. 58]
```
AGTGATGTTTTTCAAAAGAAGTTTTCAACTATGAACTCAGTCTCTACTTTTTCTGAACTT
CTTGGCTCTGAGAACGAGTCTCCGGTAGGTGGTGATTACTGTCCCATGTTGGCGGCGAGC
TGTCCGAAGAAGCCGGCGGGTAGGAAGAAGTTTCGGGAGACACGTCACCCCATTTACCGA
GGAGTTCGCCTTAGAAAATCAGGTAAGTGGGTGTGTGAAGTGAGGGAGCCAAACAAGAAA
TCTAGGATTTGGCTCGGTACTTTCCTAACAGCCGAGATCGCAGCCCGTGCTCACGACGTC
GCCGCCATAGCCCTCCGCGGCAAATCAGCTTGTCTCAATTTTGCCGACTCCGCTTGGCGG
CTCCGTATCCCGGAGACAACATGCCCCAAGGAGATTCAGAAGGCGGCTGCTGAAGCCGCG
GTGGCTTTTAAGGCTGAGATAAATAATACGACGGCGGATCATGGCATTGACGTGGAGGAG
ACGATCGTTGAGGCTATTTTCACGGAGGAAAACAACGATGGTTTTTATATGGACGAGGAG
GAGTCCATGTTCGGGATGCCGGCCTTGTTGGCTAGTATGGCTGAAGGAATGCTTTTGCCG
CCTCCGTCCGTACAATTCGGACATACCTATGACTTTGACGGAGATGCTGACGTGTCCCTT
TGGAGTTATTAGTACAAAGATTTTTTATTTCCATTTTTGGTATAATACTTCTTTTTGATT
TTCGGATTCTACCTTTTTATGGGTATCATTTTTTTTTAGGAAACGGG
``` bnCBF8 Species=Brassica napus Length=953 [SEQ ID No. 60]
```
ACCGCTCGAGCAACAATGAACACATTCCCTGCTTCCACTGAAATGGTTGGCTCCGAGAAC
GAGTCTCCGGTTACTACGGTAGCAGGAGGTGATTATTATCCCATGTTGGCGGCAAGCTGT
CCGAAGAAGCCAGCGGGTAGGAAGAAGTTTCAGGAGACACGTCACCCCATTTACCGAGGA
GTTCGTCTGAGAAAGTCAGGTAAGTGGGTGTGTGAAGTGAGGGAACCAAACAAGAAATCT
AGAATTTGGCTTGGAACTTTCAAAACAGCTGAGATGGCAGCTCGTGCTCACGACGTGGCT
GCCCTAGCCCTCCGTGGAAGAGGCGCCTGCCTCAATTATGCGGACTCGGCTTCGCGGCTC
CGCATCCCGGAGACAACCTGCCACAAGGATATCCAGAAGGCTGCTGCTGAAGCCGCATTG
GCTTTTGAGGCTGAGAAAAGTGATGTGACGATGGAGGAGACGATGGCGGTGGCTTCTCAG
GCTGAAGTGAATGACACGACGACAGATCATGGCATGAACATGGAGGAGGCAACAGGCAGTG
GCTTCTCAGGCTGAGGTGAATGACACGACGACGGATCATGGCGTAGACATGGAGGAGACA
ATGGTGGAGGCTGTTTTTACTGGGGAACAAAGTGAAGGGTTTAACATGGCGAAGGAGTCG
ACGGTGGAGGCTGCTGTTGTTACGGAGGAACCGAGCAAAGGATCTTACATGGACGAGGAG
TGGATGCTCGAGATGCCGACCTTGTTGGCTGATATGGCGGAAGGGATGCTTTTGCCGCCG
CCGTCCGTACAATGGGACAGAATGATGACTTCGAAGGAGATGCGGACATGAACCTCTGG
AGTTATTAATACTCGTATTTTAAAATTATTTATTGTGCAATAATTTTTATCGAATTTC
GAATTCTGCCTTTAATTTTTAATGGGATCTTTATTTGCCAAAAAAAAAAAAA
``` bnCBF9 Species=Brassica napus Length=889 [SEQ ID No. 62]
```
CTAGTGATTACCGCTCGAGCAACAATGAACACATTCCCTGCTTCCACTGAAATGGTTGGC
TCCGAGAACGAGTCTCCGGTTACTACGGTAGCAGGAGGTGATTATTATCCCATGTTGGCG
GCAAGCTGTCCGAAGAAGCCAGCGGGTAGGAAGAAGTTTCAGGAGACACGTCACCCCATT
TACCGAGGAGTTCGTCTGAGAAAGTCAGGTAAGTGGGTGTGTGAAGTGAGGGAACCAAAC
AAGAAATCTAGAATTTGGCCCGGAACTTTCAAAACAGCTGAGATGGCAGCTCGTGCTCAC
GACGTCGCTGCCCTAGCCCTCCGTGGAAGAGGCGCCGCCTCAATTATGCGGACTCAGCT
TGGCGGCTCCGCATCCCGGAGACAACCTGCCACAAGGATATCCAGAAGGCTGCTGCTGAA
GCCGCATTGGCTTTTGAGGCTGAGAAAAGTGATGTGACGATGCAAAATGGCCTGAACATG
GAGGAGACGACGGCGGTGGCTTCTCAGGCTGAAGTGAATGACACGACGACAGAACATGGC
ATGAACATGGAGGAGGCAACGGCAGTGGCTTCTCAGGCTGAGGTGAATGACACGACGACG
GATCATGGCGTAGACATGGAGGAGACAATGGTGGAGGCTGTTTTTACTGGGGAACAAAGT
GAAGGGTTTAACATGGCGAAGGAGTCGACGGTGGAGGCTGCTGTTGTTACGGAGGAACCG
AGCAAAGGATCTTACATGGACGAGGAGTGGATGCTCGAGATGCCGACCTTGTTGGCTGAT
ATGGCGGAAGGGATGCTTTTGCCGCCGCCGTCCGTACAATGGGACAGAATGATGACTTC
```

FIGURE 18A-continued

GAAGGAGATGCGCACATGAACCTCTGGAGTTATTAAGGATCCGCGAATC boCBF1 Species=Brassica oleracea Length=563 [SEQ ID No. 64]
CACCCTATCTACCGGGGAGTTCGCCTGAGAAAGTCAGGTAAGTGGGTGTGTGAAGTGAGG
GAGCCAAACAAGAAATCTAGGATTTGGCTTGGAACTTTCAAAACCGCAGAGATCGCTGCT
CGTGCTCACGACGTTGCCGCCTTAGCCCTCCGTGGAAGAGCGGCCTGTCTCAACTTCGCC
GACTCGGCTTGGCGGCTCCGTATCCCGGAGACAACTTGCGCCAAGGATATCCAGAAGGCT
GCTGCTGAAGCTGCGTTGGCTTTTGGGGCCGAAAAGAGTGATACCACGACGAATGATCAA
GGCATGAACATGGAGGAGATGACGGTGGTGGCTTCTCAGGCTGAGGTGAGCGACACGACG
ACATATCATGGCCTGGACATGGAGGAGACTATGGTGGAGGCTGTTTTTGCTGAGGAACAG
AGAGAAGGGTTTTACTTGGCGGAGGAGACGACGGTGGAGGGTGTTGTTACGGAGGAACAG
AGCAAAGGGTTTTATATGGACGAGGAGTGGACGTTCGGGATGCAGTCCTTTTTGGCCGAT
ATGGCTGAAGGCATGCTCTTTCC boCBF2 Species=Brassica oleracea Length=533 [SEQ ID No. 66]
GAAACATAGATCTTTGTACTTACTATACTTCACCTTATCCAGTTTTATTTTTTTATTTAT
AAAGAGTTTTCAACAATGACCTCATTTTCTACCTTTTCTGAACTGTTGGGCTCCGAGCAT
GAGTCTCCGGTTACATTAGGCGAAGAGTATTGTCCGAAGCTGGCCGCAAGCTGTCCGAAG
AAACCAGCCGGCCGGAAGAAGTTTCGAGAGACGCGTCACCCAGTTTACAGAGGAGTTCGT
CTGAGAAACTCAGGTAAGTGGGTGTGTGAAGTGAGGGAGCCAAACAAGAAATCTAGGATT
TGGCTCGGTACTTTCCTAACAGCCGAGATCGCAGCCCGTGCTCACGACGTCGCCGCCATA
GCCCTCCGCGGCAAATCAGCTTGTCTCAATTTTGCCGACTCCGCTTGGCGGCTCCGTATC
CCGGAGACAACATGCCCCAAGGAGATTCAGAAGGCGGCTGCTGAAGCCGCGGTGGCTTTT
AAGGCTGAGATAAATAATACGACGGCGGATCACGGCCTCGACATGGAAGAGAC boCBF3 Species=Brassica oleracea Length=887 [SEQ ID No. 68]
ACTCAGCCTTATCCAGTTTTTCTCAAAAGATTTTTCAACAATGAACACATTCCCTGCTTC
CACTGAAATGGTTGGCTCCGAGAACGAGTCTCCGGTTACTACGGTAGTAGGAGGTGATTA
TTATCCCATGTTGGCGGCAAGCTGTCCGAAGAAGCCAGCGGGTAGGAAGAAGTTTCAGGA
GACACGTCACCCCATTTACCGAGGAGTTCGTCTGAGAAAGTCAGGTAAGTGGGTGTGTGA
AGTGAGGGAACCAAACAAGAAATCTAGAATTTGGCTTGGAACTTTCAAAACAGCTGAGAT
GGCAGCTCGTGCTCACGACGTGGCTGCCCTAGCCCTCCGTGGAAGAGGCGCCTGCCTCAA
TTATGCGGACTCGGCTTGGCGGCTCCGCATCCCGGAGACAACCTGCCACAAGGATATCCA
GAAGGCTGCTGCTGAAGCCGCATTGGCTTTTGAGGCTGAGAAAGTGATGTGACGATGGA
GGAGACGATGGCGGTGGCTTCTCAGGCTGAAGTGAATGACACGACGACAGATCATGGCAT
GAACATGGAGGAGGCAACAGCGGTGGCTTCTCAGGCTGAGGTGAATGACACGACGACAGA
TCATGGCGTAGACATGGAGGAGACGATGGTGGAGGCTGTTTTTACGGAGGAACAAAGTGA
AGGGTTCAACATGGCGGAGGAGTCGACGGTGGAGGCTGCTGTTGTTACGGATGAACTGAG
CAAAGGATTTTACATGGACGAGGAGTGGACGTACGAGATGCCGACCTTGTTGGCTGATAT
GGCGGCAGGGATGCTTTTGCCGCCACCATCTGTACAATGGGGACATAATGATGACTTGGA
AGGAGATGCGGACATGAACCTCTGGAGTTATTAATACTCGTATTTTT boCBF4 Species=Brassica oleracea Length=950 [SEQ ID No. 70]
CTGAAAAGAAGATAAAAGAGAGAGAAATAAATATCTTATCAAACCAGACAGAACAGAGAT
CTTGTTACTTACTATACTACACTCAGCCTTATCCAGTTTTTCAAAAGAAGTTTTCAACTA
TGAACTCAGTCTCTACTTTTTCTGAACTTCTTGGCTCTGAGAACGAGTCTCCGGTAGGTG
GTGATTACTGTCCCATGTTGGCGGCGAGCTGTCCGAAGAAGCCGGCGGGTAGGAAGAAGT
TTCGGGAGACACGTCACCCCATTTACCGAGGAGTTCGCCTTAGAAAATCAGGTAAGTGGG
TGTGTGAAGTGAGGGAACCAAACAAAAAATCTAGGATTTGGCTCGGAACTTTCAAAACAG
CTGAGATCGCAGCTCGTGCTCACGACGTCGCCGCCTTAGCTCTCCGTGGAAGAGGCGCCT
GCCTCAACTTCGCCGACTCGGCTTGGCGGCTCCGTATCCCGGAGACAACCTGCGCCAAGG
ATATCCAGAAGGCTGCTGCTGAAGCCGCATTGGCTTTTGAGGCCGAGAAGAGTGATACCA
CGACGAATGATCATGGCATGAACATGGCTTCTCAGGCTGAGGTTAATGACACGACGGATC
ATGGCCTGGACATGGAGGAGACGATGGTGGAGGCTGTTTTACTGAGGAGCAGAGAGACG
GGTTTTACATGGCGGAGGAGACGACGGTGGAGGGTGTTGTTCCGGAGGAACAGATGAGCA
AAGGGTTTTACATGGACGAGGAGTGGATTCGGGATGCCGACCTTGTTGGCTGATATGG
CGGCAGGGATGCTCTTACCGCCGCCGTCCGTACAATGGGACATAATGATGACTTCGAAG
GAGATGCTGACATGAACCTCTGGAATTATTAGTACTCGTATTTTTTAAATTATTTTTTG
AACGAATAATATTTTATTGAATTCGGATTCTACCTGTTTTTTTAATGGAT boCBF5 Species=Brassica oleracea Length=877 [SEQ ID No. 72]
ACCGCTCGAGCAACAATGAACACATTCCCTGCTTCCACTGAAATGGTTAGCTCCGAGAAC
GAGTCTCCGGTTACTACGGTAGTAGGAGGTGATTATTATCCCATGTTGGCGGCAAGCTGT
CCGAAGAAGCCAGCGGGTAGGAAGAAGTTTCAGGAGACACGTCACCCCATTTACCGAGGA
GTTCGTCTGAGAAAGTCAGGTAAGTGGGTGTGTGAAGTGAGGGAACTAAACAAGAAATCT
AGAATTTGGCTTGGAACTTTCAAAACAGCTGAGATGGCAGCTCGTGCTCACGACGTGGCT

FIGURE 18A-continued

```
GCCCTAGCCCTCCGTGGAAGAGGCGCCTGCCTCAATTATGCGGACTCGGCTTGGCGGCTC
CGCATCCCGGAGACAACCTGCCACAAGGATATCCAGAAGGCTGCTGCTGAAGCCGCATTG
GCTTTTGAGGCTGAGAAGAGTGATGCGACGATGCAAAATGGCCTGAACATGGAGGAGACG
ACGGCGGCGGCTTCTCAGACTGAAGTGAGTGACACGACGACAGATCATGGCATGAACATG
GAGGAGACAACGGCGGTGGCTTCTCAGGCTGAGGTGAATGACACGACGACAGATCATGGC
GTAGACATGGAGGAGACGATGGTGGAGGCTGTTTTTACTGAGGAACAAAGTGAAGGGTTC
AACATGGCGAAGGAGTCGACGGCGGAGGCTGCTGTTGTTACGGAGGAACTGAGCAAAGGA
GTTTACATGGACGAGGAGTGGACGTACGAGATGCCGACCTTGTTGGCTGATATGGCGGCA
GGGATGCTTTTGCCGCCACCATCTGTACAATGGGGACATAATGATGACTTGGAAGGAGAT
GCGGACATGAACCTACTGGAGTTATTAAGGATCCGCG
``` brCBF1 Species=Brassica rapa Length=374 [SEQ ID No. 74]
```
CATCCCATTTACAGGGGGGTTCGTTTAAGAAAGTCAGGTAAGTGGGTGTGTGAAGTGAGG
GAACCAAACAAGAAATCTAGGATTTGGCTCGGAACTTTCAAAACCGCTGAGATCGCTGCT
CGTGCTCACGACGTTGCTGCCTTAGCCCTCCGCGGGAGAGGCGCCTGCCTCAACTTCGCC
GACTCGGCTTGGCGGCTCCGTATCCCGGAGACAACCTGCGCCAAGGACATCCAGAAGGCG
GCTGCTGAAGCTGCATTGGCTTTTGAGGCCGAGAAGAGTGATCATGGCATGAACATCAAG
AATACTACGGCGGTGGTTTCTCAGGTTGAGGTGAATGACACGACGACGGACCACGGCTTG
GACATGGAGGAGAC
``` brCBF2 Species=Brassica rapa Length=884 [SEQ ID No. 76]
```
TACACTCAGCCTTATCCAGTTTTTTTCAAAAGACTTTTCAACAATGAACACATTCCCTGC
GTCCACTGAAATGGTTGGCTCCGAGAACGAGTCTCCGGTTACTACGGTAGCAGGAGGTGA
TTATTATCCCATGTTGGCGGCAAGCTGTCCGAAGAAGCCAGCGGGTAGGAAGAAGTTTCA
GGAGACACGTCACCCCATTTACCGAGGAGTTCGTCTGAGAAAGTCAGGTAAGTGGGTGTG
TGAAGTGAGGGAACCAAACAAGAAATCTAGAATTTGGCTTGGAACTTTCAAAACAGCTGA
GATGGCAGCTCGTGCTCACGACGTCGCTGCCCTAGCCCTCCGTGGAAGAGGCGCCTGCCT
CAATTATGCGGACTCGGCTTGGCGGCTCCGCATCCCGGAGACAACCTGCCACAAGGATAT
CCAGAAGGCTGCTGCTGAAGCCGCATTGGCTTTTGAGGCTGAGAAAAGTGATGTGACGAT
GCAAAATGGCCTGAACATGGAGGAGATGACGGCGGTGGCTTCTCAGGCTGAAGTGAATGA
CACGACGACAGAACATGGCATGAACATGGAGGAGGCAACGGCAGTGGCTTCTCAGGCTGA
GGTGAATGACACGACGACGGATCATGGCGTAGACATGGAGGAGACAATGGTGGAGGCTGT
TTTTACTGAGGAACAAAGTGAAGGGTTTAACATGGCGAAGGAGTCGACGGTGGAGGCTGC
TGTTGTTACGGAGGAACCGAGCAAAGGATCTTACATGGACGAGGAGTGGATGCTCGAGAT
GCCGACCTTGTTGGCTGATATGGCGGAAGGGATGCTTTTGCCGCCGCCGTCCGTACAATG
GGGACAGAATGATGACTTCGAAGGAGATGCTGACATGAACCTCT
``` brCBF3 Species=Brassica rapa Length=806 [SEQ ID No. 78]
```
ACACTCAGCCTTATCCAGTTTTCAAAAAAAGTATTCAACGATGAACTCAGTCTCTACTTT
TTCTGAACTGCTCTGCTCCGAGAACGAGTCTCCGGTTAATACGGAAGGTGGTGATTACAT
TTTGGCGGCGAGCTGTCCCAAGAAACCTGCTGGTAGGAAGAAGTTTCAGGAGACACGCCA
CCCCATTTACAGAGGAGTTCGTCTGAGGAAGTCAGGTAAGTGGGTGTGTGAAGTGAGGGA
ACCAAACAAGAAATCTAGAATTTGGCTCGGAACTTTCAAAACAGCTGAGATCGCAGCTCG
TGCTCACGACGTTGCCGCCTTAGCTCTCCGTGGAAGAGGCGCCTGCCTCAACTTCGCCGA
CTCGGCTTGGCGGCTCCGTATCCCGGAGACGACCTGCGCCAAGGATATCCAGAAGGCTGC
TGCTGAAGCCGCATTGGCTTTTGAGGCCGAGAAGAGTGATACCACGACGAATGATCGTGG
CATGAACATGGAGGAGACGTCGGCGGTGGCTTCTCCGGCTGAGTTGAATGATACGACGGC
GGATCATGGCCTGGACATGGAGGAGACGATGGTGGAGGCTGTTTTTAGGGAGGAACAGAG
AGAAGGGTTTTACATGGCGGAGGAGACGACGGTGGAGGGTGTTGTTCCGGAGTAACAGAT
GAGCAAAGGGTTTTACATGGACGAGGAGTGGACGTTCGAGATGCCGAGGTTGTTGGCTGA
TATGGCGGAAGGGATGCTTTTGCCGCCCCCGTCCGTACAATGGGGACATAACGATGACTT
CGAAGGAGATGCTGACATGAACCTCT
``` brCBF4 Species=Brassica rapa Length=755 [SEQ ID No. 80]
```
ACCGCTCGAGTACTTACTATACTACACTCAGCCTTATCCAGTTTTTCTTCCAACGATGGA
CTCAATCTCTACTTTTCCTGAACTGCTTGGCTCAGAGAACGAGTCTCCGGTTACTACGGT
AGTAGGAGGTGATTATTGTCCCAGGTTGGCGGCAAGCTGTCCGAAGAAGCCAGCGGGTAG
GAAGAAGTTTCAGGAGACACGTCACCCCATTTACCGTGGAGTTCGTTTAAGAAAGTCCGG
TAAGTGGGTGTGTGAAGTGAGGGAACCAAACAAGAAATCTAGGATTTGGCTCGGAACTTT
CAAAACCGCTGAGATCGCTGCTCGTGCTCACGACGTTGCTGCCTTAGCCCTCCGCGGAAG
AGGCGCCTGCCTCAACTTCGCCGACTCGGCTTGGCGGCTCCGTATCCCGGAGACAACCTG
CGCCAAGGATATCCAGAAGGCTGCTGCTGAAGCTGCATTGGCTTTTGAGGCCGAGAAGAG
TGATCATGGCATGAACATGAAGAATACTACGGCGGTGGCTTCTCAGGTTGAGGTGAATGA
TACGACGACGGACCATGGCGTGGACATGGAGGAGACGAGGGTGGAGGGTGTTGTTACGGA
GGAACAGAACAATTGGTTTTACATGGACGAGGAGTGGATGTTTGGGATGCCGACGTTGTT
GGTTGATATGGCGGAAGGGATGCTTATACCGCGGCAGTCCGTACAATCGGGACACTACGA
```

FIGURE 18A-continued

TGACTTCGAAGGAGATGCTGACATGAACCTCTGGA brCBF5 Species=Brassica rapa Length=832 [SEQ ID No. 82]
ACCGCTCGAGTACTTACTATACTACACTCAGCCTTATCCAGTTTTTCTTCCAACGATGGA
CTCAATCTCTACTTTTCCTGAACTGCTTGGCTCAGAGAACGAGTCTCCGGTTACTACGGT
AGTAGGAGGTGATTATTGTCCCAGGTTGGCGGCAAGCTGTCCGAAGAAGCCAGCGGGTAG
GAAGAAGTTTCAGGAGACACGTCACCCCATTTACCGTGGAGTTCGTTTAAGAAAGTCCGG
TAAGTGGGTGTGTGAAGTGAGGGAACCAAACAAGAAATCTAGGATTTGGCTCGGAACTTT
CAAAACCGCTGAGATCGCTGCTCGTGCTCACGACGTTGCTGCCTTAGCCCTCCGCGGAAG
AGGCGCCTGCCTCAACTTCGCCGACTCGGCTTGGCGGCTCCGTATCCCGGAGACAACCTG
CGCCAAGGATATCCAGAAGGCTGCTGCTGAAGCTGCTTTGGCTTTTGAGGCCGAGAAGAG
TGATCATGGCATGAACATGAAGAATACTACGGCGGTGGCTTCTCAGGTTGAGGTGAATGA
TACGACGACGGACCATGGCGTGGACATGGAGGAGACGTTGGTGGAGGCTGTTTTTACGGA
GGAACAGAGAGAAGGGTTTTACATGACGGAGGAGACGAGGGTGGAGGGTGTTGTTACGGA
GGAACAGAACAATTGGTTTTACATGGACGAGGAGTGGATGTTTGGGATGCCGACGTTGTT
GGTTGATATGGCGGAAGGGATGCTTATACCGCGGCAGTCCGTACAATCGGGACACTACGA
TGACTTCGAAGGAGATGCTGACATGAACCTCTGGAATTATTAGGGATCCGCG brCBF6 Species=Brassica rapa Length=830 [SEQ ID No. 84]
TACTACACTCAGCCTTATCCAGTTTTCAAAAAAAGTATTCAACTATGAACTCAGTCTCTA
CTTTTTCTGAACTGCTCTGCTCCGAGAACAAGTCTCCGGTTAATACGGAAGGTGGTGATT
ACATTTTGGCGGCGAGCTGTCCCAAGAAACCTGCTGGTAGGAAGAAGTTTCAGGAGACAC
GCCACCCCATTTACAGAGGAGTTCGCCTAAGAAAGTCAGGTAAGTGGGTGTGTGAAGTGA
GGGAACCAAACAAGAAATCTAGAATTTGGCTCGGAACTTTCAAAACAGCTGAGATAGCAG
CTCGTGCTCACGACGTCGCCGCCTTAGCTCTCCGTGGAAGAGGCGCCTGCCTCAACTTCG
CCGACTCGGCTTGGCGGCTCCGTATCCCAGAGACAACCTGCGCCAAGGATATCCAGAAGG
CTGCTGCTGAAGCCGCATTGGCTTTTGAGGCCGAGAAGAGTGATACCACGACGAATGATC
GTGGCATGAACATGGAGGAGACGTCCGCGGTGGCTTCTCCGGCTGAGTTGAATGATACGA
CGGCGGATCATGGCCTGGACATGGAGGAGACGATGGTGGAGGCTGTTTTTAGGGACGAAC
AGAGAGAAGGGTTTTACATGGCGGAGGAGACGACGGTGGAGGGTGTTGTTCCGGAGGAAC
AGATGAGCAAAGGGTTTTACATGGACGAGGAGTGGACGTTCGAGATGCCGAGGTTGTTGG
CTGATATGGCGGAAGGGATGCTTCTGCCTCCCCCGTCCGTACAATGGGGACATAACGATG
ACTTCGAAGGAGATGCTGACATGAACCTCTGGAATTATTAGGGATCCGCG brCBF7 Species=Brassica rapa Length=854 [SEQ ID No. 86]
CTATACTACACACAGCCTTATCCAGCCGCTCGAGTACTTACTATACTACACTCAGCCTTT
TCCAGTTTTTCAAAAGAAGTTTTCAACGATGAACTCAGTCTCTACTCTTTCTGAAGTTCT
TGGCTCCCAGAACGAGTCTCCCGTAGGTGGTGATTACTGTCCCATGTTGGCGGCGAGCTG
TCCGAAGAAGCCGGCGGGTAGGAAGAAGTTTCGGGAGACACGTCACCCCATTTACAGAGG
AGTTCGTCTTAGAAAGTCAGGTAAGTGGGTGTGTGAAGTGAGGGAACCAAACAAGAAATC
TAGGATTTGGCTCGGAACTTTCAAAACAGCTGAGATCGCAGCTCGTGCTCACGACGTTGC
CGCCTTAGCTCTCCGTGGAAGAGGCGCCTGCCTCAACTTCGCCGACTCGGCTTGGCGGCT
CCGTATCCCGGAGACAACCTGCGCCAAGGATATCCAGAAGGCTGCTGCTGAAGCCGCATT
GGCTTTTGAGGCGGAGAAGAGTGATACCACGACGACGAATGATCATGGCATGAACATGGC
TTCTCAGGTTGAGGTTAATGACACGGACGGATCATGACCTGGACATGGAGGAGACGATGGT
GGAGGCTGTTTTTAGGGAGGAACAGAGAGAAGGGTTTTACATGGCGGAGGAGACGACGGT
GGAGGGTATTGTTCCGGAGGAACAGATGAGCAAAGGGTTTTACATGGACGAGGAGTGGAT
GTTCGGGATGCCGACCTTGTTGGCTGATATGGCGGCAGGGATGCTCTTACCGCCGCCGTC
CGTACAATGGGGACATAATGATGACTTCGAAGGAGATGCTGACATGAACCTCTGGAATTA
TTAAGGGATCCGCG gmCBF1 Species=Glycine max Length=738 [SEQ ID No. 88]
CATCCGATTTATAGTGGCGTGAGGAGGAGGAACACGGATAAGTGGGTAAGTGAGGTGAGG
GAGCCCAACAAAAAGACCAGGATTTGGCTGGGGACTTTTCCCACGCCGGAGATGGCGGCA
CGGGCCCACGACGTGGCGGCAATGGCCCTGAGGGGCCGGTATGCCTGTCTCAACTTCGCT
GACTCGACGTGGCGGTTACCAATTCCCGCCACTGCTAACGCAAAGGATATACAGAAAGCA
GCAGCAGAGGCTGCCGAGGCTTTCAGACCAAGTCAGACCTTAGAAAATACGAATACAAAG
CAAGAGTGTGTAAAAGTGGTGACGACAACAACGATCACAGAACAAAAACGAGGAATGTTT
TATACGGAGGAAGAAGAGCAAGTGTTAGATATGCCTGAGTTGCTTAGGAATATGGTGCTT
ATGTCCCCAACACATTGCATAGGGTATGAGTATGAAGATGCTGACTTGGATGCTCAAGAT
GCTGAGGTGTCCCTATGGAGTTTCTCAATTTAATAACGTGCTTTTGGTTTGGTTTTTTAT
GTTAGTTTTGGAGTGTGACTGTCTGTACTGGTTTTTTATTAGTAGTACGGATACTAGCTA
TAGGTGGCAGATTGAAAGGGACCAAAAGGAATTTTCTTTTGAAACCCTTTTTGTCAAAGT
AATCAATCGCGTATCATCAAGTGAATCCCTTGATCAAGTTTATGTATGAATTAAATAAAA
GAAGAATCTAGTTTTGGT

FIGURE 18A-continued rsCBF1 Species= Raphanus sativus Length=793 [SEQ ID No. 90]
ACTACACTCAGCCTTATCCAGTTTTTCTTCCAACGATGGACTCAATCTCTACTTTTTCTG
AACTGCTTGGCTCCGAGAACGAGTCTCCGGTTACTACGGTAGTAGGAGGTGATTATTTTC
CCAGGTTGGCGGCAAGCTGTCCGAAGAAGCCAGCGGGTAGGAAGAAGTTTCAGGAGACAC
GTCACCCCATTTACCGCGGAGTTCGTTTAAGAAAGTCAGGTAAGTGGGTGTGTGAAGTGA
GGGAACCAAACAAGAAATCTAGGATTTGGCTCGGAACTTTCAAAACCGCTGAGATCGCTG
CTCGTGCTCACGACGTTGCTGCCTTAGCCCTCCGCGGAAGAGGCGCCTGCCTCAACTTCG
CCGACTCGGCTTGGCGGCTCCGTATCCCGGAGACAACCTGCGCCAAGGATATCCAGAAGG
CTGCTGCTGAAGCTGCATTGGCTTTTGAGGCCGAGAAGAGTGATCATGGCATGAACATGA
AGAATACTACGGCGGTGGCTTCTCAGGTTGAGGTGAATGACACGACGACGACCATGGCG
TGGACATGGAGGAGACGTTGGTGGAGGCTGTTTTTACGGAGGAACAGAGAGAAGGGTTTT
ACATGACGGAGGAGACGAGGGTGGAGGGTGTTGTTACGGAGGAACAGAACAATTGGTTTT
ACATGGACGAGGAGTGGATGTTTGGGATGCCGACGTTGTTGGTTGATATGGCGGAAGGGA
TGCTTTTACCGCGGCCGTCCGTACAATCGGGACACTACGATGACTTCGAAGGAGATGCTG
ACATGAACCTCTG rsCBF2 Species= Raphanus sativus Length=682 [SEQ ID No. 92]
ACACCTAAACCTTATCCAGGTTTAACTTTTTTTTTCATAAAGAGTTTTCAACAATGACCA
CATTTTCTACCTTTTCCGAAATGTTGGGCTCCGAGTACGAGTCTCCGGTTACATTAGGCG
GAGAGTATTGTCCGAAGCTGGCCGCGAGCTGTCCGAAGAAACCAGCTGGTCGTAAGAAGT
TTCGAGAGACGCGCCACCCAATATACAGAGGAGTTCGTCTGAGAAACTCAGGTAAGTGGG
TGTGTGAAGTGAGGGAGCCAAACAAGAAATCTAGGATTTGGCTCGGTACTTTCCTAACCG
CCGAGATCGCAGCGCGTGCCCACGACGTCGCCGCCATAGCCCTCCGCGGCAAATCCGCAT
GTCTCAATTTCGCTGACTCGGCTTGGCGGCTCCGTATCCCGGAGACAACATGCCCCAAGG
ATATACAGAAGGCGGCTGCTGAAGCCGCGGTGGCTTTTCAGGCTGAGATAAATGATACGA
CGACGGATCATGGCCTGGACTTGGAGGAGACGATCGTGGAGGCTATTTTTACGGAGGTAA
ACAACGATGAGTTTTATATGGACGAGGAGTCCATGTTCGGGATGCCGTCTTTGTTGGCTA
GTATGGCGGAAGGGATGCTTTTGCCGCTGCCGTCCGTACAATCTGAACATAACTGTGACT
TCGACGGAGATGCTGACATGAA zmCBF1 Species=Zea maize Length=349 [SEQ ID No. 94]
CGGAGTCCGCGGACGGCGGCGGCGGCGACGACGAGTACGCGACGGTGCTGTCGGCGC
CACCCAAGCGGCCGGCGGGGCGGACCAAGTTCCGGGAGACGCGGCACCCCGTGTACCGCG
GCGTGCGGCGGCGCGGGCCCGCGGGGCGCTGGGTGTGCGAGGTCCGCGAGCCCAACAAGA
AGTCGCGCATCTGGCTCGGCACCTTCGCCACCCCCGAGGCCGCCGCGCGCGCACGACG
TGGCCGCGCTGGCCCTGCGGGGCCGCGCCGCGTGCCTCAACTTCGCCGACTCGGCGCGCC
TGCTCCAAGTCGACCCCGCCACGCTCGCCACCCCCGACGACATCCGCCG

FIGURE 18B

BJCBF1-PEP Species=Brassica juncea length=130 [SEQ ID No. 39]
LPGVRLRKSGKWVCEVREPNKKSRIWLGTFKTAEIAARAHDVAALALRGRAACLNFADSA
WRLRIPETTCAKDIQKAAAEAALAFGAEKSDTTTNDQGMNMEEMTAVASQAEVSDTTTYH
GLDMEETMVD

BJCBF2-PEP Species=Brassica juncea length=143 [SEQ ID No. 41]
HPIYRGVRLRKSGKWVCEVREPNKRSRIWLGTFLTAEIAARAHDVAAIALRGKSACLNFA
DSAWRLRISETTCPKEIQKAAAEAAVAFQAELNDTTADHGLDVEETIVEAIFTEESSEGF
YMDEEFMFGMPTLWASMAEGMLL

BJCBF3-PEP Species=Brassica juncea length=143 [SEQ ID No. 43]
HPIYRGVRLRKSGKWVCEVREPNKKSRIWPGTFLTAEIAARAHDVAAIALRGKSACLNFA
DSAWRLRIPETTCPKEIQKAAAEAAVAFQAELNDTTADHGLDVEETIVEAIFTEESSEGF
YMAEEFMFGMPTLWASVAEGMLL

BJCBF4-PEP Species=Brassica juncea length=142 [SEQ ID No. 45]
HPIYRGVRQRNSGKWVCEVREPNKKSRIWLGTFPTVEMAARAHDVAALALRGRSACLNFA
DSAWCLRIPESTCPKEIQKAAAEAAMAFQNEETATTETTMVEGVIPAEETVGQTRVETAE
ENGVEYMDDPRFLENMAEGMLF

BNCBF1-PEP Species=Brassica napus length=210 [SEQ ID No. 47]
HPIYRGVRLRKSGKWVCEVREPNKKSRIWLGTFKTAEMAARAHDVAALALRGRGACLNYA
DSAWRLRIPETTCHKDIQKAAAEAALAFEAEKSDVTMQNGQNMEETTAVASQAEVNDTTT
EHGMNMEEATAVASQAEVNDTTTDHGVDMEETMVEAVFTGEQSEGFNMAKESTVEAAVVT
EEPSKGSYMDEEWMLEMPTLLADMAEGMLL

BNCBF2-PEP Species=Brassica napus length=283 [SEQ ID No. 49]
MNTFPASTEMVGSENESPVTTVVGGDYYPMLAASCPKKPAGRKKFQETRHPIYRGVRLRK
SGKWVCEVREPNKKSRIWPGTFKTAEMAARAHDVAALALRGRGACLNYADSAWRLRIPET
TCHKDIQKAAAEAALAFEAEKSDVTMQNGLNMEETTAVASQAEVNDTTTEHGMNMEEATA
VASQAEVNDTTTDHGVDMEETMVEAVFTEEQSEGFNMAEESTVEAAVVTDELSKGFYMDE
EWTYEMPTLLADMAAGMLLPPPSVQWGHNDDLEGDADMNLWSY

BNCBF3-PEP Species=Brassica napus length=279 [SEQ ID No. 51]
MNTFPASTEMVGSENESPVTTVAGGDYYPMLAASCPKKPAGRKKFQETRHPIYRGVRLRK
SGKWVCEVREPNKKSRIWPGTFKTAEMAARAHDVAALALRGRGACLNYADSAWRLRIPET
TCHKDIQKAAAEAALAFEAEKSDVTMQNGLNMEETTAVASQAEVNDTTTEHGMNMEEATA
VASQAEVNDTTTDHGVDMEETMVEAVFTGEQSEGFNMAKESTVEAAVVTEEPSKGSYMDE
EWMLEMPTLLADMAEGMLLPPPSVQWGQNDDFEGDADMN

BNCBF4-PEP Species=Brassica napus length=250 [SEQ ID No. 53]
MNSVSTFSELLGSENESPVGGDYCPMLAASCPKKPAGRKKFRETRHPIYRGVRLRKSGKW
VCEVREPNKKSRIWLGTFKTAEIAARAHDVAALALRGRGACLNFADSAWRLRIPETTCAK
DIQKAAAEAALAFEAEKSDTTTNDHGMNMASQAEVNDTTDHGLDMEETMVEAVFTEEQRD
GFYMAEETTVEGVVPEEQMSKGFYMDEEWMFGMPTLLADMAAGMLLPPPSVQWGHNDDFE
GDVDMNLWNY

BNCBF5-PEP Species=Brassica napus length=251 [SEQ ID No. 55]
MNSVSTFSELLRSENESPVNTEGGDYILAASCPKKPAGRKKFQETRHPIYRGVRLRKSGK
WVCEVREPNKKSRIWLGTFKTAEIAARAHDVAALALRGRGACLNFADSAWRLRIPETTCA
KDIQKAAAEAALAFEAEKSDTTTNDHGMNMASQVEVNDTTDHDLDMEETIVEAVFREEQR
EGFYMAEETTVVGVVPEEQMSKGFYMDEEWMFGMPTLLADMAAGMLLPLPSVQWGHNDDF
EGDADMNLWNY

BNCBF6-PEP Species=Brassica napus length=277 [SEQ ID No. 57]
MNTFPASTEMVGSENESPVTTVVGGDYYPMLAASCPKKPAGRKKFRETRHPIYRGVRLRK
SGKWVCEVREPNKKSRIWLGTFKTAEMAARAHDVAALALRGRGACLNYADSASRLRIPET
TCHKDIQKAAAEAALAFEAEKSDVTMEETMAVASQAEVNDTTTDHGMNMEEATAVASQAE
VNDTTTDHGVDMEETMVEAVFTEEQSEGFNMAEESTVEAAVVTDELSKGFYMDEEWTYEM
PTLLADMAAGMLLPPPSVQWGHNDDLEGDADMNLWNY

BNCBF7-PEP Species=Brassica napus length=213 [SEQ ID No. 59]
MNSVSTFSELLGSENESPVGGDYCPMLAASCPKKPAGRKKFRETRHPIYRGVRLRKSGKW
VCEVREPNKKSRIWLGTFLTAEIAARAHDVAAIALRGKSACLNFADSAWRLRIPETTCPK
EIQKAAAEAAVAFKAEINNTTADHGIDVEETIVEAIFTEENNDGFYMDEEESMFGMPALL

FIGURE 18B-continued

ASMAEGMLLPPPSVQFGHTYDFDGDADVSLWSY

BNCBF8-PEP Species=Brassica napus length=277 [SEQ ID No. 61]
MNTFPASTEMVGSENESPVTTVAGGDYYPMLAASCPKKPAGRKKFQETRHPIYRGVRLRK
SGKWVCEVREPNKKSRIWLGTFKTAEMAARAHDVAALALRGRGACLNYADSASRLRIPET
TCHKDIQKAAAEAALAFEAEKSDVTMEETMAVASQAEVNDTTTDHGMNMEEATAVASQAE
VNDTTTDHGVDMEETMVEAVFTGEQSEGFNMAKESTVEAAVVTEEPSKGSYMDEEWMLEM
PTLLADMAEGMLLPPPSVQWGQNDDFEGDADMNLWSY

BNCBF9-PEP Species=Brassica napus length=283 [SEQ ID No. 63]
MNTFPASTEMVGSENESPVTTVAGGDYYPMLAASCPKKPAGRKKFQETRHPIYRGVRLRK
SGKWVCEVREPNKKSRIWPGTFKTAEMAARAHDVAALALRGRGARLNYADSAWRLRIPET
TCHKDIQKAAAEAALAFEAEKSDVTMQNGLNMEETTAVASQAEVNDTTTEHGMNMEEATA
VASQAEVNDTTTDHGVDMEETMVEAVFTGEQSEGFNMAKESTVEAAVVTEEPSKGSYMDE
EWMLEMPTLLADMAEGMLLPPPSVQWGQNDDFEGDAHMNLWSY

BOCBF1-PEP Species=Brassica olercea Length=188 [SEQ ID No. 65]
HPIYRGVRLRKSGKWVCEVREPNKKSRIWLGTFKTAEIAARAHDVAALALRGRAACLNFA
DSAWRLRIPETTCAKDIQKAAAEAALAFGAEKSDTTTNDQGMNMEEMTVVASQAEVSDTT
TYHGLDMEETMVEAVFAEEQREGFYLAEETTVEGVVTEEQSKGFYMDEEWTFGMQSFLAD
MAEGMLFP

BOCBF2-PEP Species=Brassica olercea Length=152 [SEQ ID No. 67]
MTSFSTFSELLGSEHESPVTLGEEYCPKLAASCPKKPAGRKKFRETRHPVYRGVRLRNSG
KWVCEVREPNKKSRIWLGTFLTAEIAARAHDVAAIALRGKSACLNFADSAWRLRIPETTC
PKEIQKAAAEAAVAFKAEINNTTADHGLDMEE

BOCBF3-PEP Species=Brassica olercea Length=277 [SEQ ID No. 69]
MNTFPASTEMVGSENESPVTTVVGGDYYPMLAASCPKKPAGRKKFQETRHPIYRGVRLRK
SGKWVCEVREPNKKSRIWLGTFKTAEMAARAHDVAALALRGRGACLNYADSAWRLRIPET
TCHKDIQKAAAEAALAFEAEKSDVTMEETMAVASQAEVNDTTTDHGMNMEEATAVASQAE
VNDTTTDHGVDMEETMVEAVFTEEQSEGFNMAEESTVEAAVVTDELSKGFYMDEEWTYEM
PTLLADMAAGMLLPPPSVQWGHNDDLEGDADMNLWSY

BOCBF4-PEP Species=Brassica olercea Length=250 [SEQ ID No. 71]
MNSVSTFSELLGSENESPVGGDYCPMLAASCPKKPAGRKKFRETRHPIYRGVRLRKSGKW
VCEVREPNKKSRIWLGTFKTAEIAARAHDVAALALRGRGACLNFADSAWRLRIPETTCAK
DIQKAAAEAALAFEAEKSDTTTNDHGMNMASQAEVNDTTDHGLDMEETMVEAVFTEEQRD
GFYMAEETTVEGVVPEEQMSKGFYMDEEWMFGMPTLLADMAAGMLLPPPSVQWGHNDDFE
GDADMNLWNY

BOCBF5-PEP Species=Brassica olercea Length=287 [SEQ ID No. 73]
MNTFPASTEMVSSENESPVTTVVGGDYYPMLAASCPKKPAGRKKFQETRHPIYRGVRLRK
SGKWVCEVRELNKKSRIWLGTFKTAEMAARAHDVAALALRGRGACLNYADSAWRLRIPET
TCHKDIQKAAAEAALAFEAEKSDATMQNGLNMEETTAAASQTEVSDTTTDHGMNMEETTA
VASQAEVNDTTTDHGVDMEETMVEAVFTEEQSEGFNMAKESTAEAAVVTEELSKGVYMDE
EWTYEMPTLLADMAAGMLLPPPSVQWGHNDDLEGDADMNLLELLRIR

BRCBF1-PEP Species=Brassica rapa Length=124 [SEQ ID No. 75]
HPIYRGVRLRKSGKWVCEVREPNKKSRIWLGTFKTAEIAARAHDVAALALRGRGACLNFA
DSAWRLRIPETTCAKDIQKAAAEAALAFEAEKSDHGMNIKNTTAVVSQVEVNDTTTDHGL
DMEE

BRCBF2-PEP Species=Brassica rapa Length=280 [SEQ ID No. 77]
MNTFPASTEMVGSENESPVTTVAGGDYYPMLAASCPKKPAGRKKFQETRHPIYRGVRLRK
SGKWVCEVREPNKKSRIWLGTFKTAEMAARAHDVAALALRGRGACLNYADSAWRLRIPET
TCHKDIQKAAAEAALAFEAEKSDVTMQNGLNMEEMTAVASQAEVNDTTTEHGMNMEEATA
VASQAEVNDTTTDHGVDMEETMVEAVFTEEQSEGFNMAKESTVEAAVVTEEPSKGSYMDE
EWMLEMPTLLADMAEGMLLPPPSVQWGQNDDFEGDADMNL

BRCBF3-PEP Species=Brassica rapa Length=204 [SEQ ID No. 79]
MNSVSTFSELLCSENESPVNTEGGDYILAASCPKKPAGRKKFQETRHPIYRGVRLRKSGK
WVCEVREPNKKSRIWLGTFKTAEIAARAHDVAALALRGRGACLNFADSAWRLRIPETTCA
KDIQKAAAEAALAFEAEKSDTTTNDRGMNMEETSAVASPAELNDTTADHGLDMEETMVEA
VFREEQREGFYMAEETTVEGVVPE

FIGURE 18B-continued

BRCBF4-PEP Species=Brassica rapa Length=112 [SEQ ID No. 81]
MDSISTFPELLGSENESPVTTVVGGDYCPRLAASCPKKPAGRKKFQETRHPIYRGVRLRK
SGKWVCEVREPNKKSRIWLGTFKTAEIAARAHDVAALALRGRGACLNFADSA

BRCBF5-PEP Species=Brassica rapa Length=255 [SEQ ID No. 83]
MDSISTFPELLGSENESPVTTVVGGDYCPRLAASCPKKPAGRKKFQETRHPIYRGVRLRK
SGKWVCEVREPNKKSRIWLGTFKTAEIAARAHDVAALALRGRGACLNFADSAWRLRIPET
TCAKDIQKAAAEAALAFEAEKSDHGMNMKNTTAVASQVEVNDTTTDHGVDMEETLVEAVF
TEEQREGFYMTEETRVEGVVTEEQNNWFYMDEEWMFGMPTLLVDMAEGMLIPRQSVQSGH
YDDFEGDADMNLWNY

BRCBF6-PEP Species=Brassica rapa Length=258 [SEQ ID No. 85]
MNSVSTFSELLCSENKSPVNTEGGDYILAASCPKKPAGRKKFQETRHPIYRGVRLRKSGK
WVCEVREPNKKSRIWLGTFKTAEIAARAHDVAALALRGRGACLNFADSAWRLRIPETTCA
KDIQKAAAEAALAFEAEKSDTTTNDRGMNMEETSAVASPAELNDTTADHGLDMEETMVEA
VFRDEQREGFYMAEETTVEGVVPEEQMSKGFYMDEEWTFEMPRLLADMAEGMLLPPPSVQ
WGHNDDFEGDADMNLWNY

BRCBF7-PEP Species=Brassica rapa Length=251 [SEQ ID No. 87]
MNSVSTLSEVLGSQNESPVGGDYCPMLAASCPKKPAGRKKFRETRHPIYRGVRLRKSGKW
VCEVREPNKKSRIWLGTFKTAEIAARAHDVAALALRGRGACLNFADSAWRLRIPETTCAK
DIQKAAAEAALAFEAEKSDTTTTNDHGMNMASQVEVNDTTDHDLDMEETMVEAVFREEQR
EGFYMAEETTVEGIVPEEQMSKGFYMDEEWMFGMPTLLADMAAGMLLPPPSVQWGHNDDF
EGDADMNLWNY

GMCBF1-PEP Species=Glycine max Length=170 [SEQ ID No. 89]
HPIYSGVRRRNTDKWVSEVREPNKKTRIWLGTFPTPEMAARAHDVAAMALRGRYACLNFA
DSTWRLPIPATANAKDIQKAAAEAAEAFRPSQTLENTNTKQECVKVVTTTTITEQKRGMF
YTEEEEQVLDMPELLRNMVLMSPTHCIGYEYEDADLDAQDAEVSLWSFSI

RSCBF1-PEP Species=Raphanus sativus Length=252 [SEQ ID No. 91]
MDSISTFSELLGSENESPVTTVVGGDYFPRLAASCPKKPAGRKKFQETRHPIYRGVRLRK
SGKWVCEVREPNKKSRIWLGTFKTAEIAARAHDVAALALRGRGACLNFADSAWRLRIPET
TCAKDIQKAAAEAALAFEAEKSDHGMNMKNTTAVASQVEVNDTTTDHGVDMEETLVEAVF
TEEQREGFYMTEETRVEGVVTEEQNNWFYMDEEWMFGMPTLLVDMAEGMLLPRPSVQSGH
YDDFEGDADMNL

RSCBF2-PEP Species=Raphanus sativus Length=209 [SEQ ID No. 93]
MTTFSTFSEMLGSEYESPVTLGGEYCPKLAASCPKKPAGRKKFRETRHPIYRGVRLRNSG
KWVCEVREPNKKSRIWLGTFLTAEIAARAHDVAAIALRGKSACLNFADSAWRLRIPETTC
PKDIQKAAAEAAVAFQAEINDTTTDHGLDLEETIVEAIFTEVNNDEFYMDEESMFGMPSL
LASMAEGMLLPLPSVQSEHNCDFDGDADM

ZMCBF1-PEP Species=Zea maize Length=115 [SEQ ID No. 95]
ESADGGGGGDDEYATVLSAPPKRPAGRTKFRETRHPVYRGVRRRGPAGRWVCEVREPNKK
SRIWLGTFATPEAAARAHDVAALALRGRAACLNFADSARLLQVDPATLATPDDIR

FIGURE 19A

```
                 1                                                          50                 64
ap2{atcbf2}     HPiYrGVRqR .nsgkWVcEl REpNKk..tRI WlGTFqTaEm AARAHDVAAi ALRGrsAcLN fADS
ap2{atcbf3}     HPiYrGVRrR .nsgkWVcEv REpNKk..tRI WlGTFqTaEm AARAHDVAAl ALRGrsAcLN fADS
ap2{atcbf1}     HPiYrGVRqR .nsgkWVsEv REpNKk..tRI WlGTFqTaEm AARAHDVAAl ALRGrsAcLN fADS
ap2{bjcbf4}     HPiYrGVRqR .nsgkWVcEv REpNKk..sRI WlGTFpTvEm AARAHDVAAl ALRGrsAcLN fADS
ap2{bocbf2}     HPvYrGVRlR .nsgkWVcEv REpNKk..sRI WlGTFlTaEi AARAHDVAAi ALRGksAcLN fADS
ap2{rscbf2}     HPiYrGVRlR .nsgkWVcEv REpNKr..sRI WlGTFlTaEi AARAHDVAAi ALRGksAcLN fADS
ap2{bjcbf2}     HPiYrGVRlR .ksgkWVcEv REpNKk..sRI WlGTFlTaEi AARAHDVAAi ALRGksAcLN fADS
ap2{bncbf7}     HPiYrGVRlR .ksgkWVcEv REpNKk..sRI WlGTFlTaEi AARAHDVAAi ALRGksAcLN fADS
ap2{bjcbf3}     HPiYrGVRlR .ksgkWVcEv REpNKk..sRI WpGTFlTaEi AARAHDVAAi ALRGksAcLN fADS
ap2{bncbf2}     HPiYrGVRlR .ksgkWVcEv REpNKk..sRI WpGTFkTaEm AARAHDVAAl ALRGrgAcLN yADS
ap2{bncbf3}     HPiYrGVRlR .ksgkWVcEv REpNKk..sRI WpGTFkTaEm AARAHDVAAl ALRGrgAcLN yADS
ap2{bncbf1}     HPiYrGVRlR .ksgkWVcEv REpNKk..sRI WlGTFkTaEm AARAHDVAAl ALRGrgAcLN yADS
ap2{bncbf6}     HPiYrGVRlR .ksgkWVcEv REpNKk..sRI WlGTFkTaEm AARAHDVAAl ALRGrgAcLN yADS
ap2{bncbf8}     HPiYrGVRlR .ksgkWVcEv REpNKk..sRI WlGTFkTaEm AARAHDVAAl ALRGrgAcLN yADS
ap2{bocbf3}     HPiYrGVRlR .ksgkWVcEv REpNKk..sRI WlGTFkTaEm AARAHDVAAl ALRGrgAcLN yADS
ap2{brcbf2}     HPiYrGVRlR .ksgkWVcEv REpNKk..sRI WlGTFkTaEm AARAHDVAAl ALRGrgAcLN yADS
ap2{brcbf4}     HPiYrGVRlR .ksgkWVcEv REpNKk..sRI WlGTFkTaEi AARAHDVAAl ALRGrgAcLN fADS
ap2{brcbf5}     HPiYrGVRlR .ksgkWVcEv REpNKk..sRI WlGTFkTaEi AARAHDVAAl ALRGrgAcLN fADS
ap2{brcbf6}     HPiYrGVRlR .ksgkWVcEv REpNKk..sRI WlGTFkTaEi AARAHDVAAl ALRGrgAcLN fADS
ap2{bocbf4}     HPiYrGVRlR .ksgkWVcEv REpNKk..sRI WlGTFkTaEi AARAHDVAAl ALRGrgAcLN fADS
ap2{bncbf1}     HPiYrGVRlR .ksgkWVcEv RElNKk..sRI WlGTFkTaEi AARAHDVAAl ALRGrgAcLN fADS
ap2{brcbf1}     HPiYrGVRlR .ksgkWVcEv REpNKk..sRI WlGTFkTaEi AARAHDVAAl ALRGrgAcLN fADS
ap2{brcbf3}     HPiYrGVRlR .ksgkWVcEv REpNKk..sRI WlGTFkTaEi AARAHDVAAl ALRGrgAcLN fADS
ap2{brcbf4}     HPiYrGVRlR .ksgkWVcEv REpNKk..sRI WlGTFkTaEi AARAHDVAAl ALRGrgAcLN fADS
ap2{brcbf5}     HPiYrGVRlR .ksgkWVcEv REpNKk..sRI WlGTFkTaEi AARAHDVAAl ALRGrgAcLN fADS
ap2{brcbf6}     HPiYrGVRlR .ksgkWVcEv REpNKk..sRI WlGTFkTaEi AARAHDVAAl ALRGrgAcLN fADS
ap2{brcbf7}     HPiYrGVRlR .ksgkWVcEv REpNKk..sRI WlGTFkTaEi AARAHDVAAl ALRGrgAcLN fADS
ap2{rscbf1}     HPiYrGVRlR .ksgkWVcEv REpNKk..sRI WlGTFkTaEi AARAHDVAAl ALRGrgAcLN fADS
ap2{bocbf1}     HPiYrGVRlR .ksgkWVcEv REpNKk..sRI WlGTFkTaEm AARAHDVAAl ALRGrgAcLN yADS
ap2{bocbf5}     HPiYrGVRlR .ksgkWVcEv REpNKk..sRI WlGTFkTaEm AARAHDVAAl ALRGrgAcLN yADS
ap2{bncbf9}     HPiYrGVRlR .ksgkWVcEv REpNKk..sRI WpGTFkTaEm AARAHDVAAl ALRGraAcLN yADS
ap2{zmcbf1}     HPvYrGVRrR gpagrWVcEv REpNKk..sRI WlGTFaTpEa AARAHDVAAl ALRGrgArLN yADS
ap2{gmcbf1}     HPiYsGVR.R rntdkWvsEv REpNKk..tRI WlGTFpTpEm AARAHDVAAm ALRGryAcLN fADS
Consensus       HP-Y-GVR-R -----WV-E- RE-NK---RI W-GTF-T-E- AARAHDVAA- ALRG--A-LN -ADS ap2{erebp2}     grhYrGVRqR p.wgkfaaEi RdpaKngaRv WlGTyeTaEe AAlAyDkAAy rmRGskAlLN fphr
```

FIGURE 19B

```
                    1                                                                      50              64
ap2{atcbf2}         HPiYrGVRqR .nsgkWVcEl REpNKk.tRl WlGTFqTaEm AARAHDVAAi ALRGrsAcLN fADS
ap2{atcbf3}         HPiYrGVRrR .nsgkWVcEv REpNKk.tRl WlGTFqTaEm AARAHDVAAi ALRGrsAcLN fADS
ap2{atcbf1}         HPiYrGVRqR .nsgkWVsEv REpNKk.tRl WlGTFqTaEm AARAHDVAAi ALRGrsAcLN fADS
ap2{bjcbf4}         HPiYrGVRqR .nsgkWVcEv REpNKk.sRI WlGTFpTvEm AARAHDVAAi ALRGrsAcLN fADS
ap2{bocbf2}         HPvYrGVRlR .nsgkWVcEv REpNKk.sRI WlGTFlTaEi AARAHDVAAi ALRGksAcLN fADS
ap2{rscbf2}         HPiYrGVRlR .nsgkWVcEv REpNKr.sRI WlGTFlTaEi AARAHDVAAi ALRGksAcLN fADS
ap2{bjcbf2}         HPiYrGVRlR .ksgkWVcEv REpNKk.sRI WlGTFlTaEi AARAHDVAAi ALRGksAcLN fADS
ap2{bncbf7}         HPiYrGVRlR .ksgkWVcEv REpNKk.sRI WlGTFlTaEi AARAHDVAAi ALRGksAcLN fADS
ap2{bjcbf3}         HPiYrGVRlR .ksgkWVcEv REpNKk.sRI WpGTFlTaEi AARAHDVAAi ALRGrgAcLN yADS
ap2{bncbf2}         HPiYrGVRlR .ksgkWVcEv REpNKk.sRI WpGTFkTaEm AARAHDVAAi ALRGrgAcLN yADS
ap2{bncbf3}         HPiYrGVRlR .ksgkWVcEv REpNKk.sRI WpGTFkTaEm AARAHDVAAi ALRGrgAcLN yADS
ap2{bncbf1}         HPiYrGVRlR .ksgkWVcEv REpNKk.sRI WlGTFkTaEm AARAHDVAAi ALRGrgAcLN yADS
ap2{bncbf6}         HPiYrGVRlR .ksgkWVcEv REpNKk.sRI WlGTFkTaEm AARAHDVAAi ALRGrgAcLN yADS
ap2{bncbf8}         HPiYrGVRlR .ksgkWVcEv REpNKk.sRI WlGTFkTaEi AARAHDVAAi ALRGrgAcLN fADS
ap2{bocbf3}         HPiYrGVRlR .ksgkWVcEv REpNKk.sRI WlGTFkTaEi AARAHDVAAi ALRGrgAcLN fADS
ap2{brcbf2}         HPiYrGVRlR .ksgkWVcEv REpNKk.sRI WlGTFkTaEi AARAHDVAAi ALRGrgAcLN fADS
ap2{brcbf4}         HPiYrGVRlR .ksgkWVcEv REpNKk.sRI WlGTFkTaEi AARAHDVAAi ALRGrgAcLN fADS
ap2{bncbf5}         HPiYrGVRlR .ksgkWVcEv REpNKk.sRI WlGTFkTaEi AARAHDVAAi ALRGrgAcLN fADS
ap2{brcbf4}         HPiYrGVRlR .ksgkWVcEv REpNKk.sRI WlGTFkTaEi AARAHDVAAi ALRGrgAcLN fADS
ap2{bocbf4}         HPiYrGVRlR .ksgkWVcEv REpNKk.sRI WlGTFkTaEi AARAHDVAAi ALRGrgAcLN fADS
ap2{brcbf1}         HPiYrGVRlR .ksgkWVcEv REpNKk.sRI WlGTFkTaEi AARAHDVAAi ALRGrgAcLN fADS
ap2{brcbf3}         HPiYrGVRlR .ksgkWVcEv REpNKk.sRI WlGTFkTaEi AARAHDVAAi ALRGrgAcLN fADS
ap2{brcbf4}         HPiYrGVRlR .ksgkWVcEv REpNKk.sRI WlGTFkTaEi AARAHDVAAi ALRGrgAcLN fADS
ap2{brcbf5}         HPiYrGVRlR .ksgkWVcEv REpNKk.sRI WlGTFkTaEm AARAHDVAAi ALRGrgAcLN fADS
ap2{brcbf6}         HPiYrGVRlR .ksgkWVcEv REpNKk.sRI WlGTFkTaEi AARAHDVAAi ALRGrgAcLN fADS
ap2{brcbf7}         HPiYrGVRlR .ksgkWVcEv REpNKk.sRI WlGTFkTaEi AARAHDVAAi ALRGrgAcLN fADS
ap2{rscbf1}         HPiYrGVRlR .ksgkWVcEv REpNKk.sRI WlGTFkTaEi AARAHDVAAi ALRGraAcLN fADS
ap2{bocbf1}         HPiYrGVRlR .ksgkWVcEv RElNKk.sRI WlGTFkTaEm AARAHDVAAi ALRGrgAcLN fADS
ap2{bocbf5}         HPiYrGVRlR .ksgkWVcEv REpNKk.sRI WlGTFkTaEm AARAHDVAAi ALRGrgAcLN fADS
ap2{bncbf9}         HPiYrGVRlR .ksgkWVcEv REpNKk.sRI WlGTFaTpEa AARAHDVAAi ALRGrgArLN yADS
ap2{zmcbf1}         HPvYrGVRrR gpagrWVcEv REpNKk.sRI WlGTFpTpEm AARAHDVAAm ALRGraAcLN yADS
ap2{gmcbf1}         HPiYsGVR.R rntdkwVsEv                       AARAHDVAAm ALRGryAcLN fADS ap2{dreb2a}         rcsfrGVRqR i.wgkWVaEi REpnrg.sRl WlGTFpTaqe AAsAyDeAAk AmyGplArLN fprS
ap2{dreb2b}         hcsfrGVRqR i.wgkWVaEi REpkig.tRl WlGTFpTaek AAsAyDeAAt AmyGslArLN fpqS
Consensus           -----GVR-R ------WV-E- RE------RI W-GTF-T--- AA-A-D-AA- A--G--A-LN ---S
```

FIGURE 19C

```
                    1                                                                       50                           64
ap2{atcbf2}     HPiYrGVRqR .nsgkWVcEl REpNKk.tRI WlGTFqTaEm AARAHDVAAi ALRGrsAcLN fADS
ap2{atcbf3}     HPiYrGVRrR .nsgkWVcEv REpNKk.tRI WlGTFqTaEm AARAHDVAAl ALRGrsAcLN fADS
ap2{atcbf1}     HPiYrGVRqR .nsgkWVsEv REpNKk.tRI WlGTFqTaEm AARAHDVAAi ALRGrsAcLN fADS
ap2{bjcbf4}     HPvYrGVRqR .nsgkWVcEv REpNKk.sRI WlGTFpTvEm AARAHDVAAl ALRGrsAcLN fADS
ap2{bocbf2}     HPiYrGVRlR .nsgkWVcEv REpNKk.sRI WlGTFlTaEi AARAHDVAAi ALRGksAcLN fADS
ap2{rscbf2}     HPiYrGVRlR .nsgkWVcEv REpNKr.sRI WlGTFlTaEi AARAHDVAAi ALRGksAcLN fADS
ap2{bjcbf2}     HPiYrGVRlR .ksgkWVcEv REpNKk.sRI WlGTFlTaEi AARAHDVAAi ALRGksAcLN fADS
ap2{bncbf7}     HPiYrGVRlR .ksgkWVcEv REpNKk.sRI WlGTFlTaEi AARAHDVAAi ALRGksAcLN fADS
ap2{bjcbf3}     HPiYrGVRlR .ksgkWVcEv REpNKk.sRI WpGTFlTaEi AARAHDVAAi ALRGksAcLN fADS
ap2{bncbf2}     HPiYrGVRlR .ksgkWVcEv REpNKk.sRI WpGTFkTaEm AARAHDVAAl ALRGrgAcLN yADS
ap2{bncbf3}     HPiYrGVRlR .ksgkWVcEv REpNKk.sRI WpGTFkTaEm AARAHDVAAl ALRGrgAcLN yADS
ap2{bncbf1}     HPiYrGVRlR .ksgkWVcEv REpNKk.sRI WlGTFkTaEm AARAHDVAAl ALRGrgAcLN yADS
ap2{bncbf6}     HPiYrGVRlR .ksgkWVcEv REpNKk.sRI WlGTFkTaEm AARAHDVAAl ALRGrgAcLN yADS
ap2{bncbf8}     HPiYrGVRlR .ksgkWVcEv REpNKk.sRI WlGTFkTaEi AARAHDVAAl ALRGrgAcLN yADS
ap2{bocbf3}     HPiYrGVRlR .ksgkWVcEv REpNKk.sRI WlGTFkTaEm AARAHDVAAl ALRGrgAcLN yADS
ap2{brcbf2}     HPiYrGVRlR .ksgkWVcEv REpNKk.sRI WlGTFkTaEi AARAHDVAAl ALRGrgAcLN fADS
ap2{bncbf4}     HPiYrGVRlR .ksgkWVcEv REpNKk.sRI WlGTFkTaEi AARAHDVAAl ALRGrgAcLN fADS
ap2{bncbf5}     HPiYrGVRlR .ksgkWVcEv REpNKk.sRI WlGTFkTaEi AARAHDVAAl ALRGrgAcLN fADS
ap2{brcbf5}     HPiYrGVRlR .ksgkWVcEv REpNKk.sRI WlGTFkTaEi AARAHDVAAl ALRGrgAcLN fADS
ap2{bocbf4}     HPiYrGVRlR .ksgkWVcEv REpNKk.sRI WlGTFkTaEi AARAHDVAAl ALRGrgAcLN fADS
ap2{brcbf6}     HPiYrGVRlR .ksgkWVcEv REpNKk.sRI WlGTFkTaEi AARAHDVAAl ALRGrgAcLN fADS
ap2{brcbf7}     HPiYrGVRlR .ksgkWVcEv REpNKk.sRI WlGTFkTaEi AARAHDVAAl ALRGrgAcLN fADS
ap2{rscbf1}     HPiYrGVRlR .ksgkWVcEv REpNKk.sRI WlGTFkTaEi AARAHDVAAl ALRGrgAcLN fADS
ap2{bocbf1}     HPiYrGVRlR .ksgkWVcEv RElNKk.sRI WlGTFkTaEm AARAHDVAAl ALRGrgAcLN fADS
ap2{bocbf5}     HPiYrGVRlR .ksgkWVcEv REpNKk.sRI WlGTFkTaEm AARAHDVAAl ALRGrgAcLN yADS
ap2{bncbf9}     HPiYrGVRlR .ksgkWVcEv REpNKk.sRI WpGTFkTaEm AARAHDVAAl ALRGrgArLN yADS
ap2{zmcbf1}     HPvYrGVRrR gpagrWVcEv REpNKk.sRI WlGTFaTpEa AARAHDVAAl ALRGraAcLN yADS
ap2{gmcbf1}     HPiYsGVR.R rntdkWVsEv REpNKk.tRI WlGTFpTpEm AARAHDVAAm ALRGryAcLN fADS ap2{dreb2a}     rcsfrGVRqR i.wgkWVaEi REpnrg.sRI WlGTFptaqe AAsAyDeAAk amyGplArLN fprs
ap2{dreb2b}     hcsfrGVRqR i.wgkWVaEi REpkig.tRI WlGTFptaek AAsAyDeAAt amyGslArLN fpqs
ap2{tiny}       hPvYrGVRkR .nwgkWVsEi REprKk.sRI WlGTFpspem AArAhDvAAl sikGasAiLN fpDl
Consensus       -----GVR-R ------WV-E- RE------RI W-GTF----- AA-A-D-AA- ---G--A-LN ----
```

FIGURE 19D

```
                 1                                                              50                        64
ap2{atcbf2}     HPiYrGVRqR .nsgkWvCEl REpNKk.tRI WlGTFqTaEm AARAHDVAAi ALRGrsAcLN fADS
ap2{atcbf3}     HPiYrGVRrR .nsgkWvCEv REpNKk.tRI WlGTFqTaEm AARAHDVAAl ALRGrsAcLN fADS
ap2{atcbf1}     HPiYrGVRqR .nsgkWvsEv REpNKk.tRI WlGTFqTaEm AARAHDVAAl ALRGrsAcLN fADS
ap2{bjcbf4}     HPiYrGVRqR .nsgkWvCEv REpNKk.sRI WlGTFpTvEm AARAHDVAAl ALRGrsAcLN fADS
ap2{bocbf2}     HPvYrGVR1R .nsgkWvCEv REpNKk.sRI WlGTFlTaEi AARAHDVAAi ALRGksAcLN fADS
ap2{rscbf2}     HPiYrGVR1R .nsgkWvCEv REpNKk.sRI WlGTFlTaEi AARAHDVAAi ALRGksAcLN fADS
ap2{bjcbf2}     HPiYrGVR1R .ksgkWvCEv REpNKr.sRI WlGTFlTaEi AARAHDVAAi ALRGksAcLN fADS
ap2{bncbf7}     HPiYrGVR1R .ksgkWvCEv REpNKk.sRI WlGTFlTaEi AARAHDVAAi ALRGksAcLN fADS
ap2{bjcbf3}     HPiYrGVR1R .ksgkWvCEv REpNKk.sRI WpGTFlTaEi AARAHDVAAi ALRGksAcLN fADS
ap2{bncbf2}     HPiYrGVR1R .ksgkWvCEv REpNKk.sRI WpGTFkTaEm AARAHDVAAl ALRGrgAcLN yADS
ap2{bncbf3}     HPiYrGVR1R .ksgkWvCEv REpNKk.sRI WlGTFkTaEm AARAHDVAAl ALRGrgAcLN yADS
ap2{bncbf1}     HPiYrGVR1R .ksgkWvCEv REpNKk.sRI WlGTFkTaEm AARAHDVAAl ALRGrgAcLN yADS
ap2{bncbf6}     HPiYrGVR1R .ksgkWvCEv REpNKk.sRI WlGTFkTaEm AARAHDVAAl ALRGrgAcLN yADS
ap2{bncbf8}     HPiYrGVR1R .ksgkWvCEv REpNKk.sRI WlGTFkTaEi AARAHDVAAl ALRGrgAcLN yADS
ap2{bocbf3}     HPiYrGVR1R .ksgkWvCEv REpNKk.sRI WlGTFkTaEi AARAHDVAAl ALRGrgAcLN yADS
ap2{brcbf2}     HPiYrGVR1R .ksgkWvCEv REpNKk.sRI WlGTFkTaEi AARAHDVAAl ALRGrgAcLN yADS
ap2{bncbf4}     HPiYrGVR1R .ksgkWvCEv REpNKk.sRI WlGTFkTaEi AARAHDVAAl ALRGrgAcLN fADS
ap2{bncbf5}     HPiYrGVR1R .ksgkWvCEv REpNKk.sRI WlGTFkTaEi AARAHDVAAl ALRGrgAcLN fADS
ap2{bocbf4}     HPiYrGVR1R .ksgkWvCEv REpNKk.sRI WlGTFkTaEi AARAHDVAAl ALRGrgAcLN fADS
ap2{brcbf1}     HPiYrGVR1R .ksgkWvCEv REpNKk.sRI WlGTFkTaEi AARAHDVAAl ALRGrgAcLN fADS
ap2{brcbf3}     HPiYrGVR1R .ksgkWvCEv REpNKk.sRI WlGTFkTaEi AARAHDVAAl ALRGrgAcLN fADS
ap2{brcbf4}     HPiYrGVR1R .ksgkWvCEv REpNKk.sRI WlGTFkTaEi AARAHDVAAl ALRGrgAcLN fADS
ap2{brcbf5}     HPiYrGVR1R .ksgkWvCEv REpNKk.sRI WlGTFkTaEi AARAHDVAAl ALRGrgAcLN fADS
ap2{brcbf6}     HPiYrGVR1R .ksgkWvCEv REpNKk.sRI WlGTFkTaEi AARAHDVAAl ALRGrgAcLN fADS
ap2{brcbf7}     HPiYrGVR1R .ksgkWvCEv REpNKk.sRI WlGTFkTaEi AARAHDVAAl ALRGrgAcLN fADS
ap2{rscbf1}     HPiYrGVR1R .ksgkWvCEv REpNKk.sRI WlGTFkTaEi AARAHDVAAl ALRGrgAcLN fADS
ap2{bocbf1}     HPiYrGVR1R .ksgkWvCEv REpNKk.sRI WlGTFkTaEi AARAHDVAAl ALRGraAcLN fADS
ap2{bocbf5}     HPiYrGVR1R .ksgkWvCEv RElNKk.sRI WlGTFkTaEi AARAHDVAAl ALRGrgAcLN fADS
ap2{bncbf9}     HPiYrGVR1R .ksgkWvCEv REpNKk.sRI WlGTFkTaEm AARAHDVAAl ALRGrgArLN yADS
ap2{zmcbf1}     HPvYrGVRrR gpagrWvCEv REpNKk.sRI WlGTFaTpEa AARAHDVAAl ALRGraAcLN yADS
ap2{gmcbf1}     HPiYsGVR.R rntdkWvsEv REpNKk.tRI WlGTFpTpEm AARAHDVAAm ALRGryAcLN fADS
Consensus       HP-Y-GVR-R -----WV-E- RE-NK---RI W-GTF-T-E- AARAHDVAA- ALRG--A-LN -ADS ap2{tiny}       HPvYrGVRkR .nwgkWvsEi REprKk.sRI WlGTFpspEm AARAHDVAAl sikGasAilN fpDl Consensus
 - ap2{tiny}    ---------- ---------- ---N------ ---------- ---------- ALR------- -A-S
```

FIGURE 19E

```
                    1                                                          50                    64
ap2{atcbf2}         HPiYrGVRqR .nsgkWvcEl REpNKk.tRI WlGTFqTaEm AARAHDVAAi ALRGrsAcLN fADS
ap2{atcbf3}         HPiYrgVRrrR .nsgkWvcEv REpNKk.tRI WlGTFqTaEm AARAHDVAAl ALRGrsAcLN fADS
ap2{atcbf1}         HPiYrGVRqR .nsgkWVsEv REpNKk.tRI WlGTFqTaEm AARAHDVAAi ALRGrsAcLN fADS
ap2{bjcbf4}         HPiYrGVRqR .nsgkWvcEv REpNKk.sRI WlGTFpTvEm AARAHDVAAl ALRGrsAcLN fADS
ap2{bocbf2}         HPvYrGVRqR .nsgkWvcEv REpNKk.sRI WlGTFlTaEi AARAHDVAAi ALRGrsAcLN fADS
ap2{rscbf2}         HPiYrGVRlR .nsgkWvcEv REpNKk.sRI WlGTFlTaEi AARAHDVAAl ALRGksAcLN fADS
ap2{bjcbf2}         HPiYrGVRlR .ksgkWvcEv REpNKr.sRI WlGTFlTaEi AARAHDVAAi ALRGksAcLN fADS
ap2{bncbf7}         HPiYrgVRlR .ksgkWvcEv REpNKk.sRI WlGTFlTaEi AARAHDVAAi ALRGksAcLN fADS
ap2{bjcbf3}         HPiYrGVRlR .ksgkWvcEv REpNKk.sRI WpGTFlTaEi AARAHDVAAi ALRGksAcLN fADS
ap2{bncbf2}         HPiYrGVRlR .ksgkWvcEv REpNKk.sRI WpGTFKTaEm AARAHDVAAi ALRGrgAcLN yADS
ap2{bncbf3}         HPiYrGVRlR .ksgkWvcEv REpNKk.sRI WpGTFKTaEm AARAHDVAAl ALRGrgAcLN yADS
ap2{bncbf1}         HPiYrGVRlR .ksgkWvcEv REpNKk.sRI WlGTFKTaEm AARAHDVAAl ALRGrgAcLN yADS
ap2{bncbf6}         HPiYrGVRlR .ksgkWvcEv REpNKk.sRI WlGTFKTaEm AARAHDVAAl ALRGrgAcLN yADS
ap2{bncbf8}         HPiYrGVRlR .ksgkWvcEv REpNKk.sRI WlGTFKTaEi AARAHDVAAl ALRGrgAcLN yADS
ap2{bocbf3}         HPiYrGVRlR .ksgkWvcEv REpNKk.sRI WlGTFKTaEm AARAHDVAAl ALRGrgAcLN yADS
ap2{brcbf2}         HPiYrGVRlR .ksgkWvcEv REpNKk.sRI WlGTFKTaEi AARAHDVAAl ALRGrgAcLN fADS
ap2{bncbf4}         HPiYrGVRlR .ksgkWvcEv REpNKk.sRI WlGTFKTaEi AARAHDVAAl ALRGrgAcLN fADS
ap2{bncbf5}         HPiYrGVRlR .ksgkWvcEv REpNKk.sRI WlGTFKTaEi AARAHDVAAl ALRGrgAcLN fADS
ap2{bocbf4}         HPiYrGVRlR .ksgkWvcEv REpNKk.sRI WlGTFKTaEi AARAHDVAAl ALRGrgAcLN fADS
ap2{brcbf1}         HPiYrGVRlR .ksgkWvcEv REpNKk.sRI WlGTFkTaEi AARAHDVAAl ALRGrgAcLN fADS
ap2{brcbf3}         HPiYrGVRlR .ksgkWvcEv REpNKk.sRI WlGTFkTaEi AARAHDVAAl ALRGrgAcLN fADS
ap2{brcbf4}         HPiYrGVRlR .ksgkWvcEv REpNKk.sRI WlGTFKTaEi AARAHDVAAl ALRGrgAcLN fADS
ap2{brcbf5}         HPiYrGVRlR .ksgkWvcEv REpNKk.sRI WlGTFKTaEi AARAHDVAAl ALRGrgAcLN fADS
ap2{brcbf6}         HPiYrGVRlR .ksgkWvcEv REpNKk.sRI WlGTFKTaEi AARAHDVAAl ALRGrgAcLN fADS
ap2{brcbf7}         HPiYrGVRlR .ksgkWvcEv REpNKk.sRI WlGTFKTaEi AARAHDVAAl ALRGrgAcLN fADS
ap2{rscbf1}         HPiYrGVRlR .ksgkWvcEv REpNKk.sRI WlGTFKTaEi AARAHDVAAl ALRGraAcLN fADS
ap2{bocbf1}         HPiYrGVRlR .ksgkWvcEv RElNKk.sRI WlGTFKTaEm AARAHDVAAl ALRGrgAcLN fADS
ap2{bocbf5}         HPiYrGVRlR .ksgkWvcEv REpNKk.sRI WpGTFKTaEm AARAHDVAAl ALRGrgArLN yADS
ap2{bncbf9}         HPvYrGVRrR gpagrWvcEv REpNKk.sRI WlGTFaTpEa AARAHDVAAl ALRGraAcLN yADS
ap2{zmcbf1}         HPvYrGVRrR rntdkWvsEv REpNKk.tRI WlGTFpTpEm AARAHDVAAm ALRGryAcLN fADS
ap2{gmcbf1}         HPiYsGVR.R rcsfrGVRqR i.wgkWvaEi REpnrg.sRI WlGTFpTaqe AAsAyDeAAk AmyGplArLN fprS
ap2{dreb2a}         hcsfrGVRqR i.wgkWvaEi REpkig.trI WlGTFpTaek AAsAyDeAAt AmyGslArLN fpqS
ap2{dreb2b}
Consensus           ----GVR-R ----WV-E- RE------RI W-GTF-T--- AA-A-D-AA- A--G--A-LN ---S
ap2{tiny}
Consensus           -------- --------- --------- -T------- --------- A-------- ---S
- ap2{tiny}
```

FIGURE 20

```
                    1                                                      49
n{brCBF3N}   MnsvstfsEl  lcSenespvn  te.GgdY..i  LAaSCPKKPA  GRKKFqETR
n{brCBF6N}   MnsvstfsEl  lcSenkspvn  te.GgdY..i  LAaSCPKKPA  GRKKFqETR
n{bnCBF5N}   MnsvstfsEl  lrSenespvn  te.GgdY..i  LAaSCPKKPA  GRKKFqETR
n{atCBF2N}   MnsfsafsEm  fgSdyespvs  s..GgdYspk  LAtSCPKKPA  GRKKFrETR
n{atCBF3N}   MnsfsafsEm  fgSdyessvs  s..GgdYipt  LAsSCPKKPA  GRKKFrETR
n{atCBF1N}   MnsfsafsEm  fgSdye...p  q..GgdYcpt  LAtSCPKKPA  GRKKFrETR
n{bnCBF2N}   MntfpastEm  vgSenespvt  tvvGgdYypm  LAaSCPKKPA  GRKKFqETR
n{bnCBF6N}   MntfpastEm  vgSenespvt  tvvGgdYypm  LAaSCPKKPA  GRKKFqETR
n{boCBF3N}   MntfpastEm  vgSenespvt  tvvGgdYypm  LAaSCPKKPA  GRKKFqETR
n{bnCBF3N}   MntfpastEm  vgSenespvt  tvaGgdYypm  LAaSCPKKPA  GRKKFqETR
n{bnCBF8N}   MntfpastEm  vgSenespvt  tvaGgdYypm  LAaSCPKKPA  GRKKFqETR
n{bnCBF9N}   MntfpastEm  vgSenespvt  tvaGgdYypm  LAaSCPKKPA  GRKKFqETR
n{brCBF2N}   MntfpastEm  vgSenespvt  tvaGgdYypm  LAaSCPKKPA  GRKKFqETR
n{boCBF5N}   MntfpastEm  vsSenespvt  tvvGgdYypm  LAaSCPKKPA  GRKKFqETR
n{boCBF2N}   MtsfstfsEl  lgSehespvt  ..lGeeYcpk  LAaSCPKKPA  GRKKFrETR
n{rsCBF2N}   MttfstfsEm  lgSeyespvt  ..lGgeYcpk  LAaSCPKKPA  GRKKFrETR
n{bnCBF4N}   MnsvstfsEl  lgSenesp..  ..vGgdYcpm  LAaSCPKKPA  GRKKFrETR
n{bnCBF7N}   MnsvstfsEl  lgSenesp..  ..vGgdYcpm  LAaSCPKKPA  GRKKFrETR
n{boCBF4N}   MnsvstfsEl  lgSenesp..  ..vGgdYcpm  LAaSCPKKPA  GRKKFrETR
n{brCBF7N}   MnsvstlsEv  lgSqnesp..  ..vGgdYcpm  LAaSCPKKPA  GRKKFrETR
n{brCBF4N}   MdsistfpEl  lgSenespvt  tvvGgdYcpr  LAaSCPKKPA  GRKKFqETR
n{brCBF5N}   MdsistfpEl  lgSenespvt  tvvGgdYcpr  LAaSCPKKPA  GRKKFqETR
n{rsCBF1N}   MdsistfsEl  lgSenespvt  tvvGgdYfpr  LAaSCPKKPA  GRKKFqETR
  Consensus  M-------E-  --S-------  ---G--Y---  LA-SCPKKPA  GRKKF-ETR
```

FIGURE 21A

```
1                                                                    50
c{bnCBF3C}   AwRLRIpEtT  ChKdIQKAAA  EAAlaFeaek  sdvtmqngln  meettavasq
c{bnCBF9C}   AwRLRIpEtT  ChKdIQKAAA  EAAlaFeaek  sdvtmqngln  meettavasq
c{brCBF2C}   AwRLRIpEtT  ChKdIQKAAA  EAAlaFeaek  sdvtmqngln  meemtavasq
c{bnCBF1C}   AwRLRIpEtT  ChKdIQKAAA  EAAlaFeaek  sdvtmqngqn  meettavasq
c{bnCBF8C}   AsRLRIpEtT  ChKdIQKAAA  EAAlaFeaek  sdvt......  meetmavasq
c{bnCBF6C}   AsRLRIpEtT  ChKdIQKAAA  EAAlaFeaek  sdvt......  meetmavasq
c{boCBF3C}   AwRLRIpEtT  ChKdIQKAAA  EAAlaFeaek  sdvt......  meetmavasq
c{bnCBF2C}   AwRLRIpEtT  ChKdIQKAAA  EAAlaFeaek  sdvtmqngln  meettavasq
c{boCBF5C}   AwRLRIpEtT  ChKdIQKAAA  EAAlaFeaek  sdatmqngln  meettaaasq
c{brCBF5C}   AwRLRIpEtT  CaKdIQKAAA  EAAlaFeaek  s.........  ..........
c{rsCBF1C}   AwRLRIpEtT  CaKdIQKAAA  EAAlaFeaek  s.........  ..........
c{bnCBF4C}   AwRLRIpEtT  CaKdIQKAAA  EAAlaFeaek  sd.t......  ..........
c{boCBF4C}   AwRLRIpEtT  CaKdIQKAAA  EAAlaFeaek  sd.t......  ..........
c{bnCBF5C}   AwRLRIpEtT  CaKdIQKAAA  EAAlaFeaek  sd.t......  ..........
c{brCBF7C}   AwRLRIpEtT  CaKdIQKAAA  EAAlaFeaek  sdtt......  ..........
c{brCBF6C}   AwRLRIpEtT  CaKdIQKAAA  EAAlaFeaek  sd.t......  ..........
c{boCBF1C}   AwRLRIpEtT  CaKdIQKAAA  EAAlaFgaek  sd.t......  ..........
c{bjCBF2C}   AwRLRIsEtT  CpKeIQKAAA  EAAvaF....  ..........  ..........
c{bjCBF3C}   AwRLRIpEtT  CpKeIQKAAA  EAAvaF....  ..........  ..........
c{bnCBF7C}   AwRLRIpEtT  CpKeIQKAAA  EAAvaF....  ..........  ..........
c{rsCBF2C}   AwRLRIpEtT  CpKdIQKAAA  EAAvaF....  ..........  ..........
c{atCBF1C}   AwRLRIpEsT  CaKdIQKAAA  EAAlaF....  ..........  ..........
c{atCBF2C}   AwRLRIpEsT  CaKeIQKAAA  EAAlnF....  ..........  ..........
c{atCBF3C}   AwRLRIpEsT  CaKdIQKAAA  EAAlaF....  ..........  ..........
Consensus    A-RLRI-E-T  C-K-IQKAAA  EAA--F----  ----------  ----------

51                                                     100
c{bnCBF3C}   aevndttteh  gmnmeeatav  asqaEvndtt  td.HgvDmEE  TmVEAvftgE
c{bnCBF9C}   aevndttteh  gmnmeeatav  asqaEvndtt  td.HgvDmEE  TmVEAvftgE
c{brCBF2C}   aevndttteh  gmnmeeatav  asqaEvndtt  td.HgvDmEE  TmVEAvfteE
c{bnCBF1C}   aevndttteh  gmnmeeatav  asqaEvndtt  td.HgvDmEE  TmVEAvftgE
c{bnCBF8C}   aevndtttdh  gmnmeeatav  asqaEvndtt  td.HgvDmEE  TmVEAvftgE
c{bnCBF6C}   aevndtttdh  gmnmeeatav  asqaEvndtt  td.HgvDmEE  TmVEAvfteE
c{boCBF3C}   aevndtttdh  gmnmeeatav  asqaEvndtt  td.HgvDmEE  TmVEAvfteE
c{bnCBF2C}   aevndttteh  gmnmeeatav  asqaEvndtt  td.HgvDmEE  TmVEAvfteE
c{boCBF5C}   tevsdtttdh  gmnmeettav  asqaEvndxx  td.HgvDmEE  TmVEAvfteE
c{brCBF5C}   ........dh  gmnmknttav  asqvEvndtt  td.HgvDmEE  TlVEAvfteE
c{rsCBF1C}   ........dh  gmnmknttav  asqvEvndtt  td.HgvDmEE  TlVEAvfteE
c{bnCBF4C}   .....ttndh  gmnm......  asqaEvndtt  .d.HglDmEE  TmVEAvfteE
c{boCBF4C}   .....ttndh  gmnm......  asqaEvndtt  .d.HglDmEE  TmVEAvfteE
c{bnCBF5C}   .....ttndh  gmnm......  asqvEvndtt  .d.HdlDmEE  TiVEAvfreE
c{brCBF7C}   .....ttndh  gmnm......  asqvEvndtt  .d.HdlDmEE  TmVEAvfreE
c{brCBF6C}   .....ttndr  gmnmeetsav  aspaElndtt  ad.HglDmEE  TmVEAvfrdE
c{boCBF1C}   .....ttndq  gmnmeemtvv  asqaEvsdtt  ty.HglDmEE  TmVEAvfaeE
c{bjCBF2C}   ..........  ..........  ..qaElndtt  ad.HglDvEE  TiVEAift.E
c{bjCBF3C}   ..........  ..........  ..qaElndtt  ad.HglDvEE  TiVEAift.E
c{bnCBF7C}   ..........  ..........  ..kaEinntt  ad.HgiDvEE  TiVEAift.E
c{rsCBF2C}   ..........  ..........  ..qaEindtt  td.HglDlEE  TiVEAift.E
c{atCBF1C}   ..........  ..........  ..qdEtcdtt  ttdHglDmEE  TmVEAiytpE
c{atCBF2C}   ..........  ..........  ..qdEmchmt  tdaHglDmEE  TlVEAiytpE
c{atCBF3C}   ..........  ..........  ..qdEmcdat  td.HgfDmEE  TlVEAiytaE
Consensus    ----------  ----------  ----E-----  ---H--D-EE  T-VEA----E
```

FIGURE 21A-continued

```
             101                                                              150
c{bnCBF3C}   qsegfnmake  stveaavvte  epskgsYMd.  eEwmleMptl  ladmAeGMLl
c{bnCBF9C}   qsegfnmake  stveaavvte  epskgsYMd.  eEwmleMptl  ladmAeGMLl
c{brCBF2C}   qsegfnmake  stveaavvte  epskgsYMd.  eEwmleMptl  ladmAeGMLl
c{bnCBF1C}   qsegfnmake  stveaavvte  epskgsYMd.  eEwmleMptl  ladmAeGMLl
c{bnCBF8C}   qsegfnmake  stveaavvte  epskgsYMd.  eEwmleMptl  ladmAeGMLl
c{bnCBF6C}   qsegfnmaee  stveaavvtd  elskgfYMd.  eEwtyeMptl  ladmAaGMLl
c{boCBF3C}   qsegfnmaee  stveaavvtd  elskgfYMd.  eEwtyeMptl  ladmAaGMLl
c{bnCBF2C}   qsegfnmaee  stveaavvtd  elskgfYMd.  eEwtyeMptl  ladmAaGMLl
c{boCBF5C}   qsegfnmake  staeaavvte  elskgvYMd.  eEwtyeMptl  ladmAaGMLl
c{brCBF5C}   qregfymtee  trvegvvtee  q.nnwfYMd.  eEwmfgMptl  lvdmAeGMLi
c{rsCBF1C}   qregfymtee  trvegvvtee  q.nnwfYMd.  eEwmfgMptl  lvdmAeGMLl
c{bnCBF4C}   qrdgfymaee  ttvegvvpee  qmskgfYMd.  eEwmfgMptl  ladmAaGMLl
c{boCBF4C}   qrdgfymaee  ttvegvvpee  qmskgfYMd.  eEwmfgMptl  ladmAaGMLl
c{bnCBF5C}   qregfymaee  ttvvgvvpee  qmskgfYMd.  eEwmfgMptl  ladmAaGMLl
c{brCBF7C}   qregfymaee  ttvegivpee  qmskgfYMd.  eEwmfgMptl  ladmAaGMLl
c{brCBF6C}   qregfymaee  ttvegvvpee  qmskgfYMd.  eEwtfeMprl  ladmAeGMLl
c{boCBF1C}   qregfylaee  ttvegvvtee  q.skgfYMd.  eEwtfgMqsf  ladmAeGMLf
c{bjCBF2C}   esse......  ..........  ....gfYMd.  eEfmfgMptl  wasmAeGMLl
c{bjCBF3C}   esse......  ..........  ....gfYMa.  eEfmfgMptl  wasvAeGMLl
c{bnCBF7C}   ennd......  ..........  ....gfYMde  eEsmfgMpal  lasmAeGMLl
c{rsCBF2C}   vnnd......  ..........  ....efYMd.  eEsmfgMpsl  lasmAeGMLl
c{atCBF1C}   qseg......  ..........  ....afYMd.  eEtmfgMptl  ldnmAeGMLl
c{atCBF2C}   qsqd......  ..........  ....afYMd.  eEamlgMssl  ldnmAeGMLl
c{atCBF3C}   qsen......  ..........  ....afYMh.  dEamfeMpsl  lanmAeGMLl
Consensus    ----------  ----------  ------YM--  -E----M---  ----A-GML-
```

FIGURE 21B

```
                1                                                              50
C{CbnCBF3}      AwRLRIPETT CHKDIQKAAA EAALAFEAEK SDvTmqngln MEEttAvASQ
C{CbnCBF9}      AwRLRIPETT CHKDIQKAAA EAALAFEAEK SDvTmqngln MEEttAvASQ
C{CbrCBF2}      AwRLRIPETT CHKDIQKAAA EAALAFEAEK SDvTmqngln MEEmtAvASQ
C{CbnCBF1}      AwRLRIPETT CHKDIQKAAA EAALAFEAEK SDvTmqngqn MEEttAvASQ
C{CbnCBF8}      AsRLRIPETT CHKDIQKAAA EAALAFEAEK SDvT...... MEEtmAvASQ
C{CbnCBF6}      AsRLRIPETT CHKDIQKAAA EAALAFEAEK SDvT...... MEEtmAvASQ
C{CboCBF3}      AwRLRIPETT CHKDIQKAAA EAALAFEAEK SDvT...... MEEtmAvASQ
C{CbnCBF2}      AwRLRIPETT CHKDIQKAAA EAALAFEAEK SDvTmqngln MEEttAvASQ
C{CboCBF5}      AwRLRIPETT CHKDIQKAAA EAALAFEAEK SDaTmqngln MEEttAaASQ
  Consensus     A-RLRIPETT CHKDIQKAAA EAALAFEAEK SD-T------ MEE--A-ASQ 51                                                             100
C{CbnCBF3}      aEVnDTTTeH GMNMEEaTAV ASQAEVNDTT TDHGVDMEET MVEAVFTgEQ
C{CbnCBF9}      aEVnDTTTeH GMNMEEaTAV ASQAEVNDTT TDHGVDMEET MVEAVFTgEQ
C{CbrCBF2}      aEVnDTTTeH GMNMEEaTAV ASQAEVNDTT TDHGVDMEET MVEAVFTeEQ
C{CbnCBF1}      aEVnDTTTeH GMNMEEaTAV ASQAEVNDTT TDHGVDMEET MVEAVFTgEQ
C{CbnCBF8}      aEVnDTTTdH GMNMEEaTAV ASQAEVNDTT TDHGVDMEET MVEAVFTgEQ
C{CbnCBF6}      aEVnDTTTdH GMNMEEaTAV ASQAEVNDTT TDHGVDMEET MVEAVFTeEQ
C{CboCBF3}      aEVnDTTTdH GMNMEEaTAV ASQAEVNDTT TDHGVDMEET MVEAVFTeEQ
C{CbnCBF2}      aEVnDTTTeH GMNMEEaTAV ASQAEVNDTT TDHGVDMEET MVEAVFTeEQ
C{CboCBF5}      tEVsDTTTdH GMNMEEtTAV ASQAEVNDTT TDHGVDMEET MVEAVFTeEQ
  Consensus     -EV-DTTT-H GMNMEE-TAV ASQAEVNDTT TDHGVDMEET MVEAVFT-EQ 101                                                            150
C{CbnCBF3}      SEGFNMAkES TvEAAVVTeE pSKGsYMDEE WmlEMPTLLA DMAeGMLLpp
C{CbnCBF9}      SEGFNMAkES TvEAAVVTeE pSKGsYMDEE WmlEMPTLLA DMAeGMLLpp
C{CbrCBF2}      SEGFNMAkES TvEAAVVTeE pSKGsYMDEE WmlEMPTLLA DMAeGMLLpp
C{CbnCBF1}      SEGFNMAkES TvEAAVVTeE pSKGsYMDEE WmlEMPTLLA DMAeGMLL~~
C{CbnCBF8}      SEGFNMAkES TvEAAVVTeE pSKGsYMDEE WmlEMPTLLA DMAeGMLLpp
C{CbnCBF6}      SEGFNMAeES TvEAAVVTdE lSKGfYMDEE WtyEMPTLLA DMAaGMLLpp
C{CboCBF3}      SEGFNMAeES TvEAAVVTdE lSKGfYMDEE WtyEMPTLLA DMAaGMLLpp
C{CbnCBF2}      SEGFNMAeES TvEAAVVTdE lSKGfYMDEE WtyEMPTLLA DMAaGMLLpp
C{CboCBF5}      SEGFNMAkES TaEAAVVTeE lSKGvYMDEE WtyEMPTLLA DMAaGMLLpp
  Consensus     SEGFNMA-ES T-EAAVVT-E -SKG-YMDEE W--EMPTLLA DMA-GMLL--
```

PLANT HAVING ALTERED ENVIRONMENTAL STRESS TOLERANCE

RELATIONSHIP TO COPENDING APPLICATIONS

This application is a continuation-in-part of the following U.S. applications: U.S. application Ser. No.: 09/018,233, filed: Feb. 3, 1998 entitled "ISOLATED DNA ENCODING ENVIRONMENTAL STRESS TOLERANCE REGULATORY BINDING PROTEIN;" now abandoned U.S. application Ser. No.: 09/017,816, filed: Feb. 3, 1998 entitled "CONSTRUCT FOR TRANSFORMING CELL WITH SEQUENCE ENCODING ENVIRONMENTAL STRESS TOLERANCE REGULATORY BINDING PROTEIN;" now abandoned U.S. application Ser. No.: 09/018,235, filed: Feb. 3, 1998 entitled "ENVIRONMENTAL STRESS TOLERANCE REGULATORY BINDING PROTEIN TRANSFORMED CELL EXPRESSING ENVIRONMENTAL;" now abandoned U.S. application Ser. No.: 09/017,575 filed: Feb. 3, 1998 entitled "STRESS TOLERANCE REGULATORY BINDING PROTEIN;" now abandoned U.S. application Ser. No.: 09/018,227, filed: Feb. 3, 1998 entitled "TRANSFORMED PLANT WITH MODIFIED ENVIRONMENTAL STRESS TOLERANCE GENE EXPRESSION;" now abandoned U.S. application Ser. No.: 09/018, 234, filed: Feb. 3, 1998 entitled "METHOD FOR REGULATING EXPRESSION OF STRESS TOLERANCE GENES IN A TRANSFORMED PLANT;" now abandoned and U.S. application Ser. No.: 08/706,270; filed: Sep. 4, 1996, entitled "now U.S. Pat. No. 5,892,009, " each of which are incorporated herein by reference.

The US government has rights to the present invention under grants from the USDA/NRICGP-.

FIELD OF THE INVENTION

The present invention relates to the regulatory response of plants to environmental stresses such as cold and to drought. More specifically, the present invention relates to genes which regulate the response of a plant to environmental stresses such as cold or drought and their use to enhance the stress tolerance of recombinant plants into which these genes are introduced.

BACKGROUND OF THE INVENTION

Environmental factors serve as cues to trigger a number of specific changes in plant growth and development. One such factor is low temperature. Prominent examples of cold-regulated processes include cold acclimation, the increase in freezing tolerance that occurs in response to low non-freezing temperatures (Guy, C. L., Annu. Rev. Plant Physiol. Plant Mol. Biol. 41:187–223 (1990)); vernalization, the shortening of time to flowering induced by low temperature (Lang, A., in Encyclopedia of Plant Physiology, Vol.15-1, ed. Ruhland, W. (Springer, Berlin), pp. 1489–1536 (1965)); and stratification, the breaking of seed dormancy by low temperature (Berry, J. A. and J. K. Raison, in Encyclopedia of Plant Physiology, Vol. 12A, eds. Lange, O. L., Nobel, P. S., Osmond, C. B. and Ziegler, H. (Springer, Berlin), pp. 277–338 (1981)). Due to the fundamental nature and agronomic importance of these processes, there is interest in understanding how plants sense and respond to low temperature. One approach being taken is to determine the signal transduction pathways and regulatory mechanisms involved in cold-regulated gene expression.

Strong evidence exists for calcium having a role in low temperature signal transduction and regulation of at least some COR (cold-regulated) genes. Dhindsa and colleagues (Monroy, A. F., et al, Plant Physiol. 102:1227–1235 (1993); Monroy, A. F., and R. S., The Plant Cell, 7:321–331 (1995)) have shown that, in alfalfa, calcium chelators and calcium channel blockers prevent low temperature induction of COR genes and that calcium ionophores and calcium channel agonists induce expression of COR genes at normal growth temperatures. Similarly, Knight et al (The Plant Cell 8:489–503 (1996)) have shown that cold-induced expression of the Arabidopsis thaliana COR gene KIN1 is inhibited by calcium chelators and calcium channel blockers. These results suggest that low temperature triggers an influx of extracellular calcium that activates a signal transduction pathway that induces the expression of COR genes. Consistent with this notion is the finding that low temperature evokes transient increases in cytosolic calcium levels in plants (Knight, M. R. et al, Nature 352:524–526 (1991); Knight, H., et al., The Plant Cell 8:489–503 (1996)). In addition, low temperatures have been shown to stimulate the activity of mechanosensitive calcium-selective cation channels in plants (Ding, J. P. and B. G. Pickard, Plant J. 3:713–720 (1993)).

Recent efforts have led to the identification of a cis-acting cold-regulatory element in plants, the C-repeat/DRE (Yamaguchi-Shinozaki, et al., The Plant Cell 6:251–264 (1994); Baker, S. S., et al., Plant. Mol. Biol. 24:701–713 (1994); Jiang, C., et al., Plant Mol. Biol. 30:679–684 (1996)). The element, which has a 5 base pair core sequence for CCGAC, is present once to multiple times in all plant cold-regulated promoters that have been described to date; these include the promoters of the COR15a (Baker, S. S., et al, Plant. Mol. Biol. 24:701–713 (1994)), COR78/RD29A (Horvath, D. P., et al, Plant Physiol. 103:1047–1053 (1993); Yamaguchi-Shinozaki, K., et al., The Plant Cell 6:251–264 (1994)), COR6.6 (Wang, H., et al., Plant Mol. Biol. 28:605–617 (1995)) and KIN1 (Wang, H., et al, Plant Mol. Biol. 28:605–617 (1995)) genes of Arabidopsis and the BN115 gene of Brassica napus (White, T. C., et al, Plant Physiol. 106:917–928 (1994)). Deletion analysis of the Arabidopsis COR15a gene suggested that the CCGAC sequence, designated the C-repeat, might be part of a cis-acting cold-regulatory element (Baker, S. S., et al., Plant Mol. Biol. 24:701–713 (1994)). That this was the case was first demonstrated by Yamaguchi-Shinozaki and Shinozaki (Yamaguchi-Shinozaki, K., et al., The Plant Cell 6:251–264 (1994)) who showed that two of the C-repeat sequences present in the promoter of COR78/RD29A induced cold-regulated gene expression when fused to a reporter gene. It was also found that these two elements stimulate transcription in response to dehydration and high salinity and thus, was designated the DRE (dehydration, low temperature and high salt regulatory element). Recent studies by Jiang et al (Jiang, C., et al., Plant Mol. Biol. 30:679–684 (1996)) indicate that the C-repeats (referred to as low temperature response elements) present in the promoter of the B. napus BN115 gene also impart cold-regulated gene expression.

U.S. Pat. Nos. 5,296,462 and 5,356,816 to Thomashow describe the genes encoding the proteins involved in cold adaptation in Arabidopsis thaliana. In particular the DNA encoding the COR15 proteins is described. These proteins are significant in promoting cold tolerance in plants.

A need exists for the identification of genes which regulate the expression of cold tolerance genes and drought tolerance genes. A further need exists for DNA constructs useful for introducing these regulatory genes into a plant in order to cause the plant to begin expressing or enhance their expression of native or non-native cold tolerance genes and drought tolerance genes. These and other needs are provided by the present invention.

SUMMARY OF THE INVENTION

DNA in isolated form is provided which includes a sequence encoding a binding protein capable of selectively binding to a DNA regulatory sequence which regulates expression of one or more environmental stress tolerance genes in a plant. The binding protein is preferably capable of regulating expression of one or more environmental stress tolerance genes in a plant by selectively binding to a DNA regulatory sequence which regulates the one or more environmental stress tolerance genes. In one embodiment, the binding protein is a non-naturally occurring protein formed by combining an amino acid sequence capable of binding to a CCG regulatory sequence, preferably a CCGAC regulatory sequence with an amino acid sequence which forms a transcription activation region which regulates expression of one or more environmental stress tolerance genes in a plant by regulating expression of one or more environmental stress tolerance genes when the binding protein binds to the regulatory region.

DNA in isolated form is also provided which includes a promoter and the sequence encoding the binding protein. In one variation, the promoter causes expression of the binding protein in a manner which is different than how the binding protein is expressed in its native state. For example, the promoter may increase the level at which the binding protein is expressed, express the binding protein without being induced by an environmental stress and/or express the binding protein in response to a different form or degree of environmental stress than would otherwise be needed to induce expression of the binding protein. The promoter may also be inducible by an exogenous agent. The promoter can also be selected with regard to the type or types of plant tissues that the binding protein will be expressed as well as when in the plant's life the promoter will function to regulate expression of the binding protein.

A nucleic acid construct capable of transforming a plant is also provided which includes a sequence encoding a binding protein capable of selectively binding to a DNA regulatory sequence which regulates expression of one or more environmental stress tolerance genes in a plant. The binding protein is preferably capable of regulating expression of one or more environmental stress tolerance genes in a plant by selectively binding to a DNA regulatory sequence which regulates the one or more environmental stress tolerance genes. The nucleic acid construct may be an RNA or DNA construct. Examples of types of constructs include, but are not limited to DNA and RNA viral vectors and plasmids.

A nucleic acid construct capable of transforming a plant is also provided which includes a sequence which when transformed into a plant expresses a binding protein capable of selectively binding to a DNA regulatory sequence which regulates one or more environmental stress tolerance genes in the plant. The binding protein preferably regulates expression of one or more environmental stress tolerance genes in the plant by selectively binding to a DNA regulatory sequence which regulates the one or more environmental stress tolerance genes.

In one variation of the above constructs, the construct also includes a promoter which regulates expression of the binding protein encoding sequence. The promoter may optionally be homologous or heterologous relative to the binding protein encoding sequence. The promoter and binding protein encoding sequence may also optionally be native to the same or a different plant species. In one variation, the promoter causes expression of the binding protein in a manner which is different than how the binding protein is expressed in its native state. For example, the promoter may increase the level at which the binding protein is expressed, express the binding protein without being induced by an environmental stress and/or express the binding protein in response to a different form or degree of environmental stress than would otherwise be needed to induce expression of the binding protein. The promoter may also be inducible by an exogenous agent. The promoter can also be selected with regard to the type or types of plant tissues that the binding protein will be expressed as well as when in the plant's life the promoter will function to regulate expression of the binding protein.

A binding protein in isolated form is also provided which is capable of selectively binding to a DNA regulatory sequence which regulates expression of one or more environmental stress tolerance genes in a plant. The binding protein is preferably capable of regulating expression of one or more environmental stress tolerance genes in the plant by selectively binding to a DNA regulatory sequence which regulates the one or more environmental stress tolerance genes.

A recombinant binding protein expressed within a plant is also provided which is capable of selectively binding to a DNA regulatory sequence in the plant which regulates expression of one or more environmental stress tolerance genes in the plant. The recombinant binding protein is preferably capable of regulating expression of one or more environmental stress tolerance genes in the plant by selectively binding to a DNA regulatory sequence which regulates the one or more environmental stress tolerance genes. The recombinant binding protein may be native or non-native to the plant. Further, the recombinant binding protein may be homologous or heterologous relative to the DNA binding protein present in the plant in which the binding protein is expressed.

A transformed cell of an organism is also provided which includes a recombinant sequence encoding a binding protein capable of selectively binding to a DNA regulatory sequence which regulates expression of one or more environmental stress tolerance genes in a plant. The binding protein is preferably capable of regulating expression of one or more environmental stress tolerance genes in a plant by selectively binding to a DNA regulatory sequence which regulates the one or more environmental stress tolerance genes. The transformed cell may be a unicellular organism such as a bacterium, yeast or virus, or from a multicellular organism such as a fungus or a plant.

A transformed cell is also provided which includes a promoter and a sequence encoding a binding protein where at least one of the promoter and sequence under regulatory control of the promoter is recombinant. Optionally, one or both of the promoter and sequence under regulatory control of the promoter is not native to the cell. In one variation, the promoter causes expression of the binding protein in a manner which is different than how the binding protein is expressed in its native state. For example, the promoter may increase the level at which the binding protein is expressed, express the binding protein without being induced by an environmental stress and/or express the binding protein in response to a different form or degree of environmental stress than would otherwise be needed to induce expression of the binding protein. The promoter may also be inducible by an exogenous agent. The promoter can also be selected with regard to the type or types of plant tissues that the binding protein will be expressed as well as when in the plant's life the promoter will function to regulate expression of the binding protein.

A transformed cell is also provided which includes a recombinant binding protein expressed within the cell which is capable of selectively binding to a DNA regulatory sequence in the plant which regulates expression of one or more environmental stress tolerance genes in the plant. The binding protein is preferably capable of regulating expression of one or more environmental stress tolerance genes in the plant by selectively binding to a DNA regulatory sequence which regulates the one or more environmental stress tolerance genes. The binding protein may be native or non-native to the cell.

A transformed plant with modified environmental stress tolerance gene expression is also provided. In one embodiment, the transformed plant includes one or more environmental stress tolerance genes; a DNA regulatory sequence which regulates expression of the one or more environmental stress tolerance genes; and a recombinant sequence encoding a binding protein capable of selectively binding to the DNA regulatory sequence.

In another embodiment, the transformed plant includes one or more environmental stress tolerance genes; a DNA regulatory sequence which regulates expression of the one or more environmental stress tolerance genes; a sequence encoding a binding protein capable of selectively binding to the DNA regulatory sequence; and a recombinant promoter which regulates expression of the sequence encoding the binding protein.

In yet another embodiment, the transformed plant includes one or more environmental stress tolerance genes; a recombinant DNA regulatory sequence which regulates expression of the one or more environmental stress tolerance genes; and a sequence encoding a binding protein capable of selectively binding to the DNA regulatory sequence.

In yet another embodiment, the transformed plant includes at least one recombinant environmental stress tolerance gene; a DNA regulatory sequence which regulates expression of the at least one environmental stress tolerance gene; and a sequence encoding a binding protein capable of selectively binding to the DNA regulatory sequence.

In yet another embodiment, the transformed plant includes at least one recombinant environmental stress tolerance gene; a DNA regulatory sequence which regulates expression of the at least one environmental stress tolerance gene; and a recombinant binding protein expressed by the plant which is capable of selectively binding to the DNA regulatory sequence.

A method for altering an environmental stress tolerance of a plant is also provided. In one embodiment, the method includes transforming a plant with at least one copy of a gene encoding a binding protein capable of binding to a DNA regulatory sequence which regulates one or more environmental stress tolerance genes in the plant; expressing the binding protein encoded by the gene; and stimulating expression of at least one environmental stress tolerance gene through binding of the binding protein to the DNA regulatory sequence.

In another embodiment, the method includes transforming a plant with a promoter which regulates expression of at least one copy of a gene encoding a binding protein capable of binding to a DNA regulatory sequence which regulates one or more environmental stress tolerance genes in the plant; expressing the binding protein encoded by the gene; and stimulating expression of at least one environmental stress tolerance gene through binding of the binding protein to the DNA regulatory sequence.

In another embodiment, the method includes transforming a plant with one or more environmental stress tolerance genes whose expression is regulated by a DNA regulatory sequence; and expressing a binding protein capable of binding to the DNA regulatory sequence and activating expression of the one or more environmental stress tolerance genes.

According to any one of the above embodiments of the present invention, the binding protein may optionally be selected such that it selectively binds to a member of a class of DNA regulatory sequences which includes the subsequence CCG or more particularly one of the following subsequences: CCGM, CCGAT, CCGAC, CCGAG, CCGTA, CCGTT, CCGTC, CCGTG, CCGCA, CCGCT, CCGCG, CCGCC, CCGGA, CCGGT, CCGGC, CCGGG, AACCG, ATCCG, ACCCG, AGCCG, TACCG, TTCCG, TCCCG, TGCCG, CACCG CCCG, GACCG, GTCCG, GCCCG, GGCCG, ACCGA, ACCGT, ACCGC, ACCGG, TCCGA, TCCGT, TCCGC, TCCGG, CCCGA, CCCGT, CCCGC, CCCGG, GCCGA, GCCGT, GCCGC, and GCCGG. The binding protein may also be selected such that the binding protein includes an AP2 domain.

In each of the above embodiments, the level of expression of the binding protein may be the same or different than the level of expression of the binding protein in its native state. Expression of the binding protein in the transformed cell may be regulated by a recombinant promoter which may have the effect of increasing the level at which the binding protein is expressed, expressing the binding protein without being induced by an environmental stress and/or expressing the binding protein in response to a different form or degree of environmental stress than is otherwise needed to induce expression of the binding protein. Expression may also be induced by an exogenous agent. Expression may also be limited to selected types of plant tissues or selected periods in the plant's life based on which promoter is used. By selecting in what tissues and when in a plant's life the binding protein is expressed, in combination with the selecting how the binding protein is expressed (level of expression and/or type of environmental or chemical induction), an incredible range of control over the environmental stress responses of a plant can be achieved by the present invention.

In each of the above embodiments, the binding protein comprises an amino acid sequence which is capable of binding to a DNA regulatory sequence which regulates one or more environmental stress tolerance genes. In a preferred embodiment, the binding protein further comprises a transcription activation region which acts in concert with the binding sequence to regulate expression of one or more environmental stress tolerance genes in the plant by regulating expression of one or more environmental stress tolerance genes. The environmental stress tolerance gene, DNA regulatory sequence, sequence encoding the binding sequence, and the sequence encoding the transcription activation region may each independently be native or non-native to the plant and may each independently be homologous or heterologous relative to each other.

Optionally, the binding protein satisfies one or more of the following requirements:

the binding protein comprises an AP2 domain which comprises a consensus sequence sufficiently homologous to any one of the consensus sequences shown in FIGS. 19A, 19B, or 19C that the binding protein is capable of binding to a CCG regulatory sequence, preferably a CCGAC regulatory sequence;

the binding protein comprises an AP2 domain which comprises a consensus sequence shown in FIGS. 19A, 19B or 19C;

the binding protein comprises an AP2 domain which comprises the amino acid residues shown in FIGS. 19D or 19E;

the binding protein comprises an AP2 domain which is sufficiently homologous to at least one of the AP2 domains shown in the application such that it is capable of binding to a CCG regulatory sequence, preferably a CCGAC regulatory sequence;

the binding protein comprises one of the AP2 domain sequences shown in this application, including, but not limited to SEQ. I.D. Nos. 2, 13, 15, 39, 41, 43, 45, 47, 49, 51, 53, 55, 57, 59, 61, 63, 65,67, 69, 71, 73,75, 77, 79,81, 83, 85, 87, 89, 91, 93, and 95;

the binding protein comprises a sequence which comprises one of the amino terminus domains shown in FIG. 20 (it is noted that the sequence need not be at the amino terminus of the binding protein);

the binding protein comprises the consensus sequence for the amino terminus domains shown in FIG. 20, (it is noted that the sequence need not be at the amino terminus of the binding protein);

the binding protein comprises a sequence which comprises one of the carboxy terminus domains shown in FIG. 21A (it is noted that the sequence need not be at the carboxy terminus of the binding protein);

the binding protein comprises the consensus sequence for the carboxy terminus domains shown in FIG. 21A (it is noted that the sequence need not be at the carboxy terminus of the binding protein); and the binding protein comprises the consensus sequence for the carboxy terminus domains shown in FIG. 21B (it is noted that the sequence need not be at the carboxy terminus of the binding protein).

The amino acid sequence encoding the binding protein may be a naturally occurring sequence such as the ones shown in SEQ. ID. Nos. 2, 13, 15, 39, 41, 43, 45, 47, 49, 51, 53, 55, 57, 59, 61, 63, 65, 67, 69, 71, 73, 75, 77, 79, 81, 83, 85, 87, 89, 91, 93, and 95 or may be a non-naturally occurring sequence. It is noted, however, that binding proteins according to the present invention are intended to encompass non-naturally occurring sequences which are derivatives of the classes of binding proteins taught herein. For example, additional binding proteins may be constructed using one of the AP2 domains taught herein or the consensus sequence of these AP2 domains. It may be desirable to include with the AP2 domain a transcription activation region. The transcription activation region may be native to the plant or non-native to the plant in which the binding protein will be used. For example, the sequence may include a subsequence which encodes a binding domain for the DNA regulatory sequence fused to a transcription activating region, such as the transcription activating region of VP16 or GAL4. Optionally, one can include in the binding protein one of the amino terminus domains, the consensus sequence for the amino terminus domain, one of the carboxy terminus domains and/or the consensus sequence for the carboxy terminus domains. It is noted that the amino terminus domain may be positioned away from the amino terminus of the new binding protein and the carboxy terminus domain may be positioned away from the carboxy terminus of the new binding protein.

Optionally, the binding protein can be viewed as comprising one of the amino terminus domains, the consensus sequence for the amino terminus domain, one of the carboxy terminus domains and/or the consensus sequence for the carboxy terminus domains. It is noted that the amino terminus domain may be positioned away from the amino terminus of the new binding protein and the carboxy terminus domain may be positioned away from the carboxy terminus of the new binding protein.

A method is also provided for identifying from a cDNA library of at least a portion of a plant genome a gene sequence encoding a protein capable of binding to a target DNA regulatory sequence. In one embodiment, the method comprises taking a microorganism which includes a target DNA regulatory sequence for one or more environmental stress tolerance genes, a transcription activator for activating expression of a reporter gene, and a reporter gene whose expression is activated by a protein which includes a binding domain capable of binding to the target DNA regulatory sequence and an activation domain capable of activating the transcription activator;

fusing sequences from a cDNA library of at least a portion of a plant genome to a sequence which encodes a functional activation domain in the microorganism;

introducing the fused sequences into the microorganism; and selecting microorganisms which express the reporter gene, expression of the reporter gene indicating expression of a fusion protein which includes a binding domain for the target DNA regulatory sequence and the activation domain; and identifying the gene sequence from the cDNA library introduced into the microorganism. The target DNA regulatory sequence may optionally include the subsequence CCG or the subsequence CCGAC. This embodiment of the invention also relates to DNA in substantially isolated form, nucleic add constructs capable of transforming a plant, cells, and transformed plants which include a gene sequence identified by this method.

While the present invention is described with regard to the use of binding proteins which can bind to a DNA regulatory sequence that regulates environmental stress tolerance genes in a plant, it is noted that these same binding proteins can also be used to regulate genes other than environmental stress tolerance genes by placing these other genes under the regulatory control of the DNA regulatory sequence. For example, protein kinases that induce cold and drought inducible genes can be regulated by placing a protein kinase gene under the control of a promoter whose expression is regulated by the DNA regulatory sequence. PCT/US97/23019 (Intl Publication Number WO 98/26045) describes protein kinases that when constitutively expressed, induce cold and drought inducible genes. The ATCDPK1a and the ATCDPK1 constitutive protein kinase coding regions (PCT/US97/23019) can be isolated by PCR and inserted into the drought and cold inducible promoters described in Example 8 by one skilled in the art. The expression of these ATCDPK1 constitutive protein kinase coding regions (PCT/US97/23019) from the drought and cold inducible promoters will increase the drought and cold tolerance of plants and should be synergistic with the the drought and cold tolerance induced by CBF expression under inducible promoters.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 1A is a schematic diagram showing the screening strategy.

FIG. 1B is a chart showing activity of the "positive" cDNA clones in yeast reporter strains.

FIGS. 2A, 2B, 2C and 2D provide an analysis of the pACT-11 cDNA clone.

FIG. 2A is a schematic drawing of the pACT-11 cDNA insert indicating the location and 5' to 3' orientation of the 24 kDa polypeptide and 25s rRNA sequences.

FIG. 2B is a DNA and amino acid sequence of the 24 kDa polypeptide (SEQ ID NO:1 and SEQ ID NO:2).

FIG. 2C is a schematic drawing indicating the relative positions of the potential nuclear localization signal (NLS), the AP2 domain and the acidic region of the 24 kDa polypeptide.

FIG. 2D is a chart showing comparison of the AP2 domain of the 24 kDa polypeptide with that of the tobacco DNA binding protein EREBP2.

FIG. 7A is a photograph of a membrane RNA isolated from Arabidopsis plants that were grown at 22 C or grown at 22 C and transferred to 2.5 C for the indicated times.

FIG. 7B is a graph showing relative transcript levels of CBF1 in control and cold-treated plants.

FIG. 7C is a graph showing relative transcript levels of COR15a in control and cold-treated plants.

FIG. 12 shows the DNA sequence for CBF2 encoding CBF2.

FIG. 13 shows the DNA sequence for CBF3 encoding CBF3.

FIG. 14 shows the amino acid alignment of proteins CBF1, CBF2 and CBF3.

FIG. 16 shows the amino acid sequence of a canola homolog and its alignment to the amino acid sequence of CBF1.

FIG. 18A shows the DNA sequences for the CBF homologs from *Brassica juncea, Brassica napus, Brassica oleracea, Brassica rapa, Glycine max, Raphanus sativus* and *Zea Maize*.

FIG. 18B shows the amino acid sequences (one-letter abbreviations) encoded by the DNA sequences (shown in FIG. 18A) for CBF homologs from *Brassica juncea, Brassica napus, Brassica oleracea, Brassica rapa, Glycine max, Raphanus sativus* and *Zea Maize*.

FIG. 19A shows an amino acid alignment of the AP2 domains of several CBF proteins with the consensus sequence between the proteins highlighted as well as a comparison of the AP2 domains with that of the tobacco DNA binding protein EREBp2.

FIG. 19B shows an amino acid alignment of the AP2 domains of several CBF proteins including dreb2a and dreb2b with the consensus sequence between the proteins highlighted.

FIG. 19C shows an amino acid alignment of the AP2 domains of several CBF proteins including dreb2a, dreb2b, and tiny with the consensus sequence between the proteins highlighted.

FIG. 19D shows a difference between the consensus sequence shown in FIG. 19A and tiny.

FIG. 19E shows a difference between the consensus sequence shown in FIG. 19B and tiny.

FIG. 20 shows an amino acid alignment of the amino terminus of several CBF proteins with their consensus sequence highlighted.

FIGS. 21A and 21B show an amino acid alignment of the carboxy terminus of several CBF proteins, with their consensus sequences highlighted.

DETAILED DESCRIPTION

Figures 1A, 1B:
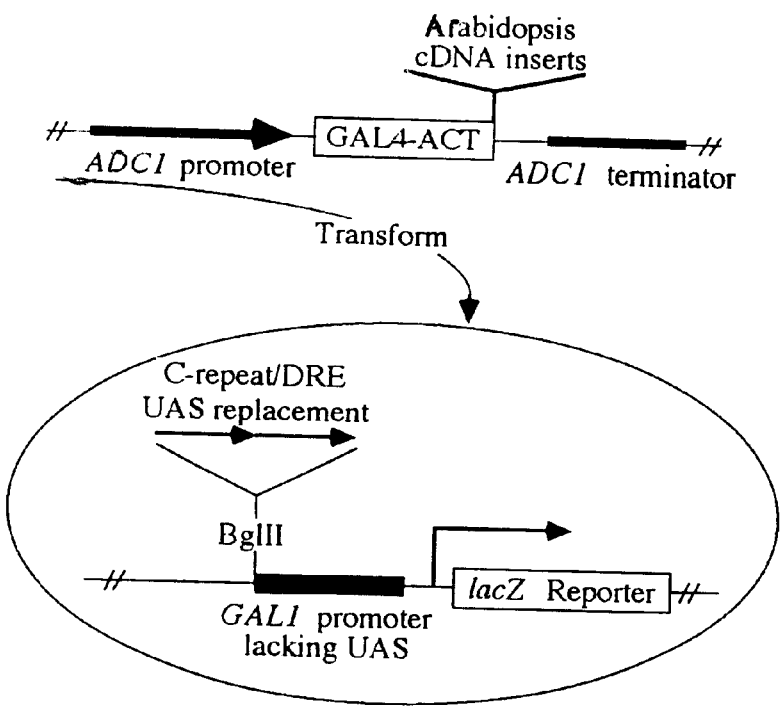
FIGS. 1A and 1B show how the yeast reporter strains were constructed.

The present invention relates to DNA encoding binding proteins capable of binding to a DNA regulatory sequence which regulates expression of one or more environmental stress tolerance genes in a plant. The present invention also relates to the binding proteins encoded by the DNA. The DNA and binding proteins may be native or non-native relative to the DNA regulatory sequence of the plant. The DNA and binding proteins may also be native or non-native relative to environmental stress tolerance genes of the plant which are regulated by the DNA regulatory sequence.

The present invention also relates to methods for using the DNA and binding proteins to regulate expression of one or more native or non-native environmental stress tolerance genes in a plant. These methods may include introducing DNA encoding a binding protein capable of binding to a DNA regulatory sequence into a plant, introducing a promoter into a plant which regulates expression of the binding protein, introducing a DNA regulatory sequence into a plant to which a binding protein can bind, and/or introducing one or more environmental stress tolerance genes into a plant whose expression is regulated by a DNA regulatory sequence.

The present invention also relates to recombinant cells, plants and plant materials (e.g., plant tissue, seeds) into which one or more gene sequences encoding a binding protein have been introduced as well as cells, plants and plant materials within which recombinant binding proteins encoded by these gene sequences are expressed. By introducing a gene sequence encoding a binding protein into a plant, a binding protein can be expressed within the plant which regulates expression of one or more stress tolerance genes in the plant. Regulation of expression can include causing one or more stress tolerance genes to be expressed under different conditions than those genes would be in the plant's native state, increasing a level of expression of one or more stress tolerance genes, and/or causing the expression of one or more stress tolerance genes to be inducible by an exogenous agent. Expression of the binding protein can be under the control of a variety of promoters. For example, promoters can be used to overexpress the binding protein, change the environment conditions under which the binding protein is expressed, or enable the expression of the binding protein to be induced, for example by the addition of an exogenous inducing agent.

The present invention also relates to cells, recombinant plants and plant materials into which a recombinant promoter is introduced which controls a level of expression of one or more gene sequences encoding a binding protein. The one or more gene sequences may be recombinant native or non-native sequences or may be native, non-recombinant gene sequences whose expression is altered by the introduction of the recombinant promoter.

The present invention also relates to cells, recombinant plants and plant materials into which a recombinant native or non-native DNA regulatory sequence is introduced which regulates expression of one or more native or non-native environmental stress tolerance genes.

Examples of environmental stresses for which stress tolerance genes are known to exist include, but are not limited to, cold tolerance, dehydration tolerance, and salinity tolerance. As used herein, environmental stress tolerance genes refer to genes which function to acclimate a plant to an environment stress. For example, cold tolerance genes, also referred to as COR genes (COld Regulated), refer to genes which function to acclimate a plant to a cold temperature environment. These genes typically are activated when a plant is exposed to cold temperatures. Dehydration tolerance genes refer to genes which function to acclimate a plant to dehydration stress. These genes typically are activated in response to dehydration conditions which can be associated with drought or cold temperatures which cause water in the plant to freeze and thereby dehydrate the plant tissue. It is noted that some cold tolerance genes may function to provide a plant with a degree of dehydration tolerance and visa versa. For example, COR genes are known to also be activated by dehydration stress. This application is intended to encompass genes which regulate one or more environmental stress tolerance genes such as cold tolerance genes, dehydration tolerance genes, and genes which perform a dual function of cold and dehydration tolerance.

One embodiment of the invention relates to a DNA sequence in isolated form which includes a sequence encoding a binding protein capable of selectively binding to a DNA regulatory sequence which regulates expression of one or more environmental stress tolerance genes in a plant. The binding protein is preferably capable of regulating expression of one or more environmental stress tolerance genes in a plant by selectively binding to a DNA regulatory sequence which regulates the one or more environmental stress tolerance genes. In one variation, the binding protein is a non-naturally occurring protein formed by combining an amino acid sequence capable of binding to a CCG regulatory sequence, preferably a CCGAC regulatory sequence with an amino acid sequence which forms a transcription activation region which regulates expression of one or more environmental stress tolerance genes in a plant by regulating expression of one or more environmental stress tolerance genes when the binding protein binds to the regulatory region.

The DNA sequence may exist in a variety of forms including a plasmid or vector and can include sequences unrelated to the gene sequence encoding the binding protein. For example, the DNA sequence can include a promoter which regulates expression of the regulatory gene.

In one variation of this embodiment, the DNA regulatory sequence is a C-repeat cold and drought regulation element (C-repeat/DRE). As will be explained and demonstrated herein, C-repeat/DRE regulatory sequences appear to be conserved in plants with some degree of variability plant to plant. Using the teachings of the present invention, C-repeat/DRE regulatory sequences native to different plants can be identified as well as the native stress tolerance regulatory genes which encode for proteins which bind to the C-repeat/DRE DNA regulatory sequences. Hence, although the examples provided herein to describe the present invention are described with regard to the Arabadopsis C-repeat/DRE DNA regulatory sequence, the present invention is not intended to be limited to the Arabadopsis C-repeat/DRE DNA regulatory sequence. Rather, the Arabadopsis C-repeat/DRE DNA regulatory sequence is believed to be a member of a class of environmental stress response regulatory elements which includes the subsequence CCGAC which in turn is believed to be a member of a class of environmental stress response regulatory elements which includes the subsequence CCG. Other different classes of environmental stress response regulatory elements may also exist. The teachings of the present invention may be used to identify sequences which bind to these and other classes of environmental stress response regulatory elements once they are identified.

In one variation of this embodiment, the gene sequence encodes a binding protein which selectively binds to a member of a class of DNA regulatory sequences which includes the subsequence CCG. In another variation, the gene sequence encodes a binding protein which selectively binds to a member of a class of DNA regulatory sequences which includes the subsequence CCGAC. The CCGAC subsequence has been found to present in the C-repeat/DRE DNA regulatory sequences of Arabadopsis and Brassica and to function in Tobacco based on the ability of the C-repeat/DRE to direct cold and tolerance regulated gene expression.

In yet another variation, the stress tolerance regulatory gene sequence encodes a binding protein which includes an AP2 domain. It is believed that a significant class of environmental stress tolerance regulatory genes encode for binding proteins with an AP2 domain capable of binding to the DNA regulatory sequence. The AP2 domain of the binding protein is preferably a homolog of the AP2 domain of one of the CBF binding proteins described herein. The subsequence encoding the AP2 domain is preferably a homolog of a subsequence of one of the CBF genes described herein which encodes an AP2 domain.

In another variation, the DNA sequence encoding the binding protein satisfies one or more of the following requirements:

the binding protein comprises an AP2 domain which comprises a consensus sequence sufficiently homologous to any one of the consensus sequences shown in FIGS. 19A, 19B, or 19C that the binding protein is capable of binding to a CCG regulatory sequence, preferably a CCGAC regulatory sequence;

the binding protein comprises an AP2 domain which comprises a consensus sequence shown in FIGS. 19A, 19B or 19C;

the binding protein comprises an AP2 domain which comprises the amino acid residues shown in FIGS. 19D or 19E;

the binding protein comprises an AP2 domain which is sufficiently homologous to at least one of the AP2 domains shown in the application such that it is capable of binding to a CCG regulatory sequence, preferably a CCGAC regulatory sequence;

the binding protein comprises one of the AP2 domain sequences shown in this application, including, but not limited to SEQ. I.D. Nos. 2, 13, 15, 39, 41, 43, 45, 47, 49, 51, 53, 55, 57, 59, 61, 63, 65, 67, 69, 71, 73, 75, 77, 79, 81, 83, 85, 87, 89, 91, 93, and 95;

the binding protein comprises a sequence which comprises one of the amino terminus domains shown in FIG. 20 (it is noted that the sequence need not be at the amino terminus of the binding protein);

the binding protein comprises the consensus sequence for the amino terminus domains shown in FIG. 20, (it is noted that the sequence need not be at the amino terminus of the binding protein);

the binding protein comprises a sequence which comprises one of the carboxy terminus domains shown in FIG. 21A (it is noted that the sequence need not be at the carboxy terminus of the binding protein);

the binding protein comprises the consensus sequence for the carboxy terminus domains shown in FIG. 21A (it is noted that the sequence need not be at the carboxy terminus of the binding protein);

the binding protein comprises the consensus sequence for the carboxy terminus domains shown in FIG. 21B (it is noted that the sequence need not be at the carboxy terminus of the binding protein);

one of SEQ. I.D. Nos. 1, 12, 14, 40, 42, 44, 46, 48, 50, 52, 54, 56, 58, 60, 62, 64, 66, 68, 70, 72, 74, 76, 78, 80, 82, 84, 86, 88, 90, 92, and 94; or a sequence which has substantially the same degree of homology to SEQ. I.D. Nos. 1, 12, 14, 40, 42, 44, 46, 48, 50, 52, 54, 56, 58, 60, 62, 64, 66, 68, 70, 72, 74, 76, 78, 80, 82, 84, 86, 88, 90, 92, and 94 as these sequences have with each other.

The present invention also relates to a method for identifying gene sequences from at least a portion of a plant genome which encode binding proteins capable of binding to a target DNA regulatory sequence which regulates expression of one or more stress tolerance genes in a plant.

In one embodiment, the method includes:

taking a microorganism which includes a target DNA regulatory sequence for one or more environmental stress tolerance genes, a transcription activator for activating expression of a reporter gene, and a reporter gene whose expression is activated by a protein which includes a binding domain capable of binding to the target DNA regulatory sequence and an activation domain capable of activating the transcription activator;

fusing sequences from a cDNA library of at least a portion of a plant genome to a sequence which encodes a functional activation domain in the microorganism;

introducing the fused sequences into the microorganism; and selecting microorganisms which express the reporter gene, expression of the reporter gene indicating expression of a fusion protein which includes a binding domain for the target DNA regulatory sequence and the activation domain; and identifying the gene sequence from the cDNA library introduced into the microorganism.

In one variation of the method, the target DNA regulatory sequence includes the subsequence CCG and in another embodiment includes the subsequence CCGAC. In yet another variation, the target DNA regulatory sequence is the C-repeat/DRE for Arabadopsis. According to the above method, the target DNA regulatory sequence is preferably native to the plant family and more preferably to the plant species from which the cDNA library is derived.

In another variation of this embodiment, the cDNA library used in the method consists of sequences which encode for a protein having an AP2 domain since it is believed that a significant class of genes encoding binding proteins for stress tolerance genes encode an AP2 domain. As will be explained herein, screening for DNA sequences from a plant genome which exhibit this functional feature has been shown to be effective for isolating gene sequences encoding binding proteins of the present invention.

In another variation of this method, the sequences from the cDNA library are fused to a sequence which includes a selectable marker, the method further including the step of selecting for microorganisms expressing the selectable marker.

While the above methodology of the present invention is described herein with regard to identifying binding protein gene sequences from Arabidopsis cDNA using the C-repeat/DRE regulatory sequence for Arabidopsis, it is noted that this methodology can be readily used to identify regulatory binding protein gene sequences for other plants by using a DNA regulatory sequence native to those plants. Alternatively, different permutations of the CCG subsequence can be used as the target DNA regulatory sequence.

An example of a microorganism which may be used in the above method is yeast. cDNA can be introduced into the microorganism by a variety of mechanisms including plasmids and vectors. In one particular embodiment, the reporter gene is beta-galactosidase.

The present invention also relates to any DNA sequences and binding proteins encoded by those DNA sequences which are identified by the above screening method.

The present invention also relates to a protein expressed by an environmental stress tolerance regulatory gene according to the present invention which can function in vivo in a plant to regulate expression of one or more environmental stress tolerance genes.

According to one embodiment, the protein is a recombinant binding protein expressed by a copy of a recombinant gene which is either not native to the plant or is native to the plant but introduced into the plant by recombinant methodology. For example, one might wish to introduce one or more copies of a regulatory gene which is native to the plant but is under the control of a promoter which overexpresses the binding protein, expresses the binding protein independent of an environmental stress, expresses the binding protein at a higher level in response to the same environmental stress than would a plant in its native state, expresses the binding protein in response to different environmental stress conditions, and/or be induced to express the binding protein by an exogenous agent to which the plant can be exposed. Alternatively, one might wish to introduce one or more copies of a regulatory gene which is not native to the plant. For example, the non-native regulatory gene may be used to alter the way in which native environmental stress tolerance genes are regulated. Alternatively, the non-native regulatory gene may be used to regulate environmental stress tolerance genes which are also not native to the plant. The non-native regulatory gene may be used to bind to a DNA regulatory region which is not native to the plant.

In another embodiment, the proteins have been isolated from a recombinant organism. The organism may be a microorganism (e.g., bacteria, yeast) or a multicellular organism such as a plant. In one variation, the protein is in substantially isolated form.

In yet another embodiment, the protein is a native, non-recombinant binding protein whose expression is regulated within a plant by a recombinant native or non-native promoter. For example, one might wish to replace a native promoter with a recombinant promoter which overexpresses the binding protein, expresses the binding protein independent of an environmental stress, expresses the binding protein at a higher level in response to the same environmental stress than would a plant in its native state, expresses the binding protein in response to different environmental stress conditions, and/or be induced to express the binding protein by an exogenous agent to which the plant can be exposed.

In one variation of the above embodiments, the protein is capable of selectively binding to a DNA regulatory sequence for one or more environmental stress tolerance genes in a plant. In another variation, the protein includes an AP2 domain which is capable of selectively binding to a DNA regulatory sequence for one or more environmental stress tolerance genes in a plant. One method which may be used to determine whether the protein binds selectively to the DNA regulatory sequence is a gel shift assay. The DNA regulatory sequence may optionally include a CCG subsequence, a CCGAC subsequence and optionally the C-repeat/DRE sequence of Arabadopsis.

In another variation of the above embodiments, the binding protein satisfies one or more of the following requirements:

the binding protein comprises an AP2 domain which comprises a consensus sequence sufficiently homologous to any one of the consensus sequences shown in FIGS. 19A, 19B, or 19C that the binding protein is capable of binding to a CCG regulatory sequence, preferably a CCGAC regulatory sequence;

the binding protein comprises an AP2 domain which comprises a consensus sequence shown in FIGS. 19A, 19B or 19C;

the binding protein comprises an AP2 domain which comprises the amino acid residues shown in FIGS. 19D or 19E;

the binding protein comprises an AP2 domain which is sufficiently homologous to at least one of the AP2 domains shown in the application such that it is capable of binding to a CCG regulatory sequence, preferably a CCGAC regulatory sequence;

the binding protein comprises one of the AP2 domain sequences shown in this application, including, but not limited to SEQ. I.D. Nos. 2, 13, 15, 39, 41, 43, 45, 47, 49, 51, 53, 55, 57, 59, 61, 63, 65, 67, 69, 71, 73, 75, 77, 79, 81, 83, 85, 87, 89, 91, 93, and 95;

the binding protein comprises a sequence which comprises one of the amino terminus domains shown in FIG. 20 (it is noted that the sequence need not be at the amino terminus of the binding protein);

the binding protein comprises the consensus sequence for the amino terminus domains shown in FIG. 20, (it is noted that the sequence need not be at the amino terminus of the binding protein);

the binding protein comprises a sequence which comprises one of the carboxy terminus domains shown in FIG. 21A (it is noted that the sequence need not be at the carboxy terminus of the binding protein);

the binding protein comprises the consensus sequence for the carboxy terminus domains shown in FIG. 21A (it is noted that the sequence need not be at the carboxy terminus of the binding protein); and the binding protein comprises the consensus sequence for the carboxy terminus domains shown in FIG. 21B (it is noted that the sequence need not be at the carboxy terminus of the binding protein).

The sequence of the binding protein may be a naturally occurring sequence such as the ones shown in SEQ. ID. Nos. 2, 13, 15, 39, 41, 43, 45, 47, 49, 51, 53, 55, 57, 59, 61, 63, 65, 67, 69, 71, 73, 75, 77, 79, 81, 83, 85, 87, 89, 91, 93, and 95 or may be a non-naturally occurring sequence. It is noted, however, that binding proteins according to the present invention are intended to encompass non-naturally occurring sequences which are derivatives of the classes of binding proteins taught herein. For example, additional binding proteins may be constructed using one of the AP2 domains taught herein or the consensus sequence of these AP2 domains. It may be desirable to include with the AP2 domain a transcription activation region. The transcription activation region may be native to the plant or non-native to the plant in which the binding protein will be used. For example, the sequence may include a subsequence which encodes a binding domain for the DNA regulatory sequence fused to a transcription activating region, such as the transcription activating region of VP16 or GAL4. Optionally, one can include in the binding protein one of the amino terminus domains, the consensus sequence for the amino terminus domain, one of the carboxy terminus domains and/or the consensus sequence for the carboxy terminus domains. It is noted that the amino terminus domain may be positioned away from the amino terminus of the new binding protein and the carboxy terminus domain may be positioned away from the carboxy terminus of the new binding protein.

Optionally, the binding protein can be viewed as comprising one of the amino terminus domains, the consensus sequence for the amino terminus domain, one of the carboxy terminus domains and/or the consensus sequence for the carboxy terminus domains. It is noted that the amino terminus domain may be positioned away from the amino terminus of the new binding protein and the carboxy terminus domain may be positioned away from the carboxy terminus of the new binding protein.

In another embodiment, the binding protein is an isolated protein or a recombinantly produced protein which has a molecular weight of about 26 kDa as measured in an electrophoresis gel and binds to a DNA regulatory sequence which regulates a cold or dehydration regulated gene of *Arabidopsis thaliana*.

The present invention also relates to DNA and RNA constructs, such as plasmids, vectors, and the like, which are capable of transforming a plant. The constructs include a sequence which encodes a binding protein capable of selectively binding to a DNA regulatory sequence which regulates the one or more environmental stress tolerance genes. The binding protein is preferably able to regulate expression of one or more environmental stress tolerance genes in a plant by selectively binding to the DNA regulatory sequence. More preferably, when transformed into a plant, the sequence regulates expression of one or more environmental stress tolerance genes in the plant by expressing the binding protein. In one embodiment, the DNA construct includes a promoter and a regulatory gene sequence whose expression is under the control of the promoter. Different promoters may be used to select the degree of expression or conditions under which the regulatory gene is expressed. For example, the promoter can be used to cause overexpression of the regulatory gene, expression of the regulatory gene independent of an environmental stress, expression of the regulatory gene at a higher level in response to the same environmental stress than would a plant in its native state, expression of the regulatory gene in response to different environmental stress conditions, and/or induction of expression of the regulatory gene by an exogenous agent to which the plant can be exposed.

In another embodiment, the DNA construct comprises a sequence which encodes:

- a binding protein comprising an AP2 domain which comprises a consensus sequence sufficiently homologous to any one of the consensus sequences shown in FIGS. 19A, 19B, or 19C that the binding protein is capable of binding to a CCG regulatory sequence, preferably a CCGAC regulatory sequence;
- a binding protein comprising an AP2 domain which comprises a consensus sequence shown in FIGS. 19A, 19B or 19C;
- a binding protein comprising an AP2 domain which comprises the amino acid residues shown in FIGS. 19D or 19E;
- a binding protein comprising an AP2 domain which is sufficiently homologous to at least one of the AP2 domains shown in the application such that it is capable of binding to a CCG regulatory sequence, preferably a CCGAC regulatory sequence;
- a binding protein comprising one of the AP2 domain sequences shown in this application, including, but not limited to SEQ. I.D. Nos. 2, 13, 15, 39, 41, 43, 45, 47, 49, 51, 53, 55, 57, 59, 61, 63, 65, 67, 69, 71, 73, 75, 77, 79, 81, 83, 85, 87, 89, 91, 93, and 95;
- a binding protein comprising a sequence which comprises one of the amino terminus domains shown in FIG. 20 (it is noted that the sequence need not be at the amino terminus of the binding protein);
- a binding protein comprising the consensus sequence for the amino terminus domains shown in FIG. 20, (it is noted that the sequence need not be at the amino terminus of the binding protein);
- a binding protein comprising a sequence which comprises one of the carboxy terminus domains shown in FIG. 21A (it is noted that the sequence need not be at the carboxy terminus of the binding protein);
- a binding protein comprising the consensus sequence for the carboxy terminus domains shown in FIG. 21A (it is noted that the sequence need not be at the carboxy terminus of the binding protein);
- a binding protein comprising the consensus sequence for the carboxy terminus domains shown in FIG. 21B (it is noted that the sequence need not be at the carboxy terminus of the binding protein);
- one of SEQ. I.D. Nos. 1, 12, 14, 40, 42, 44, 46, 48, 50, 52, 54, 56, 58, 60, 62, 64, 66, 68, 70, 72, 74, 76, 78, 80, 82, 84, 86, 88, 90, 92, and 94; or
- a sequence which has substantially the same degree of homology to SEQ. I.D. Nos. 1, 12, 14, 40, 42, 44, 46, 48, 50, 52, 54, 56, 58, 60, 62, 64, 66, 68, 70, 72, 74, 76, 78, 80, 82, 84, 86, 88, 90, 92, and 94 as these sequences have with each other.

The present invention also relates to plasmids pCBF1 (ATCC 98063), pCBF2, and pCBF3.

The present invention also relates to a recombinant microorganism, such as a bacterium, yeast, fungus, virus, into which at least one copy of a regulatory gene encoding a binding protein of the present invention has been introduced by a recombinant methodology.

The present invention also relates to recombinant plants into which at least one copy of a regulatory gene encoding a binding protein of the present invention has been introduced by a recombinant methodology. The recombinant copy of the regulatory gene may be native or non-native to the plant and express a binding protein which is either native or non-native to the plant.

Expression of the recombinant copy of the regulatory gene may be under the control of the promoter. The promoter may increase the level at which the regulatory gene is expressed, express the regulatory gene without being induced by an environmental stress and/or express the regulatory gene in response to a different form or degree of environmental stress than would otherwise be needed to induce expression of the regulatory gene. For example, a promoter can be used which turns on at a temperature that is warmer than the temperature at which the plant normally exhibits cold tolerance. This would enable the cold tolerance thermostat of a plant to be altered. Similarly, a promoter can be used which turns on at a dehydration condition that is wetter than the dehydration condition at which the plant normally exhibits dehydration tolerance. This would enable the level at which a plant responds to dehydration to be altered. A promoter can also be used which causes a higher level of expression to occur at a given environmental condition (e.g. temperature and/or dryness) than the plant would express in its native state. The promoter may also be inducible by an exogenous agent, i.e., express the regulatory gene in response to the presence of an agent to which the promoter is exposed. This would enable stress tolerance to be induced by applying an inducing agent to the plant.

Selection of the promoter can also be used to determine what tissues in the plant express the binding protein as well as when expression occurs in the plant's lifecycle. By selecting a promoter which regulates in what tissues and when in a plant's life the promoter functions to regulate expression of the binding protein, in combination with the selecting how that promoter regulates expression (level of expression and/or type of environmental or chemical induction), an incredible range of control over the environmental stress responses of a plant can be achieved according to the present invention.

The environmental stress tolerance gene regulated by the recombinantly expressed regulatory gene may be native or non-native to the plant. Hence, in one embodiment, the plant includes a recombinant copy of a regulatory gene which is native to the plant and expresses a native protein which functions within the plant to regulate expression of a native environmental stress tolerance gene. In this embodiment, the recombinant plant expresses a higher level of the native regulatory gene than the plant would otherwise.

In another embodiment, at least one of the regulatory genes and the environmental stress tolerance genes is not native to the plant. For example, the regulatory gene can be native and the environmental stress tolerance gene is non-native, or the regulatory gene is non-native and the environmental stress tolerance gene is native to the plant.

In yet another embodiment, the plant can include a recombinant copy of a regulatory gene which is not native to the plant as well as a recombinant copy of one or more environmental stress tolerance genes which also is not native to the plant. According to this embodiment, the non-native regulatory gene expresses a non-native binding protein which functions within the plant to regulate expression of the one or more non-native environmental stress tolerance genes. In this regard, it is envisioned that the present invention can be used to introduce, change and/or augment the environmental stress tolerance of a plant by introducing and causing the expression of environmental stress tolerance which the plant does not have in its native form. Accordingly, plants from warmer climates can be engineered to include one or more cold tolerance genes along with a regulatory gene needed to cause expression of the cold tolerance genes in the plant so that the engineered plant can survive better in a colder climate. Similarly, a plant can be engineered to include one or more dehydration tolerance genes along with a regulatory gene needed to cause expression of the dehydration tolerance gene so that the engineered plant can grow better in a dryer climate. In this regard, it should be possible to take a plant which grows well in a first climate and engineer it to include stress tolerance genes and regulatory genes native to a second climate so that the plant can grow well in the second climate.

The present invention also relates to a method for changing or enhancing the environmental stress tolerance of a plant.

In one embodiment, the method includes introducing at least one copy of a regulatory gene encoding a binding protein of the present invention into a plant; expressing the binding protein encoded by the regulatory gene; and using the expressed binding protein to stimulate expression of at least one environmental stress tolerance gene through binding to a DNA regulatory sequence. According to this embodiment, the regulatory gene may be non-recombinant or recombinant native or non-native to the plant. Similarly, the DNA regulatory sequence and the environmental stress tolerance gene may each independently be native or non-native to the plant. In one variation of this embodiment, the method further includes recombinantly introducing an environmental stress tolerance gene into the plant which is regulated by the recombinant regulatory gene.

In another embodiment, the method includes introducing a recombinant promoter which regulates expression of a regulatory gene encoding a binding protein of the present invention into a plant; expressing the binding protein under the control of the recombinant promoter, and using the expressed binding protein to stimulate expression of at least one environmental stress tolerance gene through binding to a DNA regulatory sequence. According to this embodiment, the regulatory gene, the DNA regulatory sequence and the environmental stress tolerance gene may each independently be non-recombinant or recombinant native or non-native to the plant.

In yet another embodiment, the method includes introducing at least one recombinant environmental stress tolerance gene into a plant; expressing a binding protein; and using the expressed binding protein to stimulate expression of the recombinant environmental stress tolerance gene through binding to a DNA regulatory sequence. According to this embodiment, the gene encoding the regulatory protein, and the DNA regulatory sequence may each independently be non-recombinant or recombinant native or non-native to the plant. The recombinant environmental stress tolerance gene may be either native or non-native to the plant.

1. Definitions

The term "C-repeat cold and drought regulation element" or "C-repeat/DRE" refers to a sequence which includes CCG and functions as a binding domain in a plant to regulate expression of one or more environmental stress tolerance genes, such as cold or dehydration stress tolerance genes.

The term "cold stress" refers to a decrease in ambient temperature, including a decrease to freezing temperatures, which causes a plant to attempt to acclimate itself to the decreased ambient temperature.

The term "dehydration stress" refers to drought, high salinity and other conditions which cause a decrease in cellular water potential in a plant.

Transformation means the process for changing the genotype of a recipient organism by the stable introduction of DNA by whatever means.

A transgenic plant is a plant containing DNA sequences which were introduced by transformation. Horticultural and crop plants particularly benefit from the present invention.

Translation means the process whereby the genetic information in an mRNA molecule directs the order of specific amino acids during protein synthesis.

The term "essentially homologous" means that the DNA or protein is sufficiently duplicative of that set forth in FIG. 2B to produce the same result. Such DNA can be used as a probe to isolate DNA's in other plants.

A promoter is a DNA fragment which causes transcription of genetic material. For the purposes described herein, promoter is used to denote DNA fragments that permit transcription in plant cells.

A poly-A addition site is a nucleotide sequence which causes certain enzymes to cleave mRNA at a specific site and to add a sequence of adenylic acid residues to the 3'-end of the mRNA.

The phrase "DNA in isolated form" refers to DNA sequence which has been at least partially separated from other DNA present in its native state in an organism. A cDNA library of genomic DNA is not "DNA in isolated form" whereas DNA which has been at least partially purified by gel electrophoresis corresponds to "DNA in isolated form".

2. C-Repeat/DRE Regulatory Elements in Plants

C-repeat cold and drought regulation elements (C-repeat/DRE) are sequences which function as a cis-acting regulatory element that stimulates transcription in response to an environmental stress, such as low temperature (Yamaguchi-Shinozaki, K., et al., The Plant Cell 6:251–264 (1994); and Baker, S. S., et al., Plant Mol. Biol. 24:701–713 (1994); Jiang, C., et al., Plant Mol. Biol. 30:679–684 (1996)) or dehydration stress and high salinity (Yamaguchi-Shinozaki, K., et al., The Plant Cell 6:251–264 (1994)). An object of the research leading to the present invention was the determination of how a C-repeat/DRE stimulates gene expression in response to these environmental factors, and whether cold, dehydration and high salinity affect independent or overlapping regulatory systems.

The first step toward determining how a C-repeat/DRE regulation element stimulates gene expression was the identification of the C-repeat cold and drought regulation element itself. The 5 base pair core sequence, CCGAC, has been found to be present once to multiple times in a variety of plant cold-regulated promoters in Arabidopsis and Brassica including the COR15a (Baker, S. S., et al, Plant. Mol. Biol. 24:701–713 (1994)); COR78/RD29A (Horvath, D. P., et al, Plant Physiol. 103:1047–1053 (1993) and Yamaguchi-Shinozaki, K., et al., The Plant Cell 6:251–264 (1994)); COR6.6 (Wang, H., et al., Plant Mol. biol. 28:605–617 (1995)); and KIN1 (Wang, H., et al, Plant Mol. Biol. 28:605–617 (1995)) genes of Arabidopsis and the BN115 gene of *Brassica napus* (White, T. C., et al, Plant Physiol.

106:917–928 (1994)). As shown in the examples herein, core sequence CCGAC was used to identify proteins encoded by genes within the Arabidopsis genome which bind to this core sequence.

Applicants believe that the CCGAC core sequence is a member of family of core sequences having the common subsequence CCG. The binding of CBF1 to the C-repeat/DRE involves the AP2 domain. In this regard, it is germane to note that the tobacco ethylene response element, AGCCGCC, closely resembles the C-repeat/DRE sequences present in the promoters of the Arabidopsis genes COR15a, GGCCGAC, and COR78lRD29A, TACCGAC. While the specific teachings in the present invention used only a DNA regulatory sequence which includes a CCGAC subsequence as the C-repeat/DRE core regulatory sequence, Applicants believe that other C-repeat/DRE regulatory sequences exist which belong to a broader CCG family of regulatory sequences. By screening plant genomes according to the methodology taught herein using other members of the CCG family, additional regulatory sequences as well as the binding proteins which bind to these regulatory sequences can be identified. For example, plants which are known to exhibit a form of environmental stress tolerance can be screened according to the blue colony assay and other screening methodologies used in the present invention with other members of the CCG family in order to identify other binding proteins and their gene sequences. Examples of other members of the CCG family include, but are not limited to, environmental stress response regulatory elements which include one of the following sequences: CCGM, CCGAT, CCGAC, CCGAG, CCGTA, CCGTT, CCGTC, CCGTG, CCGCA, CCGCT, CCGCG, CCGCC, CCGGA, CCGGT, CCGGC, CCGGG, AACCG, ATCCG, ACCCG, AGCCG, TACCG, TTCCG, TCCCG, TGCCG, CACCG, CTCCG, CGCCG, CCCCG, GACCG, GTCCG, GCCCG, GGCCG, ACCGA, ACCGT, ACCGC, ACCGG, TCCGA, TCCGT, TCCGC, TCCGG, CCCGA, CCCGT, CCCGC, CCCGG, GCCGA, GCCGT, GCCGC, and GCCGG.

Applicants also believe that other families of environmental stress tolerance DNA regulatory sequences, other than the CCG family may exist. The methodologies of the present invention may be used once such other families are identified in order to identify specific environmental stress tolerance DNA regulatory sequences and associated binding proteins.

3. Identification of Environmental Stress Tolerance Regulatory Gene Sequences Using Target Regulatory Sequence It is possible to take a cDNA library of at least a portion of a plant genome and screen the cDNA library for the presence of regulatory gene sequences which encode binding proteins capable of binding to a target regulatory sequence. As used here, a target DNA regulatory sequence refers to a sequence to which a binding protein for one or more environmental stress tolerance genes binds. Permutations of the CCG and CCGAC families of DNA regulatory sequences represent examples of target DNA regulatory sequences. As detailed in Example 1 herein, this was the approach was used to identify CBF1, a sequence which encodes a binding protein for the Arabadopsis DNA regulatory sequence, from an Arabadopsis cDNA library.

First a target regulatory sequence is selected. The target regulatory sequence is preferably native to the plant from which the cDNA library being screened is derived.

Once a target regulatory sequence is selected, the target regulatory sequence is fused to a reporter gene and introduced into a microorganism. Expression of the reporter gene can be activated by a protein which includes a binding domain capable of binding to the target DNA regulatory sequence and an activation domain capable of activating transcription.

Sequences from a cDNA library of at least a portion of a plant genome are then fused to a sequence which encodes a functional activation domain in the microorganism. The fused sequences are then introduced into the microorganism. It is possible that the sequence from the cDNA library may already encode a functional activation domain, for example as described herein in Example 1.

Microorganisms which express the reporter gene are then selected. Since only those microorganisms which express a fusion protein which includes a binding domain for the target DNA regulatory sequence and an activation domain will stimulate expression of the reporter gene, expression of the reporter gene indicates expression of such a fusion protein.

The gene sequence from the cDNA library introduced into the microorganism which stimulates expression of the reporter gene is then identifed.

According to the above method, the target DNA regulatory sequence preferably includes the subsequence CCG and more preferably includes the subsequence CCGAC.

The "one-hybrid" strategy described in Li, J. J. and I. Herskowitz, Science 262:1870–1874 (1993) and used in Example 1 to screen Arabidopsis cDNA is an example of this method. This method can be used to screen any plant species for cDNAs that encode a target regulatory sequence, such as a C-repeat/DRE regulatory sequence. According to the "one hybrid" strategy, yeast strains are constructed that contain a lacZ reporter gene with either wild-type or mutant versions of target regulatory sequences in place of the normal UAS (upstream activator sequence) of the GAL1 promoter. Yeast strains carrying these reporter constructs produce low levels of βbeta-galactosidase and form white colonies on filters containing X-gal. Reporter strains carrying wild-type target regulatory sequences are transformed with a cDNA expression library that contains random cDNA inserts fused to the acidic activator domain of the yeast GAL4 transcription factor "GAL4-ACT". Recombinant plasmids in the expression library that contain a cDNA insert encoding a C-repeatlDRE binding domain fused to GAL4-ACT will express fusion proteins which bind upstream of the lacZ reporter genes carrying the wild-type target regulatory sequence, activate transcription of the lacZ gene, and result in yeast forming blue colonies on X-gal-treated filters. Alternatively, the sequence from the cDNA library introduced into the microorganism may, as was observed in Example 1, include a sequence encoding an activator domain and thus not utilize the acidic activator domain of the yeast GAL4 transcription factor "GAL4-ACT".

Recombinant plasmids from such "blue yeast" are then isolated and transformed back into reporter strains that contain either a wild-type or mutant version of target regulatory sequence fused to the lacZ gene. The plasmids that are desired are those that turn the former strains blue, but not the later, indicating that the cloned DNA binding domain is specific for the target regulatory sequence.

Based on presence of an AP2 binding domain in CBF1, CBF2 and CBF3, Applicants believe that an AP2 binding domain is present in a significant number of the environmental stress tolerance regulatory binding proteins.

Accordingly, it is believed that the specificity of the above method for screening for gene sequences encoding a regulatory binding protein can optionally be improved by first selecting cDNA from a plant genome library which includes a potential AP2 domain site. This can be routinely done by selecting probes for selecting sequences in the library which include potential AP2 domain sequences.

4. Screening for Expression of Environmental Stress Tolerance Regulatory Protein Once one or more microorganisms are selected which are believed to express a protein capable of binding to the target regulatory element and activate expression of the reporter gene, further analysis can be performed to identify and isolate full length cDNAs; i.e. cDNAs that encode the entire protein that binds to the target regulatory sequence. The coding sequence for the protein can then cloned into an expression vector, such as the pET bacterial expression vectors (Novagen), and used to produce the protein at high levels. The protein can then be analyzed by gel retardation experiments (See Example 1F) to confirm that it binds specifically to the target regulatory sequence.

Potential sequences can be further screened using known regulatory gene sequences, such as CBF1, CB2, and CBF3, or the presence of an AP2 domain which is believed to be common to a significant class of this genes. Once identified, particular sequences can be transformed into yeast to test for activation of expression of a reporter gene, for example as described in Example 1E.

5. Screening for Binding to Target Regulatory Sequence

Once a regulatory gene sequence is identified, the sequence can be introduced into a microorganism in order to express the protein encoded by the sequence. A gel shift assay, such as the one described in Example 1F, can then be used to test for in vitro binding of the expressed protein to the target DNA regulatory sequence.

Figure 5:
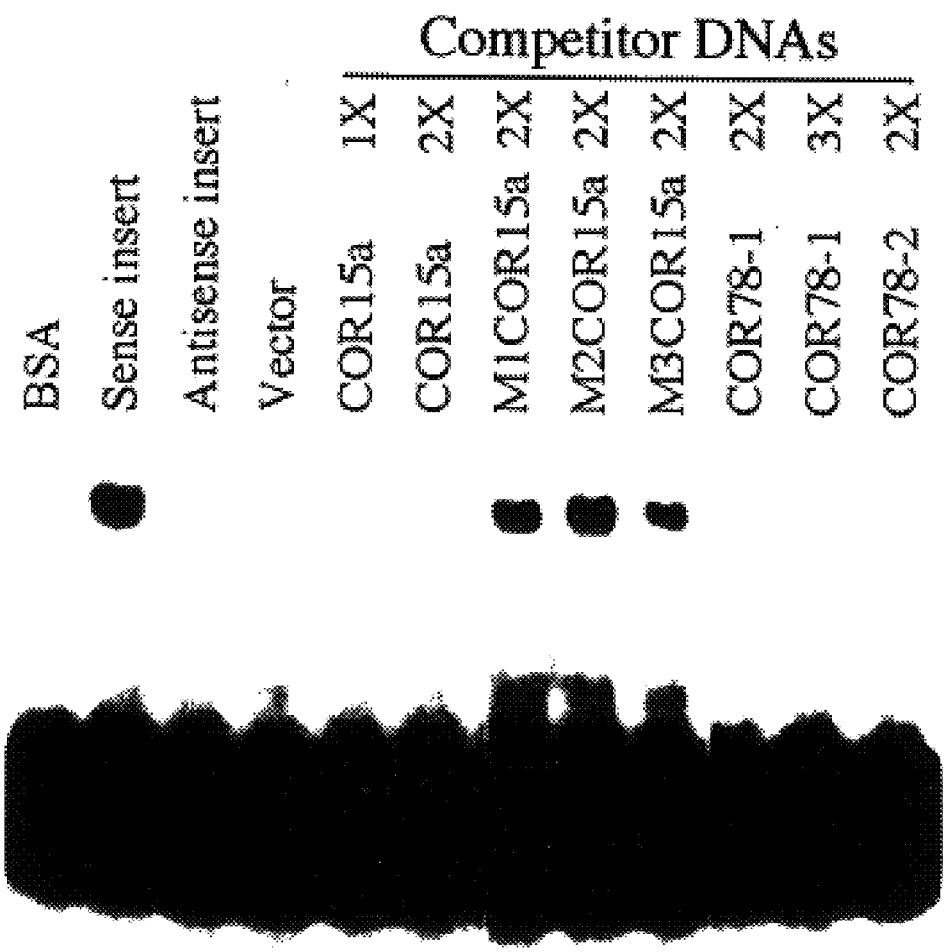
FIG. 5 is a photograph of a gel for shift assays indicating that CBF1 binds to the C-repeat/DRE.

Mutagenesis of the target DNA regulatory sequence can also be performed in order to evaluate the binding selectivity of the expressed protein. It is preferred that the expressed protein selectively bind to the target DNA regulatory sequence over related sequences with one or more base differences from the target DNA regulatory sequence. For example, FIG. 5 is a photograph of a gel from a shift assay in which CBF1 was shown to selectively bind to the wild-type C-repeat/DRE CCGAC.

6. Altering the Environmental Stress Tolerance of a Plant

The present invention also provides a method for recombinant engineered plants with a new or altered response to one or more environmental stresses.

According to one embodiment, a copy of a gene native to a plant which encodes a binding protein according to the present invention is recombinantly introduced into the plant such that the plant expresses a recombinant binding protein encoded by the recombinant copy of the gene.

According to another embodiment, a non-native gene which encodes a binding protein according to the present invention is recombinantly introduced into a plant such that the plant expresses a recombinant binding protein encoded by the recombinant non-native gene.

According to yet another embodiment, a native or non-native DNA regulatory sequence is recombinantly introduced into a plant such that the recombinant DNA regulatory sequence regulates the expression of one or more environmental stress tolerance genes in the plant. The plant includes a gene which encodes a binding protein capable of binding to the recombinant DNA regulatory sequence.

In yet another embodiment, a native or non-native promoter is recombinantly introduced into a plant such that the recombinant promoter regulates the expression of a binding protein which binds to a DNA regulatory sequence.

According to each of the above embodiments, unless otherwise specified, the gene encoding the binding protein, the promoter promoting the expression of the binding protein, the DNA regulatory sequence, and the environmental stress tolerance genes may be non-recombinant or recombinant sequences. The recombinant sequences may be native to the plant or may be non-native to the plant. All the above permutations are intended to fall within the scope of the present invention.

As an example, many plants increase in freezing tolerance in response to low non-freezing temperatures, a process known as cold acclimation. A large number of biochemical changes occur during cold acclimation including the activation of COR (COld Regulated) genes. These genes, which are also expressed in response to dehydration (e.g., drought and high salinity), are thought to help protect plant cells against the potentially deleterious effects of dehydration associated with freezing, drought and high salinity stress. Indeed, expression of the COR15a gene in plants grown at normal temperatures (22° C.) enhances the freezing tolerance of chloroplasts.

By manipulating the expression of COR genes, the stress tolerance of crop and horticultural plants could be improved, e.g., engineer broader climate ranges; target stress resistance to stress-sensitive parts of plants; render plants stress-resistant when a stress condition (frost and drought) is imminent. To bring about these effects, however, the expression of the COR genes must be manipulated. The gene, CBF1, that encodes the transcription factor that binds to the C-repeat/DRE regulatory element present in the promoters of all COR genes described to date has been isolated. CBF1 in yeast activates expression of reporter genes that have been fused to the C-repeat/DRE element. Further, expression of CBF1 in plants has been shown to activate the expression of COR genes.

By introducing modified versions of sequences encoding regulatory binding proteins, such as CBF1, into plants, the expression of COR genes can be modified, and thereby enhance the freezing and dehydration tolerance of plants.

In each of the above embodiments, expression of the recombinant copy of the regulatory gene may be under the control of a promoter. The promoter may be recombinant or non-recombinant. In the case of recombinant promoters, the promoter may be native or non-native to the plant.

When a recombinant promoter is used, the promoter can be selected to cause expression of the binding protein in a manner which is different than how the binding protein is expressed by the plant in its native state. For example, the promoter may increase the level at which the binding protein is expressed, express the binding protein without being induced by an environmental stress and/or express the binding protein in response to a different form or degree of environmental stress than would otherwise be needed to induce expression of the binding protein. The promoter may also be inducible by an exogenous agent. For example, a strong constitutive promoter could be used to cause increased levels of COR gene expression in both non-stress and stressed plants which in turn, results in enhanced freezing and dehydration tolerance. A tissue specific promoter could be used to alter COR gene expression in tissues that are highly sensitive to stress (and thereby enhance the stress tolerance of these tissues). Examples of such strong constitutive promoters-include but are not limited to the nopaline synthase (NOS) and octopine synthase (OCS) promoters, the cauliflower mosaic virus (CaMV) 19S and 35S (Odell et al., Nature 313: 810–812 (1985)) promoters or the enhanced CaMV 35S promoters (Kay et al., Science 236: 1299–1302 (1987)).

A tissue-specific promoter could also be used to alter COR gene expression in tissues that are highly sensitive to stress, thereby enhancing the stress tolerance of these tissues. Examples tissue-specific promoters include, but are not limited to, seed-specific promoters for the B. napus napin gene (U.S. Pat. No. 5,420,034), the soybean 7S promoter, the Arabidopsis 12S globulin (cruiferin) promoter (Pang, et al. Plant Molecular Biology 11: 805–820 (1988)), the maize 27 kd zein promoter, the rice glutelin 1 promoter and the phytohemaglutinin gene, fruit active promoters such as the E8 promoter from tomatoes, tuber-specific promoters such as the patatin promoter, and the promoter for the small subunit of ribuloe-1,5-bis-phosphate carboxylase (ssRUBISCO) whose expression is activated in photosynthetic tissues such as leaves.

Alternatively, an inducible promoter may be used to control the expression of the regulatory binding protein, such as CBF1, in plants. Because, in some cases, constitutive expression of higher levels of CBF proteins may have some detrimental effects on plant growth and development, the controlled expression of CBF genes is especially advantageous. For example, a promoter could be used to induce the expression of CBF proteins only at a proper time, such as prior to a frost that may occur earlier or later in the growing season of a plant, thereby prolonging the growing season of a crop and increasing the productivity of the land. This may be accomplished by applying an exogenous inducer by a grower whenever desired. Alternatively, a promoter could be used which turns on at a temperature that is warmer than the temperature at which the plant normally exhibits cold tolerance. This would enable the cold tolerance thermostat of a plant to be altered. Similarly, a promoter can be used which turns on at a dehydration condition that is wetter than the dehydration condition at which the plant normally exhibits dehydration tolerance. This would enable the level at which a plant responds to dehydration to be altered.

Promoters which are known or are found to cause inducible transcription of the DNA into mRNA in plant cells can be used in the present invention. Such promoters may be obtained from a variety of sources such as plant and inducible microbial sources, and may be activated by a variety of exogenous stimuli, such as cold, heat, dehydration, pathogenesis and chemical treatment. The particular promoter selected is preferably capable of causing sufficient expression of the regulatory binding protein, such as CBF1, to enhance plant tolerance to environmental stresses. Examples of promoters which may be used include, but are not limited to, the promoter for the DRE (C-repeat) binding protein gene dreb2a (Liu, et al. Plant Cell 10: 1391–1406 (1998)) that is activated by dehydration and high-salt stress, the promoter for delta 1-pyrroline-5-carboxylate synthetase (P5CS) whose expression is induced by dehydration, high salt and treatment with plant hormone abscisic acid (ABA) (Yoshiba, et al., Plant J. 7 751–760 (1987)), the promoters for the rd22 gene from Arabidopsis whose transcription is induced under by salt stress, water deficit and endogenous ABA (Yamaguchi-Shinozaki and Shinozaki, Mol Gen Genet 238 17–25 (1993)), the promoter for the rd29b gene (Yamaguchi-Shinizaki and Shinozaki, Plant Physiol., 101 1119–1120 (1993)) whose expression is induced by desiccation, salt stress and exogenous ABA treatment (Ishitani et al., Plant Cell 10 1151–1161 (1998)), the promoter for the rab1 8 gene from Arabidopsis whose transcripts accumulate in plants exposed to water deficit or exogenous ABA treatment, and the promoter for the pathogenesis-related protein 1a (PR-1a) gene whose expression is induced by pathogenesis organisms or by chemicals such as salicylic acid and polyacrylic acid.

It should be noted that the promoters described above may be further modified to alter their expression characteristics. For example, the drought/ABA inducible promoter for the rab18 gene may be incorporated into seed-specific promoters such that the rab 18 promoter is drought/ABA inducible only when developing seeds. Similarly, any number of chimeric promoters can be created by ligating a DNA fragment sufficient to confer environmental stress inducibility from the promoters described above to constitute promoters with other specificities such as tissue-specific promoters, developmentally regulated promoters, light-regulated promoters, hormone-responsive promoters, etc. This should result in the creation of chimeric promoters capable of being used to cause expression of the regulatory binding proteins in any plant tissue or combination of plant tissues. Expression can also be made to occur either at a specific time during a plant's life cycle or throughout the plant's life cycle.

According to the present invention, an expression vector can be constructed to express the regulatory binding protein in the transformed plants to enhance their tolerance to environmental stresses. In one embodiment, the DNA construct may contain (1) an inducible promoter that activates expression of the regulatory binding protein in response to environmental stimuli; (2) a sequence encoding the regulatory binding protein; and (3) a 3' non-translated region which enables 3' transcriptional termination and polyadenylation of the mRNA transcript. The inducible promoter may be any one of the natural or recombinant promoters described above. The gene encoding the regulatory binding protein can be any one disclosed in the present invention. The 3' region downstream from this gene should be capable of providing a polyadenylation signal and other regulatory sequences that may be required for the proper expression and processing of a mRNA may be operably linked to the 3' end of a structural gene to accomplish the invention. This may include the native 3' end of the homologous gene form which the regulatory binding protein and/or the inducible promoter is derived, the 3' end from a heterologous gene encoding the same protein from other species, the 3' end from viral genes such as the 3' end of the 35S or the 19S cauliflower mosaic virus transcripts, the 3' end of the opine synthesis genes of *Agrobacterium tumefaciens*, or the 3' end sequences from any source such that the sequence employed provides the necessary regulatory information within its nucleic acid sequence to result in the proper expression of the promoter/coding region combination to which the 3' end sequence is operably linked.

A variety of expression vectors can be used to transfer the gene encoding the regulatory binding protein as well as the desired promoter into the plant. Examples include but not limited to those derived from a Ti plasmid of *Agrobacterium tumefaciens*, as well as those disclosed by Herrera-Estrella, L., et al., Nature 303: 209(1983), Bevan, M., Nucl. Acids Res. 12: 8711–8721 (1984), Klee, H. J., Bio/Technology 3: 637–642 (1985), and EPO Publication 120,516 (Schilperoort et al.) for dicotyledonous plants. Alternatively, non-Ti vectors can be used to transfer the DNA constructs of this invention into monotyledonous plants and plant cells by using free DNA delivery techniques. Such methods may involve, for example, the use of liposomes, electroporation, microprojectile bombardment, silicon carbide wiskers, viruses and pollen. By using these methods transgenic plants such as wheat, rice (Christou, P., Bio/Technology 9: 957–962 (1991)) and corn (Gordon-Kamm, W., Plant Cell 2: 603–618 (1990)) are produced. An immature embryo can also be a good target tissue for monocots for direct DNA delivery techniques by using the particle gun (Weeks, T. et al., Plant Physiol. 102: 1077–1084 (1993); Vasil, V., Bio/Technology 10: 667–674 (1993); Wan, Y. and Lemeaux, P., Plant Physiol. 104: 37–48 (1994), and for Agrobacterium-mediated DNA transfer (Hiei et al., Plant J. 6: 271–282 (1994); Rashid et al., Plant Cell Rep. 15: 727–730 (1996); Dong, J., et al., Mol. Breeding 2: 267–276 (1996); Aldemita, R. and Hodges, T., Planta 199: 612–617 (1996); Ishida et al., Nature Biotech. 14: 745–750 (1996)).

In one embodiment, the plasmid vector pMEN020 is preferred, which is derived from a Ti plasmid pMON10098 which is the type of binary vector described in U.S. Pat. Nos. 5,773,701 and 5,773,696. PMEN20 differs from pMON10098 by the substitution of a Kpnl, Sall, Sacl, Sacll, Notl, and Xbal restriction sites between the ECaMV 35S promoter and the E9 3' region. Plasmid pMON10098 contains the following DNA segments. Starting at the bottom of the plasmid map is the origin of bacterial replication for maintenance in *E. coli* (ori-322). Moving in a counter-clockwise direction on the map, next is ori-V, which is the vegetative origin of replication (Stalker et al. *Mol. Gen. Genet.* 181:8–12 (1981)). Next is the left border of the T-DNA. Next is the chimeric gene used as the selectable marker. The chimera includes the 0.35 kilobase (kb) of the cauliflower mosaic virus 35S promoter (P-35S) (Odell et al. (1985) Nature 313:810–812). a 0.84 kb neomycin phosphotransferase type 11 gene (KAN) and a 0.25 kb 3' non-translated region of the nopaline synthase gene (NOS 3') (Fraley et al. (1983) Proc. Natl. Acad. Sci. USA 80:1803–1807). The next sequence contains the enhanced CaMV 35S promoter and E9 3' region gene cassette and restriction sites for inserting genes such as the coding region of CBF genes. This chimeric gene cassette ends with the 0.65 kb of the E9 3' region from the pea small subunit of RUBISCO gene (U.S. Pat. No. 5,773,701). Next is the right border of the T-DNA. Next is the 0.93 kb fragment isolated from transposon Tn7 that encodes the bacterial spectinomycin/streptomycin resistance (Spc/Str), which is a determinant for selection in *E. coli* and *Agrobacterium tumefaciens* (Fling et al., *Nucl. Acids Res.* 13:7095–7106 (1985)).

The pMEN020 plasmid construct is a binary cloning vector that contains both *E. coli* and *Agrobacterium tumefaciens* origins of DNA replication but no vir genes encoding proteins essential for the transfer and integration of the target gene inserted in the T-DNA region. PMEN020 requires the trfA gene product to replicate in Agrobacterium. The strain of Agrobacterium containing this trfA gene is called the ABI strain and is described below and in U.S. Pat. Nos. 5,773,701 and 5,773,696. This cloning vector serves as an *E. coli*-*Agrobacterium tumefaciens* shuttle vector. All of the cloning steps are carried out in *E. coli* before the vector is introduced into ABI strain of *Agribacterium tumefaciens*.

The recipient ABI strain of Agribacterium carries a modified defective Ti plasmid that serves as a helper plasmid containing a complete set of vir genes but lacks portions or all of the T-DNA region. ABI is the A208 Agrobacterium tumefaciens strain carrying the disarmed pTiC58 plasmid pMP90RK (Koncz et al. Mol. Gen. Genet. 204:383–396 (1986)). The disarmed Ti plasmid provides the trfA gene functions that are required for autonomous replication of the binary vectors after transfer into the ABI strain. When plant tissue is incubated with the ABI::binary vector strains, the vectors are transferred to the plant cells by the vir functions encoded by the disarmed pMP90RK Ti plasmid. After the introduction of the binary vector into the recipient Agribacterium, the vir gene products mobilize the T-DNA region of the pMEN020 plasmid to insert the target gene, e.g. the gene encoding the regulatory binding protein, into the plant chromosomal DNA, thus transforming the cell.

After transformation of cells or protoplasts, the choice of methods for regenerating fertile plants is not particularly important. Suitable protocols are available for Leguminosae (alfalfa, soybean, clover, etc.), Umbelliferae (Carrot, celery, parsnip), Cruciferae (cabbage, radish, rapeseed, broccoli, etc.), Curcurbitaceae (melons and cucumber), Gramineae (wheat, corn, rice, barley, millet, etc.), Solanaceae (potato, tomato, tobacco, peppers, etc.), and various other crops See protocols described in Ammirato et al. (1984) *Handbook of Plant Cell Culture—Crop Species*. Macmillan Publ. Co. Shimamoto et al. Nature 338:274–276 (1989); Fromm et al., *Bio/Technology* 8:833–839 (1990); Vasil et al. *Bio/Technology* 8:429–434 (1990).

It is envisioned that the present invention can be used to introduce, change and/or augment the environmental stress tolerance of a plant by introducing and causing the expression of environmental stress tolerance in a manner which the plant does not exhibit in its native form. For example, by using different promoters in combination with recombinant regulatory genes, native environmental stress tolerance genes can be expressed independent of environmental stress, made responsive to different levels or types of environmental stress, or rendered inducible independent of an environmental stress. Further, selection of the promoter can also be used to determine what tissues in the plant express the binding protein as well as when the expression occurs in the plant's lifecycle. By selecting a promoter which regulates in what tissues and when in a plants life the promoter functions to regulate expression of the binding protein, in combination with the selecting how that promoter regulates expression (level of expression and/or type of environmental or chemical induction), an incredible range of control over the environmental stress responses of a plant can be achieved using the present invention.

By recombinantly introducing a native environmental stress tolerance gene into a plant in combination with a recombinant regulatory gene under the control of an inducible promoter, a plant can be engineered which includes its native environmental stress tolerance as well as inducible environmental stress tolerance. This might be useful for inducing a cold stress tolerance reaction in anticipation of a frost.

By recombinantly introducing a non-native environmental stress tolerance gene into a plant in combination with a recombinant regulatory gene, a plant can be engineered which includes environmental stress tolerance properties that the plant would not otherwise have. In this regard, plants from warmer climates can be engineered to include one or more cold tolerance genes along with a regulatory gene needed to cause expression of the cold tolerance genes in the plant so that the engineered plant can survive better in a colder climate. Similarly, a plant can be engineered to include one or more dehydration tolerance genes along with a regulatory gene needed to cause expression of the dehydration tolerance gene so that the engineered plant can grow better in a dryer climate. In this regard, it should be possible to take a plant which grows well in a first climate and engineer it to include stress tolerance genes and regulatory genes native to a second climate so that the plant can grow well in the second climate.

By modifying the promoter controlling the expression of the gene encoding a binding protein which regulates the expression of environmental stress tolerance genes, the operation of native, non-recombinant environmental stress tolerance genes and regulatory genes can be changed. For example, the conditions under which the stress tolerance genes are expressed can be changed. Expression can also be rendered inducible by an exogenous agent.

7. Methods for Detecting Stress Tolerance Regulatory Gene Homologs

Once one DNA sequence encoding an environmental stress tolerance regulatory binding protein has been identified, several methods are available for using that sequence and knowledge about the protein it encodes to identify homologs of that sequence from the same plant or different plant species. For example, let us assume that a cDNA encoding a first target binding domain has been isolated from plant species "A." The DNA sequence encoding the first target DNA regulatory sequence could be radiolabeled and used to screen cDNA libraries of plant species "A," or any other plant species, for DNA inserts that encode proteins related to the first target DNA regulatory sequence. This could be done by screening colony or phage "lifts" using either high (Tm of about −10° C.) or low (Tm of about −30° C. or lower) stringency DNA hybridization conditions (Sambrook, J. et al, Molecular Cloning. A Laboratory Manual Cold Spring Harbor Laboratory Press, Cold Spring Harbor, N.Y., 2nd Ed. (1989)). cDNA inserts that hybridize with the first target DNA regulatory sequence could be sequenced and compared to the original first target DNA regulatory sequence. If the insert is confirmed to encode a polypeptide similar to the first target DNA regulatory sequence, the insert could be cloned into an expression vector to produce the encoded protein. The protein would then be analyzed by gel retardation experiments to confirm that it binds specifically to the first target DNA regulatory sequence.

It is recognized that not all proteins that bind to a first target DNA regulatory sequence will be transcriptional activators. However, a number of routine tests may be performed in order to determine whether a particular protein is in fact a transcriptional activator. One test involves expressing the protein in yeast strains which contain the target DNA regulatory sequence fused to the lacZ reporter gene, as described above. If the protein is a transcriptional activator, it should activate expression of the reporter gene and result in blue colonies.

Another test is a plant transient assay. In this case, a reporter gene, such as GUS, carrying the target DNA regulatory sequence as an upstream activator is introduced into plant cells (e.g. by particle bombardment) with or without a the putative transcriptional activator under control of a constitutive promoter. If the protein is an activator, it will stimulate expression of the reporter (this may be further enhanced if the plant material is placed at low temperature or is subjected to water stress as the C-repeat/DRE is responsive to low temperature and dehydration).

Significantly, once a target DNA regulatory sequence is identified, the sequence can be fused to any potential activator or repressor sequence to modify expression of plant genes that carry the target regulatory sequence as a control element. That is, the DNA regulatory sequence can be used to target "managed" expression of the battery of environmental stress tolerance related genes in a given plant species.

It is possible that the target DNA regulatory sequence of the regulatory element that imparts environmental stress tolerance related gene expression in plant species "A" might be slightly different from the analogous target DNA regulatory element that imparts environmental stress tolerance in species "B." Thus, optimal regulation of the battery of environmental stress tolerance related genes in a given species may require the use of the regulatory binding proteins from that or a closely related plant species. Knowledge of gene sequences which encode for proteins which bind to the DNA regulatory sequence of the regulatory element, in combination with knowledge of the DNA regulatory sequence, greatly simplify the identification of sequences encoding binding proteins native to the plant species.

With the advent of fast and efficient DNA sequencing technologies, the number of plant genomes recorded on computer databases is growing rapidly. These computer databases can be used to search for homologs to CBF sequences identified in this application as well as other sequences which encode binding proteins which regulate cold tolerance genes. As more and more binding protein sequences are identified and the number of computerized plant genome databases increase, searching computer databases for additional sequences encoding binding proteins which regulate cold tolerance genes will become increasingly simplified.

8. Preparation of Binding Proteins Derivatives Using Sequences Identified in This Application According to the present invention, the binding protein is a protein which is capable of binding to a DNA regulatory sequence which regulates expression of one or more environmental stress tolerance genes in a plant. These DNA regulatory sequences are preferably a member of the CCG family of regulatory sequences and more preferably a member of the CCGAC family of regulatory sequences.

Numerous amino acid sequences for CBF binding protein homologs are disclosed in this application including those shown in FIGS. 2B, 14, and 18B and listed in SEQ. I.D. Nos. 2, 13, 15, 39, 41, 43, 45, 47, 49, 51, 53, 55, 57, 59, 61, 63, 65, 67, 69, 71, 73, 75, 77, 79, 81, 83, 85, 87, 89, 91, 93, and 95. Nucleic acid sequences encoding these CBF binding protein homologs are disclosed in this application in FIGS. 2B, 12, 13, and 18A and listed in SEQ. I.D. Nos. 1, 12, 14, 40, 42, 44, 46, 48, 50, 52, 54, 56, 58, 60, 62, 64, 66, 68, 70, 72, 74, 76, 78, 80, 82, 84, 86, 88, 90, 92, and 94. These sequences were derived from a variety of different plant species including Arabidopsis, *Brassica juncea, Brassica napus, Brassica oleracea, Brassica rapa, Glycine max, Raphanus sativus* and *Zea Maize*.

The sequences identified in these figures may generally be divided into three regions: AP2 domain, amino terminus domain, and carboxy terminus domain. FIGS. 19A–19E show different AP2 domains from these homologs and consensus sequences between the different AP2 domains shown. FIG. 19A shows an amino acid alignment of the AP2 domains of several CBF proteins with the consensus sequence between the proteins highlighted as well as a comparison of the AP2 domains with that of the tobacco DNA binding protein EREBp2. FIG. 19B shows an amino acid alignment of the AP2 domains of several CBF proteins including dreb2a and dreb2b with the consensus sequence between the proteins highlighted. FIG. 19C shows an amino acid alignment of the AP2 domains of several CBF proteins including dreb2a, dreb2b, and tiny with the consensus sequence between the proteins highlighted. FIG. 19D shows a consensus sequence corresponding to the difference between the consensus sequence shown in FIG. 19A and tiny. FIG. 19E shows a consensus sequence corresponding to the difference between the consensus sequence shown in FIG. 19B and tiny.

FIGS. 21A and 21B show different carboxy terminus domains from these homologs and consensus sequences between the different carboxy terminus domains shown.

The binding proteins utilized in the present invention include classes of binding proteins which satisfy one or more of the following requirements:

the binding protein comprises an AP2 domain which comprises a consensus sequence sufficiently homologous to any one of the consensus sequences shown in FIGS. 19A, 19B, or 19C that the binding protein is capable of binding to a CCG regulatory sequence, preferably a CCGAC regulatory sequence;

the binding protein comprises an AP2 domain which comprises a consensus sequence shown in FIGS. 19A, 19B or 19C;

the binding protein comprises an AP2 domain which comprises the amino acid residues shown in FIGS. 19D or 19E;

the binding protein comprises an AP2 domain which is sufficiently homologous to at least one of the AP2 domains shown in the application such that it is capable of binding to a CCG regulatory sequence, preferably a CCGAC regulatory sequence;

the binding protein comprises one of the AP2 domain sequences shown in this application, including, but not limited to SEQ. I.D. Nos. 2, 13, 15, 39, 41, 43, 45, 47, 49, 51, 53, 55, 57, 59, 61, 63, 65, 67, 69, 71, 73, 75, 77, 79, 81, 83, 85, 87, 89, 91, 93, and 95;

the binding protein comprises a sequence which comprises one of the amino terminus domains shown in FIG. 20 (it is noted that the sequence need not be at the amino terminus of the binding protein);

the binding protein comprises the consensus sequence for the amino terminus domains shown in FIG. 20, (it is noted that the sequence need not be at the amino terminus of the binding protein);

the binding protein comprises a sequence which comprises one of the carboxy terminus domains shown in FIG. 21A (it is noted that the sequence need not be at the carboxy terminus of the binding protein);

the binding protein comprises the consensus sequence for the carboxy terminus domains shown in FIG. 21A (it is noted that the sequence need not be at the carboxy terminus of the binding protein); and the binding protein comprises the consensus sequence for the carboxy terminus domains shown in FIG. 21B (it is noted that the sequence need not be at the carboxy terminus of the binding protein).

The sequence of the binding protein may be a naturally occurring sequence such as the ones shown in SEQ. ID. Nos. 2, 13, 15, 39, 41, 43, 45, 47, 49, 51, 53, 55, 57, 59, 61, 63, 65, 67, 69, 71, 73, 75, 77, 79, 81, 83, 85, 87, 89, 91, 93, and 95 or may be a non-naturally occurring sequence. It is noted, however, that binding proteins according to the present invention are intended to encompass non-naturally occurring sequences which are derivatives of the classes of binding proteins taught herein.

Additional binding proteins may be constructed using one of the AP2 domains taught herein or the consensus sequence of these AP2 domains. It may be desirable to include with the AP2 domain a transcription activation region. The transcription activation region may be native to the plant or non-native to the plant in which the binding protein will be used. For example, the sequence may include a subsequence which encodes a binding domain for the DNA regulatory sequence fused to a transcription activating region, such as the transcription activating region of VP16 or GAL4. Optionally, one can include in the binding protein one of the amino terminus domains, the consensus sequence for the amino terminus domain, one of the carboxy terminus domains and/or the consensus sequence for the carboxy terminus domains. It is noted that the amino terminus domain may be positioned away from the amino terminus of the new binding protein and the carboxy terminus domain may be positioned away from the carboxy terminus of the new binding protein.

Optionally, the binding protein can be viewed as comprising one of the amino terminus domains, the consensus sequence for the amino terminus domain, one of the carboxy terminus domains and/or the consensus sequence for the carboxy terminus domains. It is noted that the amino terminus domain may be positioned away from the amino terminus of the new binding protein and the carboxy terminus domain may be positioned away from the carboxy terminus of the new binding protein.

EXAMPLES

1. Isolation and Analysis of *Arabidopsis Thaliana* cDNA Clone (CBF1) Encoding C-repeat/DRE Binding Factor The following example describes the isolation of an *Arabidopsis thaliana* cDNA clone that encodes a C-repeat/DRE binding factor, CBF1 (C-repeat/DREBindingFactor 1). Expression of CBF1 in yeast was found to activate transcription of reporter genes containing the C-repeat/DRE (CCGAC) as an upstream activator sequence. Meanwhile, CBF1 did not activate transcription of mutant versions of the CCGAC binding element, indicating that CBF1 is a transcription factor that binds to the C-repeat/DRE. Binding of CBF1 to the C-repeat/DRE was also demonstrated in gel shift assays using recombinant CBF1 protein expressed in *Escherichia coli*. Analysis of the deduced CBF1 amino acid sequence indicated that the protein has a potential nuclear localization sequence, a possible acidic activation domain and an AP2 domain, a DNA-binding motif of about 60 amino acids that is similar to those present in Arabidopsis proteins APETALA2, AINTEGUMENTA and TINY, the tobacco ethylene response element binding proteins, and numerous other plant proteins of unknown function.

A. Materials

Plant material and cold treatment. *A thaliana* (L.) Heyn. ecotype RLD plants were grown in pots in controlled environment chambers at 22° C. under constant illumination with cool-white fluorescent lamps (100 $\mu$mol m$^{-2}$ s$^{-1}$) essentially as described (Gilmour, S. J., Plant Physiol. 87:745–750 (1988)). Plants were cold-treated by placing pots in a cold room at 2.5° C. under constant illumination with cool-white florescent lamps (25 $\mu$mol m$^{-2}$ s$^{-1}$) for the indicated times.

Arabidopsis cDNA expression library. The Arabidopsis pACT cDNA expression library was constructed by John Walker and colleagues (NSF/DOE/USDA Collaborative Research in Plant Biology Program grant USDA 92-37105-7675) and deposited in the Arabidopsis Biological Resource Center (stock #CD4-10).

Yeast reporter strains. Oligonucleotides (Table 1) (synthesized at the MSU Macromolecular Structure Facility) encoding either wild-type or mutant versions of the C-repeat/DRE were ligated into the Bg/II site of the lacZ reporter vector pBgl-lacZ (Li, J. J. and I. Herskowitz, Science 262:1870–1874 (1993); kindly provided by Joachim Li). The resulting reported constructs were integrated into the ura3 locus of *Saccharomyces cerevisiae* strain GGY1 (MAT gal4 gal80 ura3 leu2 his3 ade2 tyr) (Li, J. J. and I. Herskowitz, Science 262:1870–1874 (1993); provided by Joachim Li) by transformation and selection for uracil prototrophy.

*E. coli* strains. *Escherichia coli* strain GM2163 containing plasmid pEJS251 was deposited under the Budapest Treaty on May 17, 1996 with the American Type Culture Collection, Rockville, Md. as ATCC 98063. It is available by name and number pursuant to the provisions of the Budapest Treaty.

Science 262:1870–1874 (1993)). Plasmid DNA from "positive" transformants (those forming blue colonies on the X-gal-treated filters) was recovered (Strathern, J. N., and D. R. Higgens, Methods Enzymol. 194:319–329 (1991)), propagated in *E. coli* DH5α and transformed back into the yeast reporter strains to confirm activity.

Yeast transformation and quantitative beta-galactosidase assays. Yeast were transformed by either electroporation (Becker, D. M., et al., Methods Enzymol. 194:182–187 (1991)) or the lithium acetate/carrier DNA method (Schiestl, R. H., et al., Current Genetics 16:339–346 (1989)). Quantitative in vitro beta-galactosidase assays were done as described (Rose, M., et al., Methods Enzymol. 101:167–180 (1983)).

Expression of CBF1 protein in *E. coli* and yeast. CBF1 was expressed in *E. coli* using the pET-28a(+) vector (Novagen, Madison, Wis.). The BglII-BclI restriction fragment of pACT-11 encoding CBF1 was ligated into the BamHI site of the vector bringing CBF1 under control of the T7 phage promoter. The construct resulted in a "histidine tag," a thrombin recognition sequence and a "T7 epitope tag" being fused to the amino terminus of CBF1. The construct was transformed into *E. coli* BL21 (DE3) and the recombinant CBF1 protein was expressed as recommended

TABLE 1

Oligonucleotides encoding wild type and mutant versions of the C-repeat/DRE

| Oligonucleotide | C-repeat/DRE* | Sequence | SEQ ID NO: |
|---|---|---|---|
| MT50 | COR15a | GatcATTTCATGGCCGACCTGCTTTTT | 3 |
| MT52 | M1COR15a | CACAATTTCAaGaattcaCTGCTTTTT | 4 |
| MT80 | M2COR15a | GatcATTTCATGGtatgtCTGCTTTTT | 5 |
| MT125 | M3COR15a | GatcATTTCATGGaatcaCTGCTTTTT | 6 |
| MT68 | COR15b | GatcACTTGATGGCCGACCTCTTTTT | 7 |
| MT66 | COR78-1 | GatcAATATACTACCGACATGAGTTCT | 8 |
| MT86 | COR78-2 | ACTACCGACATGAGTTCCAAAAAGC | 9 |

*The C-repeat/DRE sequences tested are either wild-type found in the promoters of COR15a (Baker, S. S., et al., Plant. mol. Biol. 24: 701–713 (1994)), COR15b or COR78/RD29A (Horvath, D. P., et al., Plant Physiol. 103: 1047–1053 (1993); Yamaguchi-shinozaki, K., et al., The Plant Cell 6: 251–264 (1994)) or are mutant versions of the COR15a C-repeat/DRE (M1COR15a, M2COR15a and M3COR15a).
Uppercase letters designate bases in wild type C-repeat/DRE sequences. The core CCGAC sequence common to the above sequences is indicated in bold type. Lowercase letters at the beginning of a sequence indicate bases added to facilitate cloning. The lowercase letters that are underlined indicate the mutations in the C-repeat/DRE sequence of COR15a.

B. Methods

Screen of Arabidopsis cDNA library. The Arabidopsis pACT cDNA expression library was screened for clones encoding C-repeat/DRE environmental stress response regulatory elements by the following method. The cDNA library, harbored in *Escherichia coli* BNN132, was amplified by inoculating 0.5 ml of the provided glycerol stock into 1 L of M9 minimal glucose medium (Sambrook, J. et al, Molecular Cloning. A Laboratory Manual (Cold Spring Harbor Laboratory Press, Cold Spring Harbor, N.Y., 2nd Ed. (1989)) and shaking the bacteria for 20 h at 37° C. Plasmid DNA was isolated and purified by cesium chloride density gradient centrifugation (Sambrook et al (1989)) and transformed into the yeast GGY1 reporter strains selecting for leucine prototrophy. Yeast transformants that had been grown for 2 or 3 days at 30° C. were overlaid with either a nitrocellulose membrane filter (Schleicher and Schuell, Keene, N.H.) or Whatman #50 filter paper (Hillsboro, Oreg.) and incubated overnight at 30° C. The yeast impregnated filters were then lifted from the plate and treated with X-gal (5-bromo-4-chloro-3-indolyl-D-galactosidase) to assay colonies for beta-galactosidase activity (Li, J. J. and I. Herskowitz, by the supplier (Novagen). Expression of CBF1 in yeast was accomplished by ligating restriction fragments encoding CBF1 (the BclI-BglII and BglII-BglII fragments from pACT-11) into the BglII site of pDB20.1 (Berger, S. L., et al., Cell 70:251–265 (1992); kindly provided by Steve Triezenberg) bringing CBF1 under control of the constitutive ADC1 (alcohol dehydrogenase constitutive 1) promoter.

Gel shift assays. The presence of expressed protein which binds to a C-repeat/DRE binding domain was evaluated using the following gel shift assay. Total soluble *E. coli* protein (40 ng) was incubated at room temperature in 10 μl of 1×binding buffer [15 mM HEPES (pH 7.9), 1 mM EDTA, 30 mM KCl, 5% glycerol, 5% BSA, 1 mM DTT) plus 50 ng poly(dI-dC):poly(dI-dC) (Pharmacia, Piscataway, N.J.) with or without 100 ng competitor DNA. After 10 min, probe DNA (1 ng) that was $^{32}$P-labeled by end-filling (Sambrook et al, 1989) was added and the mixture incubated for an additional 10 min. Samples were loaded onto polyacrylamide gels (4% w/v) and fractionated by electrophoresis at 150V for 2 h (Sambrook et al). Probes and competitor DNAs were prepared from oligonucleotide inserts ligated into the BamHI site of pUC118 (Vieira, J., et al., Methods Enzymol.

153:3–11 (1987)). Orientation and concatenation number of the inserts were determined by dideoxy DNA sequence analysis (Sambrook, et al, (1989)). Inserts were recovered after restriction digestion with EcoRI and HindIII and fractionation on polyacrylamide gels (12% w/v) (Sambrook et al, 1989).

Northern and southern analysis. Northern and southern analysis was performed as follows. Total RNA was isolated from Arabidopsis (Gilmour, S. J., et al., Plant Physiol. 87:745–750 (1988)) and the poly(A)$^+$ fraction purified using oligo dT cellulose (Sambrook, et al (1989)). Northern transfers were prepared and hybridized as described (Hajela, R. K., et al., Plant Physiol. 93:1246–1252 (1990)) except that high stringency wash conditions were at 50 C in 0.1×SSPE [×SSPE is 3.6 M NaCl, 20 mM EDTA, 0.2 M Na$_2$—HPO$_4$ (pH7.7)], 0.5% SDS. Membranes were stripped in 0.1× SSPE, 0.5% SDS at 95° C. for 15 min prior to re-probing. Total Arabidopsis genomic DNA was isolated (Stockinger, E. J., et al., J. Heredity, 87:214–218 (1996)) and southern transfers prepared (Sambrook et al 1989) using nylon membranes (MSI, Westborough, Mass.). High stringency hybridization and wash conditions were as described by Walling et al (Walling, L. L., et al., Nucleic Acids Res. 16:10477–10492 (1988)). Low stringency hybridization was in 6×SSPE, 0.5% SDS, 0.25% low fat dried milk at 60° C. Low stringency washes were in 1×SSPE, 0.5% SDS at 50° C. Probes used for the entire CBF1 coding sequence and 3' end of CBF1 were the BclI/BglII and EcoRV/BglII restriction fragments from pACT-11, respectively, that had been gel purified (Sambrook et al (1989)). DNA probes were radiolabeled with $^{32}$P-nucleotides by random priming (Sambrook). Autoradiography was performed using hyperfilm-MP (Amersham, Arlington Heights, Ill.). Radioactivity was quantified using a Betascope 603 blot analyzer (Betagen Corp., Waltham, Mass.).

C. Screen of Arabidopsis cDNA Library for Sequence Encoding a C-repeat/DRE Binding Domain.

The "one-hybrid" strategy (Li, J. J. and I. Herskowitz, Science 262:1870–1874 (1993)) was used to screen for Arabidopsis cDNA clones encoding a C-repeat/DRE binding domain. In brief, yeast strains were constructed that contained a lacZ reporter gene with either wild-type or mutant C-repeat/DRE sequences in place of the normal UAS (upstream activator sequence) of the GAL1 promoter.

FIGS. 1A and 1B show how the yeast reporter strains were constructed. FIG. 1A is a schematic diagram showing the screening strategy. Yeast reporter strains were constructed that carried C-repeat/DRE sequences as UAS elements fused upstream of a lacZ reporter gene with a minimal GAL1 promoter. The strains were transformed with an Arabidopsis expression library that contained random cDNA inserts fused to the GAL4 activation domain (GAL4-ACT) and screened for blue colony formation on X-gal-treated filters. FIG. 1B is a chart showing activity of the "positive" cDNA clones in yeast reporter strains. The oligonucleotides (oligos) used to make the UAS elements, and their number and direction of insertion, are indicated by the arrows.

Yeast strains carrying these reporter constructs produced low levels of beta-galactosidase and formed white colonies on filters containing X-gal. The reporter strains carrying the wild-type C-repeat/DRE sequences were transformed with a DNA expression library that contained random Arabidopsis cDNA inserts fused to the acidic activator domain of the yeast GAL4 transcription factor, "GAL4-ACT" (FIG. 1A). The notion was that some of the clones might contain a cDNA insert encoding a C-repeat/DRE binding domain fused to GLA4-ACT and that such a hybrid protein could potentially bind upstream of the lacZ reporter genes carrying the wild type C-repeat/DRE sequence, activate transcription of the lacZ gene and result in yeast forming blue colonies on X-gal-treated filters.

Upon screening about 2×10$^6$ yeast transformants, three "positive" cDNA clones were isolated; i.e., clones that caused yeast strains carrying lacZ reporters fused to wild-type C-repeat/DRE inserts to form blue colonies on X-gal-treated filters (FIG. 1B). The three cDNA clones did not cause a yeast strain carrying a mutant C-repeat/DRE fused to LacZ to turn blue (FIG. 1B). Thus, activation of the reporter genes by the cDNA clones appeared to be dependent on the C-repeat/DRE sequence. Restriction enzyme analysis and DNA sequencing indicated that the three cDNA clones had an identical 1.8 kb insert (FIG. 2A). One of the clones, designated pACT-11, was chosen for further study.

D. Identification of 24 kDa Polypeptide with an AP2 Domain Encoded by pACT-11.

FIGS. 2A, 2B, 2C and 2D provide an analysis of the pACT-11 cDNA clone. FIG. 2A is a schematic drawing of the pACT-11 cDNA insert indicating the location and 5' to 3' orientation of the 24 kDa polypeptide and 25s rRNA sequences. The cDNA insert was cloned into the XhoI site of the pACT vector. FIG. 2B is a DNA and amino acid sequence of the 24 kDa polypeptide (SEQ ID NO:1 and SEQ ID NO:2). The AP2 domain is indicated by a double underline. The basic amino acids that potentially act as a nuclear localization signal are indicated with asterisks. The BclI site immediately upstream of the 24 kDa polypeptide used in subcloning the 24 kDa polypeptide and the EcoRV site used in subcloning the 3' end of CBF1 are indicated by single underlines. FIG. 2C is a schematic drawing indicating the relative positions of the potential nuclear localization signal (NLS), the AP2 domain and the acidic region of the 24 kDa polypeptide. Numbers indicate amino acid residues. FIG. 2D is a chart showing comparison of the AP2 domain of the 24 kDa polypeptide with that of the tobacco DNA binding protein EREBP2 (Okme-Takagi, M., et al., The Plant Cell 7:173–182 (1995) SEQ ID NOS: 10 and 11). Identical amino acids are indicated with single lines; similar amino acids are indicated by double dots; amino acids that are invariant in AP2 domains are indicated with asterisks (Klucher, K. M., et al., The Plant Cell 8:137–153 (1996)); and the histidine residues present in CBF1 and TINY (Wilson, K., et al., The Plant Cell 8:659–671 (1996)) that are tyrosine residues in all other described AP2 domains are indicated with a caret. A single amino acid gap in the CBF1 sequence is indicated by a single dot.

Our expectation was that the cDNA insert in pACT-11 would have a C-repeat/DRE binding domain fused to the yeast GAL4-ACT sequence. However, DNA sequence analysis indicated that an open reading frame of only nine amino acids had been added to the C-terminus of GAL4-ACT. It seemed highly unlikely that such a short amino add sequence could comprise a DNA binding domain. Also surprising was the fact that about half of the cDNA insert in pACT-11 corresponded to 25s rRNA sequences (FIG. 2A). Further analysis, however, indicated that the insert had an open reading frame, in opposite orientation to the GAL4-ACT sequence, deduced to encode a 24 kDa polypeptide (FIGS. 2A–C). The polypeptide has a basic region that could potentially serve as a nuclear localization signal (Raikhel, N., Plant Physiol. 100:1627–1632 (1992)) and an acidic C-terminal half (pI of 3.6) that could potentially act as an acidic transcription activator domain (Hahn, S., Cell 72:481–483 (1993)). A search of the nucleic acid and protein sequence databases indicated that there was no previously described homology of the 24 kDa polypeptide. However, the polypeptide did have an AP2 domain (Jofuku, K. D., et al., The Plant Cell 6:1211–1225 (1994)) (FIGS. 2B, D), a DNA binding motif of about 60 amino acids (Ohme-Takagi, M., et al., The Plant Cell 7:173–182 (1994)) that is present in numerous plant proteins including the APETALA2 (Jofuku, K. D., et al., The Plant Cell 6:1211–1225 (1994)), AINTEGUMENTA (Klucher, K. M., et al., The Plant Cell 8:137–153 (1996); Elliot, R. C., et al., The Plant Cell 8:155–168 (1996)) and TINY (Wilson, K., et al., The Plant Cell 8:659–671 (1996)) proteins of Arabidopsis and the EREBPs (ethylene response element binding proteins) of tobacco (Ohme-Takagi, M., et al., The Plant Cell 7:173–182 (1995)).

E. 24 kDa Polypeptide Binds to the C-repeat/DRE and Activates Transcription in Yeast.

We hypothesized that the 24 kDa polypeptide was responsible for activating the lacZ reporter genes in yeast. To test this, the BclI-BglII fragment of pACT-11 containing the 24 kDa polypeptide, and the BglII-BglII fragment containing the 24 kDa polypeptide plus a small portion of the 25s rRNA sequence, was inserted into the yeast expression vector pDB20.1.

Figure 3:
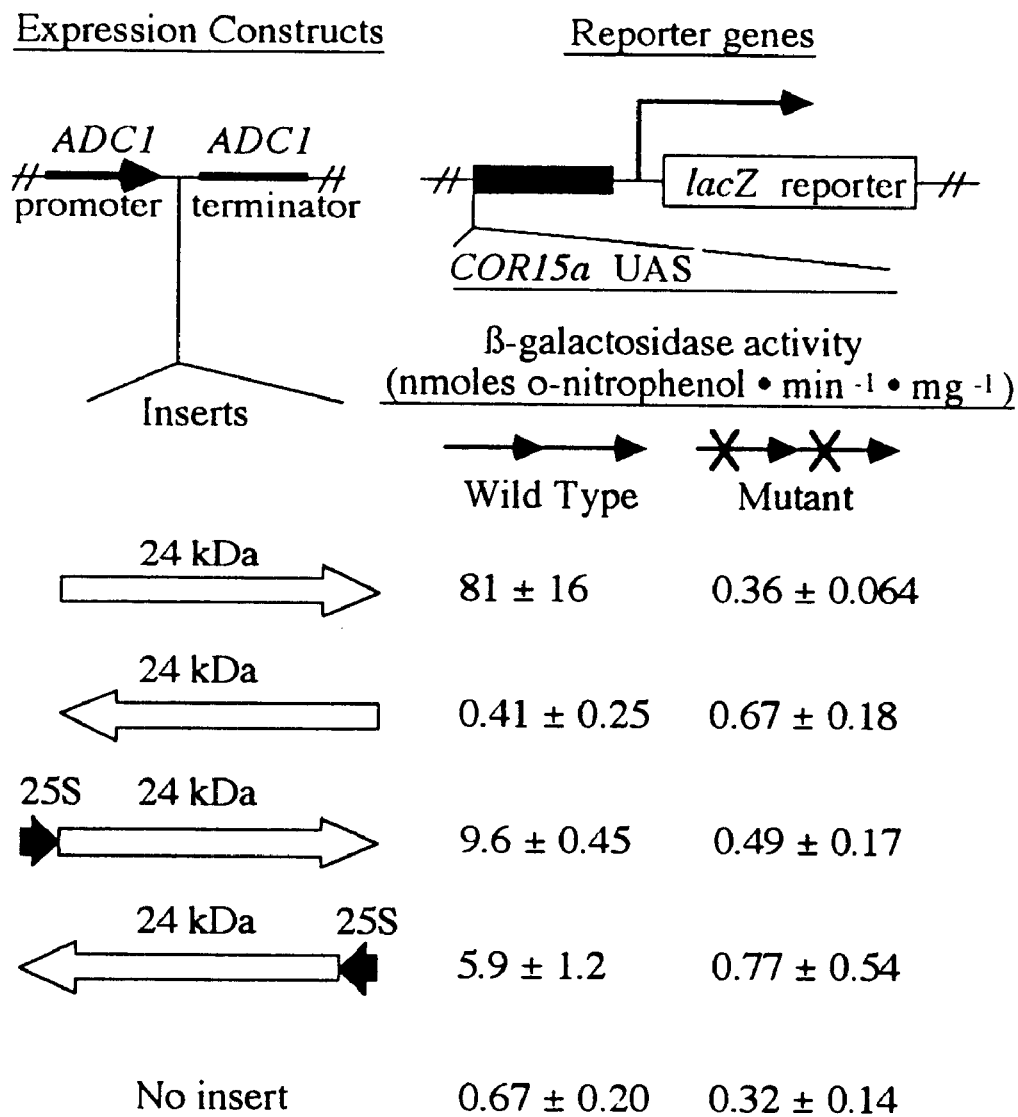
FIG. 3 is a chart showing activation of reporter genes by the 24 kDa polypeptide.

FIG. 3 is a chart showing activation of reporter genes by the 24 kDa polypeptide. Restriction fragments of pACT-11 carrying the 24 kDa polypeptide (BclI-BglII) or the 24 kDa polypeptide plus a small amount of 25s RNA sequence (BglII-BglII) were inserted in both orientations into the yeast expression vector pDB20.1 (see FIGS. 2A and 2B for location of BclI and BglII restriction sites). These "expression constructs" were transformed into yeast strains carrying the lacZ reporter gene fused to direct repeat dimers of either the wild-type COR15a C-repeat/DRE (oligonucleotide MT50) or the mutant M2COR15a C-repeat/DRE (oligonucleotide MT80). The specific activity of beta-galactosidase (nmoles o-nitrophenol produced/min$^{-1}$×mg protein$^{-1}$) was determined from cultures grown in triplicate. Standard deviations are indicated. Abbreviations: pADC1, ADC1 promoter; tADC1, ADC1 terminator.

Plasmids containing either insert in the same orientation as the ADC1 promoter stimulated synthesis of beta-galactosidase when transformed into yeast strains carrying the lacZ reporter gene fused to a wild-type COR15a C-repeat/DRE (FIG. 3). The plasmids did not, however, stimulate synthesis of beta-galactosidase when transformed into yeast strains carrying lacZ fused to a mutant version of the COR15a C-repeat/DRE (FIG. 3). These data indicated that the 24 kDa polypeptide could bind to the wild-type C-repeat/DRE and activate expression for the lacZ reporter gene in yeast. Additional experiments indicated that the 24 kDa polypeptide could activate expression of the lacZ reporter gene fused to either a wild-type COR78 C-repeat/DRE (dimer of MT66) or a wild-type COR15b C-repeat/DRE (dimer of MT 68) (not shown). A plasmid containing the BclI-BglII fragment (which encodes only the 24 kDa polypeptide) cloned in opposite orientation to the ADC1 promoter did not stimulate synthesis of beta-galactosidase in reporter strains carrying the wild-type COR15a C-repeat/DRE fused to lacZ (FIG. 3). In contrast, a plasmid carrying the BglII-BglII fragment (containing the 24 kDa polypeptide plus some 25s rRNA sequences) cloned in opposite orientation to the ADC1 promoter produced significant levels of beta-galactosidase in reporter strains carrying the wild-type COR15a C-repeat/DRE (FIG. 3). Thus, a sequence located closely upstream of the 24 kDa polypeptide was able to serve as a cryptic promoter in yeast, a result that offered an explanation for how the 24 kDa polypeptide was expressed in the original pACT-11 clone.

F. Gel Shift Analysis Indicates that the 24 kDa Polypeptide Binds to the C-repeat/DRE.

Gel shift experiments were conducted to demonstrate further that the 24 kDa polypeptide bound to the C-repeat/DRE. Specifically, the open reading frame for the 24 kDa polypeptide was inserted into the pET-28a(+) bacterial expression vector (see Materials and Methods) and the resulting 28 kDa fusion protein was expressed at high levels in E. coli. (FIG. 4).

Figure 4:
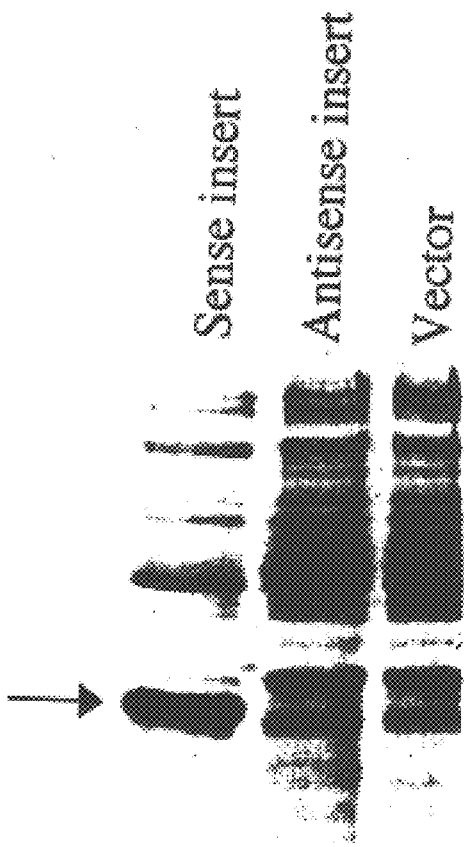
FIG. 4 is a photograph of an electrophoresis gel showing expression of the recombinant 24 kDa polypeptide in *E. coli*.

FIG. 4 is a photograph of an electrophoresis gel showing expression of the recombinant 24 kDa polypeptide in E. coli. Shown are the results of SDS-PAGE analysis of protein extracts prepared from E. coli harboring either the expression vector alone (vector) or the vector plus an insert encoding the 24 kDa polypeptide in sense (sense insert) or antisense (antisense insert) orientation. The 28 kDa fusion protein (see Materials and Methods) is indicated by an arrow.

FIG. 5 is a photograph of a gel for shift assays indicating that CBF1 binds to the C-repeat/DRE. The C-repeat/DRE probe (1 ng) used in all reactions was a $^{32}$P-labeled dimer of the oligonucleotide MT50 (wild type C-repeat/DRE from COR15a). The protein extracts used in the first four lanes were either bovine serum albumin (BSA) or the indicated CBF1 sense, antisense and vector extracts described in FIG. 4. The eight lanes on the right side of the figure used the CBF1 sense protein extract plus the indicated competitor C-repeat/DRE sequences (100 ng). The numbers 1X, 2X and 3X indicate whether the oligonucleotides were monomers, dimers or trimers, respectively, of the indicated C-repeat/DRE sequences.

Protein extracts prepared from E. coli expressing the recombinant protein produced a gel shift when a wild-type COR15a C-repeat/DRE was used as probe (FIG. 5). No shift was detected with BSA or E. coli extracts prepared from strains harboring the vector alone, or the vector with an antisense insert for the 24 kDa polypeptide. Oligonucleotides encoding wild-type C-repeat/DRE sequences from COR15a or COR78 competed effectively for binding to the COR15a C-repeat/DRE probe, but mutant version of the COR15a C-repeat/DRE did not (FIG. 5). These in vitro results corroborated the in vivo yeast expression studies indicating that the 24 kDa polypeptide binds to the C-repeat/DRE sequence. The 24 kDa polypeptide was thus designated CBF1 (C-repeat/DRE binding factor 1) and the gene encoding it named CBF1.

G. CBF1 is a Unique or Low Copy Number Gene.

Figure 6:
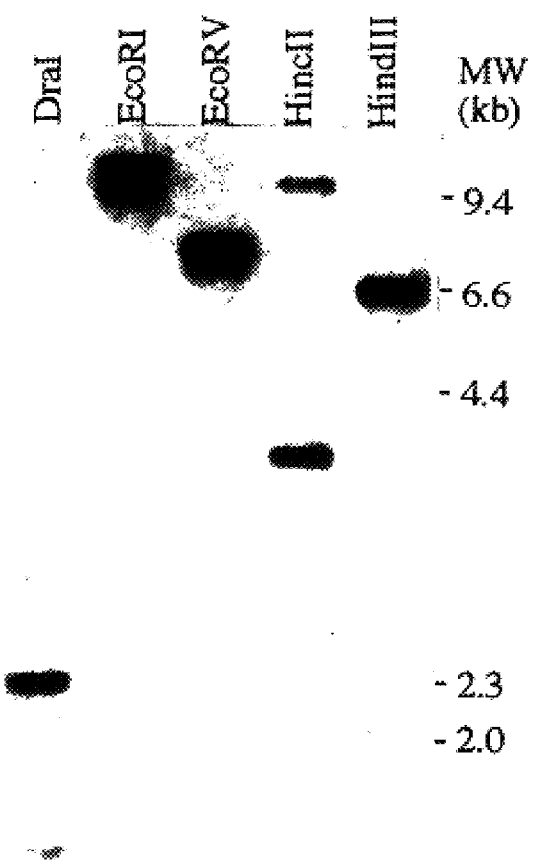
FIG. 6 is a photograph of a southern blot analysis indicating CBF1 is a unique or low copy number gene.

FIG. 6 is a photograph of a southern blot analysis indicating CBF1 is a unique or low copy number gene. Arabidopsis DNA (1 μg) was digested with the indicated restriction endonucleases and southern transfers were prepared and hybridized with a $^{32}$P-labeled probe encoding the entire CBF1 polypeptide.

The hybridization patterns observed in southern analysis of Arabidopsis DNA using the entire CBF1 gene as probe were relatively simple indicating that CBF1 is either a unique or low copy number gene (FIG. 6). The hybridization patterns obtained were not altered if only the 3' end of the gene was used as the probe (the EcoRV/BglII restriction fragment from pACT-11 encoding the acidic region of CBF1, but not the AP2 domain) or if hybridization was carried out at low stringency (not shown).

H. CBF1 Transcript Level Response to Low Temperature.

FIGS. 7A, 7B and 7C relate to CBF1 transcripts in control and cold-treated Arabidopsis. FIG. 7A is a photograph of a membrane RNA isolated from Arabidopsis plants that were grown at 22° C. or grown at 22° C. and transferred to 2.5°

C. for the indicated times. FIGS. 7B and 7C are graphs showing relative transcript levels of CBF1 and COR15a in control and cold-treated plants. The radioactivity present in the samples described in FIG. 7A were quantified using a Betascope 603 blot analyzer and plotted as relative transcript levels (the values for the 22° C. grown plants being arbitrarily set as 1) after adjusting for differences in loading using the values obtained with the pHH25 probe.

Based on FIGS. 7A–7C, northern analysis indicated that the level of CBF1 transcripts increased about 2 to 3 fold in response to low temperature (FIG. 7B). In contrast, the transcript levels for COR15a increased approximately 35 fold in cold-treated plants (FIG. 7C). Only a singly hybridizing band was observed for CBF1 at either high or low stringency with probes for either the entire CBF1 coding sequence or the 3' end of the gene (the EcoRV/BglII fragment of pACT-11) (not shown). The size of the CBF1 transcripts was about 1.0 kb.

I. Discussion Of Experimental Results.

The above example regarding CBF1 represents the first identification of a gene sequence which encodes a protein capable of binding to the C-repeat/DRE sequence CCGAC. The experimental results presented evidence that CBF1 binds to the C-repeat/DRE both in vitro via gel shift assays and in vivo via yeast expression assays. Further, the results demonstrate that CBF1 can activate transcription of reporter genes in yeast that contain the C-repeat/DRE.

The results of the southern analysis indicate that CBF1 is a unique or low copy number gene in Arabidopsis. However, the CBF1 protein contains a 60 amino acid motif, the AP2 domain, that is evolutionary conserved in plants (Weigel, D., The plant Cell 7:388–389 (1995)). It is present in the APETALA2 (Jofuku, K. D., et al., The Plant Cell 6:1211–1225 (1994)), AINTEGUMENTA (Klucher, K. M., et al., the Plant Cell 8:137–153 (1996; and Elliot, R. C., et al., The Plant Cell 8:155–168 (1996)), TINY (Wilson, K., et al., The Plant Cell 8:659–671 (1996)) and cadmium-induced (Choi, S.-Y., et al., Plant Physiol. 108:849 (1995)) proteins of Arabidopsis and the EREBPs of tobacco (Ohme-Takagi, M. et al., The Plant Cell 7:173–182 (1995)). In addition, a search of the GenBank expressed sequence tagged cDNA database indicates that there is one cDNA from *B. napus*, two from *Ricinus communes*, and more than 25 from Arabidopsis and 15 from rice, that are deduced to encode proteins with AP2 domains. The results of Ohme-Takagi and Shinshi (Ohme-Takagi, M., et al., The Plant Cell 7:173–182 (1995)) indicate that the function of the AP2 domain is DNA-binding; this region of the putative tobacco transcription factor EREBP2 is responsible for its binding to the cis-acting ethylene response element referred to as the GCC-repeat. As discussed by Ohme-Takagi and Shinshi (Ohme-Takagi, M., et al., the Plant Cell 7:173–182 (1995)), the DNA-binding domain of EREBP2 (the AP2 domain) contains no significant amino acid sequence similarities or obvious structural similarities with other known transcription factors or DNA binding motifs. Thus, the domain appears to be a novel DNA-binding motif that to date, has only been found in plant proteins.

It is believed that the binding of CBF1 to the C-repeat/DRE involves the AP2 domain. In this regard, it is germane to note that the tobacco ethylene response element, AGCCGCC, closely resembles the C-repeat/DRE sequences present in the promoters of the Arabidopsis genes COR15a, GGCCGAC, and COR781RD29A, TACCGAC. Applicants believe that CBF1, the EREBPs and other AP2 domain proteins are members of a superfamily of DNA binding proteins that recognize a family of cis-acting regulatory elements having CCG as a common core sequence. Differences in the sequence surrounding the CCG core element could result in recruitment of different AP2 domain proteins which, in turn, could be integrated into signal transduction pathways activated by different environmental, hormonal and developmental cues. Such a scenario is akin to the situation that exists for the ACGT-family of cis-acting elements (Foster et al., FASEB J. 8:192–200 (1994)). In this case, differences in the sequence surrounding the ACGT core element result in the recruitment of different bZIP transcription factors involved in activating transcription in response to a variety of environmental and developmental signals.

The results of the yeast transformation experiments indicate that CBF1 has a domain that can serve as a transcriptional activator. The most likely candidate for this domain is the acidic C-terminal half of the polypeptide. Indeed, random acidic amino acid peptides from *E. coli* have been shown to substitute for the GAL4 acidic activator domain of GAL4 in yeast (Ma, J. and M. Ptashne, Cell 51:113–199 (1987)). Moreover, acidic activator domains have been found to function across kingdoms (Hahn, S., Cell 72:481483 (1993)); the yeast GAL4 acidic activator, for instance, can activate transcription in tobacco (Ma, J., et al., Nature 334:631–633 (1988)). It has also been shown that certain plant transcription factors, such as Vp1 (McCarty, D. R., et al., Cell 66:895–905 (1991)), have acidic domains that function as transcriptional activators in plants. Significantly, the acidic activation domains of the yeast transcription factors VP16 and GCN4 require the "adaptor" proteins ADA2, ADA3, and GCN5 for full activity (see Guarente, L., Trends Biochem. Sci. 20:517–521 (1995)). These proteins form a heteromeric complex (Horiuchi, J., et al., Mol. Cell Biol. 15:1203–1209 (1995)) that bind to the relevant activation domains. The precise mechanism of transcriptional activation is not known, but appears to involve histone acetylation: there is a wealth of evidence showing a positive correlation between histone acetylation and the transcriptional activity of chromatin (Wolffe, A. P., Trends Biochem. Sci. 19:240–244 (1994)) and recently, the GCN5 protein has been shown to have histone acetyltransferase activity (Brownell, J. E., et al., Cell 84:843–851 (1996)). Genetic studies indicate that CBF1, like VP16 and GCN4, requires ADA2, ADA3 and GCN5 to function optimally in yeast. The fundamental question thus raised is whether plants have homologs of ADA2, ADA3 and GCN5 and whether these adaptors are required for CBF1 function (and function of other transcription factors with acidic activator regions) in Arabidopsis.

Figure 7:
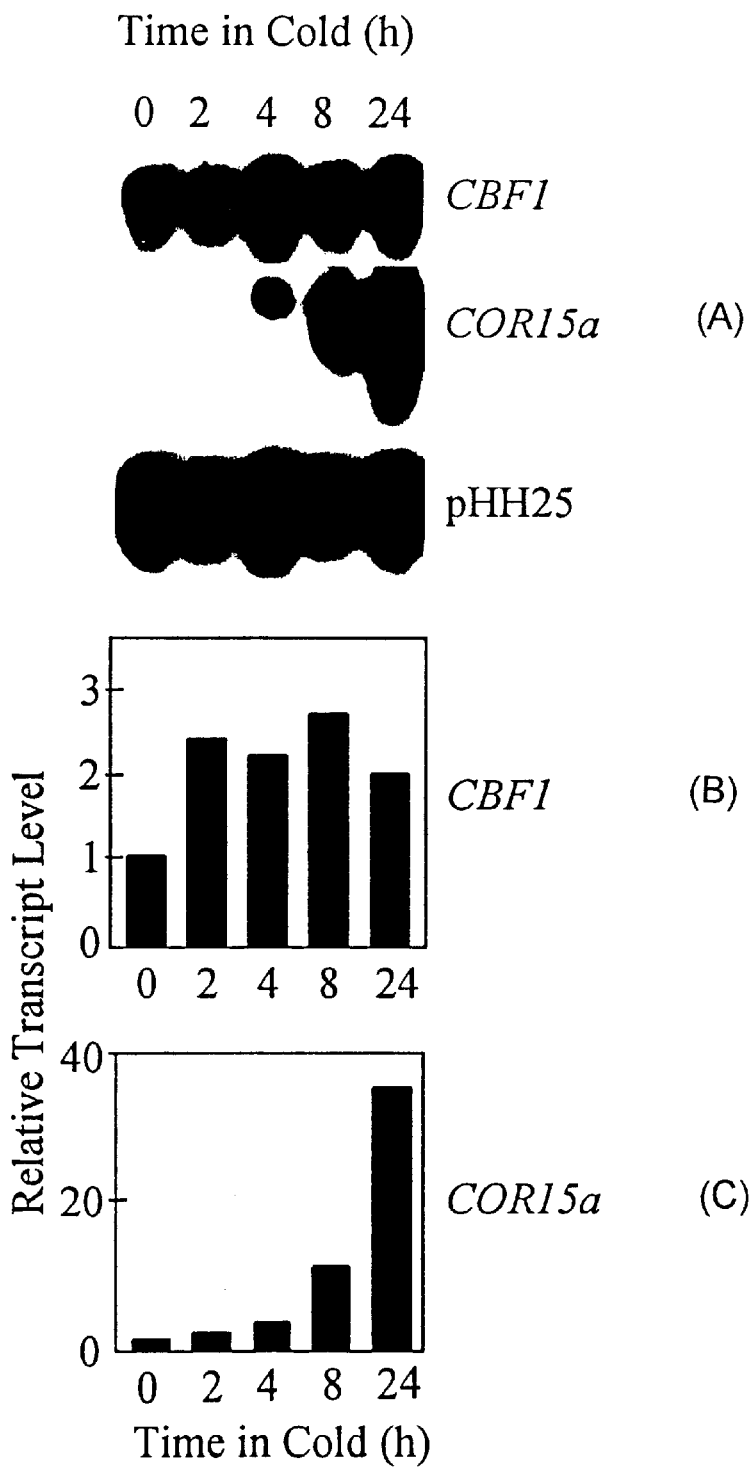
FIGS. 7A, 7B and 7C relate to CBF1 transcripts in control and cold-treated Arabidopsis.

A final point regards regulation of CBF1 activity. The results of the northern analysis indicate that CBF1 transcript levels increase only slightly in response to low temperature, while those for COR15a increase dramatically (FIG. 7). Thus, unlike in yeast, it would appear that transcription of CBF1 in Arabidopsis at warm temperatures is not sufficient to cause appreciable activation of promoters containing the C-repeat/DRE. The molecular basis for this apparent low temperature activation of CBF1 in Arabidopsis is not known. One intriguing possibility, however is that CBF1 might be modified at low temperature in Arabidopsis resulting in either stabilization of the protein, translocation of the protein from the cytoplasm to the nucleus, or activation of either the DNA binding domain or activation domain of the protein. Such modification could involve a signal transduction pathway that is activated by low temperature. Indeed, as already discussed, cold-regulated expression of COR genes in Arabidopsis and alfalfa appears to involve a signal transduction pathway that is activated by low temperature-induced calcium flux (Knight, H., et al., The Plant Cell 8:489–503 (1996); Knight, M. R., et al., Nature 352:524–526 (1991); Monroy, A. F., et al, Plant Physiol. 102:1227–1235 (1993); Monroy, A. F., and R. S., The Plant Cell, 7:321–331 (1995)). It will, therefore, be of interest to determine whether CBF1 is modified at low temperature, perhaps by phosphorylation, and if so, whether this is dependent on calcium-activated signal transduction.

2. Use of CBF1 to Induce Cold Regulated Gene Expression in Nonacclimated Arabidopsis Plants The following example demonstrates that increased expression of CBF1 induces COR gene expression in non-acclimated Arabidopsis plants. Transgenic Arabidopsis plants that overexpress CBF1 were created by placing a cDNA encoding CBF1 under the control of the strong cauliflower mosaic virus (CaMV) 35S promoter and trans-forming the chimeric gene into Arabidopsis ecotype RLD plants (Standard procedures were used for plasmid manipulations (J. Sambrook, et al., Molecular Cloning, A Laboratory Manual (Cold Spring Harbor Laboratory Press, Cold Spring Harbor, ed. 2, (1989)). The CBF1 -containing AseI-BglII fragment from pACT-Bgl+ (Stockinger, E. J., et al., Proc. Natl. Acad. Sci. U.S.A. 94:1035 (1997)) was gel-purified, BamHI linkers were ligated to both ends and the fragment was inserted into the BamHI site in pCIB710 (S. Rothstein, et al., Gene 53:153–161 (1987)) which contains the CaMV 35S promoter and terminator. The chimeric plasmid was linearized at the Kpnl site and inserted into the KpnI site of the binary vector pCIB10g (Ciba-Geigy, Research Triangle Park, N.C.). The plasmid was transformed into *Agrobacterium tumefaciens* strain C58C1 (pMP90) by electroporation. Arabidopsis plants were transformed by the vacuum infiltration procedure (N. Bechtold, J. Ellis, and G. Pelletier, C. R. Acad. Sci. Paris, Life Sci. 316:1194–1199 (1993)) as modified (A. van Hoof, P. J. Green, Plant Journal 10:415424 (1996)). Initial screening gave rise to two transgenic lines, A6 and B16, that accumulated CBF1 transcripts at elevated levels.

Figure 8:
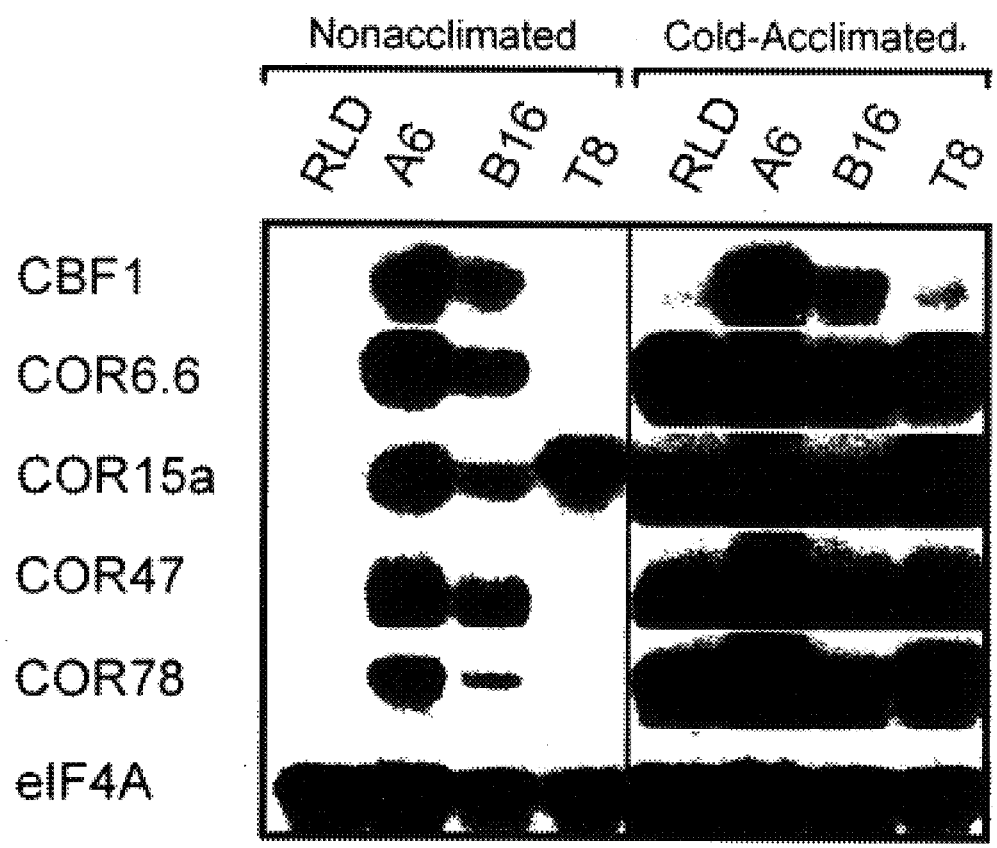
FIG. 8 is a Northern blot showing CBF1 and COR transcript levels in RLD and transgenic Arabidopsis plants.

FIG. 8 is a Northern blot showing CBF1 and COR transcript levels in RLD and transgenic Arabidopsis plants. Leaves from nonacclimated and three-day cold-acclimated plants (*Arabidopsis thaliana* ecotype RLD plants were grown in pots under continuous light (100 pE/m$^2$/sec) at 22 C for 18–25 days as described (Gilmour, S. J., et al., Plant Physiol. 87:735 (1988)). In some cases, plants were then cold-acclimated by placing them at 2.5° C. under continuous light (50 µE/m$^2$/sec) for varying amounts of time. Leaves were harvested and total RNA prepared and analyzed for CBF1 and COR transcripts by RNA blot analysis using $^{32}$P-radiolabeled probes (Total RNA was isolated from plant leaves and subjected to RNA blot analysis using high stringency hybridization and wash conditions as described (E. J. Stockinger, et al., Proc. Natl. Acad. Sci. USA 94:1035 (1997); and S. J. Gilmour, et al., Plant Physiol. 87:735 (1988)).

Figure 9:
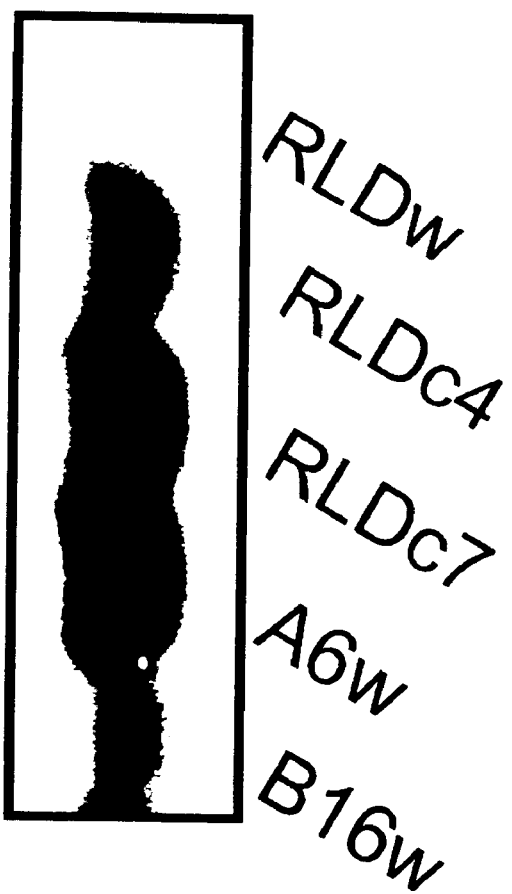
FIG. 9 is an immunoblot showing COR15am protein levels in RLD and transgenic Arabidopsis plants.

FIG. 9 is an immunoblot showing COR15am protein levels in RLD and transgenic Arabidopsis plants. Total soluble protein (100 µg) was prepared from leaves of the nonacclimated RLD (RLDw), 4-day cold-acclimated RLD (RLDc4), 7-day cold-acclimated RLD (RLDc7) and nonacclimated A6 and B16 plants and the levels of COR15am determined by immunoblot analysis using antiserum raised against the COR15am polypeptide (Total soluble protein was isolated from plant leaves, fractionated by tricine SDS-PAGE and transferred to 0.2 micron nitrocellulose as previously described (N. N. Artus et al., Proc. Natl. Acad. Sci. U.S.A. 93:13404 (1996)). COR15am protein was detected using antiserum raised to purified COR15am and protein A conjugated alkaline phosphatase (Sigma, St. Louis, Mo.) (N. N. Artus et al., Proc. Natl. Acad. Sci. U.S.A. 93:13404 (1996)). No reacting bands were observed with preimmune serum (not shown).

Southern analysis indicated that the A6 line had a single DNA insert while the B16 line had multiple inserts (not shown). Examination of fourth generation homozygous A6 and B16 plants indicated that CBF1 transcript levels were higher in nonacclimated A6 and B16 plants than they were in nonacclimated RLD plants, the levels in A6 being about three fold higher than in B16 (FIG. 8).

CBF1 overexpression resulted in strong induction of COR gene expression (FIG. 8). Specifically, the transcript levels of COR6.6, COR15a, COR47 and COR78 were dramatically elevated in nonacclimated A6 and B16 plants as compared to nonacclimated RLD plants. The effect was greater in the A6 line, where COR transcript levels in nonacclimated plants approximated those found in cold-acclimated RLD plants. The finding that COR gene expression was greater in A6 plants than in B16 plants was consistent with CBF1 transcript levels being higher in the A6 plants (FIG. 7A). Immunoblot analysis indicated that the levels of the COR 15am (FIG. 9) and COR6.6 (not shown) polypeptides were also elevated in the A6 and B16 lines, the level of expression again being higher in the A6 line. Attempts to identify the CBF1 protein in either RLD or transgenic plants were unsuccessful. Overexpression of CBF1 had no effect on the transcript levels for elF4A (eukaryotic initiation factor 4A) (Metz, A. M., et al., Gene 120:313 (1992)), a constitutively expressed gene that is not responsive to low temperature (FIG. 8) and had no obvious effects on plant growth and development.

The results from this example demonstrate that overexpression of the Arabidopsis transcriptional activator CBF1 induces expression of an Arabidopsis COR "regulon" composed of genes carrying the CRT/DRE DNA regulatory element. It appears that CBF1 binds to the CRT/DRE DNA regulatory elements present in the promoters of these genes and activates transcription which is consistent with the notion of CBF1 having a role in COR gene regulation. Significantly, there was a strong correlation between CBF1 transcript levels and the magnitude of COR gene induction in nonacclimated A6, B16, and RLD plants (FIG. 8). However, upon low temperature treatment the level of CBF1 transcripts remained relatively low in RLD plants, while COR gene expression was induced to about the same level as that in nonacclimated A6 plants (FIG. 8). Thus, it appears that CBF1 or an associated protein becomes "activated" in response to low temperature.

3. CBF1 Overexpression Resulted in a Marked Increase in Plant Freezing Tolerance The following example describes a comparison of the freezing tolerance of nonacclimated Arabidopsis plants which overexpress CBF1 to that of cold-acclimated wild-type plants. As described below, the freezing tolerance of nonacclimated Arabidopsis plants overexpressing CBF1 significantly exceeded that of non-acclimated wild-type Arabidopsis plants and approached that of cold-acclimated wild-type plants.

Freezing tolerance was determined using the electrolyte leakage test (Sukumaran, N. P., et al., HortScience 7:467 (1972)). Detached leaves were frozen to various subzero temperatures and, after thawing, cellular damage (due to freeze-induced membrane lesions) was estimated by measuring ion leakage from the tissues.

Figure 10A:
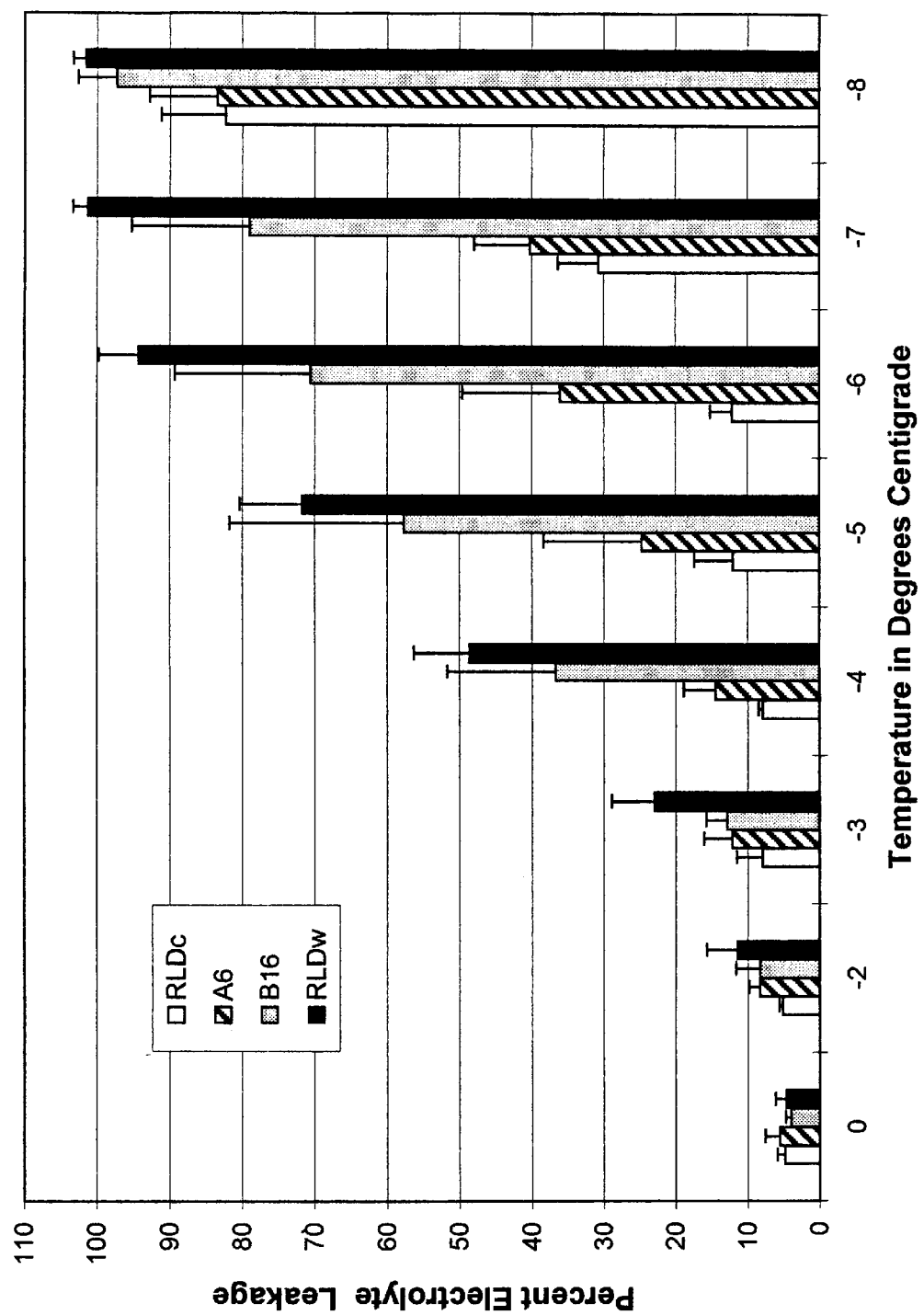
FIGS. 10A and 10B are graphs showing freezing tolerance of leaves from RLD and transgenic Arabidopsis plants.
Figure 10B:
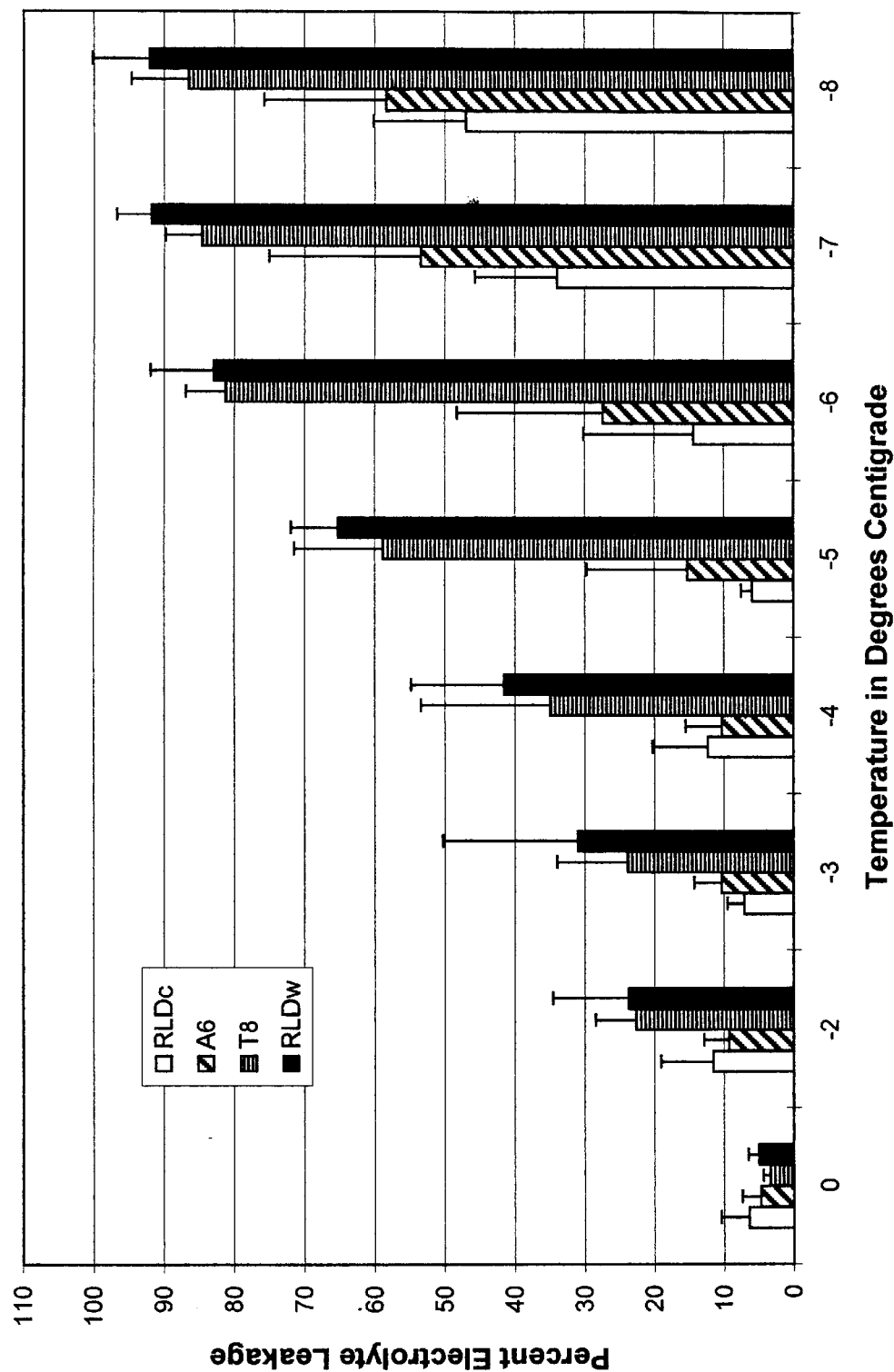

FIGS. 10A and 10B are graphs showing freezing tolerance of leaves from RLD and transgenic Arabidopsis plants. Leaves from nonacclimated RLD (RLDW) plants, cold-acclimated RLD (RLDc) plants and nonacclimated A6, B16 and T8 plants were frozen at the indicated temperatures and the extent of cellular damage was estimated by measuring electrolyte leakage (Electrolyte leakage tests were conducted as described (N. P. Sukumaran, et al., HortScience 7, 467 (1972); and S. J. Gilmour, et al., Plant Physiol. 87:735 (1988)) with the following modifications. Detached leaves (2–4) from nonacclimated or cold-acclimated plants were placed in a test tube and submerged for 1 hour in a −2° C. water-ethylene glycol bath in a completely randomized design, after which ice crystals were added to nucleate freezing. After an additional hour of incubation at −2° C., the samples were cooled in decrements of 1° C each hour until −8° C. was reached. Samples (five replicates for each data point) were thawed overnight on ice and incubated in 3 ml distilled water with shaking at room temperature for 3 hours. Electrolyte leakage from leaves was measured with a conductivity meter. The solution was then removed, the leaves frozen at −80° C. (for at least one hour), and the solution returned to each tube and incubated for 3 hours to obtain a value for 100% electrolyte leakage. In FIGS. 10A and 10B, the RLDc plants were cold-acclimated for 10 and 11 days, respectively. Error bars indicate standard deviations.

As can be seen from FIGS. 10A and 10B, CBF1 overexpression resulted in a marked increase in plant freezing tolerance. The experiment presented in FIG. 10A indicates that the leaves from both nonacclimated A6 and B16 plants were more freezing tolerant than those from nonacclimated RLD plants. Indeed, the freezing tolerance of leaves from nonacclimated A6 plants approached that of leaves from cold-acclimated RLD plants. The results also indicate that the leaves from nonacclimated A6 plants were more freezing tolerant than those from nonacclimated B1 6 plants, a result that is consistent with the greater level of CBF1 and COR gene expression in the A6 line.

The results presented in FIG. 10B further demonstrate that the freezing tolerance of leaves from nonacclimated A6 plants was greater than that of leaves from nonacclimated RLD plants and that it approached the freezing tolerance of leaves from cold-acclimated RLD plants. In addition, the results indicate that overexpression of CBF1 increases freezing tolerance to a much greater extent than overexpressing COR15a alone. This conclusion comes from comparing the freezing tolerance of leaves from nonacclimated A6 and T8 plants (FIG. 10B). T8 plants (Artus, N. N., et al., Proc. Natl. Acad. Sci. U.S.A. 93:13404 (1996)) are from a transgenic line that constitutively expresses COR15a (under control of the CaMV 35S promoter) at about the same level as in A6 plants (FIG. 1). However, unlike in A6 plants, other CRT/DRE-regulated COR genes are not constitutively expressed in T8 plants (FIG. 8).

A comparison of $EL_{50}$ values (the freezing temperature that results in release of 50% of tissue electrolytes) of leaves from RLD, A6, B16 and T8 plants is presented in Table 2.

$EL_{50}$ values were calculated and compared by analysis of variance curves fitting up to third order linear polynomial trends were determined for each electrolyte leakage experiment. To insure unbiased predictions of electrolyte leakage, trends significantly improving the model fit at the 0.2 probability level were retained. $EL_{50}$ values were calculated from the fitted models. In Table 2, an unbalanced one-way analysis of variance, adjusted for the different numbers of $EL_{50}$ values for each plant type, was determined using SAS PROC GLM [SAS Institute, Inc. (1989), SAS/STAT User's Guide, Version 6, Cory, N.C.)]. $EL_{50}$ values±SE (n) are presented on the diagonal line for leaves from nonacclimated RLD (RLDw), cold-acclimated (7 to 10 days) RLD (RLDc) and nonacclimated A6, B16 and T8 plants. P values for comparisons of $EL_{50}$ values are indicated in the intersecting cells.

TABLE 2

| | $EL_{50}$ values | | | | |
|---|---|---|---|---|---|
| | RLDw | RLDc | A6 | B16 | T8 |
| RLDw | −3.9 ± 0.21 (8) | P < 0.0001 | P < 0.0001 | P = 0.0014 | P = 0.7406 |
| RLDc | | −7.6 ± 0.30 (4) | P = 0.3261 | P < 0.0001 | P < 0.0001 |
| A6 | | | −7.2 ± 0.25 (6) | P < 0.0001 | P < 0.0001 |
| B16 | | | | −5.2 ± 0.27 (5) | P = 0.0044 |
| T8 | | | | | −3.8 ± 0.35 (3) |

The data confirm that: 1) the freezing tolerance of leaves from both nonacclimated A6 and B16 plants is greater than that of leaves from both nonacclimated RLD and T8 plants; and 2) that leaves from nonacclimated A6 plants are more freezing tolerant than leaves from nonacclimated B16 plants. No significant difference was detected in $EL_{50}$ values for leaves from nonacclimated A6 and cold-acclimated RLD plants or from nonacclimated RLD and T8 plants.

Figure 11:
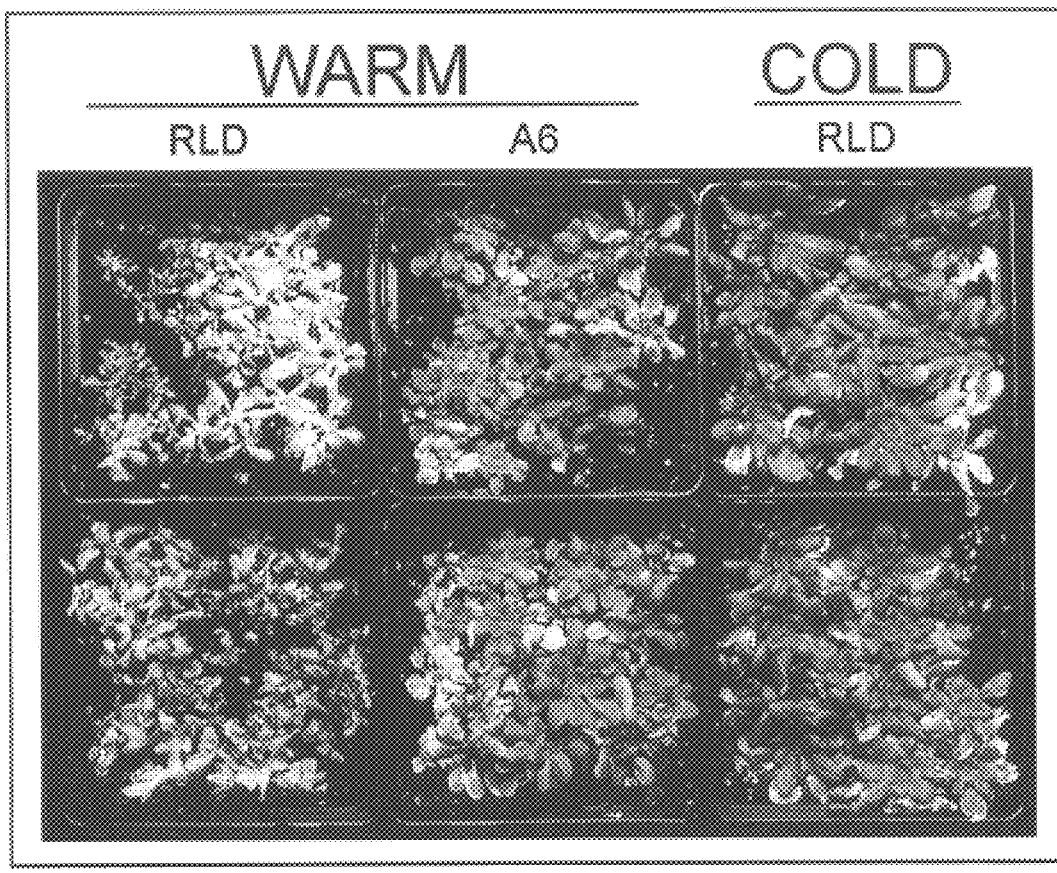
FIG. 11 is a photograph showing freezing survival of RLD and A6 Arabidopsis plants.

The enhancement of freezing tolerance in the A6 line was also apparent at the whole plant level. FIG. 11 is a photograph showing freezing survival of RLD and A6 Arabidopsis plants. Nonacclimated (WARM) RLD and A6 plants and 5-day cold-acclimated (COLD) RLD plants were frozen at −5° C. for 2 days and then returned to a growth chamber at 22° C. (Pots (3.5 inch) containing about 40 nonacclimated Arabidopsis plants (20 day old) and 4 day cold-acclimated plants (25 days old) (Arabidopsis thaliana ecotype RLD plants were grown in pots under continuous light (100 $\mu E/m^2/sec$) at 22° C. for 18–25 days as described (S. J. Gilmour, et al., Plant Physiol. 87:735 (1988)). In some cases, plants were then cold-acclimated by placing them at 2.5° C. under continuous light (50 $\mu E/m^2/sec$) for varying amounts of time) were placed in a completely randomized design in a −5° C. cold chamber in the dark. After 1 hour, ice chips were added to each pot to nucleate freezing. Plants were removed after 2 days and returned to a growth chamber at 22° C.). A photograph of the plants after 7 days of regrowth is shown.

Although the magnitude of the difference varied from experiment to experiment, nonacclimated A6 plants consistently displayed greater freezing tolerance in whole plant freeze tests than did nonacclimated RLD plants (FIG. 11). No difference in whole plant freeze survival was detected between nonacclimated B16 and RLD plants or nonacclimated T8 and RLD plants (not shown).

The results of this experiment show that CBF1-induced expression of CRT/DRE-regulated COR genes result in a dramatic increase in freezing tolerance and confirms the belief that COR genes play a major role in plant cold acclimation. The increase in freezing tolerance brought about by expressing the battery of CRT/DRE-regulated COR genes was much greater than that brought about by overexpressing COR15a alone indicating that COR genes in addition to COR15a have roles in freezing tolerance.

Traditional plant breeding approaches have met with limited success in improving the freezing tolerance of agronomic plants (Thomashow, M. F., Adv. Genet 28:99 (1990)). For instance, the freezing tolerance of the best wheat varieties today is essentially the same as the most freezing-tolerance varieties developed in the early part of this century. Thus, in recent years there has been considerable interest that biotechnology might offer new strategies to improve the freezing tolerance of agronomic plants. By the results of the present invention, Applicants demonstrate the ability to enhance the freezing tolerance of nonacclimated Arabidopsis plants by increasing the expressing of the Arabidopsis regulatory gene CBF1. As described throughout this application, the ability of the present invention to modify the expression of environmental stress tolerance genes such as core genes has wide ranging implications since the CRT/DRE DNA regulatory element is not limited to Arabidopsis (Jiang C., et al., Plant Mol. Biol. 30:679 (1996)). Rather, CBF1 and homologous genes can be used to manipulate expression of CRT/DRE-regulated COR genes in important crop species and thereby improve their freezing tolerance. By transforming modified versions of CBF1 (or homologs) into such plants, it will extend their safe growing season, increase yield and expand areas of production.

4. Selection of Promoters to Control Expression of CBF1 in Plants

The following examples describe the isolation of different promoters from plant genomic DNA, construction of the plasmid vectors carrying the CBF1 gene and the inducible promoters, transformation of Arabidoposis cells/plants with these constructs, and regeneration of transgenic plants with increased tolerance to environmental stresses.

A. Isolation of Inducible Promoters from Plant Genomic DNAs

Inducible promoters from different plant genomic DNAs were identified and isolated by PCR amplification using primers designed to flank the promoter region and contain suitable restriction sites for cloning into the expression vector. The following genes were used to BLAST search Genbank to find the inducible promoters: Dreb2a; P5CS; Rd22; Rd29a; Rd29b; Rab18; Cor47. Table 3 lists the accession numbers and positions of these promoters. Table 4 lists the forward and reverse primers that were used to isolate the promoters.

TABLE 3

| Gene Name | Accession No. | Position | Length (bps) |
|---|---|---|---|
| Dreb2a | AB010692 | 51901–53955 | 2054 |
| P5CS | AC003000 | 45472–47460 | 1988 |
| Rd22 | D10703 | 17–1046 | 1029 |
| Rd29a | D13044 | 3870–5511 | 1641 |
| Rd29b | D13044 | 90–1785 | 1695 |
| Rab18 | AB013389 | 8070–9757 | 1687 |
| Cor47 | AB004872 | 1–1370 | 1370 |

TABLE 4

| Promoter name | Primer name | Cloning sites | SEQ. ID. No. |
|---|---|---|---|
| Dreb2a | Dreb2a-reverse | HindIII (AAGCTT) | 19 |
|  | Dreb2a-forward | BglII (AGATCT) | 20 |
| P5CS | P5CS-reverse | HindIII (AAGCTT) | 21 |
|  | P5CS-forward | BglII (AGATCT) | 22 |
| Rd22 | Rd22-reverse | HindIII (AAGCTT) | 23 |
|  | Rd22-forward | KpnI (GGTACC) | 24 |
| Rd29a | Rd29a-reverse | HindIII (AAGCTT) | 25 |
|  | Rd29a-forward | KpnI (GGTACC) | 26 |
| Rd29b | Rd29b-reverse | HindIII (AAGCTT) | 27 |
|  | Rd29b-forward | KpnI (GGTACC) | 28 |
| Rab18 | Rab18-reverse | HindIII (AAGCTT) | 29 |
|  | Rab18-forward | BglII (AGATCT) | 30 |
| Cor47 | Cor47-reverse | HindIII (AAGCTT) | 31 |
|  | Cor47-forward | BglII (AGATCT) | 32 |

(1) Dreb2a promoter

A cDNA encoding DRE (C-repeat) binding protein (DREB2A) has been recently identified (Liu, et al. 1998 Plant Cell 10:1391–1406). The transcription of the DREB2A gene is activated by dehydration and high-salt stress, but not by cold stress. The upstream untranslated region (166 bps) of dreb2a was used to BLAST-search the public database. A region containing the DREB2A promoter was identified in chromosome 5 of Arabidopsis (Accession No. AB010692) between nucleotide positions 51901–53955 (Table 3).

Two PCR primers designed to amplify the promoter region from *Arabidopsis thaliana* genomic DNA are as follows: dreb2a-reverse: 5'-GCCC AAGCTTCAAGTTTAGTGAGCATATGTGCTCG-3' [SEQ ID No. 19]; and dreb2a-forward: 5'-GGA AGATCTCCTTCCCAGAAACAACACAATCTAC-3' [SEQ. ID. No. 20]. The dre2ba-reverse primer includes a Hind III (AAGCTT) restriction site near the 5'-end of the primer and dreb2a-forward primer has a Bgl II (AGATCT) restriction site at near 5'-end of the primer. These restriction sites may be used to facilitate cloning of the fragment into an expression vector.

Total genomic DNA may be isolated from *Arabidopsis thaliana* (ecotype Colombia) by using the CTAB method (Ausubel et al. (1992) Current Protocols in Molecular Biology (Greene & Wiley, New York)). Ten nanograms of the genomic DNA can be used as a template in a PCR reaction under conditions suggested by the manufacturer (Boehringer Mannheim). The reaction conditions that may be used in this PCR experiment are as follows: Segment 1: 94° C., 2 minutes; Segment 2: 94° C., 30 seconds; 60° C, 1 minute; 72° C., 3 minutes, for a total of 35 cycles; Segment 3: 72° C. for 10 minutes. A PCR product of 2054 bp is expected.

The PCR products can be subject to electrophoresis in a 0.8% agarose gel and visualized by ethidium bromide staining. The DNA fragments containing the inducible promoter will be excised and purified using a Qiaquick gel extraction kit (Qiagen, Calif.).

(2) P5CS promoter

A cDNA for delta 1-pyrroline-5-carboxylate synthetase (P5CS) has been isolated and characterized (Yoshiba, et al., 1995, Plant J. 7:751–760). The cDNA encodes an enzyme involved in the biosynthesis of proline under osmotic stress (droughtihigh salinity). The transcription of the P5CS gene was found to be induced by dehydration, high salt and treatment with plant hormone ABA, while it did not respond to heat or cold treatment.

A genomic DNA containing a promoter region of P5CS was identified by a BLAST search of Genbank using the upstream untranslated region (106 bps) of the P5CS sequence (Accession No. D32138). The sequence for the P5CS promoter is located in the region between from nucleotide positions 45472 to 47460 (Accession No. AC003000; Table 3).

Reverse and forward PCR primers designed to amplify this promoter region from *Arabidopsis thaliana* genomic DNA are P5CS-reverse primer 5'-GCCC AAGCTTGTTTCATTTTCTCCATGAAGGAGAT-3' [SEQ. ID. No. 21]; and P5CS-forward primer 5'-GGA AGATCTTATCGTCGTCGTCGTCTACCAAAACCA-CAC-3' [SEQ. ID. No. 22].

Total genomic DNA may be isolated from *Arabidopsis thaliana* (ecotype colombia) by using the CTAB method (Ausubel et al. (1992) Current Protocols in Molecular Biology (Greene & Wiley, New York)). Ten nanograms of the genomic DNA can be used as a template in a PCR reaction under conditions suggested by the manufacturer (Boehringer Mannheim). The PCR product is expected to be 1988 bps and may be PCR amplified and gel purified following the same protocol described for the dreb2a promoter.

(3) rd22promoter

A cDNA clone of rd22 was isolated from Arabidopsis under dehydration conditions (Yamaguchi-Shinizaki and Shinozaki, Mol. Gen. Genet. 238:17–25 (1993)). Transcripts of rd22 were found to be induced by salt stress, water deficit and endogenous abscisic acid (ABA) but not by cold or heat stress. A promoter region was identified from Genebank by using Nucleotide Search WWW Entrez at the NCBI with the rd22 as a search word. The sequence for the rd22 promoter is located in the region between nucleotide positions 17 to 1046 (Accession No. D10703; Table 3).

Reverse and forward PCR primers designed to amplify this promoter region from *Arabidopsis thaliana* genomic DNA are rd22-reverse primer 5'-GCTCT AAGCTTCACAAGGGGTTCGTTTGGTGC-3' [SEQ. ID. No. 23]; and rd22-forward primer 5'-GG GGTACCTTTTGGGAGTTGGAATAGAAATGGGTTTG-ATG-3' [SEQ. ID. No. 24]. The rd22-reverse primer includes a Hind III (AAGCTT) restriction site near the 5'-end of primer and rd22-forward primer has a Kpnl (GGTACC) restriction site at near 5'-end of primer.

Total genomic DNA may be isolated from *Arabidopsis thaliana* (ecotype Colombia) by using the CTAB method (Ausubel et al. (1992) Current Protocols in Molecular Biology (Greene & Wiley, New York)). Ten nanograms of the genomic DNA can be used as a template in a PCR reaction under conditions suggested by the manufacturer (Boehringer Mannheim). The PCR product is expected to be 1029 bps and may be PCR amplified and gel purified following the same protocol described for the dreb2a promoter.

(4) rd29a promoter

The rd29a and rb29b genes were isolated and characterized by Shinozaki's group in Japan (Yamaguchi-Shinizaki and Shinozaki, Plant Physiol. 101: 1119–1120 (1993)). Both rd29a and rb29b gene expressions were found to be induced by desiccation, salt stress and exogenous ABA treatment (Yamaguchi-Shinizaki and Shinozaki, Plant Physiol. 101: 1119–1120 (1993); Ishitani et al., Plant Cell 10: 1151–1161 (1998)). The rd29a gene expression was induced within 20 min after desiccation, but rd29b mRNA did not accumulate to a detectable level until 3 hours after desiccation. Expression of rd29a could also be induced by cold stress, whereas expression of rd29b could not be induced by low temperature.

A genomic clone carrying the rd29a promoter was identified by using Nucleotide Search WWW Entrez at the NCBI with the rd29a as a search word. The sequence for the rd29a promoter is located in the region between nucleotide positions 3870 to 5511 (Accession No. D13044, Table 3).

Reverse and forward primers designed to amplify this promoter region from Arabidopsis genomic DNA are: rd29a-reverse primer 5'-GCCC AAGCTTAATTTTACTCAAAATGTTTTGGTTGC-3' [SEQ. ID. No. 25]; and rd29a-forward primer 5'-CC GGTACCTTTCCAAAGATTTTTTTCTTTCCAATAGAA-GTAATC-3' [SEQ. ID. No.26]. The rd29a-reverse primer includes a Hind III (AAGCTT) restriction site near the 5'-end of primer and rd29a-forward primer has a Kpnl ( GGTACC) restriction site near 5'-end of primer.

Total genomic DNA may be isolated from *Arabidopsis thaliana* (ecotype colombia) by using the CTAB method (Ausubel et al. (1992) Current Protocols in Molecular Biology (Greene & Wiley, New York)). Ten nanograms of the genomic DNA can be used as a template in a PCR reaction under conditions suggested by the manufacturer (Boehringer Mannheim). The PCR product is expected to be 1641 bps and may be PCR amplified and gel purified following the same protocol described for the dreb2a promoter.

(5) rd29b promoter

A genomic clone carrying the rd29b promoter was identified by using Nucleotide Search WWW Entrez at the NCBI with the rd29b as a search word. The sequence for the rd29a promoter was located in the region between nucleotide positions 90 to 1785 for rd29b (Accession No. Dl 3044; Table 3).

Reverse and forward PCR primers designed to amplify this promoter region from *Arabidopsis thaliana* genomic DNA are: rd29b-reverse primer 5'-GCGG AAGCTTCATTTTCTGCTACAGAAGTG-3' [SEQ. ID. No. 27]; and rd29b-forward primer 5'-CC GGTACCTTTCCAAAGCTGTGTTTTCTCTTTTTCAAG-TG-3' [SEQ. ID. No. 28].

Total genomic DNA may be isolated from *Arabidopsis thaliana* (ecotype colombia) by using the CTAB method (Ausubel et al. (1992) Current Protocols in Molecular Biology (Greene & Wiley, New York)). Ten nanograms of the genomic DNA can be used as a template in a PCR reaction under conditions suggested by the manufacturer (Boehringer Mannheim). The PCR product is expected to be 1695 bps and may be PCR amplified and gel purified following the same protocol described for the dreb2a promoter.

(6) rab18 promoter

A rab-related (responsive to ABA) gene, rab18 from arabidopsis has been isolated. The gene encodes a hydrophilic, glycine-rich protein with the conserved serine- and lysine-rich domains. The rab18 transcripts accumulate in plants exposed to water deficit or exogenous abscisic acid (ABA) treatment. A weak induction of rab18 mRNA by low temperature was also observed (Ishitani et al., Plant Cell 10: 1151–1161 (1998)).

A genomic DNA containing a promoter region of rab18 was identified by a BLAST search of Genbank using the upstream untranslated region (757 bps) of the rab18 sequence (Accession No. L04173). The sequence of the rab18 promoter is located in the region between nucleotide positions 8070 to 9757 (Accession No. AB013389).

Reverse and forward PCR primers designed and used to amplify this promoter region from *Arabidopsis thaliana* genomic DNA are: rab18-reverse primer 5'-GCCC AAGCTTCAAATTCTGAATATTCACATATCAAACACG-TTTGC-3' [SEQ. ID. No. 29]; and rab18-forward primer 5'-GGA AGATCTGTTCTTCTTGTCTTAAGCAAACACTTTGAG-C-3' [SEQ. ID. No. 30]. The rab18-reverse primer includes a Hind III (AAGCTT) restriction site near the 5'-end of the primer and rab18-forward primer has a Bgl II (AGATCT) restriction site near the 5'-end of the primer.

Total genomic DNA may be isolated from *Arabidopsis thaliana* (ecotype colombia) by using the CTAB method (Ausubel et al. (1992) Current Protocols in Molecular Biology (Greene & Wiley, New York)). Ten nanograms of the genomic DNA can be used as a template in a PCR reaction under conditions suggested by the manufacturer (Boehringer Mannheim). The PCR product is expected to be 1687 bps and may be PCR amplified and gel purified following the same protocol described for the dreb2a promoter.

(7) Cor47promoter

The DNA sequence of cDNA for cold-regulated (cor47) gene of *Arabidopsis thaliana* was determined. Gilmour et al., Plant Molecular Biology 18: 13–21 (1992)). Expression of cor47 gene was induced by cold stress, dehydration and high NaCl treatment (Ishitani et al., *Plant Cell*. 10: 1151–1161 (1998)). The promoter region of cor47 gene was identified in Genbank by using Nucleotide Search WWW Entrez at the NCBI with the cor47 as a search word. The sequence of the cor47 promoter is located in the region between nucleotide positions 1–1370 (Accession No. AB004872; Table 3).

Reverse and forward PCR primers designed to amplify this promoter region from *Arabidopsis thaliana* genomic DNA are: cor47-reverse primer 5'-GCCC AAGCTTTCGTCTGTTATCATACAAGGCACAAAACG-AC-3' [SEQ. ID. No. 31]; and cor47-forward primer 5'-GGA AGATCTAGTTTAATCTTGATTTGATTAAAAGTTTATA-TAG-3' [SEQ. ID. No. 32]. The cor47-reverse primer includes a Hind III (AAGCTT) restriction site near the 5'-end of the primer and cor47-forward primer has a Bgl II (AGATCT) restriction site near the 5'-end of the primer.

Total genomic DNA may be isolated from *Arabidopsis thaliana* (ecotype Colombia) by using the CTAB method (Ausubel et al. (1992) Current Protocols in Molecular Biology (Greene & Wiley, New York)). Ten nanograms of the genomic DNA can be used as a template in a PCR reaction under conditions suggested by the manufacturer (Boehringer Mannheim). The PCR product is expected to be 1370 bps and may be PCR amplified and gel purified following the same protocol described for the dreb2a promoter.

B. Construction of the Plamids Containing CBF1 and Inducible Promoter

The expression binary vector pMEN020 contains a kanamycin resistance gene (neomycin phosphotransferase) for antibiotic selection of the transgenic plants and a Spc/Str gene used for bacterial or agrobacterial selections. The pMEN020 plasmid is digested with restriction enzymes such as HindIII and BglII to remove the 35S promoter. The 35S promoter is then replaced with an inducible promoter.

(1) Cloning of the inducible promoter into pMEN020

The sequences of the inducible promoters that are PCR amplified and gel purified, as well as the plasmid pMEN020, are subject to restriction digestion with their respective restriction enzymes as listed in Table 4. Both DNA samples are purified by using the Qiaquick purification kit (Qiagen, Calif.) and ligated at a ratio of 3:1 (vector to insert). Ligation reactions using T4 DNA ligase (New England Biolabs, Mass.) are carried out at 16° C. for 16 hours. The ligated DNAs are transformed into competent cells of the *E. coli* strain DH5α by using the heat shock method. The transformed cells are plated on LB plates containing 100 μg/ml spectinomycin (Sigma). Individual colonies are grown overnight in five milliliters of LB broth containing 100 μg/ml spectinomycin at 37° C.

Plasmid DNAs from transformants are purified by using Qiaquick Mini Prep kits (Qiagen, Calif.) according to the manufacturers instruction. The presence of the promoter insert is verified by restriction mapping with the respective restriction enzymes as listed in Table 4 to cut out the cloned insert. The plasmid DNA is also subject to double-strand DNA sequencing analysis using a vector primer (E9.1 primer 5'-CAAACTCAGTAGGATTCTGGTGTGT-3' [SEQ. ID. No. 33].

(2) Cjoning of the cbf1gene into the plasmids containing the inducible promoters To clone the CBF1 gene into the plasmids, different PCR primers with suitable restriction sites for each plasmid are used to isolate cbf1 gene from *Arabidopsis thaliana* genomic DNA. The primers that may be used are listed in Table 5.

TABLE 5

| Promoter name | Primer name | Cloning sites |
|---|---|---|
| Dreb2a | Cbf1-reverse1 | BglII (AGATCT) |
|  | Cbf1-forward1 | BamHI (GGATCC) |
| P5CS | Cbf1-reverse1 | BglII (AGATCT) |
|  | Cbf1-forward1 | BamHI (GGATCC) |
| Rd22 | Cbf1-reverse2 | KpnI (GGTACC |
|  | Cbf1-forward1 | BamHI (GGATCC) |
| Rd29a | Cbf1-reverse2 | KpnI (GGTACC |
|  | Cbf1-forward1 | BamHI (GGATCC) |
| Rd29b | Cbf1-reverse2 | KpnI (GGTACC |
|  | Cbf1-forwardl | BamHI (GGATCC) |
| Rab18 | Cbf1-reverse1 | BglII (AGATCT) |
|  | Cbf1-forward2 | XbaI (TCTAGA |
| Cor47 | Cbf1-reverse1 | BglII (AGATCT) |
|  | Cbf1-forward1 | BamHI (GGATCC) |

Two of the four available PCR primers (Table 5) are used for cloning the at-cbf1 gene into the expression vectors containing each inducible promoter described above. The four primers have these sequences: cbf1-reverse 5'-GGAAGATCTTGAAACAGAGTACTCTGATCAATG-AACTC-3' [SEQ. ID. No. 34], cbf1-forward 1 5'-CGCGGATCCCTCGTTTCTACAACAATAAAATAAA-ATAAAATG-3' [SEQ. ID. No. 35], cbf1-reverse 2 5'-GGGGTACCTGAAACAGAGTACTCTGATCAATGA-ACTC-3' [SEQ. ID. No. 36], and cbf1-forward 2 5'-GCTCTAGACTCGTTTCTACAACAATAAAATAAAA-TAAAATG-3' [SEQ. ID. No. 37]. For example, for the Dreb2a, P5CS, and COR47 promoters that are ligated to a BamHI and BglII flanked insert, the cbf1-reverse 1 and cbf1-forward 1 primers [SEQ. ID. No. 34 and 35, respectively] are used to isolate cbf1 gene from *Arabidopsis thaliana* genomic DNA. The cbf1-reverse primer includes a BglII (AGATCT) restriction site near the 5'-end of the primer and cbf1-forward primer has a BamHI (GGATCC) restriction site near the 5'-end of the primer. A PCR product of 764 bp is expected. The genomic DNA (10 ng) is used as a template in a PCR reaction under conditions suggested by the manufacturer (Boehringer Mannheim). The reaction conditions to be used in this PCR experiment are as follows: Segment 1: 94° C., 2 minutes; Segment 2: 94° C., 30 seconds; 55° C., 1 minute; 72° C., 1 minute, for a total of 35 cycles; Segment 3: 72° C. for 10 minutes.

The PCR products are subject to electrophoresis in a 0.8% agarose gel and visualized by ethidium bromide staining. The DNA fragment containing cbf1 is excised and purified by using a Qiaquick gel extraction kit (Qiagen, Calif.). The purified fragment and the vector pMBI2001 containing the inducible promoter (Table 5) are each digested with BgiII and BamHl restriction enzymes at 37° C. for 2 hours. Both DNA samples are purified by using the Qiaquick purification kit (Qiagen, Calif.) and ligated at a ratio of 3:1 (vector to insert). Ligation reactions using T4 DNA ligase (New England Biolabs, Mass.) are carried out at 16° C. for 16 hours. The ligated DNAs are transformed into competent cells of the E. coli strain DH5α by using the heat shock method. The transformation are plated on LB plates containing 100 (g/ml spectinomycin (Sigma).

Individual colonies are grown overnight in five milliliters of LB broth containing 100 g/ml spectinomycin at 37° C. Plasmid DNA are purified by using Qiaquick Mini Prep kits (Qiagen, Calif.). The presence of the cbf1 insert is verified by restriction mapping with BglII and BamHI. The plasmid DNA is also subject to double-strand DNA sequencing analysis by using vector primer E9.1(5'-CAAACTCAGTAGGATTCTGGTGTGT-3') [SEQ. ID. No. 33]. The other primers shown in Table 5 and appropriate restriction enzymes are used in a similar way to clone the Cbfl gene into plasmids containing the other inducible promoters. The resulting plasmids are listed in Table 6 and shown in FIGS. 17A–17G.

A similar cloning strategy may be used to clone other genes, such as cbf2, cbf3, and the other full length CBF genes listed in Table 9 and shown in FIG. 18 (new CBF gene table) into plasmids containing inducible promoters.

TABLE 6

Figure 17A:
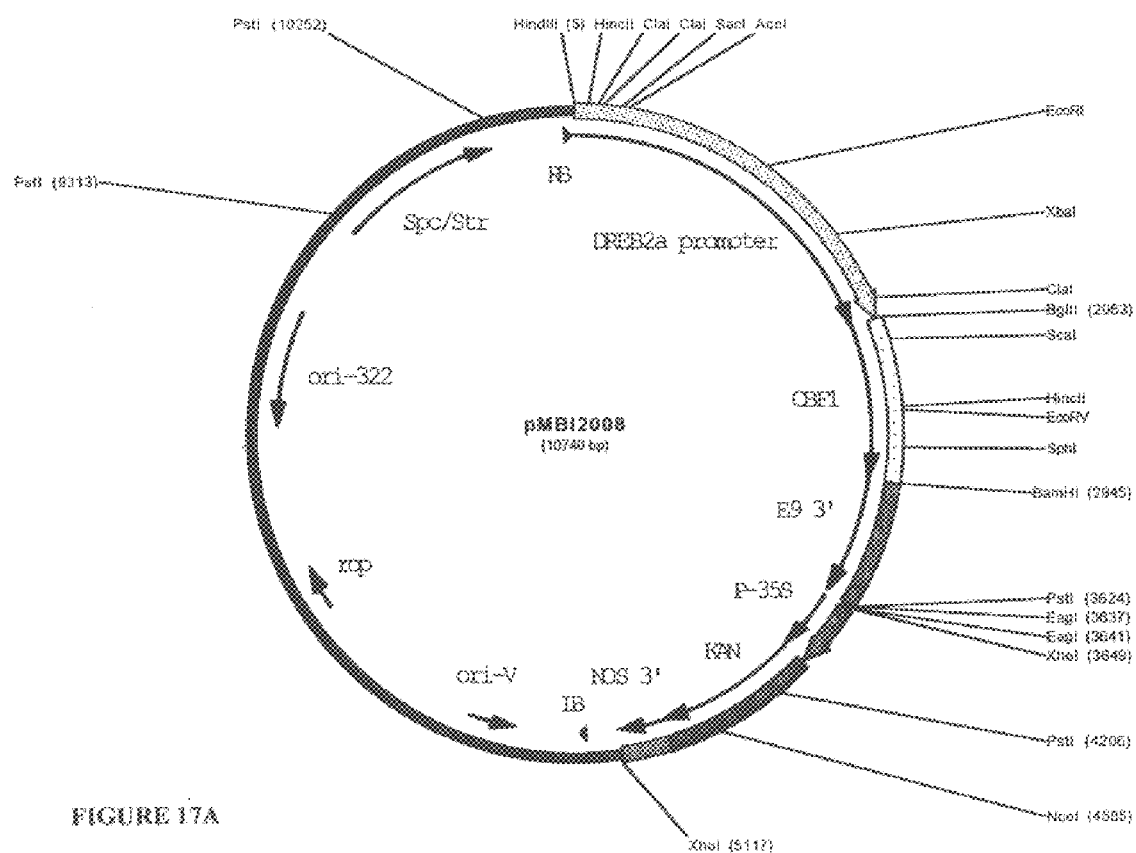
FIGS. 17A, 17B, 17C, 17D, 17E, 17F and 17G show restriction maps of plasmids pMB12008, pMB12009, pMB12010, pMB12011, pMB12012, pMB12013, and pMB12014, respectively.
Figure 17B:
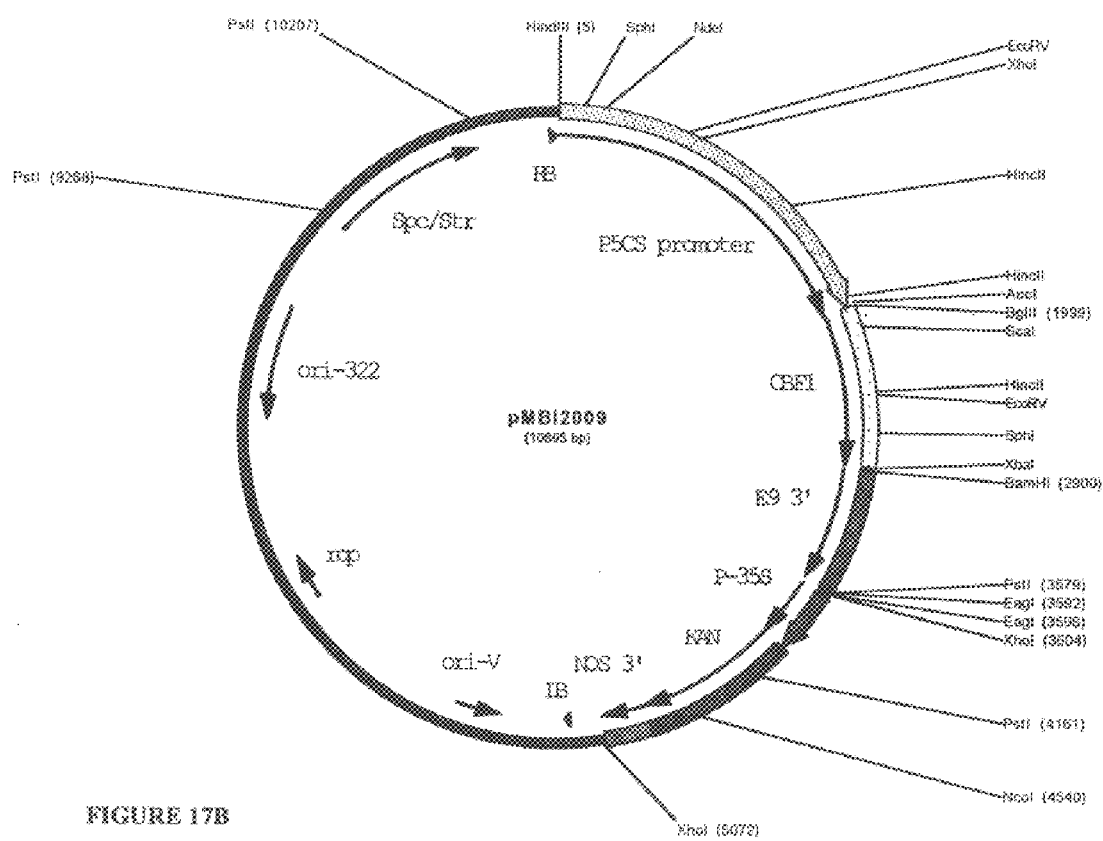
Figure 17C:
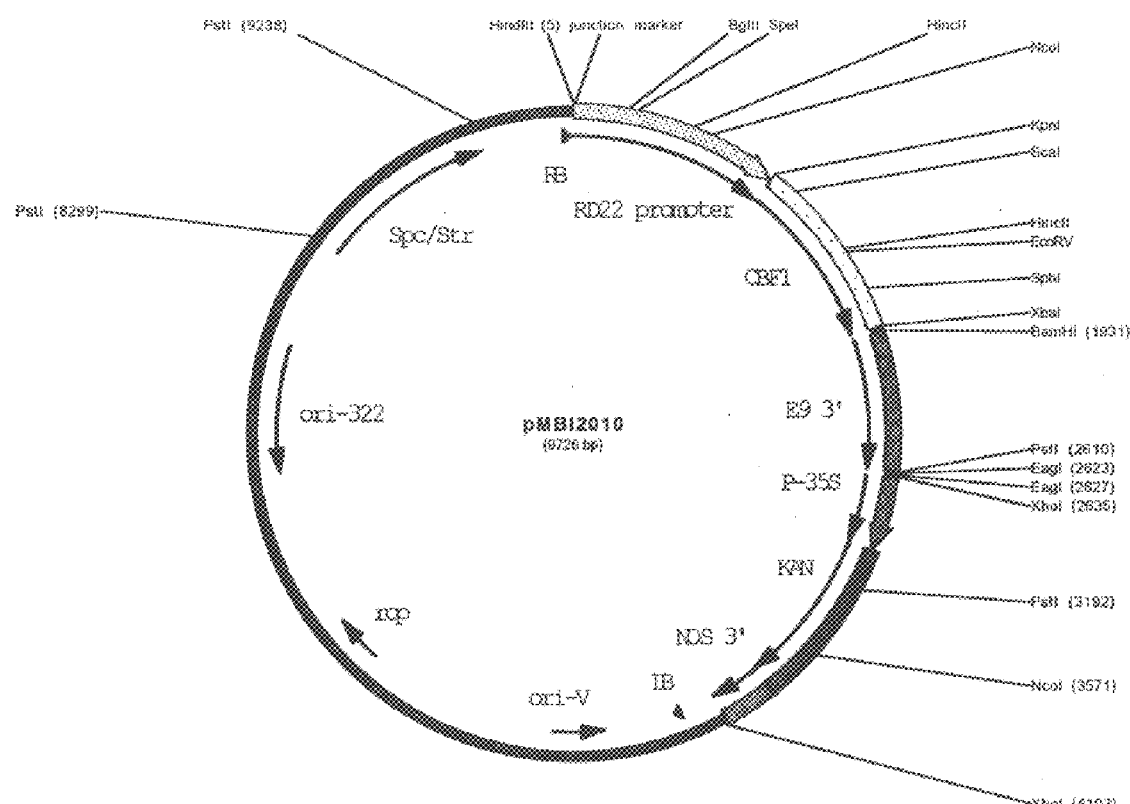
Figure 17D:
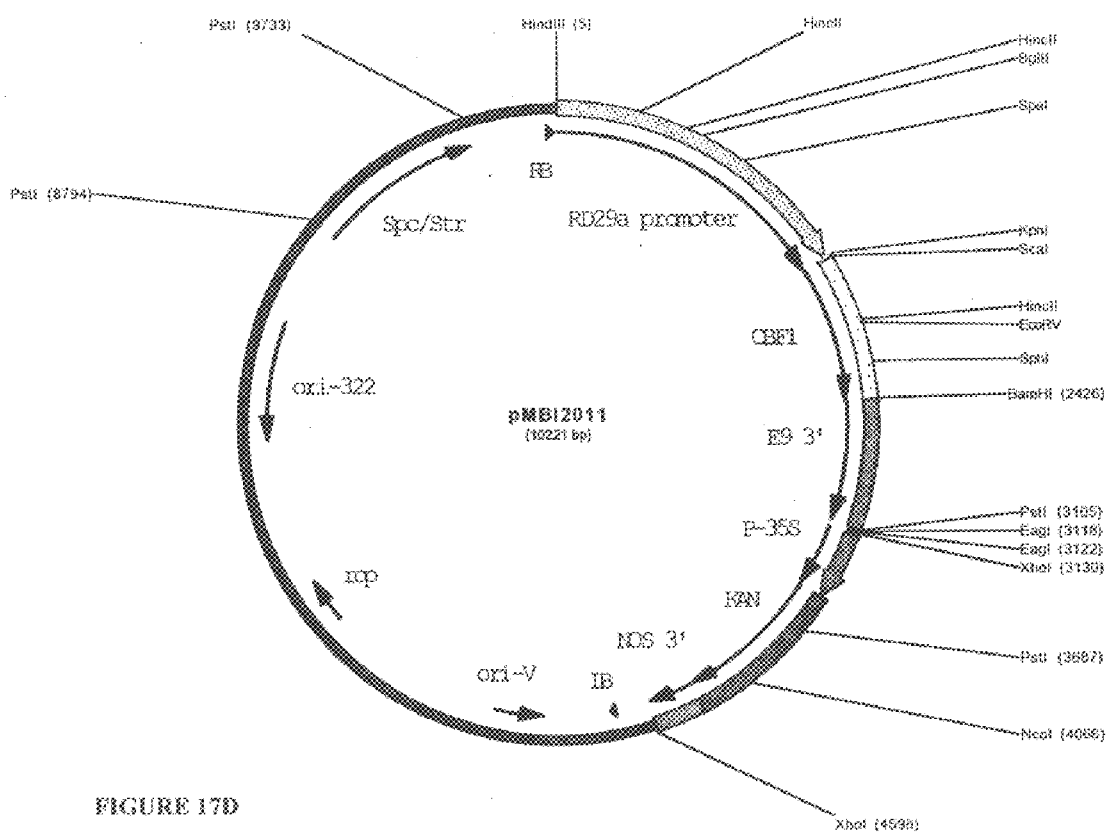
Figure 17E:
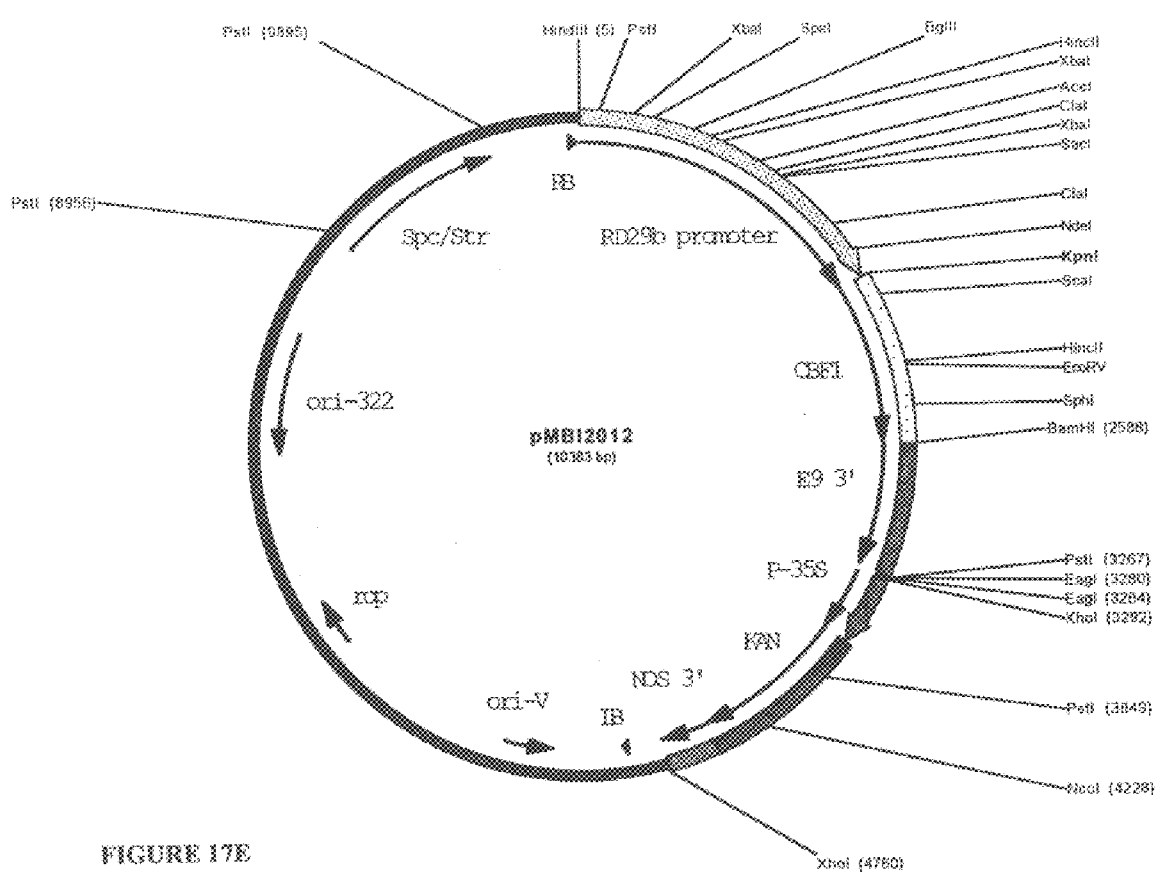
Figure 17F:
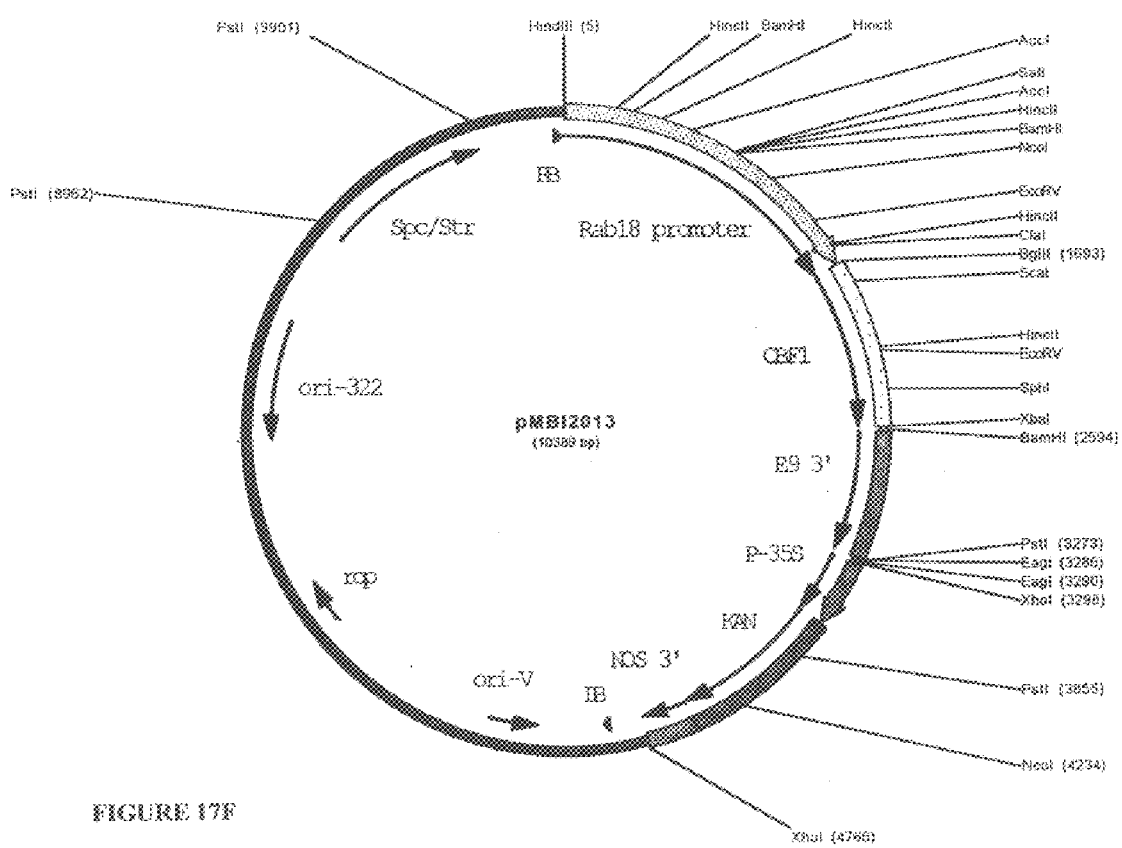
Figure 17G:
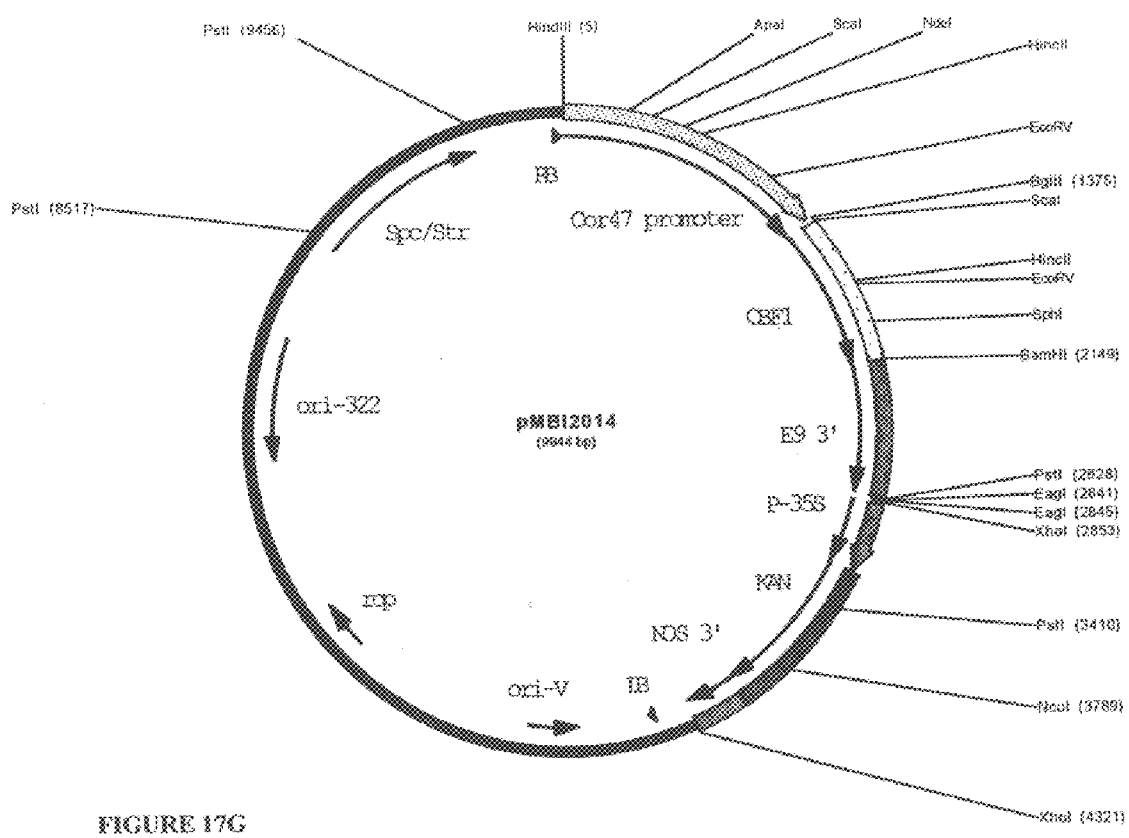

| Construct name | Promoter name | Figure name |
|---|---|---|
| PMBI2008 | Dreb2a | FIG. 17A |
| PMBI2009 | P5CS | FIG. 17B |
| PMBI2010 | Rd22 | FIG. 17C |
| PMBI2011 | Rd29a | FIG. 17D |
| PM0I2012 | Rd29b | FIG. 17E |
| PMBI2013 | Rab18 | FIG. 17F |
| PMBI2014 | Cor47 | FIG. 17G |

C. Transformation of Agrobacterium with Plasmids Containing CBF1 Gene and Inducible Promoters After the plasmid vectors containing cbf1 gene and inducible promoters are constructed, these vectors are used to transform Agrobacterium tumefaciens cells expressing the gene products. The stock of Agrobacterium tumefaciens cells for transformation are made as described by Nagel et al. FEMS Microbiol Letts 67: 325–328 (1990). Agrobacterium strain ABI is grown in 250 ml LB medium (Sigma) overnight at 28° C. with shaking until an absorbance ($A_{600}$) of 0.5–1.0 is reached. Cells are harvested by centrifugation at 4,000×g for 15 min at 4 C. Cells are then resuspended in 250 μl chilled buffer (1 mM HEPES, pH adjusted to 7.0 with KOH). Cells are centrifuged again as described above and resuspended in 125 μl chilled buffer. Cells are then centrifuged and resuspended two more times in the same HEPES buffer as described above at a volume of 100 μl and 750 μl, respectively. Resuspended cells are then distributed into 40 μl aliquots, quickly frozen in liquid nitrogen, and stored at −80 C.

Agrobacterium cells are transformed with plasmids formed as described above in Section 4B(2) following the protocol described by Nagel et al. FEMS Microbiol Letts 67: 325–328 (1990). For each DNA construct to be transformed, 50–100 ng DNA (generally resuspended in mM Tris-HCl, 1 mM EDTA, pH 8.0) is mixed with 40 μl of Agrobacterium cells. The DNA/cell mixture is then transferred to a chilled cuvette with a 2mm electrode gap and subject to a 2.5 kV charge dissipated at 25 μF and 200 μF using a Gene Pulser II apparatus (Bio-Rad). After electroporation, cells are immediately resuspended in 1.0 ml LB and allowed to recover without antibiotic selection for 2–4 hours at 28° C. in a shaking incubator. After recovery, cells are plated onto selective medium of LB broth containing 100 μg/ml spectinomycin (Sigma) and incubated for 24–48 h at 28° C. Single colonies are then picked and inoculated in fresh medium. The presence of the plasmid construct are verified by PCR amplification and sequence analysis.

D. Transformation of Arabidopsis Plants with Agrobacterium tumefaciens Carrying Expression Vector for CBF1 Protein After transformation of Agrobacterium tumefaciens with plasmid vectors containing cbf1 gene and inducible promoters, single Agrobacterium colonies containing each of pMBI2008–pMBI2014 are identified, propagated, and used to transform Arabidopsis Plants. Briefly, 500 ml cultures of LB medium containing 100 ug/ml spectinomycin are inoculated with the colonies and grown at 28 C with shaking for 2 days until an absorbance ($A_{600}$) of >2.0 is reached. Cells are then harvested by centrifugation at 4,000×g for 10 min, and resuspended in infiltration medium (½×Murashige and Skoog salts (Sigma), 1×Gamborg's B-5 vitamins (Sigma), 5.0% (w/v) sucrose (Sigma), 0.044 μM benzylamino purine (Sigma), 200 μl/L Silwet L-77 (Lehle Seeds) until an absorbance ($A_{600}$) of 0.8 is reached.

Prior to transformation, Arabidopsis thaliana seeds (ecotype Columbia) are sown at a density of ~10 plants per 4" pot onto Pro-Mix BX potting medium (Hummert International) covered with fiberglass mesh (18 mm×16 mm). Plants are grown under continuous illumination (50–75 μE/m²/sec) at 22–23 C with 65–70% relative humidity. After about 4 weeks, primary inflorescence stems (bolts) are cut off to encourage growth of multiple secondary bolts. After flowering of the mature secondary bolts, plants are prepared for transformation by removal of all siliques and opened flowers.

The pots are then immersed upside down in the mixture of Agrobacterium/infiltration medium as described above for 30 sec, and placed on their sides to allow draining into a 1'×2' flat surface covered with plastic wrap. After 24 h, the plastic wrap is removed and pots are turned upright. The immersion procedure is repeated one week later, for a total of two immersions per pot. Seeds are then collected from each transformation pot and analyzed following the protocol described below.

E. Identification of Arabidopsis Primary Transformants

Seeds collected from the transformation pots are sterilized essentially as follows. Seeds are dispersed into in a solution containing 0.1% (v/v) Triton X-100 (Sigma) and sterile $H_2O$ and washed by shaking the suspension for 20 min. The wash solution is then drained and replaced with fresh wash solution to wash the seeds for 20 min with shaking. After removal of the second wash solution, a solution containing 0.1% (v/v) Triton X-100 and 70% EtOH (Equistar) is added to the seeds and the suspension is shaken for 5 min. After removal of the ethanol/detergent solution, a solution containing 0.1% (v/v) Triton X-100 and 30% (v/v) bleach (Chlorox) is added to the seeds, and the suspension is shaken for 10 min. After removal of the bleach/detergent solution, seeds are then washed five times in sterile distilled $H_2O$. The seeds are stored in the last wash water at 4° C. for 2 days in the dark before being plated onto antibiotic selection medium (1×Murashige and Skoog salts (pH adjusted to 5.7 with 1M KOH), 1×Gamborg's B-5 vitamins, 0.9% phytagar (Life Technologies), and 50 µg/L kanamycin). Seeds are germinated under continuous illumination (50–75 µE/m$^2$/sec) at 22–23° C. After 7–10 days of growth under these conditions, kanamycin resistant primary transformants ($T_1$ generation) are visible and are obtained for each of constructs pMBI2008–pMBI2014. These seedlings are transferred first to fresh selection plates where the seedlings continued to grow for 3–5 more days, and then to soil (Pro-Mix BX potting medium). Progeny seeds ($T_2$) are collected; kanamycin resistant seedlings selected and analyzed as described above.

F. Transformation of Cereal Plants with Plasmid Vectors Containing cbf1 Gene and Inducible Promoters Cereal plants, such as corn, wheat, rice, sorghum and barley, can also be transformed with the plasmid vectors containing the cbf genes and inducible promoters to increase their tolerance to environmental stresses. In these cases, the cloning vector, pMEN020, is modified to replace the NptII coding region with the BAR gene of *Streptomyces hygroscopicus* that confers resistance to phosphinothricin. The KpnI and BglII sites of the Bar gene are removed by site-directed mutagenesis with silent codon changes. After cloning of the inducible promoters into the modified plasmid by the same procedures described above, the at-cbf coding region of cbf1gene is inserted into the plasmid following the same procedures as described above. The resulted plasmids are listed in Table 7.

TABLE 7

| Promoter name | Construct name |
| --- | --- |
| Dreb2a | PMBI2015 |
| P5CS | PMBI2016 |
| Rd22 | PMBI2017 |
| Rd29a | PMBI2018 |
| Rd29b | PMBI2019 |
| Rab18 | PMBI2020 |
| Cor47 | PMBI2021 |

It is now routine to produce transgenic plants of most cereal crops (Vasil, I., Plant Molec. Biol. 25: 925–937 (1994)) such as corn, wheat, rice, sorghum (Cassas, A. et al., Proc. Natl. Acad Sci USA 90:11212–11216 (1993) and barley (Wan, Y. and Lemeaux, P. Plant Physiol. 104:37–48 (1994) Other direct DNA transfer methods such as the microprojectile gun or *Agrobacterium tumefaciens*-mediated transformation can be used for corn (Fromm. et al. Bio/Technology 8: 833–839 (1990); Gordon-Kamm et al. Plant Cell 2: 603–618 (1990); Ishida, Y., Nature Biotechnology 14:745–750 (1990)), wheat (Vasil, et al. Bio/ Technology 10:667–674 (1992); Vasil et al., Bio/Technology 11:1553–1558 (1993); Weeks et al., Plant Physiol. 102:1077–1084 (1993)), rice (Christou Bio/Technology 9:957–962 (1991); Hiei et al. Plant J. 6:271–282 (1994); Aldemita and Hodges, Planta 199:612–617; Hiei et al., Plant Mol Biol. 35:205–18 (1997)). For most cereal plants, embryogenic cells derived from immature scutellum tissues are the preferred cellular targets for transformation (Hiei et al., Plant Mol Biol. 35:205–18 (1997); Vasil, Plant Molec. Biol. 25: 925–937 (1994)).

Plasmids according to the present invention may be transformed into corn embryogenic cells derived from immature scutellar tissue by using microprojectile bombardment, with the A188XB73 genotype as the preferred genotype (Fromm, et al., Bio/Technology 8: 833–839 (1990); Gordon-Kamm et al., Plant Cell 2: 603–618 (1990)). After microprojectile bombardment the tissues are selected on phosphinothricin to identify the transgenic embryogenic cells (Gordon-Kamm et al., Plant Cell 2: 603–618 (1990)). Transgenic plants are regenerated by standard corn regeneration techniques (Fromm, et al., Bio/Technology 8: 833–839 (1990); Gordon-Kamm et al., Plant Cell 2: 603–618 (1990)).

The plasmids prepared as described above can also be used to produce transgenic wheat and rice plants (Christou, Bio/Technology 9:957–962 (1991); Hiei et al., Plant J. 6:271–282 (1994); Aldemita and Hodges, Planta 199:612–617 (1996); Hiei et al., Plant Mol Biol. 35:205–18 (1997)) by following standard transformation protocols known to those skilled in the art for rice and wheat Vasil, et al. Bio/Technology 10:667–674 (1992); Vasil et al., Bio/ Technology 11:1553–1558 (1993); Weeks et al., Plant Physiol. 102:1077–1084 (1993)), where the BAR gene is used as the selectable marker.

5. Identification of CBF1 Homologs CBF2 and CBF3 Using CBF1

This example describes two homologs of CBF1 from *Arabidopsis thaliana* and named them CBF2 and CBF3.

CBF2 and CBF3 have been cloned and sequenced as described below. The sequences of the DNA and encoded proteins are set forth in SEQ ID NOS: 12, 13, 14 and 15. FIG. 12 shows the DNA sequence for CBF2 encoding CBF2. FIG. 13 shows the DNA sequence for CBF3 encoding CBF3.

A lambda cDNA library prepared from RNA isolated from *Arabidopsis thaliana* ecotype Columbia (Lin and Thomashow, Plant Physiol. 99: 519–525 (1992)) was screened for recombinant clones that carried inserts related to the CBF1 gene (Stockinger, E. J., et al., Proc Natl Acad Sci USA 94:1035–1040 (1997)). CBF1 was $^{32}$P-radiolabeled by random priming (Sambrook et al., Molecular Cloning. A Laboratory Manual, Ed. 2, Cold Spring Harbor Laboratory Press, New York (1989)) and used to screen the library by the plaque-lift technique using standard stringent hybridization and wash conditions (Hajela, R. K., et al., Plant Physiol 93:1246–1252 (1990); Sambrook et al., Molecular Cloning. A Laboratory Manual, Ed 2. Cold Spring Harbor laboratory Press, New York (1989) 6×SSPE buffer, 60° C. for hybridization and 0.1×SSPE buffer and 60° C. for washes). Twelve positively hybridizing clones were obtained and the DNA sequences of the cDNA inserts were determined at the MSU-DOE Plant Research Laboratory sequencing facility. The results indicated that the clones fell into three classes. One class carried inserts corresponding to CBF1. The two other classes carried sequences corresponding to two different homologs of CBF1, designated CBF2 and CBF3. The nucleic acid sequences and predicted protein coding sequences for CBF1, CBF2 and CBF3 appear at FIG. 14.

A comparison of the nucleic acid sequences of CBF1, CBF2 and CBF3 indicate that they are 83 to 85% identical as shown in Table 8. FIG. 14 shows the amino acid alignment of proteins CBF1, CBF2 and CBF3.

TABLE 8

| | Percent identity[a] | |
|---|---|---|
| | DNA[b] | Polypeptide |
| cbf1/cbf2 | 85 | 86 |
| cbf1/cbf3 | 83 | 84 |
| cbf2/cbf3 | 84 | 85 |

[a]Percent identity was determined using the Clustal algorithm from the Megalign program (DNASTAR, Inc.).
[b]Comparisons of the nucleic acid sequences of the open reading frames are shown.

Similarly, the amino acid sequences of the three CBF polypeptides range from 84 to 86% identity. An alignment of the three amino acidic sequences reveals that most of the differences in amino acid sequence occur in the acidic C-terminal half of the polypeptide. This region of CBF1 serves as an activation domain in both yeast and Arabidopsis (not shown).

Residues 47 to 106 of CBF1 correspond to the AP2 domain of the protein, a DNA binding motif that to date, has only been found in plant proteins. A comparison of the AP2 domains of CBF1, CBF2 and CBF3 indicates that there are a few differences in amino acid sequence. These differences in amino acid sequence might have an effect on DNA binding specificity.

6. Activation of Transcription in Yeast Containing C-repeat/DRE Using CBF1, CBF2 and CBF3

This example shows that CBF1, CBF2 and CBF3 activate transcription in yeast containing CRT/DREs upstream of a reporter gene. The CBFs were expressed in yeast under control of the ADC1 promoter on a 2μ plasmid (pDB20.1; Berger, S. L., et al., Cell 70:251–265 (1992)). Constructs expressing the different CBFs were transformed into yeast reporter strains which had the indicated CRT/DRE upstream of the lacZ reporter gene. Copy number of the CRT/DREs and its orientation relative to the direction of transcription from each promoter is indicated by the direction of the arrow.

Figure 15:
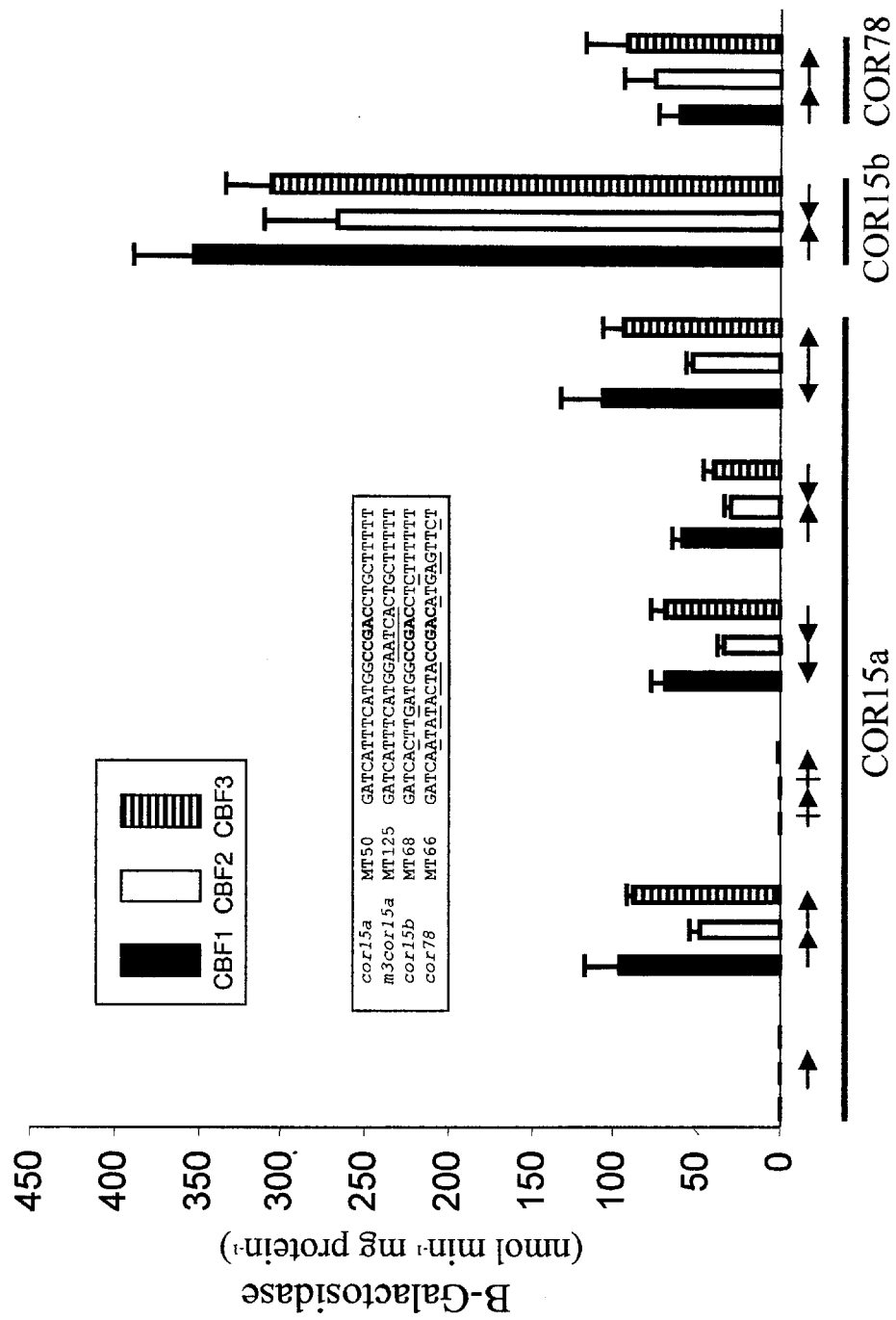
FIG. 15 is a graph showing transcription regulation of COR genes by CBF1, CBF2 and CBF3 genes in yeast.

FIG. 15 is a graph showing transcription regulation of CRT/DRE containing reporter genes by CBF1, CBF2 and CBF3 genes in yeast. In FIG. 15, the vertical lines across the arrows of the COR1 5a construct represent the m3cor15a mutant CRT/DRE construct. Each CRT/DRE-lacZ construct was integrated into the URA3 locus of yeast. Error bars represent the standard deviation derived from three replicate transformation events with the same CBF activator construct into the respective reporter strain. Quantitative B-gal assays were performed as described by Rose and Botstein (Rose, M., et al., Methods Enzymol. 101:167–180 (1983)).

7. Homologous CBF Encoding Genes in Other Plants

This example shows that homologous sequences to CBF1 are present in other plants. The presence of these homologous sequences suggest that the same or similar cold regulated environmental stress response regulatory elements such as the C-repeat/DRE of Arabidopsis (CCGAC) exist in other plants. This example serves to indicate that genes with significant homology to CBF1, CBF2 and CBF3 exist in a wide range of plant species.

Total plant DNAs from *Arabadopsis thaliana, Nicotiana tabacum, Lycopersicon pimpinellifolium, Prunis avium, Prunus cerasus, Cucumis sativus,* and *Oryza sativa* were isolated according to Stockinger al (Stockinger, E. J., et al., J. Heredity, 87:214–218 (1996)). Approximately 2 to 10 μg of each DNA sample was restriction digested, transferred to nylon membrane (Micron Separations, Westboro, Mass.) and hybridized according to Walling et al. (Walling, L. L., et al., Nucleic Acids Res. 16:10477–10492 (1988)). Hybridization conditions were: 42° C. in 50% formamide, 5×SSC, 20 mM phosphate buffer 1×Denhardt's, 10% dextran sulfate, and 100 μg/ml herring sperm DNA. Four low stringency washes at RT in 2×SSC, 0.05% Na sarcosyl and 0.02% Na$_4$ pyrophosphate were performed prior to high stringency washes at 55° C. in 0.2×SSC, 0.05% Na sarcosyl and 0.01% Na$_4$ pyrophosphate. High stringency washes were performed until no counts were detected in the washout. The BclI-BglII fragment of CBF1 (Stockinger et al., Proc Natl Acad Sci USA 94:1035–1040 (1997)) was gel isolated (Sambrook et al., Molecular Cloning. A Laboratory Manual, Ed 2. Cold Spring Harbor Laboratory Press, New York (1989)) and direct prime labelled (Feinberg and Vogelstein, Anal. Biochem 132: 6–13 (1982)) using the primer MT117 (TTGGCGGCTACGAATCCC; SEQ ID NO:16). Specific activity of the radiolabelled fragment was approximately $4 \times 10^8$ cpm/μg. Autoradiography was performed using HYPERFILM-MP (Amersham) at −80° C. with one intensifying screen for 15 hours.

Autoradiography of the gel showed that DNA sequences from *Arabadopsis thaliana, Nicotiana tabacum, Lycopersicon pimpinellifolium, Prunis avium, Prunus cerasus, Cucumis sativus,* and *Oryza sativa* hybridized to the labeled BclI, BglII fragment of CBF1. These results suggest that homologous CBF encoding genes are present in a variety of other plants.

8. Identification of Homologous Sequence to CBF1 in Canola

This example describes the identification of homologous sequences to CBF1 in canola using PCR. Degenerate primers were designed for regions of AP2 binding domain and outside of the AP2 (carboxyl terminal domain). More specifically, the following degenerate PCR primers were used:

Mol 368 (reverse) 5'- CAY CCN ATH TAY MGN GGN GT -3'

Mol 378 (forward) 5'- GGN ARN ARC ATN CCY TCN GCC -3'

(Y: C/T, N: A/C/G/T, H: A/C/T, M: A/C, R: A/G)

Primer Mol 368 is in the AP2 binding domain of CBF1 (amino acid seq: H P I Y R G V) while primer Mol 378 is outside the AP2 domain (carboxyl terminal domain)(amino acid seq: M A E G M L L P).

The genomic DNA isolated from *Brassica Napus* was PCR amplified by using these primers following these conditions: an initial denaturation step of 2 min at 93° C.; 35 cycles of 93° C. for 1 min, 55° C. for 1 min, and 72° C. for 1 min; and a final incubation of 7 min at 72° C. at the end of cycling.

The PCR products were separated by electrophoresis on a 1.2% agarose gel and, transferred to nylon membrane and hybridized with the AT CBF1 probe prepared from Arabidopsis genomic DNA by PCR amplification. The hybridized products were visualized by colormetric detection system (Boehringer Mannheim) and the corresponding bands from a similar agarose gel were isolated (By Qiagen Extraction Kit). The DNA fragments were ligated into the TA clone vector from TOPO TA Cloning Kit (Invitrogen) and transformed into *E. coli* strain TOP10 (Invitrogen).

Seven colonies were picked and the inserts were sequenced on an ABI 377 machine from both strands of sense and antisense after plasmid DNA isolation. The DNA sequence was edited by sequencer and aligned with the AtCBF1 by GCG software and NCBI blast searching.

FIG. 16 shows an amino acid sequence of a homolog [CAN1; SEQ. ID. No. 17] identified by this process and its alignment to the amino acid sequence of CBF1. The nucleic acid sequence for CAN1 is listed herein as SEQ. ID. No. 18.

As illustrated in FIG. 16, the DNA sequence alignment in four regions of BN-CBF1 shows 82% identity in the AP2 binding domain region and range from 75% to 83% with some alignment gaps due to regions of lesser homology or introns in the genomic sequence. The aligned amino acid sequences show that the BNCBF1 gene has 88% identity in the AP2 domain region and 85% identity outside the AP2 domain when aligned for two insertion sequences that are outside the AP2 domain. The extra amino acids in the 2 insertion regions are either due to the presence of introns in this region of the BNCBF1 gene, as it was derived from genomic DNA, or could be due to extra amino acids in these regions of the BNCBF1 gene. Isolation and sequencing of a cDNA of the BNCBF1 gene using the genomic DNA as a probe will resolve this.

9. Identification Of Homologous Sequence To CBF1 in Canola and other Species A PCR strategy similar to that described in Example 8 was used to isolate additional CBF homologues from *Brassica juncea*, *Brassica napus*, *Brassica oleracea*, *Brassica rapa*, *Glycine max*, *Raphanus sativus* and *Zea Maize*. The nucleotide (e.g. bjCBF1) and peptide sequences (e.g. BJCBF1-PEP) of these isolated CBF homologues are shown in FIGS. 18A and 18B, respectively. Table 9 lists the sequence names and sequence ID Nos. of these isolated CBF homologues. The PCR primers are internal to the gene so partial gene sequences are initially obtained. The full length sequences of some of these genes were further isolated by inverse PCR or ligated linker PCR. One skilled in the art can use the conserved regions in these genes to design PCR primers to isolate additional CBF genes.

TABLE 9

| DNA Seq. Name | Seq. ID No. | Peptide Seq. Name | Seq. ID No. |
| --- | --- | --- | --- |
| bjCBF1 | 38 | BJCBF1-PEP | 39 |
| bjCBF2 | 40 | BJCBF2-PEP | 41 |
| bjCBF3 | 42 | BJCBF3-PEP | 43 |
| bjCBF4 | 44 | BJCBF4-PEP | 45 |
| bnCBF1 | 46 | BNCBF1-PEP | 47 |
| bnCBF2 | 48 | BNCBF2-PEP | 49 |
| bnCBF3 | 50 | BNCBF3-PEP | 51 |
| bnCBF4 | 52 | BNCBF4-PEP | 53 |
| bnCBF5 | 54 | BNCBF5-PEP | 55 |
| bnCBF6 | 56 | BNCBF6-PEP | 57 |
| bnCBF7 | 58 | BNCBF7-PEP | 59 |
| bnCBF8 | 60 | BNCBF8-PEP | 61 |
| bnCBF9 | 62 | BNCBF9-PEP | 63 |
| boCBF1 | 64 | BOCBF1-PEP | 65 |
| boCBF2 | 66 | BOCBF2-PEP | 67 |
| boCBF3 | 68 | BOCBF3-PEP | 69 |
| boCBF4 | 70 | BOCBF4-PEP | 71 |
| boCBF5 | 72 | BOCBF5-PEP | 73 |
| brCBF1 | 74 | BRCBF1-PEP | 75 |
| brCBF2 | 76 | BRCBF2-PEP | 77 |
| brCBF3 | 78 | BRCBF3-PEP | 79 |
| brCBF4 | 80 | BRCBF4-PEP | 81 |
| brCBF5 | 82 | BRCBF5-PEP | 83 |
| brCBF6 | 84 | BRCBF6-PEP | 85 |
| brCBF7 | 86 | BRCBF7-PEP | 87 |

TABLE 9-continued

| DNA Seq. Name | Seq. ID No. | Peptide Seq. Name | Seq. ID No. |
| --- | --- | --- | --- |
| gmCBF1 | 88 | GMCBF1-PEP | 89 |
| rsCBF1 | 90 | RSCBF1-PEP | 91 |
| rsCBF2 | 92 | RSCBF2-PEP | 93 |
| zmCBF1 | 94 | ZMCBF1-PEP | 95 |

FIG. 19A shows an amino acid alignment of the AP2 domains of the CBF proteins listed in Table 9 with their consensus sequences highlighted. FIG. 19A also provides a comparison of the consensus sequence with that of the tobacco DNA binding protein EREBP2 (Okme-Takagi, M., et al., The Plant Cell 7:173–182 (1995). The sequences of these CBF proteins are BRCBF3-PEP [SEQ. ID. No. 79], BRCBF6-PEP [SEQ. ID. No.85], BNCBF5-PEP [SEQ. ID. No. 55], ATCBF2-PEP [SEQ. ID. No. 13], ATCBF3-PEP [SEQ. ID. No. 15], ATCBF1-PEP [SEQ. ID. No. 2], BNCBF2-PEP [SEQ. ID. No. 49], BNCBF6-PEP [SEQ. ID. No. 57], BOCBF3-PEP [SEQ. ID. No. 69], BNCBF3-PEP [SEQ. ID. No. 51], BNCBF8-PEP [SEQ. ID. No. 61], BNCBF9-PEP [SEQ. ID. No. 63], BRCBF2-PEP [SEQ. ID. No. 77], BOCBF5-PEP [SEQ. ID. No. 73], BOCBF2-PEP [SEQ. ID. No. 67], RSCBF2-PEP [SEQ. ID. No. 93], BNCBF4-PEP [SEQ. ID. No. 53], BNCBF7-PEP [SEQ. ID. No. 59], BOCBF4-PEP [SEQ. ID. No. 71], BRCBF7-PEP [SEQ. ID. No. 87], BRCBF4-PEP [SEQ. ID. No. 81], BRCBF5-PEP [SEQ. ID. No. 83], RSCBF1-PEP [SEQ. ID. No. 91], BJCBF2-PEP [SEQ. ID. No. 41], BJCBF3-PEP [SEQ. ID. No. 43], BNCBF1-PEP [SEQ. ID. No. 47], BOCBF1-PEP [SEQ. ID. No. 65], BRCBF1-PEP [SEQ. ID. No. 75], BJCBF4-PEP [SEQ. ID. No. 45], ZMCBF1-PEP [SEQ. ID. No. 95], and GMCBF1-PEP [SEQ. ID. No. 89].

As can be seen from the consensus sequence shown in FIG. 19A, a significant portion of the AP2 domain is conserved among the different CBF proteins. In view of this data, Applicants use the conserved sequence in the AP2 domain to define a class of AP2 domain proteins comprising this conserved sequence.

FIG. 19B shows an amino acid alignment of the AP2 domains shown in FIG. 19A and dreb2a and dreb2b and a consensus sequence between the proteins highlighted. As can be seen, a very high degree of homology exists between AP2 domains shown in FIG. 19A and dreb2a and dreb2b. Applicants employ the conserved sequence in the AP2 domain shown in FIG. 19B to define a broader class of AP2 domain proteins which are capable of binding to CCG regulatory region.

FIG. 19C shows an amino acid alignment of the AP2 domains shown in FIG. 19B and tiny and a consensus sequence between the proteins highlighted. As can be seen, a very high degree of homology exists between AP2 domains shown in FIG. 19A, dreb2a, dreb2b and tiny. Applicants employ the conserved sequence in the AP2 domain shown in FIG. 19C to define a yet broader class of AP2 domain proteins which are capable of binding to CCG regulatory region.

FIG. 19D shows a consensus sequence corresponding to the difference between the consensus sequence shown in FIGS. 19A and tiny. Applicants employ the highlighted portion of the conserved sequence shown in FIG. 19D to define a group of amino acid residues which may be critical to binding to a CCG regulatory region.

FIG. 19E shows a consensus sequence corresponding to the difference between the consensus sequence shown in FIGS. 19B and tiny. Applicants employ the highlighted portion of the conserved sequence shown in FIG. 19E to define another group of amino acid residues which may be critical to binding to a CCG regulatory region.

FIG. 20 shows the amino acid alignment of the amino terminus of the CBF proteins with their consensus sequence highlighted. The sequences of these CBF proteins are: BRCBF3-PEP [SEQ. ID. No. 79], BRCBF6-PEP [SEQ. ID. No.85], BNCBF5-PEP [SEQ. ID. No. 55], ATCBF2-PEP [SEQ. ID. No. 13], ATCBF3-PEP [SEQ. ID. No. 15], ATCBF1-PEP [SEQ. ID. No. 2], BNCBF2-PEP [SEQ. ID. No. 49], BNCBF6-PEP [SEQ. ID. No. 57], BOCBF3-PEP [SEQ. ID. No. 69], BNCBF3-PEP [SEQ. ID. No. 51], BNCBF8-PEP [SEQ. ID. No. 61], BNCBF9-PEP [SEQ. ID. No. 63], BRCBF2-PEP [SEQ. ID. No. 77], BOCBF5-PEP [SEQ. ID. No. 73], BOCBF2-PEP [SEQ. ID. No. 67], RSCBF2-PEP [SEQ. ID. No. 93], BNCBF4-PEP [SEQ. ID. No. 53], BNCBF7-PEP [SEQ. ID. No. 59], BOCBF4-PEP [SEQ. ID. No. 71], BRCBF7-PEP [SEQ. ID. No. 87], BRCBF4-PEP [SEQ. ID. No. 81], BRCBF5-PEP [SEQ. ID. No. 83], and RSCBF1-PEP [SEQ. ID. No. 91].

As can be seen from the consensus sequence shown in FIG. 20, a significant portion of the amino terminus of CBF proteins is conserved among the different CBF proteins. In view of this data, Applicants employ the conserved sequence in the amino terminus domain to define a class of proteins comprising this conserved sequence.

FIG. 21A shows the amino acid alignment of the carboxy terminus of 24 CBF proteins with their consensus sequences highlighted. The sequences of these CBF proteins are: BRCBF6-PEP [SEQ. ID. No.85], BNCBF5-PEP [SEQ. ID. No. 55], ATCBF2-PEP [SEQ. ID. No. 13], ATCBF3-PEP [SEQ. ID. No. 15], ATCBF1 -PEP [SEQ. ID. No. 2], BNCBF2-PEP [SEQ. ID. No. 49], BNCBF6-PEP [SEQ. ID. No. 57], BOCBF3-PEP [SEQ. ID. No. 69], BNCBF3-PEP [SEQ. ID. No. 51], BNCBF8-PEP [SEQ. ID. No. 61], BNCBF9-PEP [SEQ. ID. No. 63], BRCBF2-PEP [SEQ. ID. No. 77], BOCBF5-PEP [SEQ. ID. No. 73], RSCBF2-PEP [SEQ. ID. No. 93], BNCBF4-PEP [SEQ. ID. No. 53], BNCBF7-PEP [SEQ. ID. No. 59], BOCBF4-PEP [SEQ. ID. No. 71], BRCBF7-PEP [SEQ. ID. No. 87], BRCBF5-PEP [SEQ. ID. No. 83], RSCBF1-PEP [SEQ. ID. No. 91], BJCBF2-PEP [SEQ. ID. No. 41], BJCBF3-PEP [SEQ. ID. No. 43], BNCBF1-PEP [SEQ. ID. No. 47], and BOCBF1-PEP [SEQ. ID. No. 65].

As can be seen from the consensus sequence shown in FIG. 21A, a significant portion of the carboxy terminus of CBF proteins is conserved among the different CBF proteins. In view of this data, Applicants employ the conserved sequence in the carboxy terminus domain to define a class of proteins comprising this conserved sequence.

FIG. 21B shows the amino acid alignment of the carboxy terminus of 9 CBF proteins with their consensus sequences highlighted. The sequences of these CBF proteins are: BNCBF2-PEP [SEQ. ID. No. 49], BOCBF3-PEP [SEQ. ID. No. 69], BNCBF3-PEP [SEQ. ID. No. 51], BNCBF8-PEP [SEQ. ID. No. 61], BNCBF9-PEP [SEQ. ID. No. 63], BRCBF2-PEP [SEQ. ID. No. 77], BOCBF5-PEP [SEQ. ID. No. 73], BNCBF1-PEP [SEQ. ID. No.47], and BNCBF6-PEP [SEQ. ID. No. 57].

As can be seen from the consensus sequence shown in FIG. 21B, a greater portion of the carboxy terminus is conserved when these 9 CBF proteins are used. In view of this data, Applicants employ the conserved sequence in the carboxy terminus domain to define another class of proteins comprising this conserved sequence.

While the present invention is disclosed by reference to the preferred embodiments and examples detailed above, it is to be understood that these examples are intended in an illustrative rather than limiting sense, as it is contemplated that modifications will readily occur to those skilled in the art, which modifications will be within the spirit of the invention and the scope of the appended claims.

We claim:

1. A plant comprising a recombinant molecule comprising a polynucleotide that encodes a polypeptide comprising an AP2 domain having at least an 82% sequence identity to an AP2 domain from the group of sequences consisting of SEQ ID Nos:13, 15, 17, 39, 41, 43, 45, 47, 49, 51, 53, 55, 57, 59, 61, 63, 65, 67, 69, 71, 73, 75, 77, 79, 81, 83, 85, 87, 89, 91, 93 and 95.

2. The plant of claim 1, wherein said polypeptide binds to a cold or dehydration transcription regulating region comprising the sequence CCG.

3. The plant of claim 1, wherein said polypeptide binds to a member of a class of DNA regulatory sequences which includes a subsequence selected from the group consisting of CCGAA, CCGAT, CCGAC, CCGAG, CCGTA, CCGTT, CCGTC, CCGTG, CCGCA, CCGCT, CCGCG, CCGCC, CCGGA, CCGGT, CCGGC, CCGGG, AACCG, ATCCG, ACCCG, AGCCG, TACCG, TTCCG, TCCCG, TGCCG, CACCG, CTCCG, CGCCG, CCCCG, GACCG, GTCCG, GCCCG, GGCCG, ACCGA, ACCGT, ACCGC, ACCGG, TCCGA, TCCGT, TCCGC, TCCGG, CCCGA, CCCGT, CCCGC, CCCGG, GCCGA, GCCGT, GCCGC, and GCCGG.

4. The plant of claim 1, wherein said recombinant molecule comprises a polynucleotide encoding a polypeptide that elevates cold-regulated gene levels in the absence of cold acclimation compared with cold-regulated gene levels in a plant lacking said recombinant molecule.

5. The plant of claim 1, further comprising a promoter and wherein said polynucleotide is expressed under regulatory control of the promoter.

6. The plant of claim 5, wherein said promoter is regulated by the addition of an exogenous agent.

7. The plant of claim 5, wherein said promoter is a constitutive promoter.

8. The plant of claim 5, wherein said promoter is regulated by changes in environment conditions.

9. A plant comprising a recombinant molecule comprising a polynucleotide that hybridizes to the AP2 domain of a member of the group of sequences consisting of SEQ ID Nos:12, 14, 18, 38, 40, 42, 44, 46, 48, 50, 52, 54, 56, 58, 60, 62, 64, 66, 68, 70, 72, 74, 76, 78, 80, 82, 84, 86, 88, 90, 92 and 94 under high stringency conditions.

10. The plant of claim 9 comprising a recombinant polynucleotide comprising a sequence that hybridizes to a member of the group of sequences consisting of SEQ ID Nos: 12, 14, 18, 38, 40, 42, 44, 46, 48, 50, 52, 54, 56, 58, 60, 62, 64, 66, 68, 70, 72, 74, 76, 78, 80, 82, 84, 86, 88, 90, 92 and 94 under high stringency conditions.

11. A method for altering an environmental stress response of a plant, said method comprising (a) providing a recombinant molecule comprising a polynucleotide that encodes a polypeptide comprising an AP2 domain having at least an 82% sequence identity to an AP2 domain selected from the group of sequences consisting of SEQ ID Nos:2, 13, 15, 17, 39, 41, 43, 45,47, 49, 51, 53, 55, 57, 59, 61, 63, 65, 67, 69, 71, 73, 75, 77, 79, 81, 83, 85, 87, 89, 91, 93 and 95; and (b) introducing said recombinant molecule into the plant.

12. The method of claim 11, wherein said polypeptide binds to a cold or dehydration transcription regulating region comprising the sequence CCG.

13. The method of claim 12, wherein said polypeptide binds to a member of a class of DNA regulatory sequences which includes a subsequence selected from the group consisting of CCGAA, CCGAT, CCGAC, CCGAG, CCGTA, CCGTT, CCGTC, CCGTG, CCGCA, CCGCT, CCGCG, CCGCC, CCGGA, CCGGT, CCGGC, CCGGG, AACCG, ATCCG, ACCCG, AGCCG, TACCG, TTCCG, TCCCG, TGCCG, CACCG, CTCCG, CGCCG, CCCCG, GACCG, GTCCG, GCCCG, GGCCG, ACCGA, ACCGT, ACCGC, ACCGG, TCCGA, TCCGT, TCCGC, TCCGG, CCCGA, CCCGT, CCCGC, CCCGG, GCCGA, GCCGT, GCCGC, and GCCGG.

14. The method of claim 11, wherein said recombinant polynucleotide comprises a sequence encoding a polypeptide that elevates cold-regulated gene levels in the absence of cold acclimation compared with cold-regulated gene levels in a plant lacking said recombinant molecule.

15. The method of claim 11, further comprising a promoter and wherein said polynucleotide is expressed under regulatory control of the promoter.

16. The method of claim 15, wherein said promoter is regulated by the addition of an exogenous agent.

17. The method of claim 15, wherein said promoter is a constitutive promoter.

18. The method of claim 15, wherein said promoter is regulated by changes in environment conditions.

19. A method for altering an environmental stress response of a plant, comprising (a) providing a recombinant molecule comprising a polynucleotide that encodes a polypeptide comprising a polynucleotide that hybridizes to a member of the group of sequences consisting of SEQ ID Nos: 1, 12, 14, 18, 38, 40, 42, 44, 46, 48, 50, 52, 54, 56, 58, 60, 62, 64, 66, 68, 70, 72, 74, 76, 78, 80, 82, 84, 86, 88, 90, 92 and 94 under high stringency conditions; and (b) introducing said recombinant molecule into the plant.

20. A recombinant molecule comprising a polynucleotide that encodes a polypeptide comprising an AP2 domain having at least an 82% sequence identity to an AP2 domain selected from the group of sequences consisting of SEQ ID Nos: 13, 15, 17, 39, 41, 43, 45, 47,49, 51, 53, 55, 57, 59, 61, 63, 65, 67, 69, 71, 73, 75, 77, 79, 81, 83, 85, 87, 89, 91, 93 and 95.

21. The recombinant molecule of claim 20, wherein said polypeptide binds to a cold or dehydration transcription regulating region comprising the sequence CCG.

22. The recombinant molecule of claim 21, wherein said polypeptide binds to a member of a class of DNA regulatory sequences which includes a subsequence selected from the group consisting of CCGAA, CCGAT, CCGAC, CCGAG, CCGTA, CCGTT, CCGTC, CCGTG, CCGCA, CCGCT, CCGCG, CCGCC, CCGGA, CCGGT, CCGGC, CCGGG, AACCG, ATCCG, ACCCG, AGCCG, TACCG, TTCCG, TCCCG, TGCCG, CACCG, CTCCG, CGCCG, CCCCG, GACCG, GTCCG, GCCCG, GGCCG, ACCGA, ACCGT, ACCGC, ACCGG, TCCGA, TCCGT, TCCGC, TCCGG, CCCGA, CCCGT, CCCGC, CCCGG, GCCGA, GCCGT, GCCGC, and GCCGG.

23. The recombinant molecule of claim 20, wherein said recombinant polynucleotide comprises a sequence encoding a polypeptide that elevates cold-regulated gene levels in the absence of cold acclimation compared with cold-regulated gene levels in a plant lacking said recombinant molecule.

24. The recombinant molecule of claim 20, further comprising a promoter and wherein said polynucleotide is expressed under regulatory control of the promoter.

25. The recombinant molecule of claim 24, wherein said promoter is regulated by the addition of an exogenous agent.

26. The recombinant molecule of claim 24, wherein said promoter is a constitutive promoter.

27. The recombinant molecule of claim 24, wherein said promoter is regulated by changes in environment conditions.

28. A recombinant molecule comprising a polynucleotide that hybridizes to the AP2 domain of a member of the group of sequences consisting of SEQ ID Nos:12, 14, 18, 38, 40, 42, 44, 46, 48, 50, 52, 54, 56, 58, 60, 62, 64, 66, 68, 70, 72, 74, 76, 78, 80, 82, 84, 86, 88, 90, 92 and 94 under high stringency conditions.

29. The method of claim 11, wherein said environmental stress response is a response to cold or freezing.

30. The method of claim 11, wherein said environmental stress response is a response to drought.

31. The method of claim 11, wherein said environmental stress response is a response to salinity.

32. The plant of claim 1, wherein said recombinant molecule comprises a polynucleotide that encodes a polypeptide comprising an AP2 domain having at least an 82% sequence identity to an AP2 domain from the group of sequences consisting of SEQ ID Nos:13, 15, 17, 39, 41, 43, 45, 47, 49, 51, 53, 55, 57, 59, 61, 63, 65, 67, 69, 71, 73, 75, 77, 79, 81, 83, 85, 87, 89, 91, 93 and 95.

33. The method plant of claim 11, wherein said recombinant molecule comprises a polynucleotide that encodes a polypeptide comprising an AP2 domain having at least an 82% sequence identity to an AP2 domain from the group of sequences consisting of SEQ ID Nos:13, 15, 17, 39, 41, 43, 45, 47, 49, 51, 53, 55, 57, 59, 61, 63, 65, 67, 69, 71, 73, 75, 77, 79, 81, 83, 85, 87, 89, 91, 93 and 95.

* * * * *

SEQUENCE LISTING

<160> NUMBER OF SEQ ID NOS: 95

<210> SEQ ID NO 1
<211> LENGTH: 905
<212> TYPE: DNA
<213> ORGANISM: Arabidopsis thaliana
<220> FEATURE:
<223> OTHER INFORMATION: CBF1 gene

<400> SEQUENCE: 1

```
aaaagaatc  tacctgaaaa  gaaaaaaaag  agagagagat  ataaatagct  taccaagaca      60
gatatactat  cttttattaa  tccaaaaaga  ctgagaactc  tagtaactac  gtactactta     120
aaccttatcc  agtttcttga  aacagagtac  tctgatcaat  gaactcattt  tcagcttttt     180
ctgaaatgtt  tggctccgat  tacgagcctc  aaggcggaga  ttattgtccg  acgttggcca     240
cgagttgtcc  gaagaaaccg  gcgggccgta  agaagtttcg  tgagactcgt  cacccaattt     300
acagaggagt  tcgtcaaaga  aactccggta  agtgggtttc  tgaagtgaga  gagccaaaca     360
agaaaaccag  gatttggctc  gggactttcc  aaaccgctga  gatggcagct  cgtgctcacg     420
acgtcgctgc  attagccctc  cgtggccgat  cagcatgtct  caacttcgct  gactcggctt     480
ggcggctacg  aatcccggag  tcaacatgcg  ccaaggatat  ccaaaaagcg  gctgctgaag     540
```

```
cggcgttggc tttcaagat gagacgtgtg atacgacgac cacggatcat ggcctggaca    600
tggaggagac gatggtggaa gctatttata caccggaaca gagcgaaggt gcgttttata    660
tggatgagga gacaatgttt gggatgccga ctttgttgga taatatggct gaaggcatgc    720
ttttaccgcc gccgtctgtt caatggaatc ataattatga cggcgaagga gatggtgacg    780
tgtcgctttg gagttactaa tattcgatag tcgtttccat ttttgtacta tagtttgaaa    840
atattctagt tccttttta gaatggttcc ttcatttat tttatttat tgttgtagaa    900 acgag                                                                 905
```

<210> SEQ ID NO 2
<211> LENGTH: 213
<212> TYPE: PRT
<213> ORGANISM: Arabidopsis thaliana
<220> FEATURE:
<223> OTHER INFORMATION: CBF1 protein

<400> SEQUENCE: 2

```
Met Asn Ser Phe Ser Ala Phe Ser Glu Met Phe Gly Ser Asp Tyr Glu
  1               5                  10                  15

Pro Gln Gly Gly Asp Tyr Cys Pro Thr Leu Ala Thr Ser Cys Pro Lys
                 20                  25                  30

Lys Pro Ala Gly Arg Lys Lys Phe Arg Glu Thr Arg His Pro Ile Tyr
             35                  40                  45

Arg Gly Val Arg Gln Arg Asn Ser Gly Lys Trp Val Ser Glu Val Arg
         50                  55                  60

Glu Pro Asn Lys Lys Thr Arg Ile Trp Leu Gly Thr Phe Gln Thr Ala
 65                  70                  75                  80

Glu Met Ala Ala Arg Ala His Asp Val Ala Ala Leu Ala Leu Arg Gly
                 85                  90                  95

Arg Ser Ala Cys Leu Asn Phe Ala Asp Ser Ala Trp Arg Leu Arg Ile
            100                 105                 110

Pro Glu Ser Thr Cys Ala Lys Asp Ile Gln Lys Ala Ala Ala Glu Ala
            115                 120                 125

Ala Leu Ala Phe Gln Asp Glu Thr Cys Asp Thr Thr Thr Thr Asp His
        130                 135                 140

Gly Leu Asp Met Glu Glu Thr Met Val Glu Ala Ile Tyr Thr Pro Glu
145                 150                 155                 160

Gln Ser Glu Gly Ala Phe Tyr Met Asp Glu Glu Thr Met Phe Gly Met
                165                 170                 175

Pro Thr Leu Leu Asp Asn Met Ala Glu Gly Met Leu Leu Pro Pro Pro
            180                 185                 190

Ser Val Gln Trp Asn His Asn Tyr Asp Gly Glu Gly Asp Gly Asp Val
        195                 200                 205

Ser Leu Trp Ser Tyr
    210
```

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence:C-repeat/DRE

<400> SEQUENCE: 3

```
gatcatttca tggccgacct gctttt                                          27
```

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence:C-repeat/DRE

<400> SEQUENCE: 4
cacaatttca agaattcact gcttttt                                28

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence:C-repeat/DRE

<400> SEQUENCE: 5
gatcatttca tggtatgtct gcttttt                                27

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence:C-repeat/DRE

<400> SEQUENCE: 6
gatcatttca tggaatcact gcttttt                                27

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence:C-repeat/DRE

<400> SEQUENCE: 7
gatcacttga tggccgacct ctttttt                                27

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence:C-repeat/DRE

<400> SEQUENCE: 8
gatcaatata ctaccgacat gagttct                                27

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:C-repeat/DRE

<400> SEQUENCE: 9
actaccgaca tgagttccaa aaagc                                  25

<210> SEQ ID NO 10
<211> LENGTH: 60
<212> TYPE: PRT
<213> ORGANISM: Arabidopsis thaliana

<400> SEQUENCE: 10

Ile Tyr Arg Gly Val Arg Gln Arg Asn Ser Gly Lys Trp Val Ser Glu
1               5                   10                  15

Val Arg Glu Pro Asn Lys Lys Thr Arg Ile Trp Leu Gly Thr Phe Gln
            20                  25                  30

Thr Ala Glu Met Ala Ala Arg Ala His Asp Val Ala Ala Leu Ala Leu
        35                  40                  45

Arg Gly Arg Ser Ala Cys Leu Asn Phe Ala Asp Ser
    50                  55                  60

<210> SEQ ID NO 11
<211> LENGTH: 61
<212> TYPE: PRT
<213> ORGANISM: Nicotiana tabacum

<400> SEQUENCE: 11

His Tyr Arg Gly Val Arg Gln Arg Pro Trp Gly Lys Phe Ala Ala Glu
1               5                   10                  15

Ile Arg Asp Pro Ala Lys Asn Gly Ala Arg Val Trp Leu Gly Thr Tyr
            20                  25                  30

Glu Thr Ala Glu Glu Ala Ala Leu Ala Tyr Asp Lys Ala Ala Tyr Arg
        35                  40                  45

Met Arg Gly Ser Lys Ala Leu Leu Asn Phe Pro His Arg
    50                  55                  60

<210> SEQ ID NO 12
<211> LENGTH: 651
<212> TYPE: DNA
<213> ORGANISM: Arabidopsis thaliana
<220> FEATURE:
<223> OTHER INFORMATION: CBF2

<400> SEQUENCE: 12
atgaactcat tttctgcctt ttctgaaatg tttggctccg attacgagtc tccggtttcc      60
tcaggcggtg attacagtcc gaagcttgcc acgagctgcc ccaagaaacc agcgggaagg     120
aagaagtttc gtgagactcg tcacccaatt tacagaggag ttcgtcaaag aaactccggt     180
aagtgggtgt gtgagttgag agagccaaac aagaaaacga ggatttggct cgggactttc     240
caaaccgctg agatggcagc tcgtgctcac gacgtcgccg ccatagctct ccgtggcaga     300
tctgcctgtc tcaatttcgc tgactcggct tggcggctac gaatcccgga atcaacctgt     360
gccaaggaaa tccaaaaggc ggcggctgaa gccgcgttga attttcaaga tgagatgtgt     420
catatgacga cggatgctca tggtcttgac atggaggaga ccttggtgga ggctatttat     480
acgccggaac agagccaaga tgcgttttat atggatgaag aggcgatgtt ggggatgtct     540
agtttgttgg ataacatggc cgaagggatg cttttaccgt cgccgtcggt tcaatggaac     600
tataattttg atgtcgaggg agatgatgac gtgtccttat ggagctatta a              651

<210> SEQ ID NO 13
<211> LENGTH: 216
<212> TYPE: PRT
<213> ORGANISM: Arabidopsis thaliana
<220> FEATURE:
<223> OTHER INFORMATION: CBF2

<400> SEQUENCE: 13

Met Asn Ser Phe Ser Ala Phe Ser Glu Met Phe Gly Ser Asp Tyr Glu
1               5                   10                  15

Ser Pro Val Ser Ser Gly Gly Asp Tyr Ser Pro Lys Leu Ala Thr Ser

```
                20                  25                  30
Cys Pro Lys Lys Pro Ala Gly Arg Lys Lys Phe Arg Glu Thr Arg His
            35                  40                  45
Pro Ile Tyr Arg Gly Val Arg Gln Arg Asn Ser Gly Lys Trp Val Cys
        50                  55                  60
Glu Leu Arg Glu Pro Asn Lys Lys Thr Arg Ile Trp Leu Gly Thr Phe
65                  70                  75                  80
Gln Thr Ala Glu Met Ala Ala Arg Ala His Asp Val Ala Ala Ile Ala
                85                  90                  95
Leu Arg Gly Arg Ser Ala Cys Leu Asn Phe Ala Asp Ser Ala Trp Arg
            100                 105                 110
Leu Arg Ile Pro Glu Ser Thr Cys Ala Lys Glu Ile Gln Lys Ala Ala
        115                 120                 125
Ala Glu Ala Ala Leu Asn Phe Gln Asp Glu Met Cys His Met Thr Thr
    130                 135                 140
Asp Ala His Gly Leu Asp Met Glu Glu Thr Leu Val Glu Ala Ile Tyr
145                 150                 155                 160
Thr Pro Glu Gln Ser Gln Asp Ala Phe Tyr Met Asp Glu Glu Ala Met
                165                 170                 175
Leu Gly Met Ser Ser Leu Leu Asp Asn Met Ala Glu Gly Met Leu Leu
            180                 185                 190
Pro Ser Pro Ser Val Gln Trp Asn Tyr Asn Phe Asp Val Glu Gly Asp
        195                 200                 205
Asp Asp Val Ser Leu Trp Ser Tyr
    210                 215

<210> SEQ ID NO 14
<211> LENGTH: 651
<212> TYPE: DNA
<213> ORGANISM: Arabidopsis thaliana
<220> FEATURE:
<223> OTHER INFORMATION: CBF3

<400> SEQUENCE: 14
atgaactcat tttctgcttt ttctgaaatg tttggctccg attacgagtc ttcggtttcc      60
tcaggcggtg attatattcc gacgcttgcg agcagctgcc ccaagaaacc ggcgggtcgt     120
aagaagtttc gtgagactcg tcacccaata tacagaggag ttcgtcggag aaactccggt     180
aagtgggttt gtgaggttag agaaccaaac aagaaaacaa ggatttggct cggaacattt     240
caaaccgctg agatggcagc tcgagctcac gacgttgccg ctttagccct tcgtggccga     300
tcagcctgtc tcaatttcgc tgactcggct tggagactcc gaatcccgga atcaacttgc     360
gctaaggaca tccaaaaggc ggcggctgaa gctgcgttgg cgtttcagga tgagatgtgt     420
gatgcgacga cggatcatgg cttcgacatg gaggagacgt tggtggaggc tatttacacg     480
gcggaacaga gcgaaaatgc gttttatatg cacgatgagg cgatgtttga gatgccagt      540
ttgttggcta atatggcaga agggatgctt tgccgcttc cgtccgtaca gtggaatcat      600
aatcatgaag tcgacggcga tgatgacgac gtatcgttat ggagttatta a             651

<210> SEQ ID NO 15
<211> LENGTH: 216
<212> TYPE: PRT
<213> ORGANISM: Arabidopsis thaliana
<220> FEATURE:
<223> OTHER INFORMATION: CBF3

<400> SEQUENCE: 15
```

```
Met Asn Ser Phe Ser Ala Phe Ser Glu Met Phe Gly Ser Asp Tyr Glu
  1               5                  10                  15

Ser Ser Val Ser Ser Gly Gly Asp Tyr Ile Pro Thr Leu Ala Ser Ser
             20                  25                  30

Cys Pro Lys Lys Pro Ala Gly Arg Lys Lys Phe Arg Glu Thr Arg His
         35                  40                  45

Pro Ile Tyr Arg Gly Val Arg Arg Asn Ser Gly Lys Trp Val Cys
     50                  55                  60

Glu Val Arg Glu Pro Asn Lys Lys Thr Arg Ile Trp Leu Gly Thr Phe
 65                  70                  75                  80

Gln Thr Ala Glu Met Ala Ala Arg Ala His Asp Val Ala Ala Leu Ala
                 85                  90                  95

Leu Arg Gly Arg Ser Ala Cys Leu Asn Phe Ala Asp Ser Ala Trp Arg
                100                 105                 110

Leu Arg Ile Pro Glu Ser Thr Cys Ala Lys Asp Ile Gln Lys Ala Ala
                115                 120                 125

Ala Glu Ala Ala Leu Ala Phe Gln Asp Glu Met Cys Asp Ala Thr Thr
130                 135                 140

Asp His Gly Phe Asp Met Glu Glu Thr Leu Val Glu Ala Ile Tyr Thr
145                 150                 155                 160

Ala Glu Gln Ser Glu Asn Ala Phe Tyr Met His Asp Glu Ala Met Phe
                165                 170                 175

Glu Met Pro Ser Leu Leu Ala Asn Met Ala Glu Gly Met Leu Leu Pro
                180                 185                 190

Leu Pro Ser Val Gln Trp Asn His Asn His Glu Val Asp Gly Asp Asp
                195                 200                 205

Asp Asp Val Ser Leu Trp Ser Tyr
210                 215

<210> SEQ ID NO 16
<211> LENGTH: 18
<212> TYPE: DNA
<213> ORGANISM: Nicotiana tabacum

<400> SEQUENCE: 16
ttggcggcta cgaatccc                                                18

<210> SEQ ID NO 17
<211> LENGTH: 210
<212> TYPE: PRT
<213> ORGANISM: Brassica napus

<400> SEQUENCE: 17

His Pro Ile Tyr Arg Gly Val Arg Leu Arg Lys Ser Gly Lys Trp Val
  1               5                  10                  15

Cys Glu Val Arg Glu Pro Asn Lys Lys Ser Arg Ile Trp Leu Gly Thr
             20                  25                  30

Phe Lys Thr Ala Glu Met Ala Ala Arg Ala His Asp Val Ala Ala Leu
         35                  40                  45

Ala Leu Arg Gly Arg Gly Ala Cys Leu Asn Tyr Ala Asp Ser Ala Trp
     50                  55                  60

Arg Leu Arg Ile Pro Glu Thr Thr Cys His Lys Asp Ile Gln Lys Ala
 65                  70                  75                  80

Ala Ala Glu Ala Ala Leu Ala Phe Glu Ala Glu Lys Ser Asp Val Thr
                 85                  90                  95
```

```
Met Gln Asn Gly Gln Asn Met Glu Glu Thr Thr Ala Val Ala Ser Gln
            100                 105                 110
Ala Glu Val Asn Asp Thr Thr Thr Glu His Gly Met Asn Met Glu Glu
        115                 120                 125
Ala Thr Ala Val Ala Ser Gln Ala Glu Val Asn Asp Thr Thr Thr Asp
    130                 135                 140
His Gly Val Asp Met Glu Glu Thr Met Val Glu Ala Val Phe Thr Gly
145                 150                 155                 160
Glu Gln Ser Glu Gly Phe Asn Met Ala Lys Glu Ser Thr Val Glu Ala
                165                 170                 175
Ala Val Val Thr Glu Glu Pro Ser Lys Gly Ser Tyr Met Asp Glu Glu
            180                 185                 190
Trp Met Leu Glu Met Pro Thr Leu Leu Ala Asp Met Ala Glu Gly Met
        195                 200                 205
Leu Leu
    210

<210> SEQ ID NO 18
<211> LENGTH: 632
<212> TYPE: DNA
<213> ORGANISM: canola

<400> SEQUENCE: 18
cacccgatat accggggagt tcgtctgaga aagtcaggta agtgggtgtg tgaagtgagg        60
gaaccaaaca agaaatctag aatttggctt ggaactttca aaacagctga gatggcagct      120
cgtgctcacg acgtcgctgc cctagccctc cgtggaagag gcgcctgcct caattatgcg      180
gactcggctt ggcggctccg catcccggag acaacctgcc acaaggatat ccagaaggct      240
gctgctgaag ccgcattggc ttttgaggct gagaaaagtg atgtgacgat gcaaaatggc      300
cagaacatgg aggagacgac ggcggtggct tctcaggctg aagtgaatga cacgacgaca      360
gaacatggca tgaacatgga ggaggcaacg gcagtggctt ctcaggctga ggtgaatgac      420
acgacgacga atcatggcgt agacatggag gagacaatgg tggaggctgt ttttactggg      480
gaacaaagtg aagggtttaa catggcgaag gagtcgacgg tggaggctgc tgttgttacg      540
gaggaaccga gcaaaggatc ttacatggac gaggagtgga tgctcgagat gccgaccttg      600
ttggctgata tggcagaagg gatgctcctg cc                                    632

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence: PCR primer

<400> SEQUENCE: 19
gcccaagctt caagtttagt gagcactatg tgctcg                                 36

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence: PCR primer

<400> SEQUENCE: 20
ggaagatctc cttcccagaa acaacacaat ctac                                   34
```

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence: PCR primer

<400> SEQUENCE: 21
gcccaagctt gtttcatttt ctccatgaag gagat                              35

<210> SEQ ID NO 22
<211> LENGTH: 39
<212> TYPE: DNA
<213> ORGANISM: Artificial Sequence
<220> FEATURE:
<223> OTHER INFORMATION: Description of Artificial Sequence: PCR primer

<400> SEQUENCE: 22
ggaagatctt atcgtcgtcg tcgtctacca aaaccacac                          39

<210> SEQ ID NO 23
<211> LENGTH: 32
<212> TYPE: DNA
<213> ORGANISM: Artificial Sequence
<220> FEATURE:
<223> OTHER INFORMATION: Description of Artificial Sequence: PCR primer

<400> SEQUENCE: 23
gctctaagct tcacaagggg ttcgtttggt gc                                 32

<210> SEQ ID NO 24
<211> LENGTH: 40
<212> TYPE: DNA
<213> ORGANISM: Artificial Sequence
<220> FEATURE:
<223> OTHER INFORMATION: Description of Artificial Sequence: PCR primer

<400> SEQUENCE: 24
ggggtacctt ttgggagttg gaatagaaat gggtttgatg                         40

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: PCR primer

<400> SEQUENCE: 25
gcccaagctt aattttactc aaaatgtttt ggttgc                             36

<210> SEQ ID NO 26
<211> LENGTH: 44
<212> TYPE: DNA
<213> ORGANISM: Artificial Sequence
<220> FEATURE:
<223> OTHER INFORMATION: Description of Artificial Sequence: PCR primer

<400> SEQUENCE: 26
ccggtacctt tccaaagatt tttttctttc caatagaagt aatc                    44

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: PCR primer -continued

```
<400> SEQUENCE: 27
gcggaagctt cattttctgc tacagaagtg                                    30

<210> SEQ ID NO 28
<211> LENGTH: 40
<212> TYPE: DNA
<213> ORGANISM: Artificial Sequence
<220> FEATURE:
<223> OTHER INFORMATION: Description of Artificial Sequence: PCR primer

<400> SEQUENCE: 28
ccggtacctt tccaaagctg tgttttctct ttttcaagtg                         40

<210> SEQ ID NO 29
<211> LENGTH: 42
<212> TYPE: DNA
<213> ORGANISM: Artificial Sequence
<220> FEATURE:
<223> OTHER INFORMATION: Description of Artificial Sequence: PCR primer

<400> SEQUENCE: 29
gcccaagctt caaattctga atattcacat atcaaaaaag tg                      42

<210> SEQ ID NO 30
<211> LENGTH: 40
<212> TYPE: DNA
<213> ORGANISM: Artificial Sequence
<220> FEATURE:
<223> OTHER INFORMATION: Description of Artificial Sequence: PCR primer

<400> SEQUENCE: 30
ggaagatctg ttcttcttgt cttaagcaaa cactttgagc                         40

<210> SEQ ID NO 31
<211> LENGTH: 41
<212> TYPE: DNA
<213> ORGANISM: Artificial Sequence
<220> FEATURE:
<223> OTHER INFORMATION: Description of Artificial Sequence: PCR primer

<400> SEQUENCE: 31
gcccaagctt tcgtctgtta tcatacaagg cacaaaacga c                       41

<210> SEQ ID NO 32
<211> LENGTH: 42
<212> TYPE: DNA
<213> ORGANISM: Artificial Sequence
<220> FEATURE:
<223> OTHER INFORMATION: Description of Artificial Sequence: PCR primer

<400> SEQUENCE: 32
ggaagatcta gttaatcttg atttgattaa aagtttatat ag                      42

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: PCR primer

<400> SEQUENCE: 33
caaactcagt aggattctgg tgtgt                                         25

<210> SEQ ID NO 34
<211> LENGTH: 38
```

```
<212> TYPE: DNA
<213> ORGANISM: Artificial Sequence
<220> FEATURE:
<223> OTHER INFORMATION: Description of Artificial Sequence: PCR primer

<400> SEQUENCE: 34
ggaagatctt gaaacagagt actctgatca atgaactc                                38

<210> SEQ ID NO 35
<211> LENGTH: 42
<212> TYPE: DNA
<213> ORGANISM: Artificial Sequence
<220> FEATURE:
<223> OTHER INFORMATION: Description of Artificial Sequence: PCR primer

<400> SEQUENCE: 35
cgcggatccc tcgtttctac aacaataaaa taaaataaaa tg                           42

<210> SEQ ID NO 36
<211> LENGTH: 37
<212> TYPE: DNA
<213> ORGANISM: Artificial Sequence
<220> FEATURE:
<223> OTHER INFORMATION: Description of Artificial Sequence: PCR primer

<400> SEQUENCE: 36
ggggtacctg aaacagagta ctctgatcaa tgaactc                                 37

<210> SEQ ID NO 37
<211> LENGTH: 41
<212> TYPE: DNA
<213> ORGANISM: Artificial Sequence
<220> FEATURE:
<223> OTHER INFORMATION: Description of Artificial Sequence: PCR primer

<400> SEQUENCE: 37
gctctagact cgtttctaca acaataaaat aaaataaaat g                            41

<210> SEQ ID NO 38
<211> LENGTH: 577
<212> TYPE: DNA
<213> ORGANISM: Brassica juncea
<220> FEATURE:
<223> OTHER INFORMATION: bjCBF1 gene

<400> SEQUENCE: 38 tttcaccccta tctaccgggg agttcgcctg agaaagtcag gtaagtgggt gtgtgaagtg       60
agggagccaa acaagaaatc taggatttgg cttggaactt tcaaaaccgc agagatcgct      120
gctcgtgctc acgacgttgc cgccttagcc ctccgtggaa gagcggcctg tctcaacttc      180
gccgactcgg cttggcggct ccgtatcccg gagacaactt gcgccaagga tatccagaag      240
gctgctgctg aagctgcgtt ggcttttggg gccgaaaaga gtgataccac gacgaatgat      300
caaggcatga acatggagga gatgacggtg gtggcttctc aggctgaggt gagcgacacg      360
acgacatatc atggcctgga catggaggag actatggtgg aggctgtttt tgctgaggaa      420
cagagagaag ggttttactt ggcggaggag acgacggtgg agggtgttgt tacggaggaa      480
cagagcaaag ggttttatat gtacgaggag tggacgttcg ggatgcagtc cttttttggcc     540 gatatggctg aaggcatgct cttttcaaag ggcgaat                                577

<210> SEQ ID NO 39
<211> LENGTH: 130
<212> TYPE: PRT
```

```
<213> ORGANISM: Brassica juncea
<220> FEATURE:
<223> OTHER INFORMATION: bjCBF1-PEP

<400> SEQUENCE: 39
```

| Leu | Pro | Gly | Val | Arg | Leu | Arg | Lys | Ser | Gly | Lys | Trp | Val | Cys | Glu | Val |
|---|---|---|---|---|---|---|---|---|---|---|---|---|---|---|---|
| 1 | | | | 5 | | | | | 10 | | | | | 15 | |

| Arg | Glu | Pro | Asn | Lys | Lys | Ser | Arg | Ile | Trp | Leu | Gly | Thr | Phe | Lys | Thr |
|---|---|---|---|---|---|---|---|---|---|---|---|---|---|---|---|
| | | | 20 | | | | | 25 | | | | | 30 | | |

| Ala | Glu | Ile | Ala | Ala | Arg | Ala | His | Asp | Val | Ala | Ala | Leu | Ala | Leu | Arg |
|---|---|---|---|---|---|---|---|---|---|---|---|---|---|---|---|
| | | | 35 | | | | | 40 | | | | | 45 | | |

| Gly | Arg | Ala | Ala | Cys | Leu | Asn | Phe | Ala | Asp | Ser | Ala | Trp | Arg | Leu | Arg |
|---|---|---|---|---|---|---|---|---|---|---|---|---|---|---|---|
| | 50 | | | | | 55 | | | | | 60 | | | | |

| Ile | Pro | Glu | Thr | Thr | Cys | Ala | Lys | Asp | Ile | Gln | Lys | Ala | Ala | Ala | Glu |
|---|---|---|---|---|---|---|---|---|---|---|---|---|---|---|---|
| 65 | | | | | 70 | | | | | 75 | | | | | 80 |

| Ala | Ala | Leu | Ala | Phe | Gly | Ala | Glu | Lys | Ser | Asp | Thr | Thr | Thr | Asn | Asp |
|---|---|---|---|---|---|---|---|---|---|---|---|---|---|---|---|
| | | | 85 | | | | | 90 | | | | | 95 | | |

| Gln | Gly | Met | Asn | Met | Glu | Glu | Met | Thr | Ala | Val | Ala | Ser | Gln | Ala | Glu |
|---|---|---|---|---|---|---|---|---|---|---|---|---|---|---|---|
| | | | 100 | | | | | 105 | | | | | 110 | | |

| Val | Ser | Asp | Thr | Thr | Thr | Tyr | His | Gly | Leu | Asp | Met | Glu | Glu | Thr | Met |
|---|---|---|---|---|---|---|---|---|---|---|---|---|---|---|---|
| | | 115 | | | | | 120 | | | | | 125 | | | |

| Val | Asp |
|---|---|
| | 130 |

```
<210> SEQ ID NO 40
<211> LENGTH: 431
<212> TYPE: DNA
<213> ORGANISM: Brassica juncea
<220> FEATURE:
<223> OTHER INFORMATION: bjCBF2 gene

<400> SEQUENCE: 40
catccgatct acaggggagt tcgtctgaga aaatcaggta agtgggtgtg tgaagtgagg      60
gaaccaaaca agagatctag gatctggctc ggtactttcc taaccgccga gatcgcagct    120
cgcgctcacg acgtcgccgc catagccctc cgtggcaaat ccgcatgtct caatttcgct    180
gactcggctt ggcggctccg tatctcggag acaacatgcc ctaaggagat tcagaaggct    240
gctgctgaag ccgcggtggc ttttcaggct gagctaaatg atacgacggc cgatcatggc    300
cttgacgtgg aggagacgat cgtggaggct attttcacgg aggaaagcag cgaagggttt    360
tatatggacg aggagttcat gttcgggatg ccgaccttgt gggctagtat ggcagaaggg    420
atgcttcttc c                                                         431

<210> SEQ ID NO 41
<211> LENGTH: 143
<212> TYPE: PRT
<213> ORGANISM: Brassica juncea
<220> FEATURE:
<223> OTHER INFORMATION: bjCBF2 pep

<400> SEQUENCE: 41
```

| His | Pro | Ile | Tyr | Arg | Gly | Val | Arg | Leu | Arg | Lys | Ser | Gly | Lys | Trp | Val |
|---|---|---|---|---|---|---|---|---|---|---|---|---|---|---|---|
| 1 | | | | 5 | | | | | 10 | | | | | 15 | |

| Cys | Glu | Val | Arg | Glu | Pro | Asn | Lys | Arg | Ser | Arg | Ile | Trp | Leu | Gly | Thr |
|---|---|---|---|---|---|---|---|---|---|---|---|---|---|---|---|
| | | | 20 | | | | | 25 | | | | | 30 | | |

| Phe | Leu | Thr | Ala | Glu | Ile | Ala | Ala | Arg | Ala | His | Asp | Val | Ala | Ala | Ile |
|---|---|---|---|---|---|---|---|---|---|---|---|---|---|---|---|
| | | | 35 | | | | | 40 | | | | | 45 | | |

| Ala | Leu | Arg | Gly | Lys | Ser | Ala | Cys | Leu | Asn | Phe | Ala | Asp | Ser | Ala | Trp |

```
                 50                   55                  60
Arg Leu Arg Ile Ser Glu Thr Thr Cys Pro Lys Glu Ile Gln Lys Ala
 65                  70                  75                  80

Ala Ala Glu Ala Ala Val Ala Phe Gln Ala Glu Leu Asn Asp Thr Thr
                 85                  90                  95

Ala Asp His Gly Leu Asp Val Glu Glu Thr Ile Val Glu Ala Ile Phe
                100                 105                 110

Thr Glu Glu Ser Ser Glu Gly Phe Tyr Met Asp Glu Glu Phe Met Phe
                115                 120                 125

Gly Met Pro Thr Leu Trp Ala Ser Met Ala Glu Gly Met Leu Leu
                130                 135                 140

<210> SEQ ID NO 42
<211> LENGTH: 431
<212> TYPE: DNA
<213> ORGANISM: Brassica juncea
<220> FEATURE:
<223> OTHER INFORMATION: bjCBF3 gene

<400> SEQUENCE: 42
catccaattt accgtggagt tcgtctgaga aaatcaggta agtgggtgtg tgaagtgagg      60
gagccaaaca agaaatctag gatctggccc ggtactttcc taaccgccga gatcgcagct    120
cgcgctcacg acgtcgccgc catagccctc cgtggcaaat ccgcatgtct caatttcgct    180
gactcggctt ggcggctccg tatcccggag acaacatgcc ctaaggagat tcagaaggct    240
gctgctgaag ccgcggtggc ttttcaggct gagctaaatg atacgacggc cgatcatggc    300
cttgacgtgg aggagacgat cgtggaggct attttcacgg aggaaagcag cgaagggttt    360
tatatggacg aggagttcat gttcgggatg ccgaccttgt gggctagtat ggcggagggc    420
atgctccttc c                                                         431

<210> SEQ ID NO 43
<211> LENGTH: 143
<212> TYPE: PRT
<213> ORGANISM: Brassica juncea
<220> FEATURE:
<223> OTHER INFORMATION: bjCBF3-PEP

<400> SEQUENCE: 43

His Pro Ile Tyr Arg Gly Val Arg Leu Arg Lys Ser Gly Lys Trp Val
  1               5                  10                  15

Cys Glu Val Arg Glu Pro Asn Lys Lys Ser Arg Ile Trp Pro Gly Thr
                 20                  25                  30

Phe Leu Thr Ala Glu Ile Ala Ala Arg Ala His Asp Val Ala Ala Ile
                 35                  40                  45

Ala Leu Arg Gly Lys Ser Ala Cys Leu Asn Phe Ala Asp Ser Ala Trp
 50                  55                  60

Arg Leu Arg Ile Pro Glu Thr Thr Cys Pro Lys Glu Ile Gln Lys Ala
 65                  70                  75                  80

Ala Ala Glu Ala Ala Val Ala Phe Gln Ala Glu Leu Asn Asp Thr Thr
                 85                  90                  95

Ala Asp His Gly Leu Asp Val Glu Glu Thr Ile Val Glu Ala Ile Phe
                100                 105                 110

Thr Glu Glu Ser Ser Glu Gly Phe Tyr Met Ala Glu Glu Phe Met Phe
                115                 120                 125

Gly Met Pro Thr Leu Trp Ala Ser Val Ala Glu Gly Met Leu Leu
                130                 135                 140
```

<210> SEQ ID NO 44
<211> LENGTH: 425
<212> TYPE: DNA
<213> ORGANISM: Brassica juncea
<220> FEATURE:
<223> OTHER INFORMATION: bjCBF4 gene

<400> SEQUENCE: 44

| | | |
|---|---|---|
| catccaatct accggggtgt tcgacagaga aactcaggga aatgggtttg tgaagttagg | 60 |
| gagcctaata agaaatctag gatctggtta gggacttttc cgaccgtcga aatggccgct | 120 |
| cgtgctcacg acgtcgccgc tttagcccct cgtggccgct ccgcttgtct taatttcgcc | 180 |
| gactcggcgt ggtgtctacg gattcccgag tctacttgtc ctaaagagat tcagaaagct | 240 |
| gcggccgaag ctgcaatggc gtttcagaac gagacggcta cgactgagac gactatggtt | 300 |
| gagggagtca taccggcgga ggagacggtg gggcagacgc gtgtggagac agcagaggag | 360 |
| aacggtgtgt tttatatgga cgatccaagg tttcttgaga atatggcaga gggcatgttc | 420 |
| ctacc | 425 |

<210> SEQ ID NO 45
<211> LENGTH: 142
<212> TYPE: PRT
<213> ORGANISM: Brassica juncea
<220> FEATURE:
<223> OTHER INFORMATION: bjCBF4-PEP

<400> SEQUENCE: 45

His Pro Ile Tyr Arg Gly Val Arg Gln Arg Asn Ser Gly Lys Trp Val
 1               5                  10                  15

Cys Glu Val Arg Glu Pro Asn Lys Lys Ser Arg Ile Trp Leu Gly Thr
                20                  25                  30

Phe Pro Thr Val Glu Met Ala Ala Arg Ala His Asp Val Ala Ala Leu
            35                  40                  45

Ala Leu Arg Gly Arg Ser Ala Cys Leu Asn Phe Ala Asp Ser Ala Trp
        50                  55                  60

Cys Leu Arg Ile Pro Glu Ser Thr Cys Pro Lys Glu Ile Gln Lys Ala
65                  70                  75                  80

Ala Ala Glu Ala Ala Met Ala Phe Gln Asn Glu Thr Ala Thr Thr
                85                  90                  95

Glu Thr Thr Met Val Glu Gly Val Ile Pro Ala Glu Glu Thr Val Gly
            100                 105                 110

Gln Thr Arg Val Glu Thr Ala Glu Glu Asn Gly Val Glu Tyr Met Asp
        115                 120                 125

Asp Pro Arg Phe Leu Glu Asn Met Ala Glu Gly Met Leu Phe
    130                 135                 140

<210> SEQ ID NO 46
<211> LENGTH: 632
<212> TYPE: DNA
<213> ORGANISM: Brassica napus
<220> FEATURE:
<223> OTHER INFORMATION: bnCBF1 gene

<400> SEQUENCE: 46

| | | |
|---|---|---|
| cacccgatat accggggagt tcgtctgaga aagtcaggta agtgggtgtg tgaagtgagg | 60 |
| gaaccaaaca agaaatctag aatttggctt ggaactttca aaacagctga gatggcagct | 120 |
| cgtgctcacg acgtcgctgc cctagcccctc cgtggaagag gcgcctgcct caattatgcg | 180 |

-continued

```
gactcggctt ggcggctccg catcccggag acaacctgcc acaaggatat ccagaaggct        240
gctgctgaag ccgcattggc ttttgaggct gagaaaagtg atgtgacgat gcaaaatggc        300
cagaacatgg aggagacgac ggcggtggct tctcaggctg aagtgaatga cacgacgaca        360
gaacatggca tgaacatgga ggaggcaacg gcagtggctt ctcaggctga ggtgaatgac        420
acgacgacgg atcatggcgt agacatggag gagacaatgt ggaggctgt ttttactggg         480 gaacaaagtg aagggtttaa catggcgaag gagtcgacgg tggaggctgc tgttgttacg        540
gaggaaccga gcaaaggatc ttacatggac gaggagtgga tgctcgagat gccgaccttg        600
ttggctgata tggcagaagg gatgctcctg cc                                      632
```

<210> SEQ ID NO 47
<211> LENGTH: 210
<212> TYPE: PRT
<213> ORGANISM: Brassica napus
<220> FEATURE:
<223> OTHER INFORMATION: bnCBF1-PEP

<400> SEQUENCE: 47

```
His Pro Ile Tyr Arg Gly Val Arg Leu Arg Lys Ser Gly Lys Trp Val
 1               5                  10                  15

Cys Glu Val Arg Glu Pro Asn Lys Lys Ser Arg Ile Trp Leu Gly Thr
            20                  25                  30

Phe Lys Thr Ala Glu Met Ala Ala Arg Ala His Asp Val Ala Ala Leu
        35                  40                  45

Ala Leu Arg Gly Arg Gly Ala Cys Leu Asn Tyr Ala Asp Ser Ala Trp
    50                  55                  60

Arg Leu Arg Ile Pro Glu Thr Thr Cys His Lys Asp Ile Gln Lys Ala
65                  70                  75                  80

Ala Glu Ala Ala Leu Ala Phe Glu Ala Glu Lys Ser Asp Val Thr
                85                  90                  95

Met Gln Asn Gly Gln Asn Met Glu Glu Thr Thr Ala Val Ala Ser Gln
            100                 105                 110

Ala Glu Val Asn Asp Thr Thr Thr Glu His Gly Met Asn Met Glu Glu
        115                 120                 125

Ala Thr Ala Val Ala Ser Gln Ala Glu Val Asn Asp Thr Thr Thr Asp
    130                 135                 140

His Gly Val Asp Met Glu Glu Thr Met Val Glu Ala Val Phe Thr Gly
145                 150                 155                 160

Glu Gln Ser Glu Gly Phe Asn Met Ala Lys Glu Ser Thr Val Glu Ala
                165                 170                 175

Ala Val Val Thr Glu Glu Pro Ser Lys Gly Ser Tyr Met Asp Glu Glu
            180                 185                 190

Trp Met Leu Glu Met Pro Thr Leu Leu Ala Asp Met Ala Glu Gly Met
        195                 200                 205

Leu Leu
    210
```

<210> SEQ ID NO 48
<211> LENGTH: 876
<212> TYPE: DNA
<213> ORGANISM: Brassica napus
<220> FEATURE:
<223> OTHER INFORMATION: bnCBF2 gene

<400> SEQUENCE: 48

-continued

```
accgctcgag caacaatgaa cacattccct gcttccactg aaatggttgg ctccgagaac      60
gagtctccgg ttactacggt agtaggaggt gattattatc ccatgttggc ggcaagctgt     120
ccgaagaagc cagcgggtag gaagaagttt caggagacac gtcacccat ttaccgagga      180
gttcgtctga gaaagtcagg taagtgggtg tgtgaagtga gggaaccaaa caagaaatct    240
agaatttggc ccggaacttt caaaacagct gagatggcag ctcgtgctca cgacgtcgct    300
gccctagccc tccgtggaag aggcgcctgc ctcaattatg cggactcggc ttggcggctc    360
cgcatcccgg aaacaacctg ccacaaggat atccagaagg ctgctgctga agccgcattg    420
gcttttgagg ctgagaaaag tgatgtgacg atgcaaaatg gcctgaacat ggaggagacg    480
acggcggtgg cttctcaggc tgaagtgaat gacacgacga cagaacatgg catgaacatg    540
gaggaggcaa cagcggtggc ttctcaggct gaggtgaatg acacgacgac agatcatggc    600
gtagacatgg aggagacgat ggtggaggct gttttttacgg aggaacaaag tgaagggttc   660
aacatggcgg aggagtcgac ggtggaggct gctgttgtta cggatgaact gagcaaagga   720
ttttacatgg acgaggagtg gacgtacgag atgccgacct tgttggctga tatggcggca   780
gggatgcttt tgccgccacc atctgtacaa tggggacata atgatgactt ggaaggagat   840
gcggacatga acctctggag ttattaagga tccgcg                              876
```

<210> SEQ ID NO 49
<211> LENGTH: 283
<212> TYPE: PRT
<213> ORGANISM: Brassica napus
<220> FEATURE:
<223> OTHER INFORMATION: bnCBF2-PEP

<400> SEQUENCE: 49

```
Met Asn Thr Phe Pro Ala Ser Thr Glu Met Val Gly Ser Glu Asn Glu
  1               5                  10                  15

Ser Pro Val Thr Thr Val Val Gly Gly Asp Tyr Tyr Pro Met Leu Ala
             20                  25                  30

Ala Ser Cys Pro Lys Lys Pro Ala Gly Arg Lys Lys Phe Gln Glu Thr
         35                  40                  45

Arg His Pro Ile Tyr Arg Gly Val Arg Leu Arg Lys Ser Gly Lys Trp
     50                  55                  60

Val Cys Glu Val Arg Glu Pro Asn Lys Lys Ser Arg Ile Trp Pro Gly
 65                  70                  75                  80

Thr Phe Lys Thr Ala Glu Met Ala Ala Arg Ala His Asp Val Ala Ala
                 85                  90                  95

Leu Ala Leu Arg Gly Arg Gly Ala Cys Leu Asn Tyr Ala Asp Ser Ala
            100                 105                 110

Trp Arg Leu Arg Ile Pro Glu Thr Thr Cys His Lys Asp Ile Gln Lys
        115                 120                 125

Ala Ala Ala Glu Ala Ala Leu Ala Phe Glu Ala Glu Lys Ser Asp Val
    130                 135                 140

Thr Met Gln Asn Gly Leu Asn Met Glu Glu Thr Thr Ala Val Ala Ser
145                 150                 155                 160

Gln Ala Glu Val Asn Asp Thr Thr Thr Glu His Gly Met Asn Met Glu
                165                 170                 175

Glu Ala Thr Ala Val Ala Ser Gln Ala Glu Val Asn Asp Thr Thr Thr
            180                 185                 190

Asp His Gly Val Asp Met Glu Glu Thr Met Val Glu Ala Val Phe Thr
        195                 200                 205
```

```
Glu Glu Gln Ser Glu Gly Phe Asn Met Ala Glu Ser Thr Val Glu
            210                 215                 220
Ala Ala Val Val Thr Asp Glu Leu Ser Lys Gly Phe Tyr Met Asp Glu
225                 230                 235                 240
Glu Trp Thr Tyr Glu Met Pro Thr Leu Leu Ala Asp Met Ala Ala Gly
                245                 250                 255
Met Leu Leu Pro Pro Pro Ser Val Gln Trp Gly His Asn Asp Asp Leu
            260                 265                 270
Glu Gly Asp Ala Asp Met Asn Leu Trp Ser Tyr
        275                 280
```

<210> SEQ ID NO 50
<211> LENGTH: 884
<212> TYPE: DNA
<213> ORGANISM: Brassica napus
<220> FEATURE:
<223> OTHER INFORMATION: bnCBF3 gene

<400> SEQUENCE: 50

| | | | | | |
|---|---|---|---|---|---|
| actacactca | gccttatcca | gtttttttca | aaagattttt | caacaatgaa | cacattccct | 60 |
| gcgtccactg | aaatggttgg | ctccgagaac | gagtctccgg | ttactacggt | agcaggaggt | 120 |
| gattattatc | ccatgttggc | ggcaagctgt | ccgaagaagc | cagcaggtag | gaagaagttt | 180 |
| caggagacac | gtcaccccat | ttaccgagga | gttcgtctga | aaagtcagg | taagtgggtg | 240 |
| tgtgaagtga | gggaaccaaa | caagaaatct | agaatttggc | ccggaacttt | caaaacagct | 300 |
| gagatggcag | ctcgtgctca | cgacgtcgct | gccctagccc | tccgtggaag | aggcgcctgc | 360 |
| ctcaattatg | cggactcggc | ttggcggctc | cgcatcccgg | agacaacctg | ccacaaggat | 420 |
| atccagaagg | ctgctgctga | agccgcattg | gcttttgagg | ctgagaaaag | tgatgtgacg | 480 |
| atgcaaaatg | gcctgaacat | ggaggagacg | acggcggtgg | cttctcaggc | tgaagtgaat | 540 |
| gacacgacga | cagaacatgg | catgaacatg | gaggaggcaa | cggcagtggc | ttctcaggct | 600 |
| gaggtgaatg | acacgacgac | ggatcatggc | gtagacatgg | aggagacaat | ggtggaggct | 660 |
| gttttactg | gggaacaaag | tgaagggttt | aacatggcga | aggagtcgac | ggtggaggct | 720 |
| gctgttgtta | cggaggaacc | gagcaaagga | tcttacatgg | acgaggagtg | gatgctcgag | 780 |
| atgccgacct | tgttggctga | tatggcggaa | gggatgcttt | tgccgccgcc | gtccgtacaa | 840 |
| tggggacaga | atgatgactt | cgaaggagat | gctgacatga | acct | | 884 |

<210> SEQ ID NO 51
<211> LENGTH: 279
<212> TYPE: PRT
<213> ORGANISM: Brassica napus
<220> FEATURE:
<223> OTHER INFORMATION: bnCBF3-PEP

<400> SEQUENCE: 51

```
Met Asn Thr Phe Pro Ala Ser Thr Glu Met Val Gly Ser Glu Asn Glu
1               5                   10                  15
Ser Pro Val Thr Thr Val Ala Gly Gly Asp Tyr Tyr Pro Met Leu Ala
                20                  25                  30
Ala Ser Cys Pro Lys Lys Pro Ala Gly Arg Lys Phe Gln Glu Thr
            35                  40                  45
Arg His Pro Ile Tyr Arg Gly Val Arg Leu Arg Ser Gly Lys Trp
        50                  55                  60
Val Cys Glu Val Arg Glu Pro Asn Lys Lys Ser Arg Ile Trp Pro Gly
65                  70                  75                  80
```

-continued

```
Thr Phe Lys Thr Ala Glu Met Ala Ala Arg Ala His Asp Val Ala Ala
                85                  90                  95
Leu Ala Leu Arg Gly Arg Gly Ala Cys Leu Asn Tyr Ala Asp Ser Ala
            100                 105                 110
Trp Arg Leu Arg Ile Pro Glu Thr Thr Cys His Lys Asp Ile Gln Lys
        115                 120                 125
Ala Ala Ala Glu Ala Ala Leu Ala Phe Glu Ala Glu Lys Ser Asp Val
    130                 135                 140
Thr Met Gln Asn Gly Leu Asn Met Glu Glu Thr Thr Ala Val Ala Ser
145                 150                 155                 160
Gln Ala Glu Val Asn Asp Thr Thr Thr Glu His Gly Met Asn Met Glu
                165                 170                 175
Glu Ala Thr Ala Val Ala Ser Gln Ala Glu Val Asn Asp Thr Thr Thr
            180                 185                 190
Asp His Gly Val Asp Met Glu Glu Thr Met Val Glu Ala Val Phe Thr
        195                 200                 205
Gly Glu Gln Ser Glu Gly Phe Asn Met Ala Lys Glu Ser Thr Val Glu
    210                 215                 220
Ala Ala Val Val Thr Glu Glu Pro Ser Lys Gly Ser Tyr Met Asp Glu
225                 230                 235                 240
Glu Trp Met Leu Glu Met Pro Thr Leu Leu Ala Asp Met Ala Glu Gly
                245                 250                 255
Met Leu Leu Pro Pro Pro Ser Val Gln Trp Gly Gln Asn Asp Asp Phe
            260                 265                 270
Glu Gly Asp Ala Asp Met Asn
        275
```

<210> SEQ ID NO 52
<211> LENGTH: 874
<212> TYPE: DNA
<213> ORGANISM: Brassica napus
<220> FEATURE:
<223> OTHER INFORMATION: bnCBF4 gene

<400> SEQUENCE: 52

```
gtaattcgat taccgctcga gtacttacta tactacactc agccttatcc agttttttcaa     60
aagaagtttt caactatgaa ctcagtctct actttttctg aacttcttgg ctctgagaac    120
gagtctccgg taggtggtga ttactgtccc atgttggcgg cgagctgtcc gaagaagccg    180
gcgggtagga agaagtttcg ggagacacgt caccccattt accgaggagt tcgccttaga    240
aaatcaggta agtgggtgtg tgaagtgagg gaaccaaaca aaaaatctag gatttggctc    300
ggaactttca aaacagctga gatcgcagct cgtgctcacg acgtcgccgc cttagctctc    360
cgtggaagag gcgcctgcct caacttcgcc gactcggctt ggcggctccg tatcccggag    420
acaacctgcg ccaaggatat ccagaaggct gctgctgaag ccgcattggc ttttgaggcc    480
gagaagagtg ataccacgac gaatgatcat ggcatgaaca tggcttctca ggccgaggtt    540
aatgacacaa cggatcatgg cctggacatg gaggagacga tggtggaggc tgttttttact    600
gaggagcaga gagacgggtt ttacatggcg gaggagacga cggtggaggg tgttgttccg    660
gaggaacaga tgagcaaagg gttttacatg gacgaggagt ggatgttcgg gatgccgacc    720
ttgttggctg atatgcggc agggatgctc ttaccgccgc cgtccgtaca atggggacat    780
aatgatgact cgaaggaga tgttgacatg aacctctgga attattagta ctcatatttt    840
tttaaattat tttttgaacg aataatattt tatt                                874
```

<210> SEQ ID NO 53
<211> LENGTH: 250
<212> TYPE: PRT
<213> ORGANISM: Brassica napus
<220> FEATURE:
<223> OTHER INFORMATION: bnCBF4-PEP

<400> SEQUENCE: 53

```
Met Asn Ser Val Ser Thr Phe Ser Glu Leu Leu Gly Ser Glu Asn Glu
 1               5                  10                  15

Ser Pro Val Gly Gly Asp Tyr Cys Pro Met Leu Ala Ala Ser Cys Pro
             20                  25                  30

Lys Lys Pro Ala Gly Arg Lys Lys Phe Arg Glu Thr Arg His Pro Ile
         35                  40                  45

Tyr Arg Gly Val Arg Leu Arg Lys Ser Gly Lys Trp Val Cys Glu Val
     50                  55                  60

Arg Glu Pro Asn Lys Lys Ser Arg Ile Trp Leu Gly Thr Phe Lys Thr
 65                  70                  75                  80

Ala Glu Ile Ala Ala Arg Ala His Asp Val Ala Ala Leu Ala Leu Arg
                 85                  90                  95

Gly Arg Gly Ala Cys Leu Asn Phe Ala Asp Ser Ala Trp Arg Leu Arg
            100                 105                 110

Ile Pro Glu Thr Thr Cys Ala Lys Asp Ile Gln Lys Ala Ala Ala Glu
        115                 120                 125

Ala Ala Leu Ala Phe Glu Ala Glu Lys Ser Asp Thr Thr Thr Asn Asp
    130                 135                 140

His Gly Met Asn Met Ala Ser Gln Ala Glu Val Asn Asp Thr Thr Asp
145                 150                 155                 160

His Gly Leu Asp Met Glu Glu Thr Met Val Glu Ala Val Phe Thr Glu
                165                 170                 175

Glu Gln Arg Asp Gly Phe Tyr Met Ala Glu Glu Thr Thr Val Glu Gly
            180                 185                 190

Val Val Pro Glu Glu Gln Met Ser Lys Gly Phe Tyr Met Asp Glu Glu
        195                 200                 205

Trp Met Phe Gly Met Pro Thr Leu Leu Ala Asp Met Ala Ala Gly Met
    210                 215                 220

Leu Leu Pro Pro Pro Ser Val Gln Trp Gly His Asn Asp Asp Phe Glu
225                 230                 235                 240

Gly Asp Val Asp Met Asn Leu Trp Asn Tyr
                245                 250
```

<210> SEQ ID NO 54
<211> LENGTH: 898
<212> TYPE: DNA
<213> ORGANISM: Brassica napus
<220> FEATURE:
<223> OTHER INFORMATION: bnCBF5 gene

<400> SEQUENCE: 54

```
aataaatatc ttatcaaacc agtcagaaca gagatcttgt tacttactat actacactca    60
gccttatcca gttttcaaaa aaagtattca acgatgaact cagtctctac tttttctgaa   120
ctgctccgct ccgagaacga gtctccggtt aatacggaag gtggtgatta cattttggcg   180
gcgagctgtc ccaagaaacc tgctggtagg aagaagtttc aggagacacg ccaccccatt   240
tacagaggag ttcgtctgag gaagtcaggt aagtgggtgt gtgaagtgag ggaaccaaac   300
```

```
aagaaatcta gaatttggct cggaactttc aaaacagctg agatcgcagc tcgtgctcac      360
gacgttgccg ccttagctct ccgtggaaga ggcgcctgcc tcaacttcgc cgactcggct      420
tggcggctcc gtatcccgga gacgacctgc gccaaggata tccagaaggc tgctgctgaa      480
gccgcattgg cttttgaggc cgagaagagt gataccacga cgaatgatca tggcatgaac      540
atggcttctc aggttgaggt taatgacacg acggatcatg acctggacat ggaggagacg      600
atagtggagg ctgtttttag ggaggaacag agagaagggt tttacatggc ggaggagacg      660
acggttgtgg gtgttgttcc ggaggaacag atgagcaaag gttttacat ggacgaggag        720 tggatgttcg ggatgccgac cttgttggct gatatggcgg cagggatgct cttaccgctg      780
ccgtccgtac aatggggaca taatgatgac ttcgaaggag atgctgacat gaacctctgg      840
aattattagt actcatattt ttttaaatta tttttgaac gaataatatt ttattgaa         898
```

<210> SEQ ID NO 55
<211> LENGTH: 251
<212> TYPE: PRT
<213> ORGANISM: Brassica napus
<220> FEATURE:
<223> OTHER INFORMATION: bnCBF5-PEP

<400> SEQUENCE: 55

```
Met Asn Ser Val Ser Thr Phe Ser Glu Leu Leu Arg Ser Glu Asn Glu
 1               5                  10                  15

Ser Pro Val Asn Thr Glu Gly Gly Asp Tyr Ile Leu Ala Ala Ser Cys
            20                  25                  30

Pro Lys Lys Pro Ala Gly Arg Lys Lys Phe Gln Glu Thr Arg His Pro
        35                  40                  45

Ile Tyr Arg Gly Val Arg Leu Arg Lys Ser Gly Lys Trp Val Cys Glu
    50                  55                  60

Val Arg Glu Pro Asn Lys Lys Ser Arg Ile Trp Leu Gly Thr Phe Lys
65                  70                  75                  80

Thr Ala Glu Ile Ala Ala Arg Ala His Asp Val Ala Ala Leu Ala Leu
                85                  90                  95

Arg Gly Arg Gly Ala Cys Leu Asn Phe Ala Asp Ser Ala Trp Arg Leu
            100                 105                 110

Arg Ile Pro Glu Thr Thr Cys Ala Lys Asp Ile Gln Lys Ala Ala Ala
        115                 120                 125

Glu Ala Ala Leu Ala Phe Glu Ala Glu Lys Ser Asp Thr Thr Thr Asn
    130                 135                 140

Asp His Gly Met Asn Met Ala Ser Gln Val Glu Val Asn Asp Thr Thr
145                 150                 155                 160

Asp His Asp Leu Asp Met Glu Glu Thr Ile Val Glu Ala Val Phe Arg
                165                 170                 175

Glu Glu Gln Arg Glu Gly Phe Tyr Met Ala Glu Thr Thr Val Val
            180                 185                 190

Gly Val Val Pro Glu Glu Gln Met Ser Lys Gly Phe Tyr Met Asp Glu
        195                 200                 205

Glu Trp Met Phe Gly Met Pro Thr Leu Leu Ala Asp Met Ala Ala Gly
    210                 215                 220

Met Leu Leu Pro Leu Pro Ser Val Gln Trp Gly His Asn Asp Asp Phe
225                 230                 235                 240

Glu Gly Asp Ala Asp Met Asn Leu Trp Asn Tyr
                245                 250
```

-continued

<210> SEQ ID NO 56
<211> LENGTH: 1132
<212> TYPE: DNA
<213> ORGANISM: Brassica napus
<220> FEATURE:
<223> OTHER INFORMATION: bnCBF6 gene

<400> SEQUENCE: 56

| | | | | | |
|---|---|---|---|---|---|
| gattaccgct | cgagtactta | ctatactaca | ctcagcctta | tccagttttt | ctcaaaagat | 60 |
| ttttcaacaa | tgaacacatt | ccctgcttcc | actgaaatgg | ttggctccga | gaacgagtct | 120 |
| ccggttacta | cggtagtagg | aggtgattat | tatcccatgt | tggcggcaag | ctgtccgaag | 180 |
| aagccagcgg | gtaggaagaa | gtttcaggag | acacgtcacc | ccatttaccg | aggagttcgt | 240 |
| ctgagaaagt | caggtaagtg | ggtgtgtgaa | gtgagggaac | caaacaagaa | atctagaatt | 300 |
| tggcttggaa | ctttcaaaac | agctgagatg | gcagctcgtg | ctcacgacgt | ggctgcccta | 360 |
| gccctccgtg | gaagaggcgc | ctgcctcaat | tatgcggact | cggcttcgcg | gctccgcatc | 420 |
| ccggagacaa | cctgccacaa | ggatatccag | aaggctgctg | ctgaagccgc | attggctttt | 480 |
| gaggctgaga | aaagtgatgt | gacgatggag | gagacgatgg | cggtggcttc | tcaggctgaa | 540 |
| gtgaatgaca | cgacgacaga | tcatggcatg | aacatggagg | aggcaacagc | ggtggcttct | 600 |
| caggctgagt | gaatgacac | gacgacagat | catggcgtag | acatggagga | gacgatggtg | 660 |
| gaggctgttt | ttacggagga | acaaagtgaa | gggttcaaca | tggcggagga | gtcgacggtg | 720 |
| gaggctgctg | ttgttacgga | tgaactgagc | aaaggatttt | acatgacga | ggagtggacg | 780 |
| tacgagatgc | cgaccttgtt | ggctgatatg | gcggcaggga | tgcttttgcc | gccaccatct | 840 |
| gtacaatggg | gacataatga | tgacttggaa | ggagatgctg | acatgaacct | ctggaattat | 900 |
| taatactcgt | gttttaaaaa | ttatacattg | tgcaataata | ttttatcgaa | tttctaattc | 960 |
| tgcctttaac | ttttaatggg | gatctttatt | agtgtaggaa | acgagtgtaa | atgttccgcc | 1020 |
| gtggtgttgt | caaaatgctg | attattttt | gtgtcagca | taatcacgtt | tggtttcctt | 1080 |
| tacactccaa | atttagttga | aatacaaata | gaatagaaaa | gtgaaaaaat | gt | 1132 |

<210> SEQ ID NO 57
<211> LENGTH: 277
<212> TYPE: PRT
<213> ORGANISM: Brassica napus
<220> FEATURE:
<223> OTHER INFORMATION: bnCBF6-PEP

<400> SEQUENCE: 57

Met Asn Thr Phe Pro Ala Ser Thr Glu Met Val Gly Ser Glu Asn Glu
 1               5                  10                  15

Ser Pro Val Thr Thr Val Val Gly Gly Asp Tyr Tyr Pro Met Leu Ala
                20                  25                  30

Ala Ser Cys Pro Lys Lys Pro Ala Gly Arg Lys Lys Phe Gln Glu Thr
            35                  40                  45

Arg His Pro Ile Tyr Arg Gly Val Arg Leu Arg Ser Gly Lys Trp
        50                  55                  60

Val Cys Glu Val Arg Glu Pro Asn Lys Lys Ser Arg Ile Trp Leu Gly
 65                  70                  75                  80

Thr Phe Lys Thr Ala Glu Met Ala Ala Arg Ala His Asp Val Ala Ala
                85                  90                  95

Leu Ala Leu Arg Gly Arg Gly Ala Cys Leu Asn Tyr Ala Asp Ser Ala
            100                 105                 110

Ser Arg Leu Arg Ile Pro Glu Thr Thr Cys His Lys Asp Ile Gln Lys

```
                115                 120                      125
Ala Ala Ala Glu Ala Ala Leu Ala Phe Glu Ala Glu Lys Ser Asp Val
        130                 135                 140

Thr Met Glu Glu Thr Met Ala Val Ala Ser Gln Ala Glu Val Asn Asp
145                 150                 155                 160

Thr Thr Thr Asp His Gly Met Asn Met Glu Glu Ala Thr Ala Val Ala
                165                 170                 175

Ser Gln Ala Glu Val Asn Asp Thr Thr Thr Asp His Gly Val Asp Met
            180                 185                 190

Glu Glu Thr Met Val Glu Ala Val Phe Thr Glu Glu Gln Ser Glu Gly
        195                 200                 205

Phe Asn Met Ala Glu Ser Thr Val Glu Ala Val Val Thr Asp
210                 215                 220

Glu Leu Ser Lys Gly Phe Tyr Met Asp Glu Glu Trp Thr Tyr Glu Met
225                 230                 235                 240

Pro Thr Leu Leu Ala Asp Met Ala Ala Gly Met Leu Leu Pro Pro Pro
                245                 250                 255

Ser Val Gln Trp Gly His Asn Asp Asp Leu Gly Asp Ala Asp Met
            260                 265                 270

Asn Leu Trp Asn Tyr
        275

<210> SEQ ID NO 58
<211> LENGTH: 768
<212> TYPE: DNA
<213> ORGANISM: Brassica napus
<220> FEATURE:
<223> OTHER INFORMATION: bnCBF7 gene

<400> SEQUENCE: 58
agtgatgttt ttcaaaagaa gttttcaact atgaactcag tctctacttt ttctgaactt      60
cttggctctg agaacgagtc tccggtaggt ggtgattact gtcccatgtt ggcggcgagc     120
tgtccgaaga agccggcggg taggaagaag tttcgggaga cacgtcaccc catttaccga     180
ggagttcgcc ttagaaaatc aggtaagtgg gtgtgtgaag tgagggagcc aaacaagaaa     240
tctaggattt ggctcggtac tttcctaaca gccgagatcg cagcccgtgc tcacgacgtc     300
gccgccatag ccctccgcgg caaatcagct tgtctcaatt ttgccgactc cgcttggcgg     360
ctccgtatcc cggagacaac atgccccaag gagattcaga aggcggctgc tgaagccgcg     420
gtggctttta aggctgagat aaataatacg acggcggatc atggcattga cgtggaggag     480
acgatcgttg aggctatttt cacggaggaa acaacgatg  gttttatat  ggacgaggag     540 gagtccatgt tcgggatgcc ggccttgttg ctagtatgg  ctgaaggaat gcttttgccg     600
cctccgtccg tacaattcgg acataccat  gactttgacg gagatgctga cgtgtccctt     660
tggagttatt agtacaaaga ttttttattt ccattttgg  tataatactt cttttgatt     720 ttcggattct accttttat  gggtatcatt ttttttttag gaaacggg                   768

<210> SEQ ID NO 59
<211> LENGTH: 213
<212> TYPE: PRT
<213> ORGANISM: Brassica napus
<220> FEATURE:
<223> OTHER INFORMATION: bnCBF7-PEP

<400> SEQUENCE: 59

Met Asn Ser Val Ser Thr Phe Ser Glu Leu Leu Gly Ser Glu Asn Glu
```

```
 1               5                 10                15
Ser Pro Val Gly Gly Asp Tyr Cys Pro Met Leu Ala Ala Ser Cys Pro
             20                  25                30

Lys Lys Pro Ala Gly Arg Lys Lys Phe Arg Glu Thr Arg His Pro Ile
         35                  40                  45

Tyr Arg Gly Val Arg Leu Arg Lys Ser Gly Lys Trp Val Cys Glu Val
     50                  55                  60

Arg Glu Pro Asn Lys Lys Ser Arg Ile Trp Leu Gly Thr Phe Leu Thr
 65                  70                  75                  80

Ala Glu Ile Ala Ala Arg Ala His Asp Val Ala Ala Ile Ala Leu Arg
                 85                  90                  95

Gly Lys Ser Ala Cys Leu Asn Phe Ala Asp Ser Ala Trp Arg Leu Arg
             100                 105                 110

Ile Pro Glu Thr Thr Cys Pro Lys Glu Ile Gln Lys Ala Ala Ala Glu
             115                 120                 125

Ala Ala Val Ala Phe Lys Ala Glu Ile Asn Asn Thr Thr Ala Asp His
         130                 135                 140

Gly Ile Asp Val Glu Glu Thr Ile Val Glu Ala Ile Phe Thr Glu Glu
145                 150                 155                 160

Asn Asn Asp Gly Phe Tyr Met Asp Glu Glu Glu Ser Met Phe Gly Met
                 165                 170                 175

Pro Ala Leu Leu Ala Ser Met Ala Glu Gly Met Leu Leu Pro Pro Pro
             180                 185                 190

Ser Val Gln Phe Gly His Thr Tyr Asp Phe Asp Gly Asp Ala Asp Val
         195                 200                 205

Ser Leu Trp Ser Tyr
     210
```

<210> SEQ ID NO 60
<211> LENGTH: 953
<212> TYPE: DNA
<213> ORGANISM: Brassica napus
<220> FEATURE:
<223> OTHER INFORMATION: bnCBF8 gene

<400> SEQUENCE: 60

```
accgctcgag caacaatgaa cacattccct gcttccactg aaatggttgg ctccgagaac      60
gagtctccgg ttactacggt agcaggaggt gattattatc ccatgttggc ggcaagctgt     120
ccgaagaagc cagcgggtag gaagaagttt caggagacac gtcacccat ttaccgagga     180
gttcgtctga aaagtcagg taagtgggtg tgtgaagtga gggaaccaaa caagaaatct     240
agaatttggc ttggaacttt caaaacagct gagatgcag ctcgtgctca cgacgtggct     300
gccctagccc tccgtggaag aggcgcctgc ctcaattatg cggactcggc ttcgcggctc     360
cgcatcccgg agacaacctg ccacaaggat atccagaagg ctgctgctga agccgcattg     420
gcttttgagg ctgagaaaag tgatgtgacg atggaggaga cgatggcggt ggcttctcag     480
gctgaagtga atgacacgac gacagatcat ggcatgaaca tggaggaggc aacggcagtg     540
gcttctcagg ctgaggtgaa tgacacgacg acggatcatg gcgtagacat ggaggagaca     600
atggtggagg ctgtttttac tggggaacaa agtgaagggt taacatggc gaaggagtcg     660
acggtggagg ctgctgttgt tacggaggaa ccgagcaaag gatcttacat ggacgaggag     720
tggatgctcg agatgccgac cttgttggct gatatggcgg aagggatgct tttgccgccg     780
ccgtccgtac aatggggaca gaatgatgac ttcgaaggag atgcggacat gaacctctgg     840
```

```
agttattaat actcgtattt ttaaaattat ttattgtgca ataatttttt atcgaatttc        900
gaattctgcc tttaattttt aatggggatc tttatttgcc aaaaaaaaaa aaa              953
```

<210> SEQ ID NO 61
<211> LENGTH: 277
<212> TYPE: PRT
<213> ORGANISM: Brassica napus
<220> FEATURE:
<223> OTHER INFORMATION: bnCBF8-PEP

<400> SEQUENCE: 61

```
Met Asn Thr Phe Pro Ala Ser Thr Glu Met Val Gly Ser Glu Asn Glu
 1               5                  10                  15

Ser Pro Val Thr Thr Val Ala Gly Gly Asp Tyr Tyr Pro Met Leu Ala
            20                  25                  30

Ala Ser Cys Pro Lys Lys Pro Ala Gly Arg Lys Lys Phe Gln Glu Thr
        35                  40                  45

Arg His Pro Ile Tyr Arg Gly Val Arg Leu Arg Lys Ser Gly Lys Trp
    50                  55                  60

Val Cys Glu Val Arg Glu Pro Asn Lys Lys Ser Arg Ile Trp Leu Gly
65                  70                  75                  80

Thr Phe Lys Thr Ala Glu Met Ala Ala Arg Ala His Asp Val Ala Ala
                85                  90                  95

Leu Ala Leu Arg Gly Arg Gly Ala Cys Leu Asn Tyr Ala Asp Ser Ala
            100                 105                 110

Ser Arg Leu Arg Ile Pro Glu Thr Thr Cys His Lys Asp Ile Gln Lys
        115                 120                 125

Ala Ala Ala Glu Ala Ala Leu Ala Phe Glu Ala Glu Lys Ser Asp Val
    130                 135                 140

Thr Met Glu Glu Thr Met Ala Val Ala Ser Gln Ala Glu Val Asn Asp
145                 150                 155                 160

Thr Thr Thr Asp His Gly Met Asn Met Glu Glu Ala Thr Ala Val Ala
                165                 170                 175

Ser Gln Ala Glu Val Asn Asp Thr Thr Thr Asp His Gly Val Asp Met
            180                 185                 190

Glu Glu Thr Met Val Glu Ala Val Phe Thr Gly Glu Gln Ser Glu Gly
        195                 200                 205

Phe Asn Met Ala Lys Glu Ser Thr Val Glu Ala Ala Val Val Thr Glu
    210                 215                 220

Glu Pro Ser Lys Gly Ser Tyr Met Asp Glu Glu Trp Met Leu Glu Met
225                 230                 235                 240

Pro Thr Leu Leu Ala Asp Met Ala Glu Gly Met Leu Leu Pro Pro Pro
                245                 250                 255

Ser Val Gln Trp Gly Gln Asn Asp Asp Phe Glu Gly Asp Ala Asp Met
            260                 265                 270

Asn Leu Trp Ser Tyr
        275
```

<210> SEQ ID NO 62
<211> LENGTH: 889
<212> TYPE: DNA
<213> ORGANISM: Brassica napus
<220> FEATURE:
<223> OTHER INFORMATION: bnCBF9 gene

<400> SEQUENCE: 62

```
ctagtgatta ccgctcgagc aacaatgaac acattccctg cttccactga aatggttggc        60
```

```
tccgagaacg agtctccggt tactacggta gcaggaggtg attattatcc catgttggcg    120
gcaagctgtc cgaagaagcc agcgggtagg aagaagtttc aggagacacg tcaccccatt    180
taccgaggag ttcgtctgag aaagtcaggt aagtgggtgt gtgaagtgag ggaaccaaac    240
aagaaatcta gaatttggcc cggaactttc aaaacagctg agatggcagc tcgtgctcac    300
gacgtcgctg ccctagccct ccgtggaaga ggcgcccgcc tcaattatgc ggactcagct    360
tggcggctcc gcatcccgga gacaacctgc cacaaggata tccagaaggc tgctgctgaa    420
gccgcattgg cttttgaggc tgagaaaagt gatgtgacga tgcaaaatgg cctgaacatg    480
gaggagacga cggcggtggc ttctcaggct gaagtgaatg acacgacgac agaacatggc    540
atgaacatgg aggaggcaac ggcagtggct tctcaggcta ggtgaatga cacgacgacg    600 gatcatggcg tagacatgga ggagacaatg gtggaggctg tttttactgg ggaacaaagt    660
gaagggttta acatggcgaa ggagtcgacg gtggaggctg ctgttgttac ggaggaaccg    720
agcaaaggat cttacatgga cgaggagtgg atgctcgaga tgccgacctt gttggctgat    780
atggcggaag ggatgctttt gccgccgccg tccgtacaat ggggacagaa tgatgacttc    840
gaaggagatg cgcacatgaa cctctggagt tattaaggat ccgcgaatc                 889
```

<210> SEQ ID NO 63
<211> LENGTH: 283
<212> TYPE: PRT
<213> ORGANISM: Brassica napus
<220> FEATURE:
<223> OTHER INFORMATION: bnCBF9-PEP

<400> SEQUENCE: 63

```
Met Asn Thr Phe Pro Ala Ser Thr Glu Met Val Gly Ser Glu Asn Glu
  1               5                  10                  15

Ser Pro Val Thr Thr Val Ala Gly Gly Asp Tyr Tyr Pro Met Leu Ala
                 20                  25                  30

Ala Ser Cys Pro Lys Lys Pro Ala Gly Arg Lys Lys Phe Gln Glu Thr
             35                  40                  45

Arg His Pro Ile Tyr Arg Gly Val Arg Leu Arg Lys Ser Gly Lys Trp
         50                  55                  60

Val Cys Glu Val Arg Glu Pro Asn Lys Lys Ser Arg Ile Trp Pro Gly
 65                  70                  75                  80

Thr Phe Lys Thr Ala Glu Met Ala Ala Arg Ala His Asp Val Ala Ala
                 85                  90                  95

Leu Ala Leu Arg Gly Arg Gly Ala Arg Leu Asn Tyr Ala Asp Ser Ala
                100                 105                 110

Trp Arg Leu Arg Ile Pro Glu Thr Thr Cys His Lys Asp Ile Gln Lys
            115                 120                 125

Ala Ala Ala Glu Ala Ala Leu Ala Phe Glu Ala Glu Lys Ser Asp Val
        130                 135                 140

Thr Met Gln Asn Gly Leu Asn Met Glu Glu Thr Thr Ala Val Ala Ser
145                 150                 155                 160

Gln Ala Glu Val Asn Asp Thr Thr Thr Glu His Gly Met Asn Met Glu
                165                 170                 175

Glu Ala Thr Ala Val Ala Ser Gln Ala Glu Val Asn Asp Thr Thr Thr
            180                 185                 190

Asp His Gly Val Asp Met Glu Glu Thr Met Val Glu Ala Val Phe Thr
        195                 200                 205

Gly Glu Gln Ser Glu Gly Phe Asn Met Ala Lys Glu Ser Thr Val Glu
```

```
Ala Ala Val Val Thr Glu Glu Pro Ser Lys Gly Ser Tyr Met Asp Glu
225                 230                 235                 240

Glu Trp Met Leu Glu Met Pro Thr Leu Leu Ala Asp Met Ala Glu Gly
                245                 250                 255

Met Leu Leu Pro Pro Pro Ser Val Gln Trp Gly Gln Asn Asp Asp Phe
            260                 265                 270

Glu Gly Asp Ala His Met Asn Leu Trp Ser Tyr
        275                 280
```

<210> SEQ ID NO 64
<211> LENGTH: 563
<212> TYPE: DNA
<213> ORGANISM: Brassica oleracea
<220> FEATURE:
<223> OTHER INFORMATION: boCBF1 gene

<400> SEQUENCE: 64

```
caccctatct accggggagt tcgcctgaga aagtcaggta agtgggtgtg tgaagtgagg    60
gagccaaaca agaaatctag gatttggctt ggaactttca aaaccgcaga gatcgctgct   120
cgtgctcacg acgttgccgc cttagccctc cgtggaagag cggcctgtct caacttcgcc   180
gactcggctt ggcggctccg tatcccggag acaacttgcg ccaaggatat ccagaaggct   240
gctgctgaag ctgcgttggc ttttggggcc gaaaagagtg ataccacgac gaatgatcaa   300
ggcatgaaca tggaggagat gacggtggtg gcttctcagg ctgaggtgag cgacacgacg   360
acatatcatg gcctggacat ggaggagact atggtggagg ctgttttttgc tgaggaacag   420
agagaagggt tttacttggc ggaggagacg acggtggagg gtgttgttac ggaggaacag   480
agcaaagggt tttatatgga cgaggagtgg acgttcggga tgcagtcctt tttggccgat   540
atggctgaag gcatgctctt tcc                                          563
```

<210> SEQ ID NO 65
<211> LENGTH: 188
<212> TYPE: PRT
<213> ORGANISM: Brassica oleracea
<220> FEATURE:
<223> OTHER INFORMATION: boCBF1-PEP

<400> SEQUENCE: 65

```
His Pro Ile Tyr Arg Gly Val Arg Leu Arg Lys Ser Gly Lys Trp Val
1               5                   10                  15

Cys Glu Val Arg Glu Pro Asn Lys Lys Ser Arg Ile Trp Leu Gly Thr
            20                  25                  30

Phe Lys Thr Ala Glu Ile Ala Ala Arg Ala His Asp Val Ala Ala Leu
        35                  40                  45

Ala Leu Arg Gly Arg Ala Ala Cys Leu Asn Phe Ala Asp Ser Ala Trp
    50                  55                  60

Arg Leu Arg Ile Pro Glu Thr Thr Cys Ala Lys Asp Ile Gln Lys Ala
65                  70                  75                  80

Ala Ala Glu Ala Ala Leu Ala Phe Gly Ala Glu Lys Ser Asp Thr Thr
                85                  90                  95

Thr Asn Asp Gln Gly Met Asn Met Glu Glu Met Thr Val Val Ala Ser
            100                 105                 110

Gln Ala Glu Val Ser Asp Thr Thr Thr Tyr His Gly Leu Asp Met Glu
        115                 120                 125

Glu Thr Met Val Glu Ala Val Phe Ala Glu Glu Gln Arg Glu Gly Phe
```

```
            130                 135                 140
Tyr Leu Ala Glu Glu Thr Thr Val Glu Gly Val Val Thr Glu Glu Gln
145                 150                 155                 160

Ser Lys Gly Phe Tyr Met Asp Glu Glu Trp Thr Phe Gly Met Gln Ser
                165                 170                 175

Phe Leu Ala Asp Met Ala Glu Gly Met Leu Phe Pro
            180                 185

<210> SEQ ID NO 66
<211> LENGTH: 533
<212> TYPE: DNA
<213> ORGANISM: Brassica oleracea
<220> FEATURE:
<223> OTHER INFORMATION: boCBF2 gene

<400> SEQUENCE: 66
gaaacataga tctttgtact tactatactt caccttatcc agttttattt ttttatttat      60
aaagagtttt caacaatgac ctcatttcct accttttctg aactgttggg ctccgagcat     120
gagtctccgg ttacattagg cgaagagtat tgtccgaagc tggccgcaag ctgtccgaag     180
aaaccagccg gccggaagaa gtttcgagag acgcgtcacc cagtttacag aggagttcgt     240
ctgagaaact caggtaagtg ggtgtgtgaa gtgagggagc caaacaagaa atctaggatt     300
tggctcggta ctttcctaac agccgagatc gcagcccgtg ctcacgacgt cgccgccata     360
gccctccgcg gcaaatcagc ttgtctcaat tttgccgact ccgcttggcg gctccgtatc     420
ccggagacaa catgccccaa ggagattcag aaggcggctg ctgaagccgc ggtggctttt     480
aaggctgaga taaataatac gacggcggat cacggcctcg acatggaaga gac            533

<210> SEQ ID NO 67
<211> LENGTH: 152
<212> TYPE: PRT
<213> ORGANISM: Brassica oleracea
<220> FEATURE:
<223> OTHER INFORMATION: boCBF2-PEP

<400> SEQUENCE: 67

Met Thr Ser Phe Ser Thr Phe Ser Glu Leu Leu Gly Ser Glu His Glu
  1               5                  10                  15

Ser Pro Val Thr Leu Gly Glu Glu Tyr Cys Pro Lys Leu Ala Ala Ser
                20                  25                  30

Cys Pro Lys Lys Pro Ala Gly Arg Lys Lys Phe Arg Glu Thr Arg His
            35                  40                  45

Pro Val Tyr Arg Gly Val Arg Leu Arg Asn Ser Gly Lys Trp Val Cys
        50                  55                  60

Glu Val Arg Glu Pro Asn Lys Lys Ser Arg Ile Trp Leu Gly Thr Phe
 65                  70                  75                  80

Leu Thr Ala Glu Ile Ala Ala Arg Ala His Asp Val Ala Ala Ile Ala
                85                  90                  95

Leu Arg Gly Lys Ser Ala Cys Leu Asn Phe Ala Asp Ser Ala Trp Arg
            100                 105                 110

Leu Arg Ile Pro Glu Thr Thr Cys Pro Lys Glu Ile Gln Lys Ala Ala
        115                 120                 125

Ala Glu Ala Ala Val Ala Phe Lys Ala Glu Ile Asn Asn Thr Thr Ala
    130                 135                 140

Asp His Gly Leu Asp Met Glu Glu
145                 150
```

<210> SEQ ID NO 68
<211> LENGTH: 887
<212> TYPE: DNA
<213> ORGANISM: Brassica oleracea
<220> FEATURE:
<223> OTHER INFORMATION: boCBF3 gene

<400> SEQUENCE: 68

```
actcagcctt atccagtttt tctcaaaaga tttttcaaca atgaacacat tccctgcttc      60
cactgaaatg gttggctccg agaacgagtc tccggttact acggtagtag gaggtgatta     120
ttatcccatg ttggcggcaa gctgtccgaa gaagccagcg ggtaggaaga agtttcagga     180
gacacgtcac cccatttacc gaggagttcg tctgagaaag tcaggtaagt gggtgtgtga     240
agtgagggaa ccaaacaaga aatctagaat ttggcttgga actttcaaaa cagctgagat     300
ggcagctcgt gctcacgacg tggctgccct agccctccgt ggaagaggcg cctgcctcaa     360
ttatgcggac tcggcttggc ggctccgcat cccggagaca acctgccaca aggatatcca     420
gaaggctgct gctgaagccg cattggcttt tgaggctgag aaaagtgatg tgacgatgga     480
ggagacgatg gcggtggctt ctcaggctga agtgaatgac acgacgacag atcatggcat     540
gaacatggag gaggcaacag cggtggcttc tcaggctgag gtgaatgaca cgacgacaga     600
tcatggcgta gacatggagg agacgatggt ggaggctgtt tttacggagg aacaaagtga     660
agggttcaac atggcggagg agtcgacggt ggaggctgct gttgttacgg atgaactgag     720
caaaggattt tacatggacg aggagtggac gtacgagatg ccgaccttgt tggctgatat     780
ggcggcaggg atgctttttgc cgccaccatc tgtacaatgg ggacataatg atgacttgga     840
aggagatgcg gacatgaacc tctggagtta ttaatactcg tattttt                  887
```

<210> SEQ ID NO 69
<211> LENGTH: 277
<212> TYPE: PRT
<213> ORGANISM: Brassica oleracea
<220> FEATURE:
<223> OTHER INFORMATION: boCBF3-PEP

<400> SEQUENCE: 69

```
Met Asn Thr Phe Pro Ala Ser Thr Glu Met Val Gly Ser Glu Asn Glu
  1               5                  10                  15

Ser Pro Val Thr Thr Val Val Gly Gly Asp Tyr Tyr Pro Met Leu Ala
             20                  25                  30

Ala Ser Cys Pro Lys Lys Pro Ala Gly Arg Lys Lys Phe Gln Glu Thr
         35                  40                  45

Arg His Pro Ile Tyr Arg Gly Val Arg Leu Arg Lys Ser Gly Lys Trp
     50                  55                  60

Val Cys Glu Val Arg Glu Pro Asn Lys Lys Ser Arg Ile Trp Leu Gly
 65                  70                  75                  80

Thr Phe Lys Thr Ala Glu Met Ala Ala Arg Ala His Asp Val Ala Ala
                 85                  90                  95

Leu Ala Leu Arg Gly Arg Gly Ala Cys Leu Asn Tyr Ala Asp Ser Ala
            100                 105                 110

Trp Arg Leu Arg Ile Pro Glu Thr Thr Cys His Lys Asp Ile Gln Lys
        115                 120                 125

Ala Ala Ala Glu Ala Ala Leu Ala Phe Glu Ala Glu Lys Ser Asp Val
    130                 135                 140

Thr Met Glu Glu Thr Met Ala Val Ala Ser Gln Ala Glu Val Asn Asp
145                 150                 155                 160
```

Thr Thr Thr Asp His Gly Met Asn Met Glu Glu Ala Thr Ala Val Ala
            165                 170                 175

Ser Gln Ala Glu Val Asn Asp Thr Thr Thr Asp His Gly Val Asp Met
        180                 185                 190

Glu Glu Thr Met Val Glu Ala Val Phe Thr Glu Gln Ser Glu Gly
    195                 200                 205

Phe Asn Met Ala Glu Glu Ser Thr Val Glu Ala Ala Val Val Thr Asp
    210                 215                 220

Glu Leu Ser Lys Gly Phe Tyr Met Asp Glu Glu Trp Thr Tyr Glu Met
225                 230                 235                 240

Pro Thr Leu Leu Ala Asp Met Ala Ala Gly Met Leu Leu Pro Pro Pro
            245                 250                 255

Ser Val Gln Trp Gly His Asn Asp Asp Leu Glu Gly Asp Ala Asp Met
            260                 265                 270

Asn Leu Trp Ser Tyr
        275

<210> SEQ ID NO 70
<211> LENGTH: 950
<212> TYPE: DNA
<213> ORGANISM: Brassica oleracea
<220> FEATURE:
<223> OTHER INFORMATION: boCBF4 gene

<400> SEQUENCE: 70

| | | | | | |
|---|---|---|---|---|---|
| ctgaaaagaa | gataaaagag | agagaaataa | atatcttatc | aaaccagaca | gaacagagat | 60 |
| cttgttactt | actatactac | actcagcctt | atccagtttt | tcaaaagaag | ttttcaacta | 120 |
| tgaactcagt | ctctactttt | tctgaacttc | ttggctctga | gaacgagtct | ccggtaggtg | 180 |
| gtgattactg | tccatgttg | gcggcgagct | gtccgaagaa | gccggcgggt | aggaagaagt | 240 |
| tcgggagac | acgtcacccc | atttaccgag | gagttcgcct | agaaaatca | ggtaagtggg | 300 |
| tgtgtgaagt | gagggaacca | aacaaaaaat | ctaggatttg | gctcggaact | ttcaaaacag | 360 |
| ctgagatcgc | agctcgtgct | cacgacgtcg | ccgccttagc | tctccgtgga | agaggcgcct | 420 |
| gcctcaactt | cgccgactcg | gcttggcggc | tccgtatccc | ggagacaacc | tgcgccaagg | 480 |
| atatccagaa | ggctgctgct | gaagccgcat | tggcttttga | ggccgagaag | agtgatacca | 540 |
| cgacgaatga | tcatggcatg | aacatggctt | ctcaggctga | ggttaatgac | acgacggatc | 600 |
| atggcctgga | catggaggag | acgatggtgg | aggctgtttt | tactgaggag | cagagagacg | 660 |
| ggttttacat | ggcggaggag | acgacggtgg | agggtgttgt | tccggaggaa | cagatgagca | 720 |
| aagggttta | catggacgag | gagtggatgt | tcgggatgcc | gaccttgttg | gctgatatgg | 780 |
| cggcagggat | gctcttaccg | ccgccgtccg | tacaatgggg | acataatgat | gacttcgaag | 840 |
| gagatgctga | catgaacctc | tggaattatt | agtactcgta | ttttttaaa | ttattttttg | 900 |
| aacgaataat | attttattga | attcggattc | tacctgtttt | tttaatggat | | 950 |

<210> SEQ ID NO 71
<211> LENGTH: 250
<212> TYPE: PRT
<213> ORGANISM: Brassica oleracea
<220> FEATURE:
<223> OTHER INFORMATION: boCBF4-PEP

<400> SEQUENCE: 71

Met Asn Ser Val Ser Thr Phe Ser Glu Leu Leu Gly Ser Glu Asn Glu
  1               5                  10                  15

Ser Pro Val Gly Gly Asp Tyr Cys Pro Met Leu Ala Ala Ser Cys Pro
            20                  25                  30

Lys Lys Pro Ala Gly Arg Lys Lys Phe Arg Glu Thr Arg His Pro Ile
        35                  40                  45

Tyr Arg Gly Val Arg Leu Arg Lys Ser Gly Lys Trp Val Cys Glu Val
    50                  55                  60

Arg Glu Pro Asn Lys Lys Ser Arg Ile Trp Leu Gly Thr Phe Lys Thr
65                  70                  75                  80

Ala Glu Ile Ala Ala Arg Ala His Asp Val Ala Ala Leu Ala Leu Arg
                85                  90                  95

Gly Arg Gly Ala Cys Leu Asn Phe Ala Asp Ser Ala Trp Arg Leu Arg
            100                 105                 110

Ile Pro Glu Thr Thr Cys Ala Lys Asp Ile Gln Lys Ala Ala Ala Glu
        115                 120                 125

Ala Ala Leu Ala Phe Glu Ala Glu Lys Ser Asp Thr Thr Thr Asn Asp
    130                 135                 140

His Gly Met Asn Met Ala Ser Gln Ala Glu Val Asn Asp Thr Thr Asp
145                 150                 155                 160

His Gly Leu Asp Met Glu Glu Thr Met Val Glu Ala Val Phe Thr Glu
                165                 170                 175

Glu Gln Arg Asp Gly Phe Tyr Met Ala Glu Thr Thr Val Glu Gly
            180                 185                 190

Val Val Pro Glu Glu Gln Met Ser Lys Gly Phe Tyr Met Asp Glu Glu
        195                 200                 205

Trp Met Phe Gly Met Pro Thr Leu Leu Ala Asp Met Ala Ala Gly Met
    210                 215                 220

Leu Leu Pro Pro Pro Ser Val Gln Trp Gly His Asn Asp Asp Phe Glu
225                 230                 235                 240

Gly Asp Ala Asp Met Asn Leu Trp Asn Tyr
                245                 250

<210> SEQ ID NO 72
<211> LENGTH: 877
<212> TYPE: DNA
<213> ORGANISM: Brassica oleracea
<220> FEATURE:
<223> OTHER INFORMATION: boCBF5 gene

<400> SEQUENCE: 72
accgctcgag caacaatgaa cacattccct gcttccactg aaatggttag ctccgagaac      60
gagtctccgg ttactacggt agtaggaggt gattattatc ccatgttggc ggcaagctgt     120
ccgaagaagc cagcgggtag gaagaagttt caggagacac gtcaccccat ttaccgagga     180
gttcgtctga aaagtcagg taagtgggtg tgtgaagtga gggaactaaa caagaaatct     240
agaatttggc ttggaacttt caaaacagct gagatggcag ctcgtgctca cgacgtggct     300
gccctagccc tccgtggaag aggcgcctgc ctcaattatg cggactcggc ttggcggctc     360
cgcatcccgg agacaacctg ccacaaggat atccagaagg ctgctgctga agccgcattg     420
gcttttgagg ctgagaagag tgatgcgacg atgcaaaatg gcctgaacat ggaggagacg     480
acggcggcgg cttctcagac tgaagtgagt gacacgacga cagatcatgg catgaacatg     540
gaggagacaa cggcggtggc ttctcaggct gaggtgaatg acacgacgac agatcatggc     600
gtagacatgg aggagacgat ggtggaggct gttttttactg aggaacaaag tgaagggttc     660
aacatggcga aggagtcgac ggcggaggct gctgttgtta cggaggaact gagcaaagga     720

```
gtttacatgg acgaggagtg gacgtacgag atgccgacct tgttggctga tatggcggca      780
gggatgcttt tgccgccacc atctgtacaa tggggacata atgatgactt ggaaggagat      840
gcggacatga acctactgga gttattaagg atccgcg                                877
```

<210> SEQ ID NO 73
<211> LENGTH: 287
<212> TYPE: PRT
<213> ORGANISM: Brassica oleracea
<220> FEATURE:
<223> OTHER INFORMATION: boCBF5-PEP

<400> SEQUENCE: 73

```
Met Asn Thr Phe Pro Ala Ser Thr Glu Met Val Ser Ser Glu Asn Glu
 1               5                  10                  15

Ser Pro Val Thr Thr Val Val Gly Gly Asp Tyr Tyr Pro Met Leu Ala
             20                  25                  30

Ala Ser Cys Pro Lys Lys Pro Ala Gly Arg Lys Lys Phe Gln Glu Thr
         35                  40                  45

Arg His Pro Ile Tyr Arg Gly Val Arg Leu Arg Lys Ser Gly Lys Trp
     50                  55                  60

Val Cys Glu Val Arg Glu Leu Asn Lys Lys Ser Arg Ile Trp Leu Gly
 65                  70                  75                  80

Thr Phe Lys Thr Ala Glu Met Ala Ala Arg Ala His Asp Val Ala Ala
                 85                  90                  95

Leu Ala Leu Arg Gly Arg Gly Ala Cys Leu Asn Tyr Ala Asp Ser Ala
            100                 105                 110

Trp Arg Leu Arg Ile Pro Glu Thr Thr Cys His Lys Asp Ile Gln Lys
        115                 120                 125

Ala Ala Ala Glu Ala Ala Leu Ala Phe Glu Ala Glu Lys Ser Asp Ala
    130                 135                 140

Thr Met Gln Asn Gly Leu Asn Met Glu Glu Thr Thr Ala Ala Ala Ser
145                 150                 155                 160

Gln Thr Glu Val Ser Asp Thr Thr Asp His Gly Met Asn Met Glu
                165                 170                 175

Glu Thr Thr Ala Val Ala Ser Gln Ala Glu Val Asn Asp Thr Thr Thr
            180                 185                 190

Asp His Gly Val Asp Met Glu Glu Thr Met Val Glu Ala Val Phe Thr
        195                 200                 205

Glu Glu Gln Ser Glu Gly Phe Asn Met Ala Lys Glu Ser Thr Ala Glu
    210                 215                 220

Ala Ala Val Val Thr Glu Glu Leu Ser Lys Gly Val Tyr Met Asp Glu
225                 230                 235                 240

Glu Trp Thr Tyr Glu Met Pro Thr Leu Leu Ala Asp Met Ala Ala Gly
                245                 250                 255

Met Leu Leu Pro Pro Pro Ser Val Gln Trp Gly His Asn Asp Asp Leu
            260                 265                 270

Glu Gly Asp Ala Asp Met Asn Leu Leu Glu Leu Leu Arg Ile Arg
        275                 280                 285
```

<210> SEQ ID NO 74
<211> LENGTH: 374
<212> TYPE: DNA
<213> ORGANISM: Brassica rapa
<220> FEATURE:
<223> OTHER INFORMATION: brCBF1 gene

```
<400> SEQUENCE: 74
catcccattt acagggggt tcgtttaaga aagtcaggta agtgggtgtg tgaagtgagg      60
gaaccaaaca agaaatctag gatttggctc ggaactttca aaaccgctga gatcgctgct    120
cgtgctcacg acgttgctgc cttagccctc cgcgggagag gcgcctgcct caacttcgcc   180
gactcggctt ggcggctccg tatcccggag acaacctgcg ccaaggacat ccagaaggcg   240
gctgctgaag ctgcattggc ttttgaggcc gagaagagtg atcatggcat gaacatcaag   300
aatactacgg cggtggtttc tcaggttgag gtgaatgaca cgacgacgga ccacggcttg   360
gacatggagg agac                                                      374

<210> SEQ ID NO 75
<211> LENGTH: 124
<212> TYPE: PRT
<213> ORGANISM: Brassica rapa
<220> FEATURE:
<223> OTHER INFORMATION: brCBF1 PRP

<400> SEQUENCE: 75

His Pro Ile Tyr Arg Gly Val Arg Leu Arg Lys Ser Gly Lys Trp Val
  1               5                  10                  15

Cys Glu Val Arg Glu Pro Asn Lys Lys Ser Arg Ile Trp Leu Gly Thr
             20                  25                  30

Phe Lys Thr Ala Glu Ile Ala Ala Arg Ala His Asp Val Ala Ala Leu
         35                  40                  45

Ala Leu Arg Gly Arg Gly Ala Cys Leu Asn Phe Ala Asp Ser Ala Trp
     50                  55                  60

Arg Leu Arg Ile Pro Glu Thr Thr Cys Ala Lys Asp Ile Gln Lys Ala
 65                  70                  75                  80

Ala Ala Glu Ala Ala Leu Ala Phe Glu Ala Glu Lys Ser Asp His Gly
                 85                  90                  95

Met Asn Ile Lys Asn Thr Thr Ala Val Val Ser Gln Val Glu Val Asn
            100                 105                 110

Asp Thr Thr Thr Asp His Gly Leu Asp Met Glu Glu
        115                 120

<210> SEQ ID NO 76
<211> LENGTH: 884
<212> TYPE: DNA
<213> ORGANISM: Brassica rapa
<220> FEATURE:
<223> OTHER INFORMATION: brCBF2 gene

<400> SEQUENCE: 76
tacactcagc cttatccagt tttttcaaa agacttttca acaatgaaca cattccctgc      60
gtccactgaa atggttggct ccgagaacga gtctccggtt actacggtag caggaggtga   120
ttattatccc atgttggcgg caagctgtcc gaagaagcca gcgggtagga agaagtttca   180
ggagacacgt cacccccattt accgaggagt tcgtctgaga aagtcaggta agtgggtgtg   240
tgaagtgagg gaaccaaaca agaaatctag aatttggctt ggaactttca aaacagctga   300
gatggcagct cgtgctcacg acgtcgctgc cctagccctc cgtggaagag gcgcctgcct   360
caattatgcg gactcggctt ggcggctccg catcccggag acaacctgcc acaaggatat   420
ccagaaggct gctgctgaag ccgcattggc ttttgaggct gagaaaagtg atgtgacgat   480
gcaaaatggc ctgaacatgg aggagatgac ggcggtggct ctcaggctg aagtgaatga    540
cacgacgaca gaacatggca tgaacatgga ggaggcaacg gcagtggctt ctcaggctga   600
```

```
ggtgaatgac acgacgacgg atcatggcgt agacatggag agacaatggt ggaggctgt      660 ttttactgag gaacaaagtg aagggtttaa catggcgaag gagtcgacgg tggaggctgc     720
tgttgttacg gaggaaccga gcaaaggatc ttacatggac gaggagtgga tgctcgagat     780
gccgaccttg ttggctgata tggcggaagg gatgcttttg ccgccgccgt ccgtacaatg     840
gggacagaat gatgacttcg aaggagatgc tgacatgaac ctct                      884
```

<210> SEQ ID NO 77
<211> LENGTH: 280
<212> TYPE: PRT
<213> ORGANISM: Brassica rapa
<220> FEATURE:
<223> OTHER INFORMATION: brCBF2-PEP

<400> SEQUENCE: 77

```
Met Asn Thr Phe Pro Ala Ser Thr Glu Met Val Gly Ser Glu Asn Glu
 1               5                  10                  15

Ser Pro Val Thr Thr Val Ala Gly Gly Asp Tyr Tyr Pro Met Leu Ala
             20                  25                  30

Ala Ser Cys Pro Lys Lys Pro Ala Gly Arg Lys Lys Phe Gln Glu Thr
         35                  40                  45

Arg His Pro Ile Tyr Arg Gly Val Arg Leu Arg Lys Ser Gly Lys Trp
     50                  55                  60

Val Cys Glu Val Arg Glu Pro Asn Lys Lys Ser Arg Ile Trp Leu Gly
 65                  70                  75                  80

Thr Phe Lys Thr Ala Glu Met Ala Ala Arg Ala His Asp Val Ala Ala
                 85                  90                  95

Leu Ala Leu Arg Gly Arg Gly Ala Cys Leu Asn Tyr Ala Asp Ser Ala
            100                 105                 110

Trp Arg Leu Arg Ile Pro Glu Thr Thr Cys His Lys Asp Ile Gln Lys
        115                 120                 125

Ala Ala Ala Glu Ala Ala Leu Ala Phe Glu Ala Glu Lys Ser Asp Val
    130                 135                 140

Thr Met Gln Asn Gly Leu Asn Met Glu Glu Met Thr Ala Val Ala Ser
145                 150                 155                 160

Gln Ala Glu Val Asn Asp Thr Thr Glu His Gly Met Asn Met Glu
                165                 170                 175

Glu Ala Thr Ala Val Ala Ser Gln Ala Glu Val Asn Asp Thr Thr Thr
            180                 185                 190

Asp His Gly Val Asp Met Glu Glu Thr Met Val Glu Ala Val Phe Thr
        195                 200                 205

Glu Glu Gln Ser Glu Gly Phe Asn Met Ala Lys Glu Ser Thr Val Glu
    210                 215                 220

Ala Ala Val Val Thr Glu Glu Pro Ser Lys Gly Ser Tyr Met Asp Glu
225                 230                 235                 240

Glu Trp Met Leu Glu Met Pro Thr Leu Leu Ala Asp Met Ala Glu Gly
                245                 250                 255

Met Leu Leu Pro Pro Pro Ser Val Gln Trp Gly Gln Asn Asp Asp Phe
            260                 265                 270

Glu Gly Asp Ala Asp Met Asn Leu
        275                 280
```

<210> SEQ ID NO 78
<211> LENGTH: 806
<212> TYPE: DNA

```
<213> ORGANISM: Brassica rapa
<220> FEATURE:
<223> OTHER INFORMATION: brCBF3 gene

<400> SEQUENCE: 78
acactcagcc ttatccagtt ttcaaaaaaa gtattcaacg atgaactcag tctctacttt      60
ttctgaactg ctctgctccg agaacgagtc tccggttaat acggaaggtg gtgattacat     120
tttggcggcg agctgtccca agaaacctgc tggtaggaag aagtttcagg agacacgcca     180
ccccatttac agaggagttc gtctgaggaa gtcaggtaag tgggtgtgtg aagtgaggga     240
accaaacaag aaatctagaa tttggctcgg aactttcaaa acagctgaga tcgcagctcg     300
tgctcacgac gttccgcct tagctctccg tggaagaggc gcctgcctca acttcgccga      360
ctcggcttgg cggctccgta tcccggagac gacctgcgcc aaggatatcc agaaggctgc     420
tgctgaagcc gcattggctt ttgaggccga agagtgat accacgacga atgatcgtgg       480
catgaacatg gaggagacgt cggcggtggc ttctccggct gagttgaatg atacgacggc     540
ggatcatggc ctggacatgg aggagacgat ggtggaggct gtttttaggg aggaacagag     600
agaagggttt tacatggcgg aggagacgac ggtggagggt gttgttccgg agtaacagat     660
gagcaaaggg ttttacatgg acgaggagtg gacgttcgag atgccgaggt tgttggctga     720
tatggcggaa gggatgcttt tgccgccccc gtccgtacaa tggggacata cgatgactt      780
cgaaggagat gctgacatga acctct                                          806

<210> SEQ ID NO 79
<211> LENGTH: 204
<212> TYPE: PRT
<213> ORGANISM: Brassica rapa
<220> FEATURE:
<223> OTHER INFORMATION: brCBF3 PEP

<400> SEQUENCE: 79

Met Asn Ser Val Ser Thr Phe Ser Glu Leu Leu Cys Ser Glu Asn Glu
  1               5                  10                  15

Ser Pro Val Asn Thr Glu Gly Gly Asp Tyr Ile Leu Ala Ala Ser Cys
             20                  25                  30

Pro Lys Lys Pro Ala Gly Arg Lys Lys Phe Gln Glu Thr Arg His Pro
         35                  40                  45

Ile Tyr Arg Gly Val Arg Leu Arg Lys Ser Gly Lys Trp Val Cys Glu
     50                  55                  60

Val Arg Glu Pro Asn Lys Lys Ser Arg Ile Trp Leu Gly Thr Phe Lys
 65                  70                  75                  80

Thr Ala Glu Ile Ala Ala Arg Ala His Asp Val Ala Ala Leu Ala Leu
                 85                  90                  95

Arg Gly Arg Gly Ala Cys Leu Asn Phe Ala Asp Ser Ala Trp Arg Leu
            100                 105                 110

Arg Ile Pro Glu Thr Thr Cys Ala Lys Asp Ile Gln Lys Ala Ala Ala
        115                 120                 125

Glu Ala Ala Leu Ala Phe Glu Ala Glu Lys Ser Asp Thr Thr Thr Asn
    130                 135                 140

Asp Arg Gly Met Asn Met Glu Glu Thr Ser Ala Val Ala Ser Pro Ala
145                 150                 155                 160

Glu Leu Asn Asp Thr Thr Ala Asp His Gly Leu Asp Met Glu Glu Thr
                165                 170                 175

Met Val Glu Ala Val Phe Arg Glu Glu Gln Arg Glu Gly Phe Tyr Met
            180                 185                 190
```

Ala Glu Glu Thr Thr Val Glu Gly Val Val Pro Glu
        195                 200

<210> SEQ ID NO 80
<211> LENGTH: 755
<212> TYPE: DNA
<213> ORGANISM: Brassica rapa
<220> FEATURE:
<223> OTHER INFORMATION: brCBF4 gene

<400> SEQUENCE: 80

| | | | | | |
|---|---|---|---|---|---|
| accgctcgag | tacttactat | actacactca | gccttatcca | gttttcttc | caacgatgga | 60 |
| ctcaatctct | acttttcctg | aactgcttgg | ctcagagaac | gagtctccgg | ttactacggt | 120 |
| agtaggaggt | gattattgtc | ccaggttggc | ggcaagctgt | ccgaagaagc | cagcgggtag | 180 |
| gaagaagttt | caggagacac | gtcaccccat | ttaccgtgga | gttcgtttaa | gaaagtccgg | 240 |
| taagtgggtg | tgtgaagtga | gggaaccaaa | caagaaatct | aggatttggc | tcggaacttt | 300 |
| caaaaccgct | gagatcgctg | ctcgtgctca | cgacgttgct | gccttagccc | tccgcggaag | 360 |
| aggcgcctgc | ctcaacttcg | ccgactcggc | ttgacggctc | cgtatcccgg | agacaacctg | 420 |
| cgccaaggat | atccagaagg | ctgctgctga | agctgcattg | gcttttgagg | ccgagaagag | 480 |
| tgatcatggc | atgaacatga | agaatactac | ggcggtggct | tctcaggttg | aggtgaatga | 540 |
| tacgacgacg | gaccatggcg | tggacatgga | ggagacgagg | gtggagggtg | ttgttacgga | 600 |
| ggaacagaac | aattggtttt | acatggacga | ggagtggatg | tttgggatgc | cgacgttgtt | 660 |
| ggttgatatg | gcggaaggga | tgcttatacc | gcggcagtcc | gtacaatcgg | gacactacga | 720 |
| tgacttcgaa | ggagatgctg | acatgaacct | ctgga | | | 755 |

<210> SEQ ID NO 81
<211> LENGTH: 112
<212> TYPE: PRT
<213> ORGANISM: Brassica rapa
<220> FEATURE:
<223> OTHER INFORMATION: brCBF4 pep

<400> SEQUENCE: 81

Met Asp Ser Ile Ser Thr Phe Pro Glu Leu Leu Gly Ser Glu Asn Glu
1               5                   10                  15

Ser Pro Val Thr Thr Val Val Gly Gly Asp Tyr Cys Pro Arg Leu Ala
            20                  25                  30

Ala Ser Cys Pro Lys Lys Pro Ala Gly Arg Lys Lys Phe Gln Glu Thr
        35                  40                  45

Arg His Pro Ile Tyr Arg Gly Val Arg Leu Arg Lys Ser Gly Lys Trp
    50                  55                  60

Val Cys Glu Val Arg Glu Pro Asn Lys Lys Ser Arg Ile Trp Leu Gly
65                  70                  75                  80

Thr Phe Lys Thr Ala Glu Ile Ala Ala Arg Ala His Asp Val Ala Ala
                85                  90                  95

Leu Ala Leu Arg Gly Arg Gly Ala Cys Leu Asn Phe Ala Asp Ser Ala
            100                 105                 110

<210> SEQ ID NO 82
<211> LENGTH: 832
<212> TYPE: DNA
<213> ORGANISM: Brassica rapa
<220> FEATURE:
<223> OTHER INFORMATION: brCBF5 gene -continued

```
<400> SEQUENCE: 82
accgctcgag tacttactat actacactca gccttatcca gttttcttc caacgatgga      60
ctcaatctct acttttcctg aactgcttgg ctcagagaac gagtctccgg ttactacggt    120
agtaggaggt gattattgtc ccaggttggc ggcaagctgt ccgaagaagc cagcgggtag    180
gaagaagttt caggagacac gtcaccccat ttaccgtgga gttcgtttaa gaaagtccgg    240
taagtgggtg tgtgaagtga gggaaccaaa caagaaatct aggatttggc tcggaacttt    300
caaaaccgct gagatcgctg ctcgtgctca cgacgttgct gccttagccc tccgcggaag    360
aggcgcctgc ctcaacttcg ccgactcggc ttggcggctc cgtatcccgg agacaacctg    420
cgccaaggat atccagaagg ctgctgctga agctgctttg gcttttgagg ccgagaagag    480
tgatcatggc atgaacatga agaatactac ggcggtggct tctcaggttg aggtgaatga    540
tacgacgacg gaccatggcg tggacatgga ggagacgttg gtggaggctg ttttacgga    600
ggaacagaga gaagggtttt acatgacgga ggagacgagg gtggagggtg ttgttacgga    660
ggaacagaac aattggtttt acatggacga ggagtggatg tttgggatgc cgacgttgtt    720
ggttgatatg gcggaaggga tgcttatacc gcggcagtcc gtacaatcgg gacactacga    780
tgacttcgaa ggagatgctg acatgaacct ctggaattat tagggatccg cg            832
```

```
<210> SEQ ID NO 83
<211> LENGTH: 255
<212> TYPE: PRT
<213> ORGANISM: Brassica rapa
<220> FEATURE:
<223> OTHER INFORMATION: brCBF5-PEP

<400> SEQUENCE: 83
```

Met Asp Ser Ile Ser Thr Phe Pro Glu Leu Leu Gly Ser Glu Asn Glu
 1               5                  10                  15

Ser Pro Val Thr Thr Val Val Gly Gly Asp Tyr Cys Pro Arg Leu Ala
             20                  25                  30

Ala Ser Cys Pro Lys Lys Pro Ala Gly Arg Lys Lys Phe Gln Glu Thr
         35                  40                  45

Arg His Pro Ile Tyr Arg Gly Val Arg Leu Arg Lys Ser Gly Lys Trp
     50                  55                  60

Val Cys Glu Val Arg Glu Pro Asn Lys Lys Ser Arg Ile Trp Leu Gly
 65                  70                  75                  80

Thr Phe Lys Thr Ala Glu Ile Ala Ala Arg Ala His Asp Val Ala Ala
                 85                  90                  95

Leu Ala Leu Arg Gly Arg Gly Ala Cys Leu Asn Phe Ala Asp Ser Ala
            100                 105                 110

Trp Arg Leu Arg Ile Pro Glu Thr Thr Cys Ala Lys Asp Ile Gln Lys
        115                 120                 125

Ala Ala Ala Glu Ala Ala Leu Ala Phe Glu Ala Glu Lys Ser Asp His
    130                 135                 140

Gly Met Asn Met Lys Asn Thr Thr Ala Val Ala Ser Gln Val Glu Val
145                 150                 155                 160

Asn Asp Thr Thr Thr Asp His Gly Val Asp Met Glu Glu Thr Leu Val
                165                 170                 175

Glu Ala Val Phe Thr Glu Glu Gln Arg Glu Gly Phe Tyr Met Thr Glu
            180                 185                 190

Glu Thr Arg Val Glu Gly Val Val Thr Glu Glu Gln Asn Asn Trp Phe
        195                 200                 205

```
Tyr Met Asp Glu Glu Trp Met Phe Gly Met Pro Thr Leu Leu Val Asp
    210                 215                 220
Met Ala Glu Gly Met Leu Ile Pro Arg Gln Ser Val Gln Ser Gly His
225                 230                 235                 240
Tyr Asp Asp Phe Glu Gly Asp Ala Asp Met Asn Leu Trp Asn Tyr
                245                 250                 255

<210> SEQ ID NO 84
<211> LENGTH: 830
<212> TYPE: DNA
<213> ORGANISM: Brassica rapa
<220> FEATURE:
<223> OTHER INFORMATION: brCBF6 gene

<400> SEQUENCE: 84
tactacactc agccttatcc agttttcaaa aaaagtattc aactatgaac tcagtctcta    60
cttttctga actgctctgc tccgagaaca agtctccggt taatacgaaa ggtggtgatt   120
acattttggc ggcgagctgt cccaagaaac ctgctggtag aagaagtttt caggagacac   180
gccacccat ttacagagga gttcgcctaa gaaagtcagg taagtgggtg tgtgaagtga   240
gggaaccaaa caagaaatct agaatttggc tcggaacttt caaaacagct gagatagcag   300
ctcgtgctca cgacgtcgcc gcttagctc tccgtggaag aggcgcctgc ctcaacttcg   360
ccgactcggc ttggcggctc cgtatcccag agacaacctg cgccaaggat atccagaagg   420
ctgctgctga agccgcattg cttttgagg ccgagaagag tgataccacg acgaatgatc   480
gtggcatgaa catggaggag acgtccgcgg tggcttctcc ggctgagttg aatgatacga   540
cggcggatca tggcctggac atggaggaga cgatggtgga ggctgttttt agggacgaac   600
agagagaagg gttttacatg gcggaggaga cgacggtgga gggtgttgtt ccggaggaac   660
agatgagcaa agggttttac atggacgagg agtggacgtt cgagatgccg aggttgttgg   720
ctgatatggc ggaagggatg cttctgcctc ccccgtccgt acaatgggga cataacgatg   780
acttcgaagg agatgctgac atgaacctct ggaattatta gggatccgcg              830

<210> SEQ ID NO 85
<211> LENGTH: 258
<212> TYPE: PRT
<213> ORGANISM: Brassica rapa
<220> FEATURE:
<223> OTHER INFORMATION: brCBF6-PEP

<400> SEQUENCE: 85

Met Asn Ser Val Ser Thr Phe Ser Glu Leu Leu Cys Ser Glu Asn Lys
1               5                   10                  15
Ser Pro Val Asn Thr Glu Gly Gly Asp Tyr Ile Leu Ala Ala Ser Cys
                20                  25                  30
Pro Lys Lys Pro Ala Gly Arg Lys Phe Gln Glu Thr Arg His Pro
        35                  40                  45
Ile Tyr Arg Gly Val Arg Leu Arg Lys Ser Gly Lys Trp Val Cys Glu
    50                  55                  60
Val Arg Glu Pro Asn Lys Lys Ser Arg Ile Trp Leu Gly Thr Phe Lys
65                  70                  75                  80
Thr Ala Glu Ile Ala Ala Arg Ala His Asp Val Ala Ala Leu Ala Leu
                85                  90                  95
Arg Gly Arg Gly Ala Cys Leu Asn Phe Ala Asp Ser Ala Trp Arg Leu
                100                 105                 110
Arg Ile Pro Glu Thr Thr Cys Ala Lys Asp Ile Gln Lys Ala Ala Ala
```

```
                115                 120                     125
Glu Ala Ala Leu Ala Phe Glu Ala Glu Lys Ser Asp Thr Thr Thr Asn
        130                 135                 140

Asp Arg Gly Met Asn Met Glu Glu Thr Ser Ala Val Ala Ser Pro Ala
145                 150                 155                 160

Glu Leu Asn Asp Thr Thr Ala Asp His Gly Leu Asp Met Glu Glu Thr
                165                 170                 175

Met Val Glu Ala Val Phe Arg Asp Glu Gln Arg Glu Gly Phe Tyr Met
            180                 185                 190

Ala Glu Glu Thr Thr Val Glu Gly Val Val Pro Glu Glu Gln Met Ser
        195                 200                 205

Lys Gly Phe Tyr Met Asp Glu Glu Trp Thr Phe Glu Met Pro Arg Leu
    210                 215                 220

Leu Ala Asp Met Ala Glu Gly Met Leu Leu Pro Pro Pro Ser Val Gln
225                 230                 235                 240

Trp Gly His Asn Asp Asp Phe Glu Gly Asp Ala Asp Met Asn Leu Trp
                245                 250                 255

Asn Tyr

<210> SEQ ID NO 86
<211> LENGTH: 854
<212> TYPE: DNA
<213> ORGANISM: Brassica rapa
<220> FEATURE:
<223> OTHER INFORMATION: brCBF7 gene

<400> SEQUENCE: 86
ctatactaca cacagcctta tccagccgct cgagtactta ctatactaca ctcagccttt      60
tccagttttt caaaagaagt tttcaacgat gaactcagtc tctactcttt ctgaagttct     120
tggctcccag aacgagtctc ccgtaggtgg tgattactgt cccatgttgg cggcgagctg     180
tccgaagaag ccggcgggta ggaagaagtt tcgggagaca cgtcacccca tttacagagg     240
agttcgtctt agaaagtcag gtaagtgggt gtgtgaagtg agggaaccaa acaagaaatc     300
taggatttgg ctcggaactt tcaaaacagc tgagatcgca gctcgtgctc acgacgttgc     360
cgccttagct ctccgtggaa gaggcgcctg cctcaacttc gccgactcgg cttggcggct     420
ccgtatcccg gagacaacct gcgccaagga tatccagaag gctgctgctg aagccgcatt     480
ggcttttgag gcggagaaga gtgataccac gacgacgaat gatcatggca tgaacatggc     540
ttctcaggtt gaggttaatg cacgacgga tcatgacctg gacatggagg agacgatggt     600
ggaggctgtt tttagggagg aacagagaga agggttttac atggcggagg agacgacggt     660
ggagggtatt gttccggagg aacagatgag caaagggttt tacatggacg aggagtggat     720
gttcgggatg ccgaccttgt tggctgatat ggcggcaggg atgctcttac cgccgccgtc     780
cgtacaatgg ggacataatg atgacttcga aggagatgct gacatgaacc tctggaatta     840
ttaagggatc gcgg                                                       854

<210> SEQ ID NO 87
<211> LENGTH: 251
<212> TYPE: PRT
<213> ORGANISM: Brassica rapa
<220> FEATURE:
<223> OTHER INFORMATION: brCBF7 PEP

<400> SEQUENCE: 87

Met Asn Ser Val Ser Thr Leu Ser Glu Val Leu Gly Ser Gln Asn Glu
```

|   1 |       |     | 5   |     |     |     |     | 10  |     |     |     |     | 15  |     |     |
|-----|-------|-----|-----|-----|-----|-----|-----|-----|-----|-----|-----|-----|-----|-----|-----|
| Ser | Pro   | Val | Gly | Gly | Asp | Tyr | Cys | Pro | Met | Leu | Ala | Ala | Ser | Cys | Pro |
|     |       |     |     | 20  |     |     |     |     | 25  |     |     |     |     | 30  |     |

Ser Pro Val Gly Gly Asp Tyr Cys Pro Met Leu Ala Ala Ser Cys Pro
                    20                  25                  30

Lys Lys Pro Ala Gly Arg Lys Lys Phe Arg Glu Thr Arg His Pro Ile
        35                  40                  45

Tyr Arg Gly Val Arg Leu Arg Lys Ser Gly Lys Trp Val Cys Glu Val
    50                  55                  60

Arg Glu Pro Asn Lys Lys Ser Arg Ile Trp Leu Gly Thr Phe Lys Thr
65                  70                  75                  80

Ala Glu Ile Ala Ala Arg Ala His Asp Val Ala Ala Leu Ala Leu Arg
                85                  90                  95

Gly Arg Gly Ala Cys Leu Asn Phe Ala Asp Ser Ala Trp Arg Leu Arg
                100                 105                 110

Ile Pro Glu Thr Thr Cys Ala Lys Asp Ile Gln Lys Ala Ala Ala Glu
            115                 120                 125

Ala Ala Leu Ala Phe Glu Ala Glu Lys Ser Asp Thr Thr Thr Thr Asn
    130                 135                 140

Asp His Gly Met Asn Met Ala Ser Gln Val Glu Val Asn Asp Thr Thr
145                 150                 155                 160

Asp His Asp Leu Asp Met Glu Glu Thr Met Val Glu Ala Val Phe Arg
                165                 170                 175

Glu Glu Gln Arg Glu Gly Phe Tyr Met Ala Glu Thr Thr Val Glu
                180                 185                 190

Gly Ile Val Pro Glu Glu Gln Met Ser Lys Gly Phe Tyr Met Asp Glu
        195                 200                 205

Glu Trp Met Phe Gly Met Pro Thr Leu Leu Ala Asp Met Ala Ala Gly
    210                 215                 220

Met Leu Leu Pro Pro Pro Ser Val Gln Trp Gly His Asn Asp Asp Phe
225                 230                 235                 240

Glu Gly Asp Ala Asp Met Asn Leu Trp Asn Tyr
                245                 250

```
<210> SEQ ID NO 88
<211> LENGTH: 738
<212> TYPE: DNA
<213> ORGANISM: Glycine max
<220> FEATURE:
<223> OTHER INFORMATION: gmCBF1 gene

<400> SEQUENCE: 88
catccgattt atagtggcgt gaggaggagg aacacggata agtgggtaag tgaggtgagg      60
gagcccaaca aaaagaccag gatttggctg gggacttttc ccacgccgga gatggcggca     120
cgggcccacg acgtggcggc aatggccctg aggggccggt atgcctgtct caacttcgct     180
gactcgacgt ggcggttacc aattcccgcc actgctaacg caaggatat acagaaagca      240 gcagcagagg ctgccgaggc tttcagacca agtcagacct agaaaatac gaatacaaag      300 caagagtgtg taaagtggt gacgacaaca acgatcacag aacaaaaacg aggaatgttt      360
tatacggagg aagaagagca agtgttagat atgcctgagt tgcttaggaa tatggtgctt     420
atgtccccaa cacattgcat agggtatgag tatgaagatg ctgacttgga tgctcaagat     480
gctgaggtgt ccctatggag tttctcaatt taataacgtg cttttggttt ggttttttat     540
gttagttttg gagtgtgact gtctgtactg gttttttatt agtagtacgg atactagcta     600
taggtggcag attgaaaggg accaaaagga atttctttt gaaacccttt ttgtcaaagt      660
```

```
aatcaatcgc gtatcatcaa gtgaatccct tgatcaagtt tatgtatgaa ttaaataaaa    720
gaagaatcta gttttggt                                                   738
```

<210> SEQ ID NO 89
<211> LENGTH: 170
<212> TYPE: PRT
<213> ORGANISM: Glycine max
<220> FEATURE:
<223> OTHER INFORMATION: gmCBF1-PEP

<400> SEQUENCE: 89

```
His Pro Ile Tyr Ser Gly Val Arg Arg Arg Asn Thr Asp Lys Trp Val
  1               5                  10                  15

Ser Glu Val Arg Glu Pro Asn Lys Lys Thr Arg Ile Trp Leu Gly Thr
             20                  25                  30

Phe Pro Thr Pro Glu Met Ala Ala Arg Ala His Asp Val Ala Ala Met
         35                  40                  45

Ala Leu Arg Gly Arg Tyr Ala Cys Leu Asn Phe Ala Asp Ser Thr Trp
     50                  55                  60

Arg Leu Pro Ile Pro Ala Thr Ala Asn Ala Lys Asp Ile Gln Lys Ala
 65                  70                  75                  80

Ala Ala Glu Ala Ala Glu Ala Phe Arg Pro Ser Gln Thr Leu Glu Asn
                 85                  90                  95

Thr Asn Thr Lys Gln Glu Cys Val Lys Val Val Thr Thr Thr Thr Ile
            100                 105                 110

Thr Glu Gln Lys Arg Gly Met Phe Tyr Thr Glu Glu Glu Gln Val
        115                 120                 125

Leu Asp Met Pro Glu Leu Leu Arg Asn Met Val Leu Met Ser Pro Thr
    130                 135                 140

His Cys Ile Gly Tyr Glu Tyr Glu Asp Ala Asp Leu Asp Ala Gln Asp
145                 150                 155                 160

Ala Glu Val Ser Leu Trp Ser Phe Ser Ile
                165                 170
```

<210> SEQ ID NO 90
<211> LENGTH: 793
<212> TYPE: DNA
<213> ORGANISM: Raphanus sativus
<220> FEATURE:
<223> OTHER INFORMATION: rsCBF1 gene

<400> SEQUENCE: 90

```
actacactca gccttatcca gttttcttc caacgatgga ctcaatctct acttttctg      60 aactgcttgg ctccgagaac gagtctccgg ttactacgga gtaggaggt gattattttc    120 ccaggttggc ggcaagctgt ccgaagaagc cagcgggtag gaagaagttt caggagacac    180
gtcaccccat ttaccgcgga gttcgtttaa gaaagtcagg taagtgggtg tgtgaagtga    240
gggaaccaaa caagaaatct aggatttggc tcggaacttt caaaaccgct gagatcgctg    300
ctcgtgctca cgacgttgct gccttagccc tccgcggaag aggcgcctgc ctcaacttcg    360
ccgactcggc ttggcggctc cgtatcccgg agacaacctg cgccaaggat atccagaagg    420
ctgctgctga agctgcattg gcttttgagg ccgagaagag tgatcatggc atgaacatga    480
agaatactac ggcggtggct ctcaggttg aggtgaatga cacgacgacg gaccatggcg    540
tggacatgga ggagacgttg gtggaggctg ttttacgga ggaacagaga gaagggtttt    600
acatgacgga ggagacgagg gtggagggtg ttgttacgga ggaacagaac aattggtttt    660
```

```
acatggacga ggagtggatg tttgggatgc cgacgttgtt ggttgatatg gcggaaggga      720 tgctttttacc gcggccgtcc gtacaatcgg gacactacga tgacttcgaa ggagatgctg     780
acatgaacct ctg                                                          793
```

<210> SEQ ID NO 91
<211> LENGTH: 252
<212> TYPE: PRT
<213> ORGANISM: Raphanus sativus
<220> FEATURE:
<223> OTHER INFORMATION: rsCBF1-PEP

<400> SEQUENCE: 91

```
Met Asp Ser Ile Ser Thr Phe Ser Glu Leu Leu Gly Ser Glu Asn Glu
  1               5                  10                  15

Ser Pro Val Thr Thr Val Val Gly Gly Asp Tyr Phe Pro Arg Leu Ala
             20                  25                  30

Ala Ser Cys Pro Lys Lys Pro Ala Gly Arg Lys Lys Phe Gln Glu Thr
         35                  40                  45

Arg His Pro Ile Tyr Arg Gly Val Arg Leu Arg Lys Ser Gly Lys Trp
     50                  55                  60

Val Cys Glu Val Arg Glu Pro Asn Lys Lys Ser Arg Ile Trp Leu Gly
 65                  70                  75                  80

Thr Phe Lys Thr Ala Glu Ile Ala Ala Arg Ala His Asp Val Ala Ala
                 85                  90                  95

Leu Ala Leu Arg Gly Arg Gly Ala Cys Leu Asn Phe Ala Asp Ser Ala
            100                 105                 110

Trp Arg Leu Arg Ile Pro Glu Thr Thr Cys Ala Lys Asp Ile Gln Lys
        115                 120                 125

Ala Ala Ala Glu Ala Ala Leu Ala Phe Glu Ala Glu Lys Ser Asp His
    130                 135                 140

Gly Met Asn Met Lys Asn Thr Thr Ala Val Ala Ser Gln Val Glu Val
145                 150                 155                 160

Asn Asp Thr Thr Thr Asp His Gly Val Asp Met Glu Glu Thr Leu Val
                165                 170                 175

Glu Ala Val Phe Thr Glu Glu Gln Arg Glu Gly Phe Tyr Met Thr Glu
            180                 185                 190

Glu Thr Arg Val Glu Gly Val Val Thr Glu Gln Asn Asn Trp Phe
        195                 200                 205

Tyr Met Asp Glu Glu Trp Met Phe Gly Met Pro Thr Leu Leu Val Asp
    210                 215                 220

Met Ala Glu Gly Met Leu Leu Pro Arg Pro Ser Val Gln Ser Gly His
225                 230                 235                 240

Tyr Asp Asp Phe Glu Gly Asp Ala Asp Met Asn Leu
                245                 250
```

<210> SEQ ID NO 92
<211> LENGTH: 682
<212> TYPE: DNA
<213> ORGANISM: Raphanus sativus
<220> FEATURE:
<223> OTHER INFORMATION: rsCBF2 gene

<400> SEQUENCE: 92

```
acacctaaac cttatccagg tttaactttt tttttcataa agagttttca acaatgacca      60
cattttctac cttttccgaa atgttgggct ccgagtacga gtctccggtt acattaggcg     120
gagagtattg tccgaagctg gccgcgagct gtccgaagaa accagctggt cgtaagaagt     180
```

```
ttcgagagac gcgccaccca atatacagag gagttcgtct gagaaactca ggtaagtggg      240
tgtgtgaagt gagggagcca acaagaaat ctaggatttg gctcggtact ttcctaaccg      300
ccgagatcgc agcgcgtgcc cacgacgtcg ccgccatagc cctccgcggc aaatccgcat     360
gtctcaattt cgctgactcg gcttggcggc tccgtatccc ggagacaaca tgccccaagg     420
atatacagaa ggcggctgct gaagccgcgg tggcttttca ggctgagata aatgatacga     480
cgacggatca tggcctggac ttggaggaga cgatcgtgga ggctattttt acggaggtaa     540
acaacgatga gttttatatg gacgaggagt ccatgttcgg gatgccgtct ttgttggcta     600
gtatggcgga agggatgctt ttgccgctgc cgtccgtaca atctgaacat aactgtgact     660
tcgacggaga tgctgacatg aa                                              682
```

<210> SEQ ID NO 93
<211> LENGTH: 209
<212> TYPE: PRT
<213> ORGANISM: Raphanus sativus
<220> FEATURE:
<223> OTHER INFORMATION: rsCBF2-PEP

<400> SEQUENCE: 93

```
Met Thr Thr Phe Ser Thr Phe Ser Glu Met Leu Gly Ser Glu Tyr Glu
 1               5                  10                  15

Ser Pro Val Thr Leu Gly Gly Glu Tyr Cys Pro Lys Leu Ala Ala Ser
            20                  25                  30

Cys Pro Lys Lys Pro Ala Gly Arg Lys Lys Phe Arg Glu Thr Arg His
        35                  40                  45

Pro Ile Tyr Arg Gly Val Arg Leu Arg Asn Ser Gly Lys Trp Val Cys
    50                  55                  60

Glu Val Arg Glu Pro Asn Lys Lys Ser Arg Ile Trp Leu Gly Thr Phe
65                  70                  75                  80

Leu Thr Ala Glu Ile Ala Ala Arg Ala His Asp Val Ala Ala Ile Ala
                85                  90                  95

Leu Arg Gly Lys Ser Ala Cys Leu Asn Phe Ala Asp Ser Ala Trp Arg
            100                 105                 110

Leu Arg Ile Pro Glu Thr Thr Cys Pro Lys Asp Ile Gln Lys Ala Ala
        115                 120                 125

Ala Glu Ala Ala Val Ala Phe Gln Ala Glu Ile Asn Asp Thr Thr Thr
    130                 135                 140

Asp His Gly Leu Asp Leu Glu Glu Thr Ile Val Glu Ala Ile Phe Thr
145                 150                 155                 160

Glu Val Asn Asn Asp Glu Phe Tyr Met Asp Glu Glu Ser Met Phe Gly
                165                 170                 175

Met Pro Ser Leu Leu Ala Ser Met Ala Glu Gly Met Leu Leu Pro Leu
            180                 185                 190

Pro Ser Val Gln Ser Glu His Asn Cys Asp Phe Asp Gly Asp Ala Asp
        195                 200                 205

Met
```

<210> SEQ ID NO 94
<211> LENGTH: 349
<212> TYPE: DNA
<213> ORGANISM: Zea maize
<220> FEATURE:
<223> OTHER INFORMATION: zmCBF1 gene

<400> SEQUENCE: 94

-continued

```
cggagtccgc ggacggcggc ggcggcggcg acgacgagta cgcgacggtg ctgtcggcgc      60
cacccaagcg gccggcgggg cggaccaagt tccgggagac gcggcacccc gtgtaccgcg     120
gcgtgcggcg gcgcgggccc gcggggcgct gggtgtgcga ggtccgcgag cccaacaaga    180
agtcgcgcat ctggctcggc accttcgcca ccccgaggc cgccgcgcgc gcgcacgacg     240
tggccgcgct ggccctgcgg ggccgcgccg cgtgcctcaa cttcgccgac tcggcgcgcc   300
tgctccaagt cgacccccgcc acgctcgcca ccccgacga catccgccg               349
```

<210> SEQ ID NO 95
<211> LENGTH: 115
<212> TYPE: PRT
<213> ORGANISM: Zea maize
<220> FEATURE:
<223> OTHER INFORMATION: smCBF1-PEP

<400> SEQUENCE: 95

```
Glu Ser Ala Asp Gly Gly Gly Gly Asp Asp Glu Tyr Ala Thr Val
  1               5                  10                  15

Leu Ser Ala Pro Pro Lys Arg Pro Ala Gly Arg Thr Lys Phe Arg Glu
                 20                  25                  30

Thr Arg His Pro Val Tyr Arg Gly Val Arg Arg Arg Gly Pro Ala Gly
             35                  40                  45

Arg Trp Val Cys Glu Val Arg Glu Pro Asn Lys Lys Ser Arg Ile Trp
 50                  55                  60

Leu Gly Thr Phe Ala Thr Pro Glu Ala Ala Ala Arg Ala His Asp Val
 65                  70                  75                  80

Ala Ala Leu Ala Leu Arg Gly Arg Ala Ala Cys Leu Asn Phe Ala Asp
                 85                  90                  95

Ser Ala Arg Leu Leu Gln Val Asp Pro Ala Thr Leu Ala Thr Pro Asp
                100                 105                 110

Asp Ile Arg
        115
```